US012606871B2

(12) United States Patent (10) Patent No.: US 12,606,871 B2

Teixeira et al. (45) **Date of Patent: \*Apr. 21, 2026**

(54) MOLECULAR SIGNATURE

(71) Applicant: UCL Business LTD, London (GB)

(72) Inventors: Vitor Hugo De Sousa Teixeira, London (GB); Samuel Janes, London (GB); Christodoulos P. Pipinikas, London (GB); Adam James Pennycuick, London (GB)

(73) Assignee: UCL Business LTD, London (GB)

( * ) Notice: Subject to any disclaimer, the term of this patent is extended or adjusted under 35 U.S.C. 154(b) by 407 days.

This patent is subject to a terminal disclaimer.

(21) Appl. No.: 17/309,349

(22) PCT Filed: Nov. 29, 2019

(86) PCT No.: PCT/GB2019/053388

§ 371 (c)(1),
(2) Date: May 20, 2021

(87) PCT Pub. No.: WO2020/109820

PCT Pub. Date: Jun. 4, 2020

(65) Prior Publication Data

US 2022/0017967 A1 Jan. 20, 2022

(30) Foreign Application Priority Data

Nov. 29, 2018 (GB) ...................................... 1819453

(51) Int. Cl.
C12Q 1/6886 (2018.01)

(52) U.S. Cl.
CPC ...... C12Q 1/6886 (2013.01); *C12Q 2600/112* (2013.01); *C12Q 2600/118* (2013.01); *C12Q 2600/154* (2013.01)

(58) Field of Classification Search
CPC ............ C12Q 1/6886; C12Q 2600/112; C12Q 2600/118; C12Q 2600/154; C12Q 2600/156; C12Q 2600/158
See application file for complete search history.

(56) References Cited

U.S. PATENT DOCUMENTS

2013/0109644 A1 * 5/2013 MacBeth ............. A61K 31/706
514/43
2014/0080715 A1 3/2014 Lo et al.
2017/0298437 A1 10/2017 Huang et al.

FOREIGN PATENT DOCUMENTS

| WO | 2012154979 A2 | 11/2012 |
| WO | 2013096661 A1 | 6/2013 |
| WO | 2016115530 A1 | 7/2016 |
| WO | 2017106481 A1 | 6/2017 |

OTHER PUBLICATIONS

Stueve et al. Human Molecular Genetics, 2017, vol. 26, No. 15, 3014-3027.*
Um (Clinical Epigenetics, 2019, 6:131, pp. 1-10).*
Technical Note: Epigenetic Analysis. Illumina Methylation BeadChips Achieve Breadth of Coverage Using 2 Infinium® Chemistries, published in 2015 and available at: http://www.illumina.com/content/dam/illumina-marketing/documents/products/technotes/technote_hm450_data_analysis_optimization.pdf.
Technical Note: Epigenetics. CpG Loci Identification. A guide to Illumina's method for unambiguous CpG loci identification and tracking for the Golden Gate? and Infinium? Assay for Methylation, published in 2010 and available at: https://support.illumina.com/documents/products/technotes/technote_cpg_loci_identification.pdf.
Teixeira, V.H. et al.: Deciphering the genomic, epigenomic, and transcriptomic landscape of pre-invasive lung cancer lesions. Nat Med. 2019, 25(3):517-525.
Teschendorff, A. E. et al. DNA methylation outliers in normal breast tissue identify field defects that are enriched in cancer. Nat Commun 7, 10478, doi:10.1038/ncomms10478 (2016).
Thorvaldsdottir, H., Robinson, J. T. & Mesirov, J. P. Integrative Genomics Viewer (IGV): high-performance genomics data visualization and exploration. Brief Bioinform 14, 178-192, doi:10.1093/bib/bbs017 (2013).
Tibshirani, R. et al.: Class prediction by nearest shrunken centroids, with applications to DNA microarrays. Statist. Sci. 2003, 18(1): 104-117.
Tibshirani, R., Hastie, T., Narasimhan, B. & Chu, G. Diagnosis of multiple cancer types by shrunken centroids of gene expression. Proceedings of the National Academy of Sciences of the United States of America 99, 6567-6572, doi:10.1073/pnas.082099299 (2002).
Van Boerdonk, R. A et al. DNA copy number aberrations in endobronchial lesions: a validated predictor for cancer. Thorax 69, 451-457, doi:10.1136/thoraxjnl-2013-203821 (2014).

(Continued)

*Primary Examiner* — Sarae L Bausch

(74) *Attorney, Agent, or Firm* — Norton Rose Fulbright US LLP

(57) ABSTRACT

The present invention relates to a method of identifying a pre-invasive lung lesion in an individual that will progress to an invasive lung cancer involving determining the presence or absence of a molecular signature.

The present invention also relates to a method of treating a pre-invasive lung lesion and/or treating and/or preventing an invasive lung cancer in an induvial comprising involving determining the presence or absence of a molecular signature.

The present invention further relates to a molecular signature, and uses thereof, for identifying whether or not an individual has a pre-invasive lung lesion that will progress to an invasive lung cancer.

14 Claims, 30 Drawing Sheets

Specification includes a Sequence Listing.

(56) References Cited

OTHER PUBLICATIONS

Van Boerdonk, R. A et al. DNA copy number alterations in endobronchial squamous metaplastic lesions predict lung cancer. American journal of respiratory and critical care medicine 184, 948-956, doi:10.1164/rccm.201102-02180C (2011).

Van Loo, P. et al. Allele-specific copy number analysis of tumors. Proc Natl Acad Sci U S A 107, 16910-16915, doi:10.1073/pnas.1009843107 (2010).

Whitfield, M. L. et al. Identification of genes periodically expressed in the human cell cycle and their expression in tumors. Mol Biol Cell 13, 1977-2000, doi:10.1091/mbc.02-02-0030. (2002).

Xiong, Z. & Laird, P. W.: COBRA: a sensitive and quantitative DNA methylation assay. Nucleic Acids Res. 1997, 25:2532-2534.

Ye, K., Schulz, M. H., Long, Q., Apweiler, R. & Ning, Z. Pindel: a pattern growth approach to detect break points of large deletions and medium sized insertions from paired-end short reads. Bioinformatics 25, 2865-2871, doi:10.1093/bioinformatics/btp394 (2009).

Alexandrov, L. B. et al. Clock-like mutational processes in human somatic cells. Nat Genet 47, 1402-1407, doi:10.1038/ng.3441 (2015).

Alexandrov, L. B. et al. Signatures of mutational processes in human cancer. Nature 500, 415-421, doi:10.1038/nature12477 (2013).

Benjamini, Y., Drai, D., Elmer, G., Kafkafi, N. & Golani, I. Controlling the false discovery rate in behavior genetics research. Behav Brain Res 125, 279-284 (2001).

Bibikova, M. et al. High density DNA methylation array with single CpG site resolution. Genomics 98, 288-295, doi:10.1016/j.ygeno.2011.07.007 (2011).

Blokzijl, F., Janssen, R., van Boxtel, R. & Cuppen, E. MutationalPatterns: comprehensive genome-wide analysis of mutational processes. Genome Med 10, 33, doi: 10.1186/s13073-018-0539-0 (2018).

Buyer's guide. Simple, customized RNA-Seq workflows, published in 2018 and available at: https://www.illumina.com/content/dam/illumina-marketing/documents/products/other/rna-sequencing-workflow-buyers-guide-476-2015-003.pdf.

Carter, S. L., Eklund, A. C., Kohane, I. S., Harris, L. N. & Szallasi, Z. A signature of chromosomal instability inferred from gene expression profiles predicts clinical outcome in multiple human cancers. Nat Genet 38, 1043-1048, doi:10.1038/ng1861 (2006).

Chang, J.T. et al.: The impact of the Cancer Genome Atlas on lung cancer. Transl Res. 2015, 166(6):568-585.

Chari, R. et al.: Integrating the multiple dimensions of genomic and epigenomic landscapes of cancer. Cancer Metastasis Rev. 2010, 29(1):73-93.

Corney and Basturea. Material and Methods 2013, 3:203, available at: https://www.labome.com/method/RNA-seq.html.

Data Sheet: Epigenetics. Infinium® Human Methylation450 BeadChip, published in 2012 and available at: http://www.illumina.com/content/dam/illumina-marketing/documents/products/datasheets/datasheet_humanmethylation450.pdf.

Endesfelder, D. et al. Chromosomal instability selects gene copy-No. variants encoding core regulators of proliferation in ER+ breast cancer. Cancer Res 74, 4853-4863, doi:10.1158/0008-5472.CAN-13-2664 (2014).

Farmery, J. H. R., Smith, M. L. & Lynch, A. G. Telomerecat: A Ploidy-Agnostic Method For Estimating Telomere Length From Whole Genome Sequencing Data. bioRxiv, doi:10.1101/139972 (2017).

Feber, A. et al. Using high-density DNA methylation arrays to profile copy number alterations. Genome Biol 15, R30, doi:10.1186/gb-2014-15-2-130 (2014).

Forbes, S. A. et al. COSMIC: somatic cancer genetics at high-resolution. Nucleic acids research 45, D777-D783, doi:10.1093/nar/gkw1121 (2017).

Frommer, M. et al.: A genomic sequencing protocol that yields a positive display of 5-methylcytosine residues in individual DNA strands. Proc. Natl Acad. Sci. USA 1992, 89: 1827-1831.

Gene Expression Omnibus (GEO) repository of DMPs, published in 2011, available at: https://www.ncbi.nlm.nih.gov/geo/query/acc.cgi?acc=GPL13534.

Gonzalgo, M. L. & Jones, P. A.: Rapid quantitation of methylation differences at specific sites using methylationsensitive single nucleotide primer extension (Ms-SNuPE). Nucleic Acids Res. 1997, 25: 2529-2531.

Grossman, R. L. et al. Toward a Shared Vision for Cancer Genomic Data. N Engl J Med 375, 1109-1112, doi:10.1056/NEJMp1607591 (2016).

Herman, J. G., Graff, J. R., Myohanen, S., Nelkin, B. D. & Baylin, S. B.: Methylation-specific PCR: a novel PCR assay for methylation status of CpG islands. Proc. Natl Acad. Sci. USA 1996, 93: 9821-9826.

http://www.illumina.com/documents/products/technotes/technote_cpg_loci_identification.pdf.

Huber, W. et al. Orchestrating high-throughput genomic analysis with Bioconductor. Nat Methods 12, 115-121, doi:10.1038/nmeth.3252 (2015).

Jeremy George, P. et al. Surveillance for the detection of early lung cancer in patients with bronchial dysplasia. Thorax 62, 43-50, doi:10.1136/thx 2005.052191 (2007).

Johnson, W. E., Li, C. & Rabinovic, A. Adjusting batch effects in microarray expression data using empirical Bayes methods. Biostatistics 8, 118-127, doi:10.1093/biostatistics/kxj037 (2007).

Jones, D. et al. cgpCaVEManWrapper: Simple Execution of CaVE-Man in Order to Detect Somatic Single Nucleotide Variants in NGS Data. Current protocols in bioinformatics 56, 15 10 11-15 10 18, doi:10.1002/cpbi.20 (2016).

Kanehisa, M. & Goto, S. KEGG: kyoto encyclopedia of genes and genomes. Nucleic acids research 28, 27-30 (2000).

Kanehisa, M., Furumichi, M., Tanabe, M., Sato, Y. & Morishima, K. KEGG: new perspectives on genomes, pathways, diseases and drugs. Nucleic acids research 45, D353-D361, doi:10.1093/nar/gkw1092 (2017).

Kanehisa, M., Sato, Y., Kawashima, M., Furumichi, M. & Tanabe, M. KEGG as a reference resource for gene and protein annotation. Nucleic acids research 44, D457-462, doi:10.1093/nar/gkv1070 (2016).

Keilwagen, J., Grosse, I. & Grau, J. Area under precision-recall curves for weighted and unweighted data. PLoS One 9, e92209, doi:10.1371/journal.pone.0092209 (2014).

Law, C. W., Chen, Y., Shi, W. & Smyth, G. K. voom: Precision weights unlock linear model analysis tools for RNA-seq read counts. Genome biology 15, R29, doi:10.1186/GB-2014-15-2-r29 (2014).

Lu, T.P. et al.: Identification of regulatory SNPs associated with genetic modifications in lung adenocarcinoma. BMC Res Notes 2015, 8(1):92.

Luo, W., Friedman, M. S., Shedden, K., Hankenson, K. D. & Woolf, P. J. GAGE: generally applicable gene set enrichment for pathway analysis. BMC Bioinformatics 10, 161, doi:10.1186/1471-2105-10-161 (2009).

Martincorena, I. & Campbell, P. J. Somatic mutation in cancer and normal cells. Science 349, 1483-1489, doi:10.1126/science.aab4082 (2015).

Martincorena, I. et al. Universal Patterns of Selection in Cancer and Somatic Tissues. Cell 171, 1029-1041 e1021, doi:10.1016/j.cell.2017.09.042 (2017).

McGranahan, N. et al. Clonal neoantigens elicit T cell immunoreactivity and sensitivity to immune checkpoint blockade. Science 351, 1463-1469, doi:10.1126/science.aaf1490 (2016).

McLaren, W. et al. The Ensembl Variant Effect Predictor. Genome Biol 17, 122, doi:10.1186/s13059-016-0974-4 (2016).

Miller, C. A. et al. SciClone: inferring clonal architecture and tracking the spatial and temporal patterns of tumor evolution. PLoS Comput Biol 10, e1003665, doi:10.1371/journal.pcbi.1003665 (2014).

Morris, T. J. et al. ChAMP: 450k Chip Analysis Methylation Pipeline. Bioinformatics 30, 428-430, doi:10.1093/bioinformatics/btt684 (2014).

Nik-Zainal, S. et al. The life history of 21 breast cancers. Cell 149, 994-1007, doi:10.1016/j.cell.2012.04.023 (2012).

(56)         References Cited

OTHER PUBLICATIONS

Olkhov-Mitsel, E and Bapat, B: Strategies for discovery and validation of methylated and hydroxymethylated DNA biomarkers. Cancer Medicine 2012, 1(2): 237-260.

Papaemmanuil, E. et al. RAG-mediated recombination is the predominant driver of oncogenic rearrangement in ETV6-RUNX1 acute lymphoblastic leukemia. Nature genetics 46, 116-125, doi:10.1038/ng.2874 (2014).

Paul DS, Guilhamon P, Karpathakis A, Butcher LM, Thirlwell C, Feber A, Beck S: Assessment of RainDrop BS-seq as a method for large?scale, targeted bisulfite sequencing. Epigenetics 2014, 9.

Raine, K. M. et al. ascatNgs: Identifying Somatically Acquired Copy-Number Alterations from Whole-Genome Sequencing Data. Current protocols in bioinformatics 56, 15 19 11-15 19 17, doi:10.1002/cpbi.17 (2016).

Raine, K. M. et al. cgpPindel: Identifying Somatically Acquired Insertion and Deletion Events from Paired End Sequencing. Curr Protoc Bioinformatics 52, 15 17 11-12, doi:10.1002/0471250953.bi1507s52 (2015).

Ritchie, M. E. et al. limma powers differential expression analyses for RNA-sequencing and microarray studies. Nucleic acids research 43, e47, doi:10.1093/nar/gkv007 (2015).

Robin, X. et al. pROC: an open-source package for R and S+ to analyze and compare ROC curves. BMC Bioinformatics 12, 77, doi:10.1186/1471-2105-12-77 (2011).

Robinson, J. T. et al. Integrative genomics viewer. Nat Biotechnol 29, 24-26, doi: 10.1038/nbt.1754 (2011).

Robles, A.I. et al.: An Integrated Prognostic Classifier for Stage I Lung Adenocarcinoma Based on mRNA, microRNA, and DNA Methylation Biomarkers. J Thorac Oncol. 2015, 10(7):1037-1048.

Sandoval, J. et al. Validation of a DNA methylation microarray for 450,000 CpG sites in the human genome. Epigenetics 6, 692-702 (2011).

Skinner, M. E., Uzilov, A. V., Stein, L. D., Mungall, C. J. & Holmes, I. H. JBrowse: a next-generation genome browser. Genome Res 19, 1630-1638, doi:10.1101/gr.094607.109 (2009).

Chen and Lau "Advances in Mapping Tumor Progression from Precancer Atlases", Cancer Prevention Research, 2023, 16, 439-48.

Ehrlich et al: "DNA hypomethylation in cancer cells", EPIGENOMICS, vol. I, No. 2, Dec. 3, 2009 (Dec. 3, 2009), pp. 239-259.

Gene Expression Omnibus (GEO) repository of DMPs, published in 2011 and available at: https://www.ncbi.nlm.nih.gov/geo/query/acc.cgi?acc=GPL13534.

Hu et al., "Evolution of DNA methylome from precancerous lesions to invasive lung adenocarcinomas", Nature Communications, 2021, 12:687, 1-13.

Malone et al. "Molecular profiling for precision cancer therapies", Genome Medicine, 2020, 12, 8, pp. 1-19.

Nabiha Missaoui et al: "Global DNA Methylation in Precancerous and Cancerous Lesions of the Uterine Cervix", Asian Pacific Journal of Cancer Prevention J Cancer Prev, vol. 11, No. 6, Jan. 1, 2010 (Jan. 1, 2010), pp. 1741-1744.

Technical Note: Epigenetics. CpG Loci Identification. A guide to Illumina's method for unambiguous CpG loci identification and tracking for the Golden Gate? and Infinium? Assay for Methylation, published in 2010 and available at: http://www.illumina.com/documents/products/technotes/technote_cpg_loci_identification.pdf.

Teschendorff et al., "Correlation of Smoking-Associated DNA Methylation Changes in Buccal Cells with DNA Methylation Changes in Epithelial Cancer", (JAMA Oneal, 2015, 1(4):476-485).

Widschwendter et al., "Epigenome-based cancer risk prediciction: rationale, opportunties and challenges", Nature Reviews, 2018, vol. 15, p. 292-309.

* cited by examiner

Fig. 1

| Clinical Characteristics | Whole genome sequencing set (N=39) | | Methylation discovery set (N=60) | | | Methylation validation set (N=27) | | | Gene expression set (N=33) | | Gene expression validation set (N=18) | |
|---|---|---|---|---|---|---|---|---|---|---|---|---|
| | Progression | Regression | Progression | Regression | Controls | Progression | Regression | Controls | Progression | Regression | Progression | Regression |
| Patients | 21 | 8 | 13 | 7 | 16 | 9 | 7 | 8 | 16 | 14 | 9 | 8 |
| Lesions Profiled | 29 | 10 | 26 | 11 | 23 | 10 | 7 | 10 | 17 | 16 | 10 | 8 |
| Gender | | | | | | | | | | | | |
| Male | 18 | 8 | 11 | 7 | 15 | 7 | 7 | 7 | 14 | 10 | 7 | 4 |
| Female | 3 | 0 | 2 | 0 | 1 | 2 | 0 | 1 | 2 | 4 | 2 | 4 |
| Age at bronchoscopy (years) | | | | | | | | | | | | |
| Mean | 71.1 | 63.1 | 69.81 | 63.27 | 65.96 | 70.2 | 69.86 | 64.3 | 69.29 | 66.56 | 69.4 | 68.125 |
| Median | 72 | 65.5 | 70 | 67 | 68 | 73 | 68 | 63 | 70 | 67.5 | 71.5 | 68 |
| Range | 58-81 | 52-71 | 52-79 | 53-79 | 44-77 | 58-78 | 64-76 | 56-77 | 55-80 | 53-81 | 56-82 | 57-84 |
| Smoking History (pack years) | | | | | | | | | | | | |
| Mean | 54.4 | 54.9 | 58.08 | 31 | 41.95 | 57.3 | 62.14 | 37.71 | 57.07 | 47 | 49.125 | 59.2 |
| Median | 50 | 50 | 59.5 | 29 | 40 | 60 | 50 | 36 | 50 | 47.5 | 47.5 | 58 |
| Range | 30-100 | 9-141 | 32-141 | 5-88 | 20-65 | 40-75 | 30-141 | 20-60 | 22-141 | 5-141 | 30-75 | 30-96 |
| COPD status | | | | | | | | | | | | |
| Yes | 12 | 3 | 9 | 3 | 14 | 5 | 1 | 7 | 4 | 8 | 3 | 7 |
| No | 9 | 5 | 4 | 4 | 1 | 4 | 6 | 1 | 12 | 6 | 1 | 0 |
| Previous History of Lung Cancer | | | | | | | | | | | | |
| Yes | 12 | 2 | 6 | 2 | 9 | 7 | 4 | 3 | 5 | 4 | 3 | 4 |
| No | 9 | 6 | 7 | 5 | 7 | 2 | 3 | 5 | 11 | 10 | 6 | 4 |

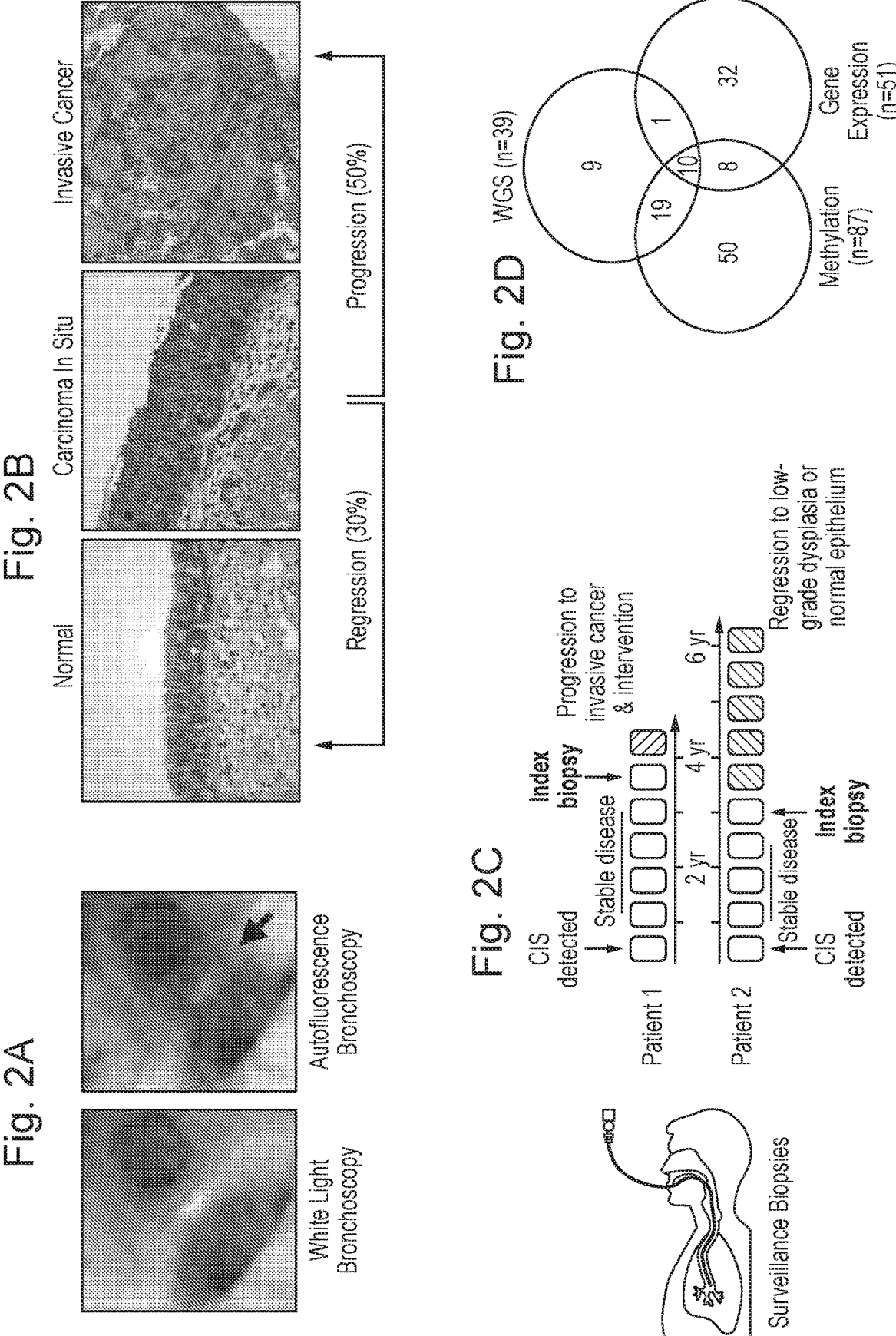

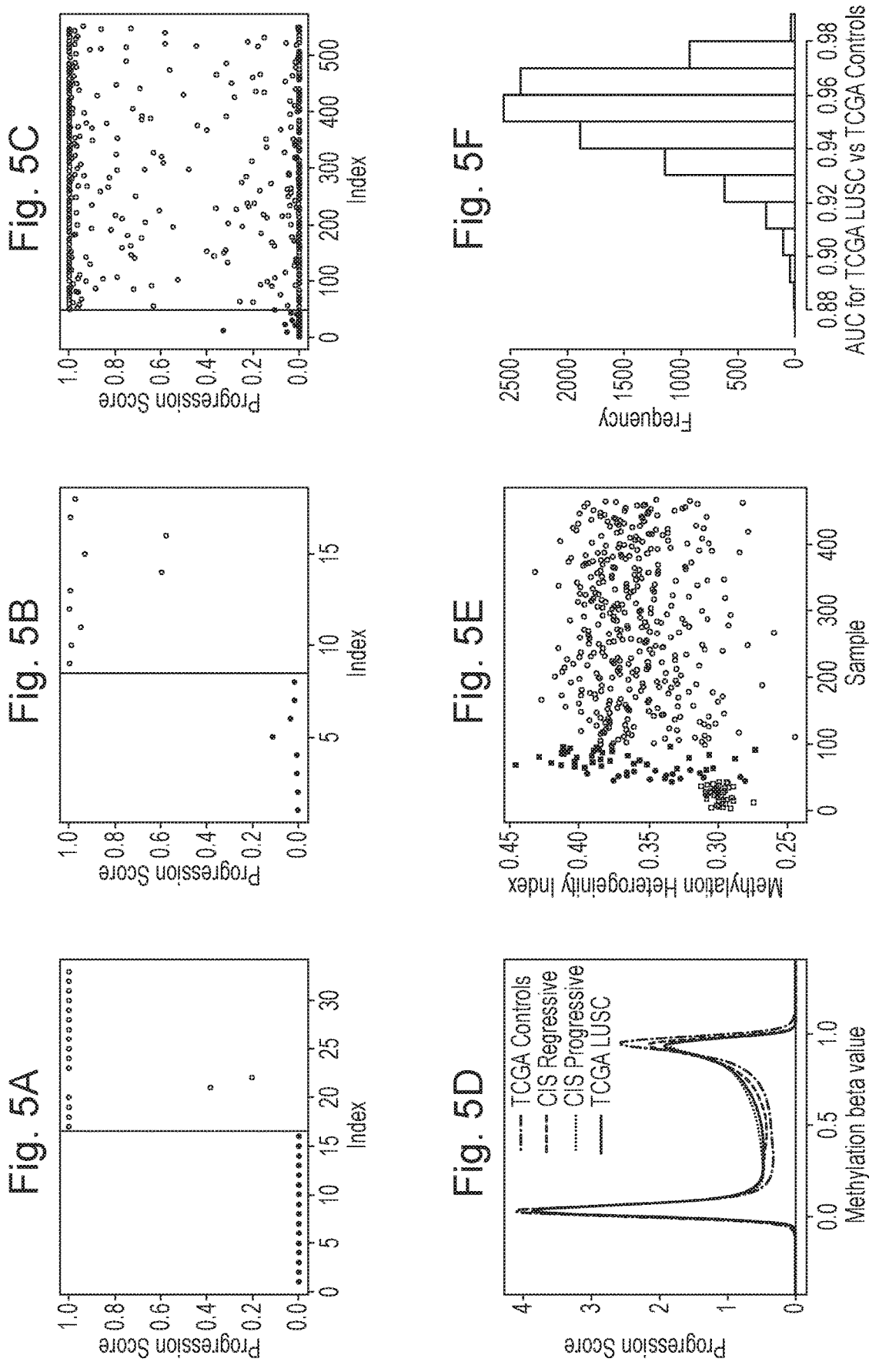

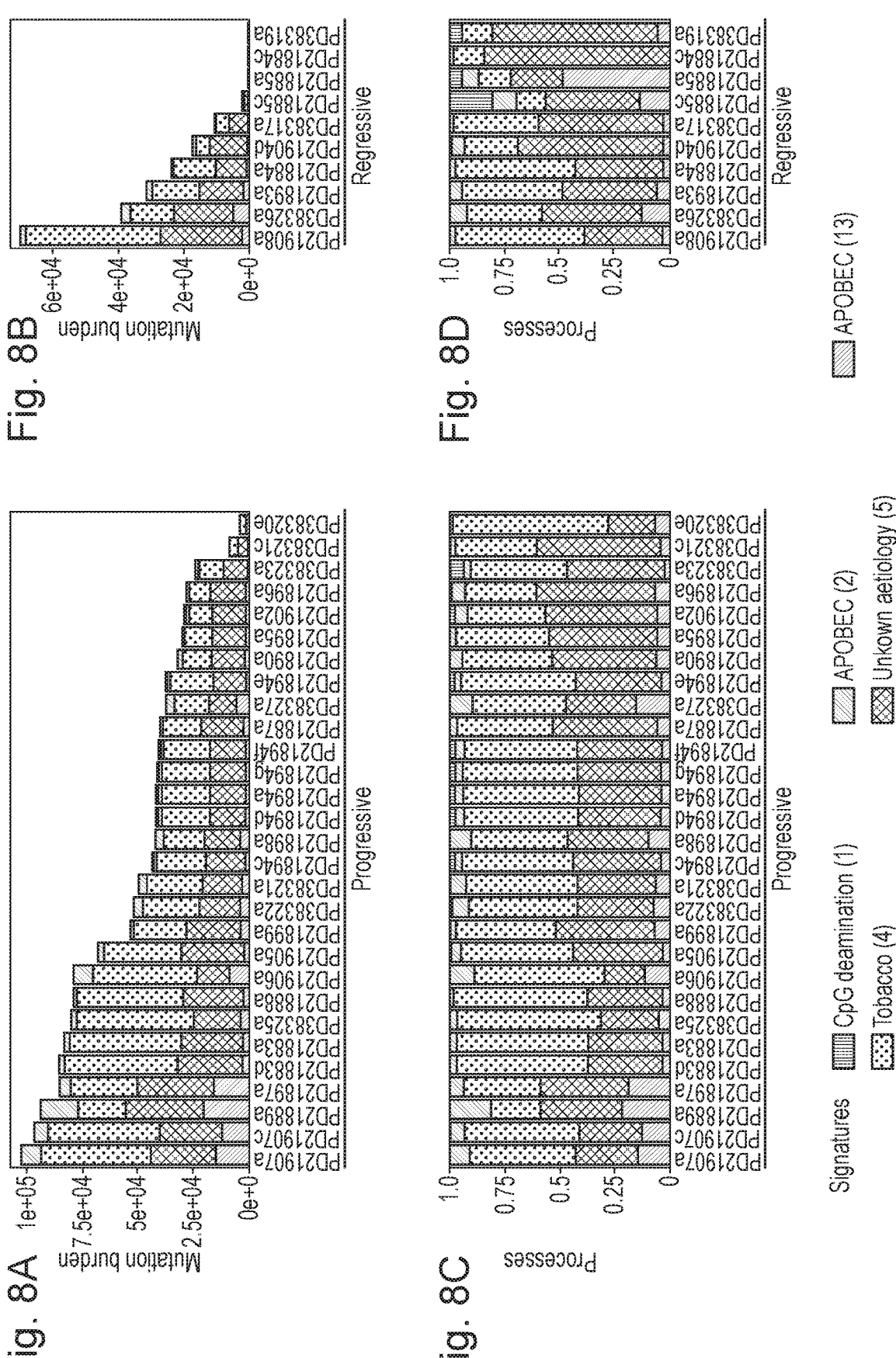

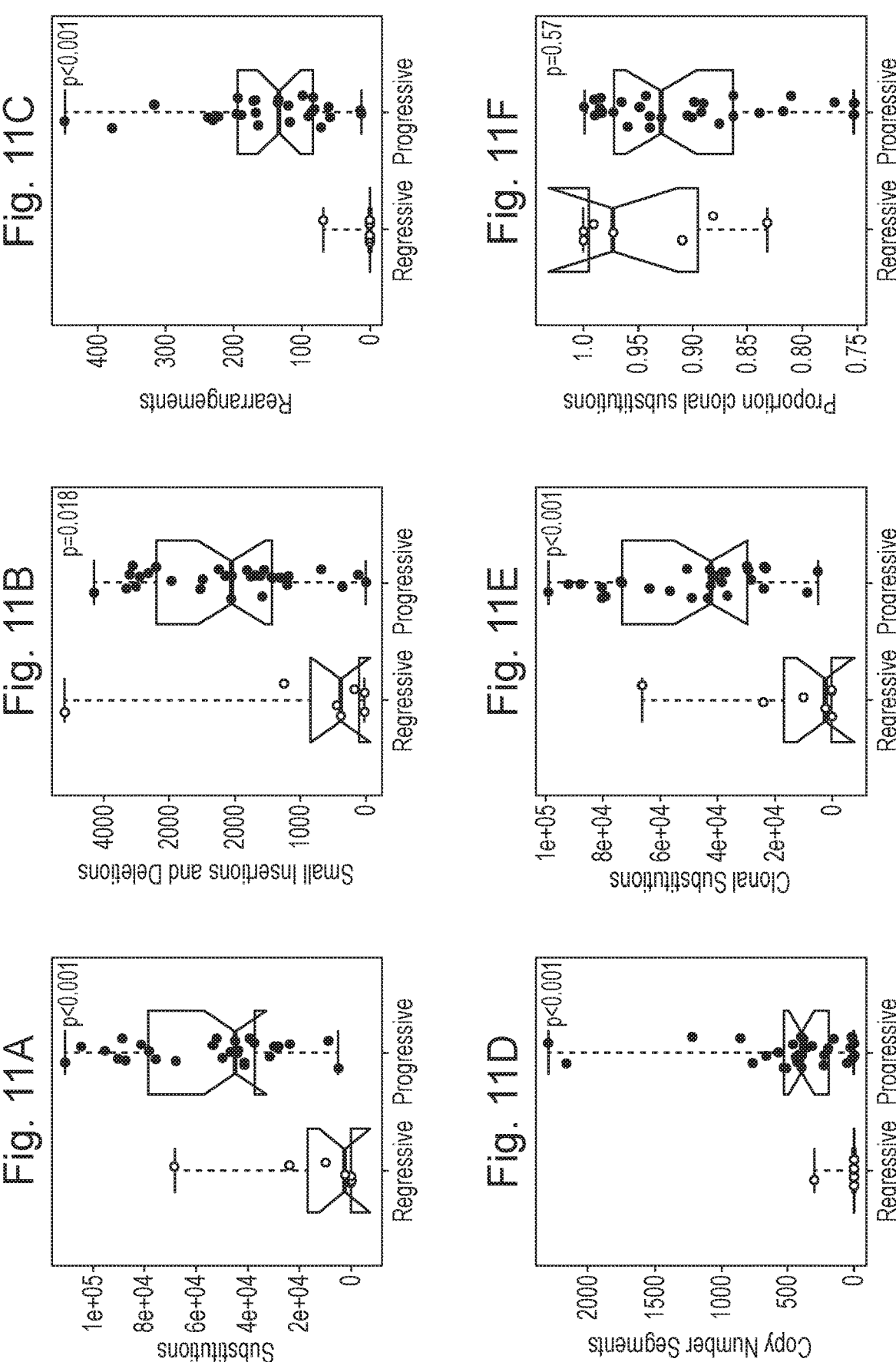

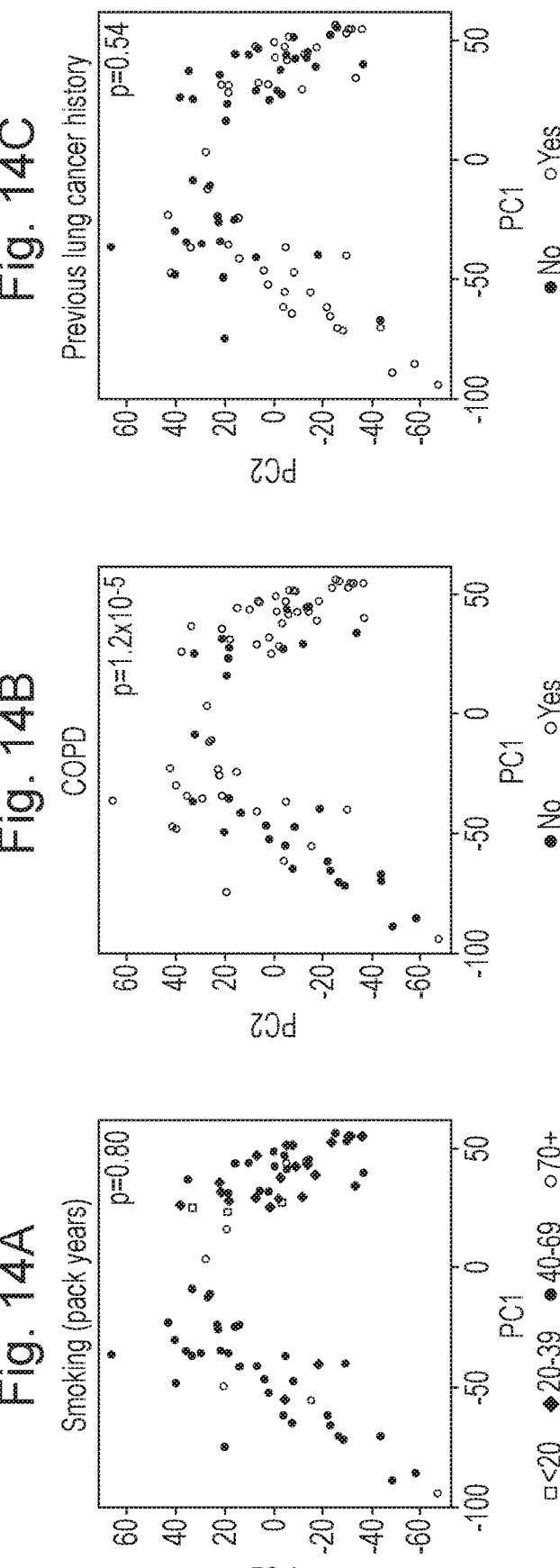

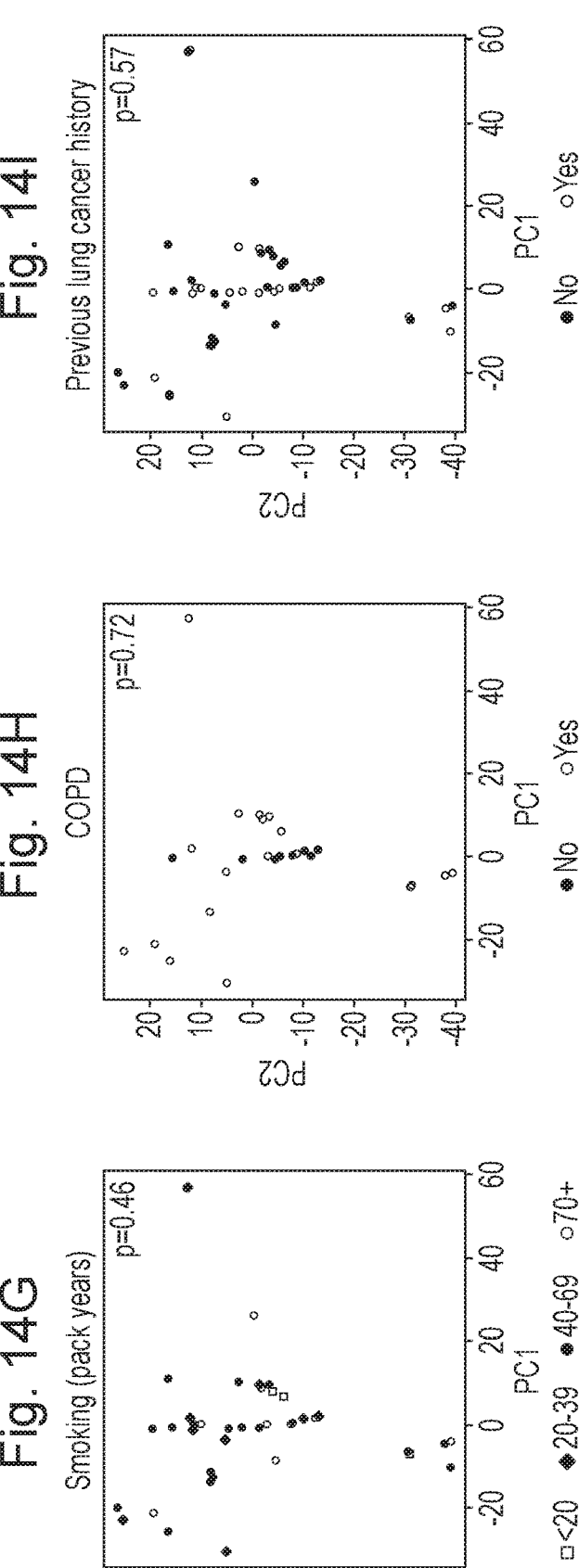

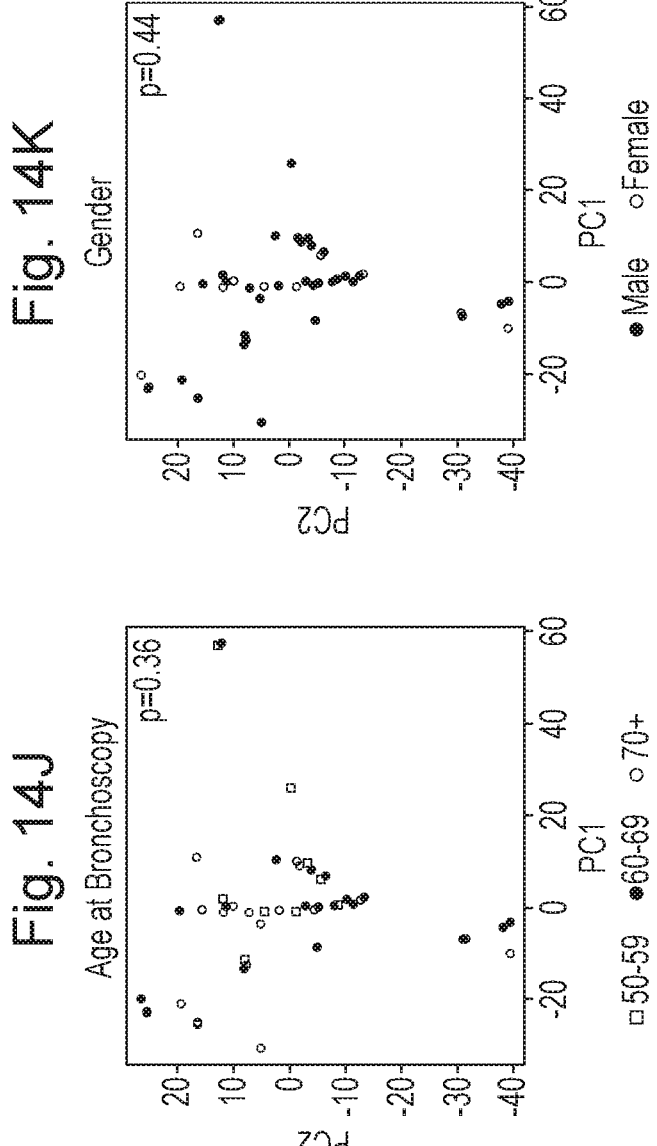

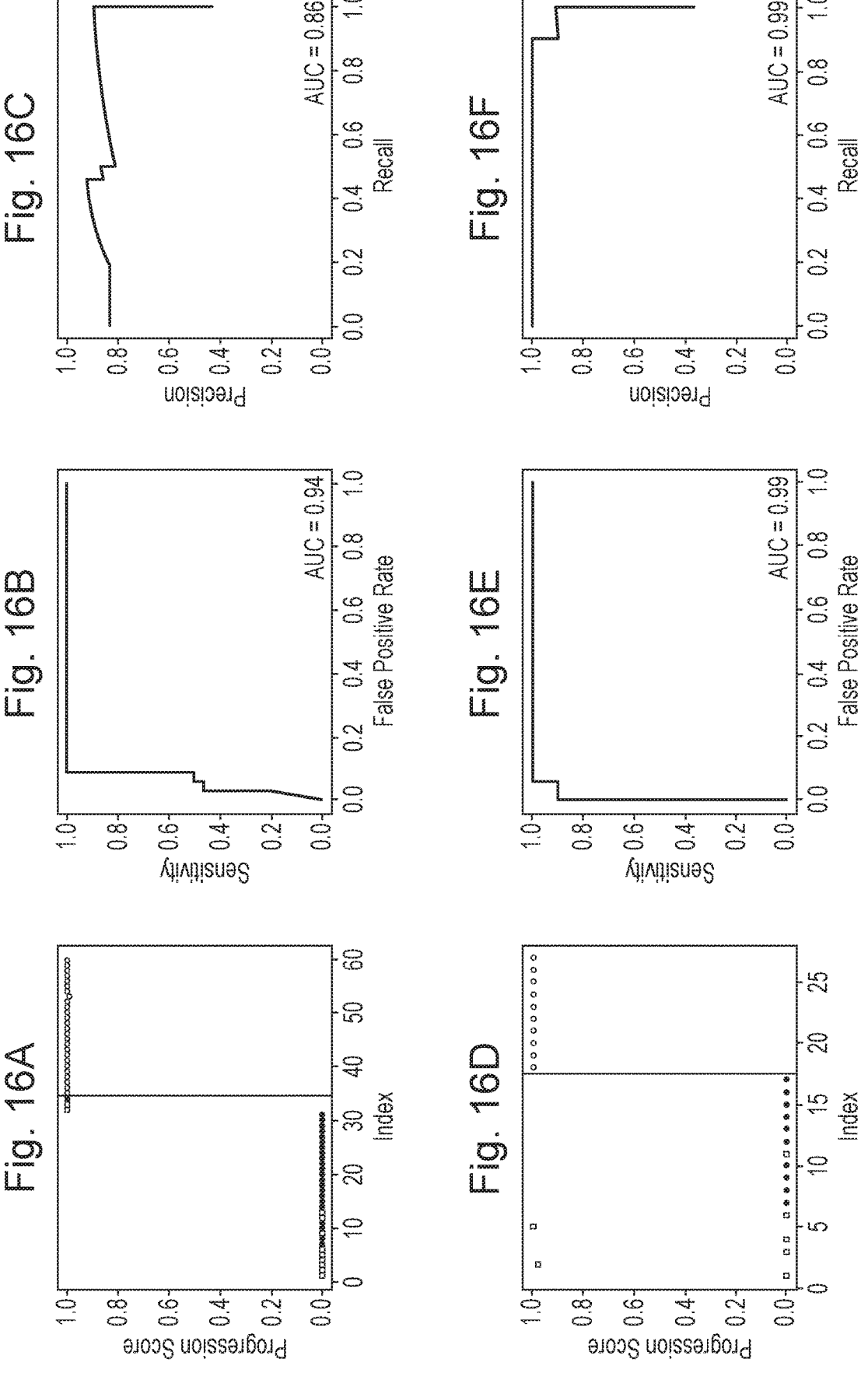

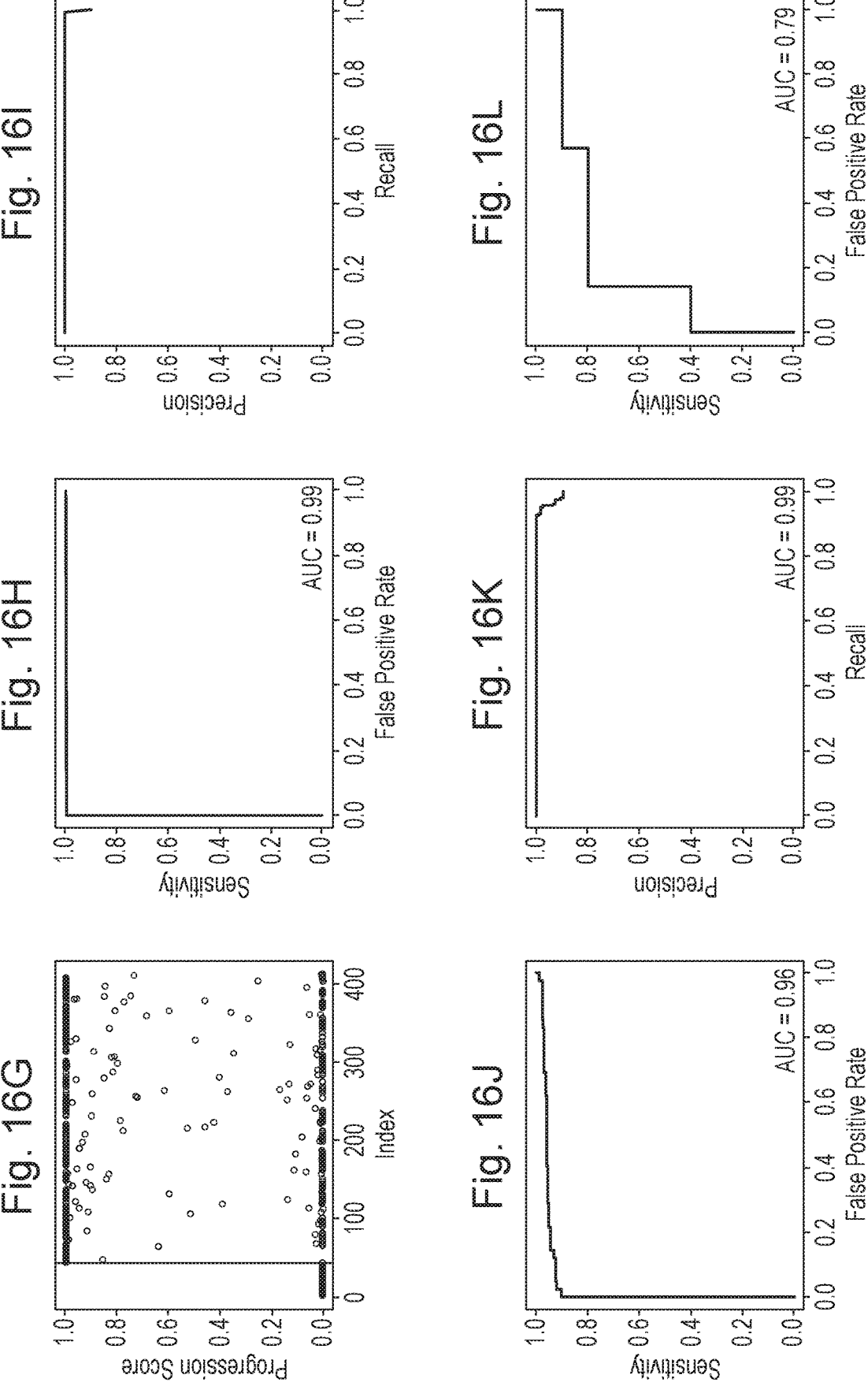

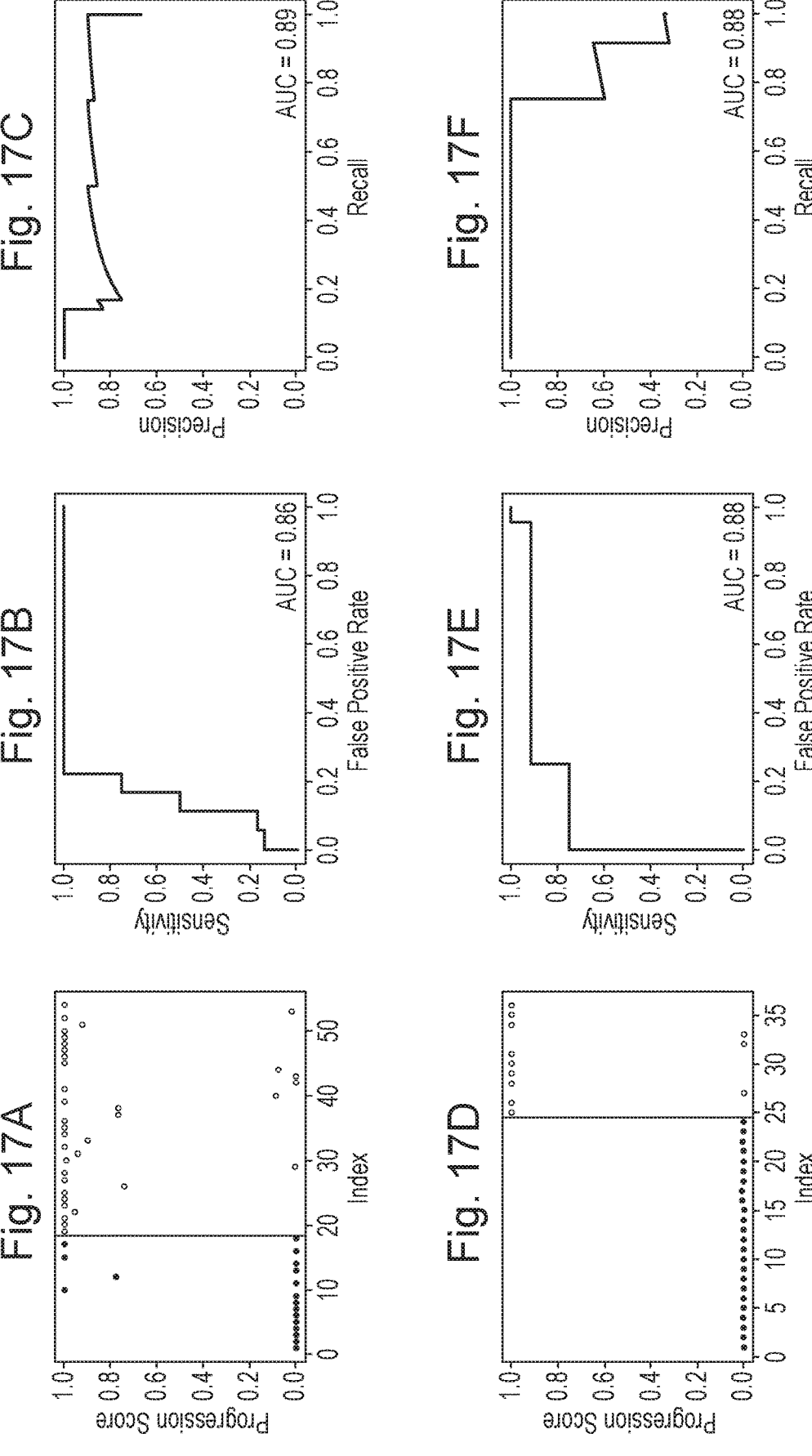

MOLECULAR SIGNATURE

CROSS-REFERENCE TO RELATED APPLICATIONS

This application is a national phase application under 35 U.S.C. § 371 that claims priority to International Application No. PCT/GB2019/053388 filed Nov. 29, 2019, which claims priority to Great Britain Patent Application No. 1819453.0 filed Nov. 29, 2018, both of which are incorporated by reference herein in their entirety.

INCORPORATION OF SEQUENCE LISTING

The instant application contains a Sequence Listing which has been submitted electronically in ASCII format and is hereby incorporated by reference in its entirety. Said ASCII copy, created on May 20, 2021, is named Sequence_listing_KEMP_P0112US.txt and is 1,134 bytes in size.

FIELD OF THE INVENTION

The present invention relates to a method of identifying a pre-invasive lung lesion in an individual that will progress to an invasive lung cancer comprising:

identifying a tissue as comprising a pre-invasive lung lesion that will progress to an invasive lung cancer where a molecular signature is present or identifying the tissue as comprising a pre-invasive lung lesion that will not progress to an invasive lung cancer where the molecular signature is absent.

The present invention also relates to a method of treating a pre-invasive lung lesion and/or treating and/or preventing an invasive lung cancer in an induvial comprising:

identifying a tissue as comprising a pre-invasive lung lesion that will progress to an invasive lung cancer where a molecular signature is present or identifying the tissue as comprising a pre-invasive lung lesion that will not progress to an invasive lung cancer where the molecular signature is absent.

The present invention further relates to a molecular signature, and uses thereof, for identifying whether or not an individual has a pre-invasive lung lesion that will progress to an invasive lung cancer.

BACKGROUND TO THE INVENTION

Lung cancer is the most common cause of cancer death worldwide with 1.5 million deaths per year [1]. Lung squamous cell carcinoma (LUSC) is the most common subtype in parts of Europe and second in the U.S.A [2]. Before progression to invasive LUSC, there is step-wise evolution of ever more disordered pre-invasive lesions, ranging from mild and moderate dysplasia (low-grade lesions) to severe dysplasia and carcinoma-in-situ (CIS; high-grade lesions) [3]. The accessibility of the proximal airways allows detection and monitoring of these lesions using high-resolution diagnostic approaches such as auto-fluorescence bronchoscopy (AFB) [4]. This technique enables the acquisition of tissue throughout the natural history of LUSC, providing an excellent model to study early tumorigenesis in human patients.

The molecular alterations that occur in cells before cancer is manifest are largely uncharted. Lung carcinoma-in-situ (CIS) lesions are the pre-invasive precursor to squamous cell carcinoma. While microscopically identical, their future is in equipoise with half progressing to invasive cancer and half regressing or remaining static. The cellular basis of this clinical observation is unknown.

Clinically, the optimal management of pre-invasive airway lesions remains unclear, despite the availability of surgery, radiotherapy and ablative techniques [5]. AFB with biopsy allows assessment of the size, gross morphology and histopathology of pre-invasive lesions but cannot distinguish lesions that will ultimately progress to invasive tumours from those that will spontaneously regress. As such, indiscriminate surgical resection of pre-invasive lesions or external beam radiotherapy represents over-treatment: lesions will spontaneously regress in 30% of cases, patient co-morbidity and poor lung function impart considerable risk, and the presence of field cancerization means independent lung cancers frequently emerge at sites outside resection or therapy margins [6].

Whilst molecular techniques have revolutionised the understanding of cancer biology, the key steps from normal cell to the point of cancer (uncontrolled growth and invasion) remain unclear. Thus, improved assays for the accurate diagnosis and management of lung CIS and/or lung cancer are sought and would be of significant clinical and economic benefit, particular assays which are minimally invasive.

SUMMARY OF THE INVENTION

Provided is a new understanding of cancer precursor biology, based on a unique collection of high-grade pre-invasive lung lesions which were followed-up under conservative clinical management. Genomic, transcriptomic and epigenomic landscape of CIS have been profiled in a unique patient cohort with longitudinally monitored pre-invasive disease. Predictive modelling identifies which lesions will progress with remarkable accuracy. Progression-specific methylation changes on a background of widespread heterogeneity, alongside a strong chromosomal instability signature have been identified. Mutations and copy number changes characteristic of cancer and chart their emergence, offering a window into early carcinogenesis have also been identified. This has enabled the provision of a novel molecular signature, with particular utility in the diagnosis of and monitoring of lung CIS and lung cancer. Methods of the invention allow more efficient patient risk stratification for the purposes of providing better treatment and/or to help plan and manage patient care.

The present disclosure delineates changes in the genomic architecture, genome-wide gene expression and DNA methylation of pre-invasive cancers with known histological evidence of subsequent disease progression or regression. The CIS genome shares many of the hallmarks of advanced, invasive LUSC but marked genomic, transcriptomic and epigenetic differences exist between lesions that are benign and those that will progress to cancer. The disclosure demonstrate the use of these differences in predicting outcome over current clinical practice.

One of the pathways associated with progression is chromosomal instability (CIN), defined as a high rate of gain or loss of whole (or parts of) chromosomes. CIN is implicated in many human cancers, including lung, and has been suggested both as a prognostic marker and therapeutic target [30], [31]. Regressive lesions do not have the wholesale genomic instability of those that will progress and their epigenetic and transcriptional profiles more closely resemble normal bronchial epithelium than invasive cancers. Despite this, CIS lesions that spontaneously regress are genuine neoplasms; they harbour many somatic mutations, which can include known potential driver mutations. The mechanism of regression remains mysterious: it is unclear whether clones become exhausted and die out, potentially abetted by immune surveillance, or whether clones persist but phenotypically revert to an architecturally normal, physiological epithelium. Likewise the mechanisms of CIN are not well understood.

This disclosure represents the first whole genome sequencing data of pre-invasive lung lesions and offers the first insight into the molecular map of early lung squamous cancer pathogenesis, foretelling an era in which molecular profiling will enable personally tailored therapeutic decisions for patients with, for example, pre-invasive lung disease.

Thus, the invention provides a method of identifying whether or not an individual has a pre-invasive lung lesion that will progress to an invasive lung cancer, the method comprising:

(a) providing a sample of nucleic acid which has been taken from a tissue of the individual, wherein the tissue is suspected of harbouring a pre-invasive lung lesion;

(b) performing an assay to determine a progression score for the sample; and (c) identifying whether or not the individual has a pre-invasive lung lesion that will progress to an invasive lung cancer by comparing the progression score to a threshold value;

wherein the progression score is determined using a molecular signature selected from:

i) a differentially expressed gene (DEG) signature;

ii) a differentially methylated position (DMP) signature;

iii) a copy number variation (CNV) signature; and iv) combinations of (i) to (iii).

The individual may be identified as having a pre-invasive lung lesion that will progress to an invasive lung cancer if the progression score determined for the sample is higher than the threshold value; or the individual may be identified as not having a pre-invasive lung lesion that will progress to an invasive lung cancer if the progression score determined for the sample is lower than the threshold value.

In some embodiments of the present invention, the DEG signature comprises the expression level of each of at least 10, at least 20, at least 30, at least 40, at least 50, at least 60, at least 75, at least 100, at least 150, at least 200, at least 250, at least 300, at least 325, least 350, at least 375, or 397 genes identified in Table 1, optionally wherein the method achieves an ROC AUC of at least 0.6, at least 0.60, at least 0.61, at least 0.62, at least 0.63, at least 0.64, at least 0.65, at least 0.66, at least 0.67, at least 0.68, at least 0.69, at least 0.7, at least 0.70, at least 0.71, at least 0.72, at least 0.73, at least 0.74, at least 0.75, at least 0.76, at least 0.77, at least 0.78, at least 0.79, at least 0.8, at least 0.80, at least 0.81, at least 0.82, at least 0.83, at least 0.84, at least 0.85, at least 0.86, or at least 0.87, optionally wherein the method achieves a sensitivity of at least about 95% and/or a specificity of at least about 55%, preferably wherein the threshold value is from about 0.02 to about 0.6.

The DEG signature may comprise the expression level of each of the genes identified in:

(i) Table 5, optionally wherein the threshold value is about 0.3, preferably wherein the method also achieves an ROC AUC of at least about 0.6 or about 0.64 and/or achieves a sensitivity of at least about 95% and/or a specificity of at least about 55%;

(ii) Table 4, optionally wherein the threshold value is about 0.035, preferably wherein the method also achieves an ROC AUC of at least about 0.65 or about 0.69 and/or achieves a sensitivity of at least about 95% and/or a specificity of at least about 55%;

(iii) Table 3, optionally wherein the threshold value is about 0.04, preferably wherein the method also achieves an ROC AUC of at least about 0.7 or about 0.76 and/or achieves a sensitivity of at least about 95% and/or a specificity of at least about 55%;

(iv) Table 2, optionally wherein the threshold value is about 0.105, preferably wherein the method also achieves an ROC AUC of at least about 0.75 or about 0.81 and/or achieves a sensitivity of at least about 95% and/or a specificity of at least about 55%; or (v) Table 1, optionally wherein the threshold value is about 0.14, preferably wherein the method achieves an ROC AUC of at least about 0.85 or about 0.87, optionally wherein the method achieves a sensitivity of at least about 95% and/or a specificity of at least about 55%.

In some embodiments of the methods of the present invention, the DMP signature comprises the methylation status (B) of least two, at least three, at least four, at least five, at least six, at least seven, at least eight, at least nine, at least 10, at least 12, least 14, at least 16, at least 18, at least 20, at least 25, at least 50, at least 75, at least 100, at least 125, or differentially methylated positions (DMPs) selected from Table 11, optionally wherein the method achieves an ROC AUC of at least 0.9, at least 0.90, at least 0.91, at least 0.92, at least 0.93, at least 0.94, at least 0.95, at least 0.96, at least 0.97, at least 0.98, or at least 0.99, optionally wherein the method achieves a sensitivity of at least about 95% and/or a specificity of at least about 50%, preferably wherein the threshold value is from about 0.3 to about 0.6.

The DMP signature may comprise the R of each of the DMPs identified in:

(i) Table 16 or Table 17, optionally wherein the threshold value is about 0.43 or about 0.44, preferably wherein the method achieves an ROC AUC of at least about 0.9 or about 0.94 and/or achieves a sensitivity of at least about 95% and/or a specificity of at least about 60%;

(ii) Table 15, optionally wherein the threshold value is about 0.45, preferably wherein the method achieves an ROC AUC of at least about 0.93 or about 0.96 and/or achieves a sensitivity of at least about 95% and/or a specificity of at least about 50%;

(iii) Table 14, optionally wherein the threshold value is about 0.45, preferably wherein the method achieves an ROC AUC of at least about 0.95 or about 0.99 and/or achieves a sensitivity of at least about 95% and/or a specificity of at least about 55%;

(iv) Table 13, optionally wherein the threshold value is about 0.46, preferably wherein the method achieves an ROC AUC of at least about 0.95 or about 0.996 and/or achieves a sensitivity of at least about 95% and/or a specificity of at least about 55%;

(v) Table 12, optionally wherein the threshold value is about 0.48, preferably wherein the method achieves an ROC AUC of at least about 0.95 or about 0.999 and/or achieves a sensitivity of at least about 95% and/or a specificity of at least about 55%; or (vi) Table 11, optionally wherein the threshold value is about 0.5, preferably wherein the method achieves an ROC AUC of at least about 0.95 or about 0.998 and/or achieves a sensitivity of at least about 95% and/or a specificity of at least about 55%. In some embodiments of the methods of the present invention, the CNV signature comprises the amplification or loss of at least 5, at least 6, least 7, at least 8, at least 9, at least 10, at least 25, at least 50, at least 75, at least 100, at least 125, at least 150, at least 175, or at least 200 CNV bands identified in Table 19, optionally wherein the method achieves an ROC AUC of at least about 0.9, at least about 0.91, at least about 0.92, at least about 0.93, at least about 0.94, at least about 0.95, at least about 0.96, at least about 0.97, at least about 0.98, at least about 0.99, optionally wherein the method achieves a sensitivity of at least about 75%, at least about 80%, at least about 85%, at least about 90%, or at least about 95%, and/or a specificity of at least about 65%, at least about 70% at least about 75%, at least about 80%, at least about 85%, at least about 90%, or at least about 95%, preferably wherein the threshold value is from about 0.05 to about 0.6.

The CNV signature may comprises the amplification or loss of the CNV bands identified in:

(i) Table 34, optionally wherein the threshold value is about 0.66, preferably wherein the method achieves an ROC AUC of at least about 0.9 or about 0.95 and/or achieves a sensitivity of at least about 95% and/or a specificity of at least about 65%;

(ii) Table 33, optionally wherein the threshold value is about 0.65, preferably wherein the method achieves an ROC AUC of at least about 0.9 or about 0.95 and/or achieves a sensitivity of at least about 95% and/or a specificity of at least about 70%;

(iii) Table 32, optionally wherein the threshold value is about 0.6, preferably wherein the method achieves an ROC AUC of at least about 0.9 or about 0.95 and/or achieves a sensitivity of at least about 95% and/or a specificity of at least about 85%;

(iv) Table 31, optionally wherein the threshold value is about 0.56, preferably wherein the method achieves an ROC AUC of at least about 0.9 or about 0.96 and/or achieves a sensitivity of at least about 95% and/or a specificity of at least about 85%;

(v) Table 30, optionally wherein the threshold value is about 0.48, preferably wherein the method achieves an ROC AUC of at least about 0.95 or about 0.96 and/or achieves a sensitivity of at least about 90% and/or a specificity of at least about 90%;

(vi) Table 29, optionally wherein the threshold value is about 0.41, preferably wherein the method achieves an ROC AUC of at least about 0.95 or about 0.96 and/or achieves a sensitivity of at least about 90% and/or a specificity of at least about 90%;

(vii) Table 28, optionally wherein the threshold value is about 0.31, preferably wherein the method achieves an ROC AUC of at least about 0.95 or about 0.95 and/or achieves a sensitivity of at least about 95% and/or a specificity of at least about 90%;

(viii) Table 27, optionally wherein the threshold value is about 0.19, preferably wherein the method achieves an ROC AUC of at least about 0.95 or about 0.97 and/or achieves a sensitivity of at least about 80% and/or a specificity of at least about 95%;

(ix) Table 26, optionally wherein the threshold value is about 0.12, preferably wherein the method achieves an ROC AUC of at least about 0.95 or about 0.97 and/or achieves a sensitivity of at least about 90% and/or a specificity of at least about 95%;

(x) Table 25, optionally wherein the threshold value is about 0.06, preferably wherein the method achieves an ROC AUC of at least about 0.95 or about 0.98 and/or achieves a sensitivity of at least about 90% and/or a specificity of at least about 90%;

(xi) Table 24, optionally wherein the threshold value is about 0.02, preferably wherein the method achieves an ROC AUC of at least about 0.95 or about 0.98 and/or achieves a sensitivity of at least about 90% and/or a specificity of at least about 95%;

(xii) Table 23, optionally wherein the threshold value is about 0.01, preferably wherein the method achieves an ROC AUC of at least about 0.95 or about 0.98 and/or achieves a sensitivity of at least about 95% and/or a specificity of at least about 95%;

(xiii) Table 22, optionally wherein the threshold value is about 0.01, preferably wherein the method achieves an ROC AUC of at least about 0.95 or about 0.98 and/or achieves a sensitivity of at least about 95% and/or a specificity of at least about 90%;

(xiv) Table 21, optionally wherein the threshold value is about 0.02, preferably wherein the method achieves an ROC AUC of at least about 0.95 or about 0.98 and/or achieves a sensitivity of at least about 95% and/or a specificity of at least about 90%;

(xv) Table 20, optionally wherein the threshold value is about 0.01, preferably wherein the method achieves an ROC AUC of at least about 0.95 or about 0.98 and/or achieves a sensitivity of at least about 95% and/or a specificity of at least about 90%; or (xvi) Table 19, optionally wherein the threshold value is about 0.02, preferably wherein the method achieves an ROC AUC of at least about 0.95 or about 0.98 and/or achieves a sensitivity of at least about 95% and/or a specificity of at least about 85%.

The present invention also provides a method of treating a pre-invasive lung lesion and/or treating and/or preventing an invasive lung cancer in an individual comprising:

identifying a pre-invasive lung lesion in an individual that will progress to an invasive lung cancer by performing a method described herein for identifying whether or not an individual has a pre-invasive lung lesion that will progress to an invasive lung cancer; and administering a lung cancer therapy to the individual, optionally wherein the therapy comprises surgical intervention.

The present invention also provides a method for determining whether or not to provide a therapeutic method of treatment to an individual, the method comprising performing a method described herein for identifying whether or not an individual has a pre-invasive lung lesion that will progress to an invasive lung cancer;

providing to the individual a therapeutic method of treatment if the individual is identified as having a pre-invasive lung lesion that will progress to an invasive lung cancer, optionally wherein the therapeutic method of treatment comprises administering to the individual a therapeutically effective amount of a lung cancer therapy.

In any of the methods of the present invention described herein, the sample may be from an individual who:

(a) is not suspected of having cancer;

(b) is suspected of having a pre-invasive lung lesion but not suspected of having cancer;

(c) has a pre-invasive lung lesion but is not suspected of having cancer;

(d) has a pre-invasive lung lesion and is suspected of having cancer;

(e) is suspected of having cancer; or (f) has cancer.

In any of the methods of the present invention described herein, the tissue from which the sample of nucleic acid has been taken may:

(i) have been obtained from a biopsy;

(iii) be processed by laser-capture micro-dissection (LCM); and/or (ii) be fresh-frozen tissue or formalin-fixed paraffin-embedded (FFPE) tissue.

The nucleic acid may be a DNA. In any of the methods of the present invention described herein, the progression score may be determined using the PAM method.

Where the progression score is determined using a DEG signature, the assay in step (b) may comprise performing a hybrisation assay. Where the progression score is determined using a DMP signature, the assay in step (b) may comprise bisulphite conversion of the DNA, optionally step (b) may comprise performing a sequencing step to determine the sequence of the DNA molecules, optionally wherein before sequencing an amplification step is performed; and/or optionally wherein step (b) comprises (i) hybridising the DNA to an array comprising probes capable of discriminating between methylated and non-methylated forms of DNA and applying a detection system to the array to discriminate methylated and non-methylated forms of DNA, optionally wherein before hybridisation an amplification step is performed; or (ii) performing an amplification step using methylation-specific primers, wherein the methylation status of the DNA is determined by the presence or absence of an amplified product, optionally wherein the amplification step is performed by PCR.

Where the progression score is determined using a CNV signature, the assay in step (b) may comprise whole genome sequencing.

The nucleic acid may be an RNA. Where the nucleic acid is an RNA, the progression score may be determined using a DEG signature and the assay in step (b) may comprise reverse transcriptase quantitative PCT (RT-qPCR).

The present invention also provides a molecular signature as described herein for identifying whether or not an individual has a pre-invasive lung lesion that will progress to an invasive lung cancer.

The present invention further provides use of a molecular signature as described herein for identifying whether or not an individual has a pre-invasive lung lesion that will progress to an invasive lung cancer. The use of the molecular signature may be in an ex-vivo method for identifying whether or not an individual has a pre-invasive lung lesion that will progress to an invasive lung cancer. Further provided by the present invention are the in vitro, in silico or ex-vivo use of a molecular signature as described herein for identifying whether or not an individual has a pre-invasive lung lesion that will progress to an invasive lung cancer.

In any of the methods, molecular signatures or uses thereof provided by the present invention described herein, the pre-invasive lung lesion may be a solid lesion and/or the invasive lung cancer may be a solid tumour. In any of the methods, molecular signatures or uses thereof provided by the present invention, the pre-invasive lung lesion may be normal epithelium, tissue hyperplasia, dysplasia, or lung carcinoma in situ (CIS). In any of the methods, molecular signatures or uses thereof provided by the present invention, the lung cancer may be lung squamous cell carcinoma (LUSC).

BRIEF DESCRIPTION OF THE FIGURES

FIG. 1. Demographic and clinical characteristics of patients in the whole-genome sequencing, methylation discovery and validation, and gene expression discovery and validation datasets.

FIG. 2. Analysis of pre-invasive lung carcinoma-in-situ (CIS) lesions. (A) Detection of bronchial pre-invasive CIS lesions by autofluorescence bronchoscopy. (B) Histological outcomes of bronchial pre-invasive lesions. (C) Overview of the study protocol. Patients with identified CIS lesions underwent repeat bronchoscopy and re-biopsy every 4 months. Definitive cancer treatment was only performed if pathological evidence of progression to invasive cancer was detected. The 'index biopsy' profiled in this study refers to the biopsy immediately preceding progression to invasive cancer or regression to low-grade dysplasia or normal epithelium. (D) Venn diagram of different-omics analyses performed on laser capture microdissection (LCM)-captured CIS lesions. Due to the small size of bronchial biopsies, not all analyses were performed on all samples.

FIG. 5. Carcinoma-in-situ (CIS) gene expression and methylation profiles are predictive of progression to cancer.

9

(A) Probability plot based on a 291-gene signature for correct class prediction (discovery set—red circles indicate progressive lesions, e.g., top right; green circles indicate regressive lesions, e.g., bottom left). (B) Challenging the 291-gene signature on a CIS validation set. Area under the curve (AUC) is 1 using Receiver Operating Characteristic (ROC) analysis. (C) Application of the 291-gene signature to TCGA LUSC data. The signature described herein classified TCGA LUSC vs TCGA controls samples with AUC of 0.81 (green circles indicate TCGA controls (left portion of graph), orange circles indicate TCGA LUSC (right portion of graph). (D) Distribution of methylation beta values across the genome in TCGA controls, CIS regressive and progressive and TCGA LUSC samples. Most probes are regulated at 0 or 1 in normal tissue but this regulation is reduced in both regressive and progressive CIS and TCGA LUSC samples. (E) Methylation Heterogeneity Index (MI), defined as counts of methylation probes with $0.26<\beta<0.88$, for each sample. MI is higher in regressive and progressive CIS and TCGA LUSC compared with TCGA controls and this can be used as an accurate predictor with AUC=0.96 for TCGA LUSC vs TCGA controls and AUC=0.74 for progressive vs regressive CIS. (F) Histogram of AUC values calculated by performing the same analysis used in (E) 10,000 times, with each run limited to a different random sample of 2,000 probes (AUC mean for TCGA LUSC vs TCGA controls is 0.95 (95% CI 0.92-0.98)). This demonstrates that a random sample of methylation probes is an accurate predictor using this method.

FIG. 6. Chromosomal instability is associated with progression to cancer. (A) Mean expression of CIN-associated genes in CIS samples. Progressive and regressive CIS samples are well differentiated with AUC=0.96. Green circles indicate regressive CIS lesions; red circles indicate progressive CIS. (B) Plot of NEK2 expression across CIS samples demonstrates increasing expression with progression to cancer. Expression of this gene alone classifies progressive vs regressive CIS with AUC=0.93. (C) Pathway analysis of gene expression data between progressive and regressive CIS shows a strong chromosomal instability (CIN) signal. This signal remains strong when cell cycle genes are removed from the CIN70 signature. (D) Pathway analysis of methylation data demonstrating several cancer-related pathways up-regulated in progressive CIS compared with regressive CIS.

Figure 7:
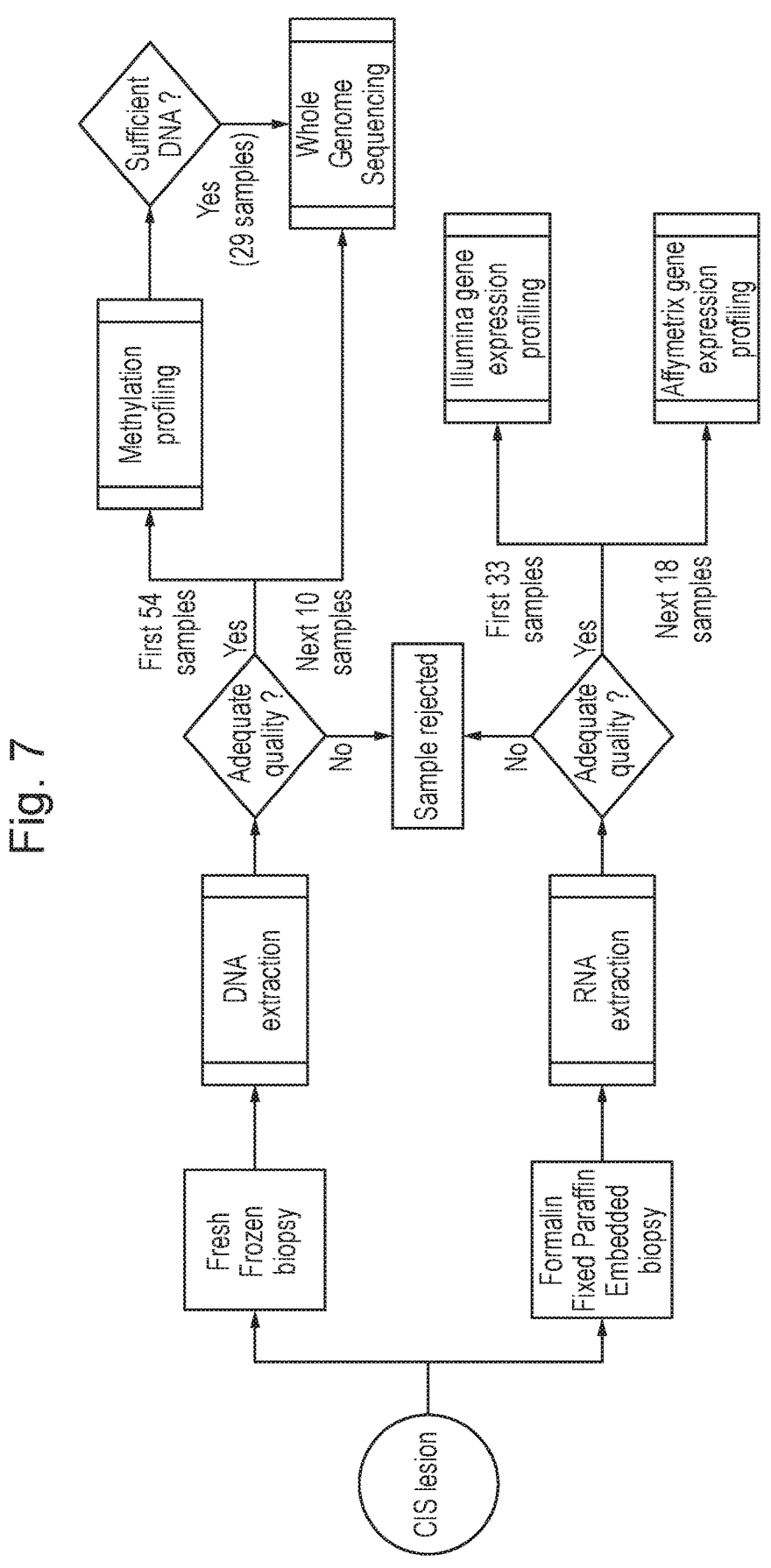
Figure 8E:
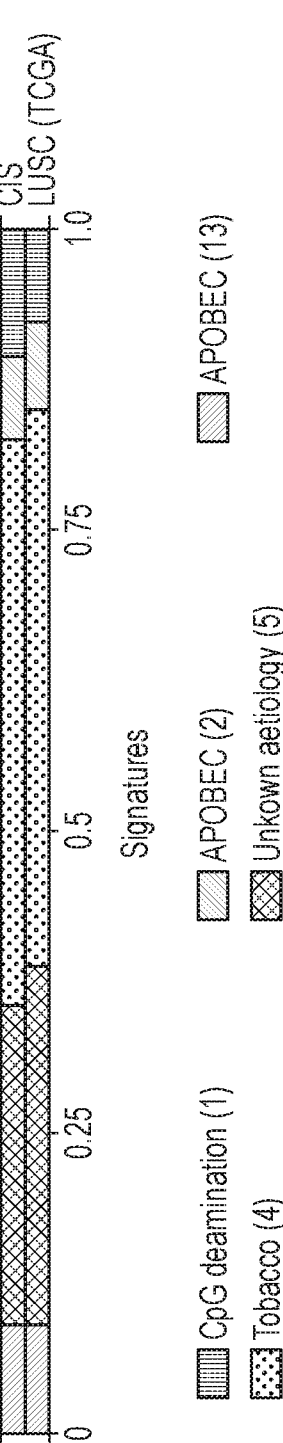
Figure 8H:
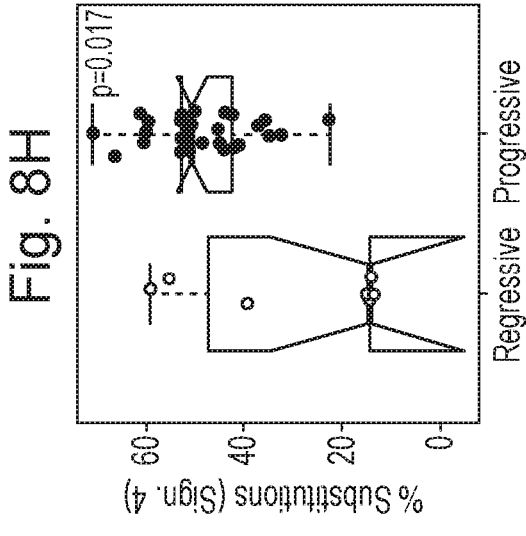
Figure 8G:
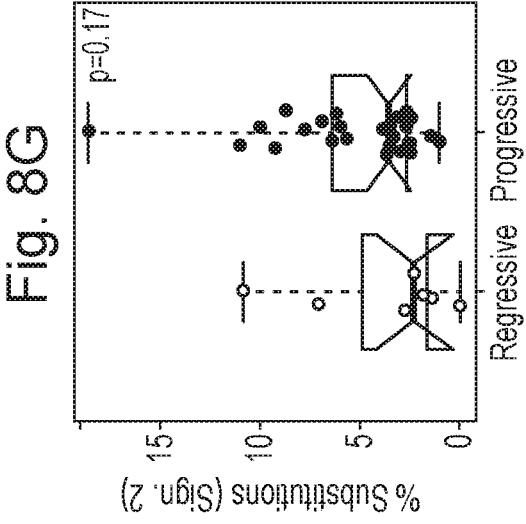
Figure 8J:
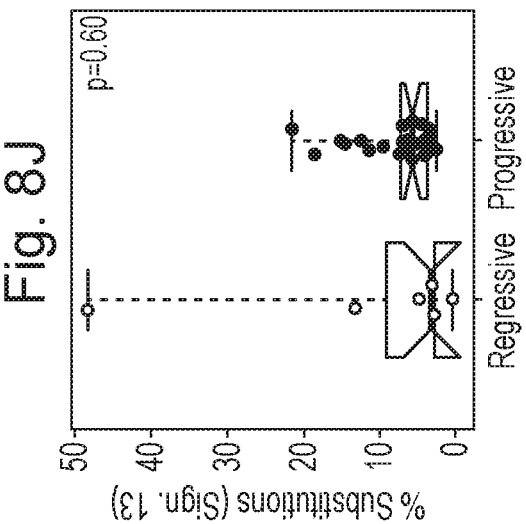
Figure 8F:
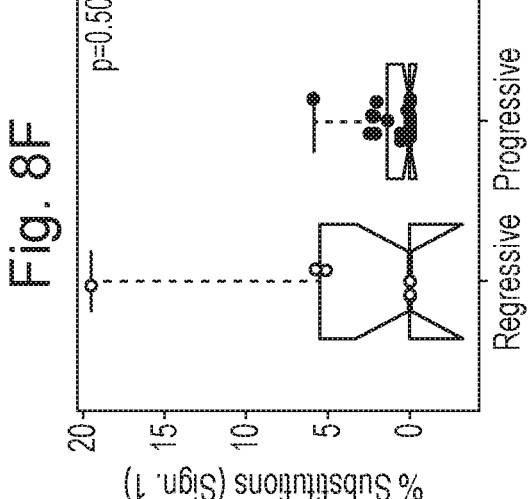
Figure 8I:
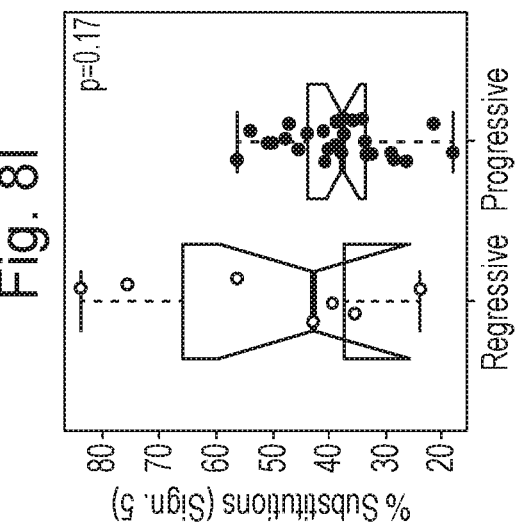

FIG. 7. Experimental workflow. Flow diagram illustrating which profiling techniques were applied to which samples. Biopsies taken from index CIS lesions were stored as fresh frozen (FF) and formalin-fixed paraffin embedded (FFPE). DNA was extracted from FF biopsies. The first 54 samples studied that had sufficient extracted DNA passing quality control (QC) underwent first methylation profiling, then whole-genome sequencing (WGS) when sufficient remaining DNA was available. Due to the low DNA quantity extracted from some biopsies, the methylation dataset (n=54) was larger than the WGS data set (n=29), therefore the subsequent 10 samples underwent WGS directly without methylation profiling. RNA was extracted from FFPE samples and underwent gene expression profiling when RNA passed QC. To ensure validity of our conclusions across orthogonal platforms we used Illumina microarrays to profile a discovery set of 33 samples, then subsequently used Affymetrix microarrays to profile an independent validation set of 18 further samples.

FIG. 8. Mutational signatures of carcinoma-in-situ (CIS) lesions. (A-D) The contribution of each of five pre-selected mutational signatures to each lesion is shown. These five mutational signatures, associated with CpG deamination (1), APOBEC (2 and 13), tobacco (4) and unknown aetiology (5), were selected based on an initial run using all 30 mutational signatures, which showed that these were present in the data and in signature extractions from lung squamous cell cancer (LUSC) datasets. The number of substitutions attributed to each signature is shown (A-B) as well as the proportion of mutations attributed to each mutational signature (C-D). Samples from the same patient share the same identifier except for the final letter; for example, PD21883a and PD21883d are two samples from the same patient. (e) Comparison of the mutational signatures of CIS lesions to those found in lung squamous cell cancer (LUSC). LUSC data were downloaded from TCGA and mutations called with our algorithms. All mutations from all samples from each cancer type were pooled for this analysis. The colour scale indicates the proportion of substitutions in each sample that are attributed to each signature. (F-J) Comparison of the relative proportion of mutations attributed to each signature between progressive (right-hand side) and regressive (left-hand side) CIS samples. P values were calculated using likelihood ratio tests of a mixed effects model with outcome (progressive or regressive) included as a fixed effect versus a model that was identical but for the fact that outcome was not included as a fixed effect. Only signature 4 (smoking-associated) was significantly different between the two groups.

Figure 9:
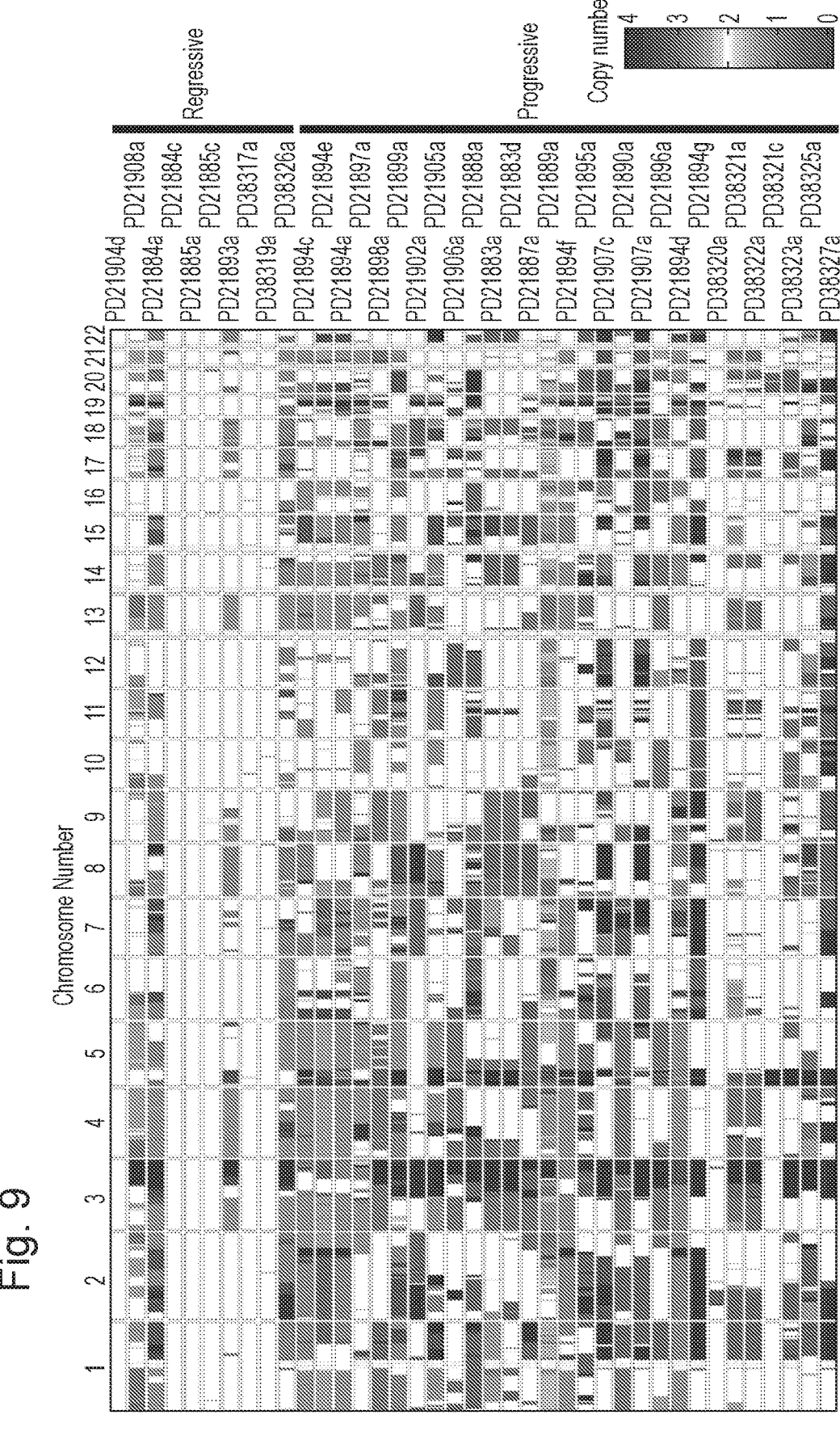

FIG. 9. Genome-wide copy number changes of carcinoma-in-situ (CIS) lesions. Visualisation of copy number changes for 39 whole-genome-sequenced CIS samples. Rows represent samples, genomic position is represented on the x-axis. Local copy number gains are illustrated in red, losses in blue. Widespread changes were observed in progressive CIS samples and a subset of regressive samples.

Figures 10A, 10B, 10C:
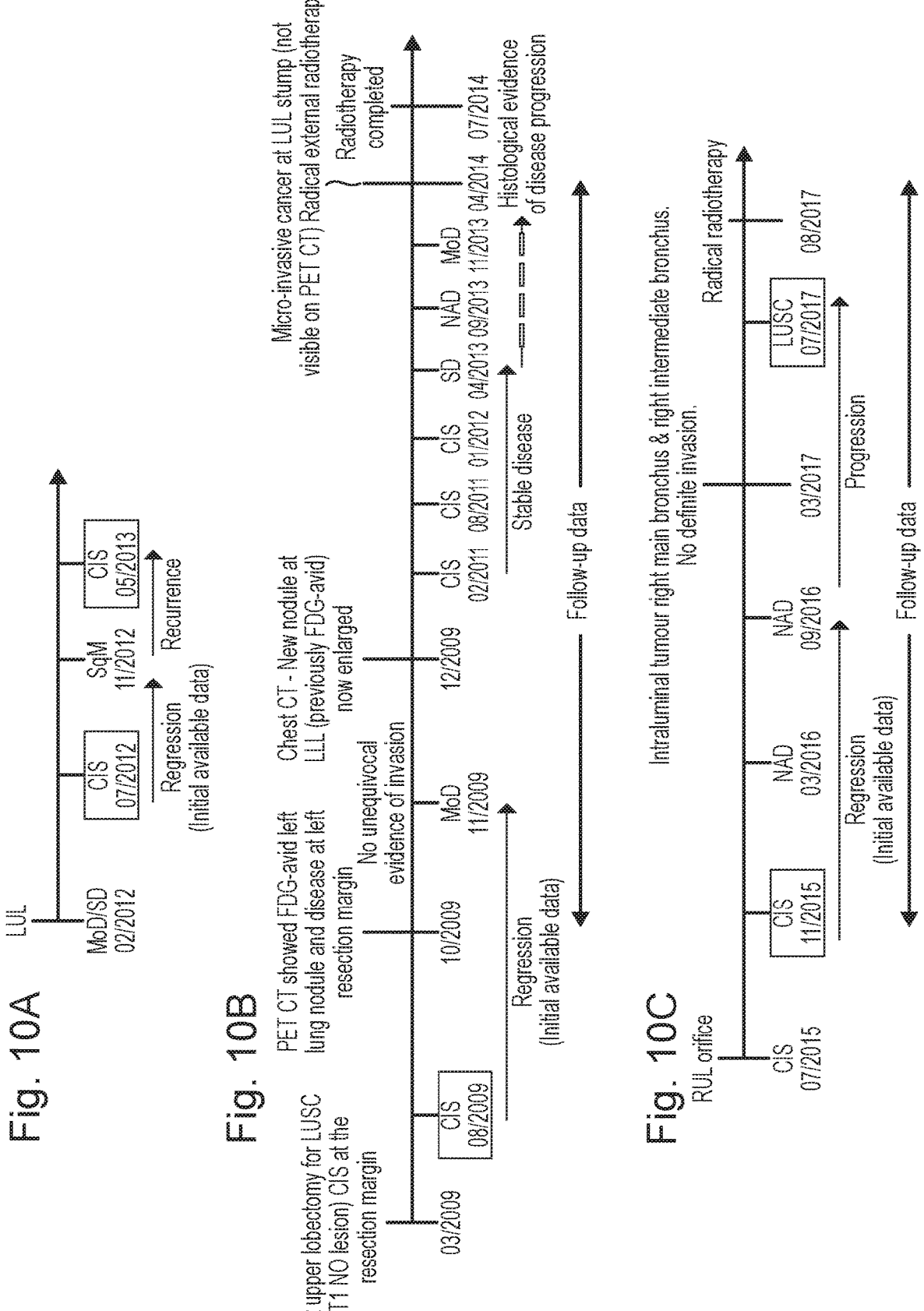

FIG. 10. Documentation of biopsy history and chronology of lesion appearance in three misclassified regressive cases. (A) Case 1 (PD21893a) appeared to regress from a CIS lesion (July 2012) to squamous metaplasia (SqM; November 2012). However, again, CIS was subsequently reconfirmed by biopsy (May 2013). (B) Case 2 (PD21884a) had a lobectomy for T1N0 lung squamous cell cancer (LUSC) in the left upper lobe (LUL) and was under surveillance for carcinoma-in-situ (CIS) at the resection margins. A subsequent, high-grade CIS lesion (August 2009) profiled for genome-wide DNA methylation changes was considered regressive since a follow-up biopsy on the same anatomical site demonstrated the presence of a low-grade, moderately dysplastic (MoD) lesion (November 2009). A subsequent biopsy, however, was classified as CIS (February 2011) and the lesion then remained static for 26 months but eventually progressed into invasive cancer (April 2014). (C) Case 3 (PD38326a) had an initial diagnosis of CIS (November 2015) followed by regression to normal epithelium (March 2016). CIS was subsequently identified at the same site (March 2017), with invasive cancer diagnosed on subsequent biopsy (July 2017).

FIG. 11. Genomic aberrations in pre-invasive lung carcinoma-in-situ (CIS) lesions. Comparisons of the number of substitutions (A), small insertions and deletions (B), genome rearrangements (C) and copy number changes (D), showing significantly more genomic changes in progressive than regressive lesions. Although there were more clonal substitutions in progressive than regressive lesions (E), the proportion of substitutions that were clonal and the number of clones were similar (F-G). Progressive lesions had more putative driver mutations (H). Telomere lengths (base pairs) were similar between the two groups (I). All P values were calculated using likelihood ratio tests of a mixed effects model with outcome (progressive or regressive) included as a fixed effect versus a model that was identical but for the fact that outcome was not included as a fixed effect.

Figure 12:
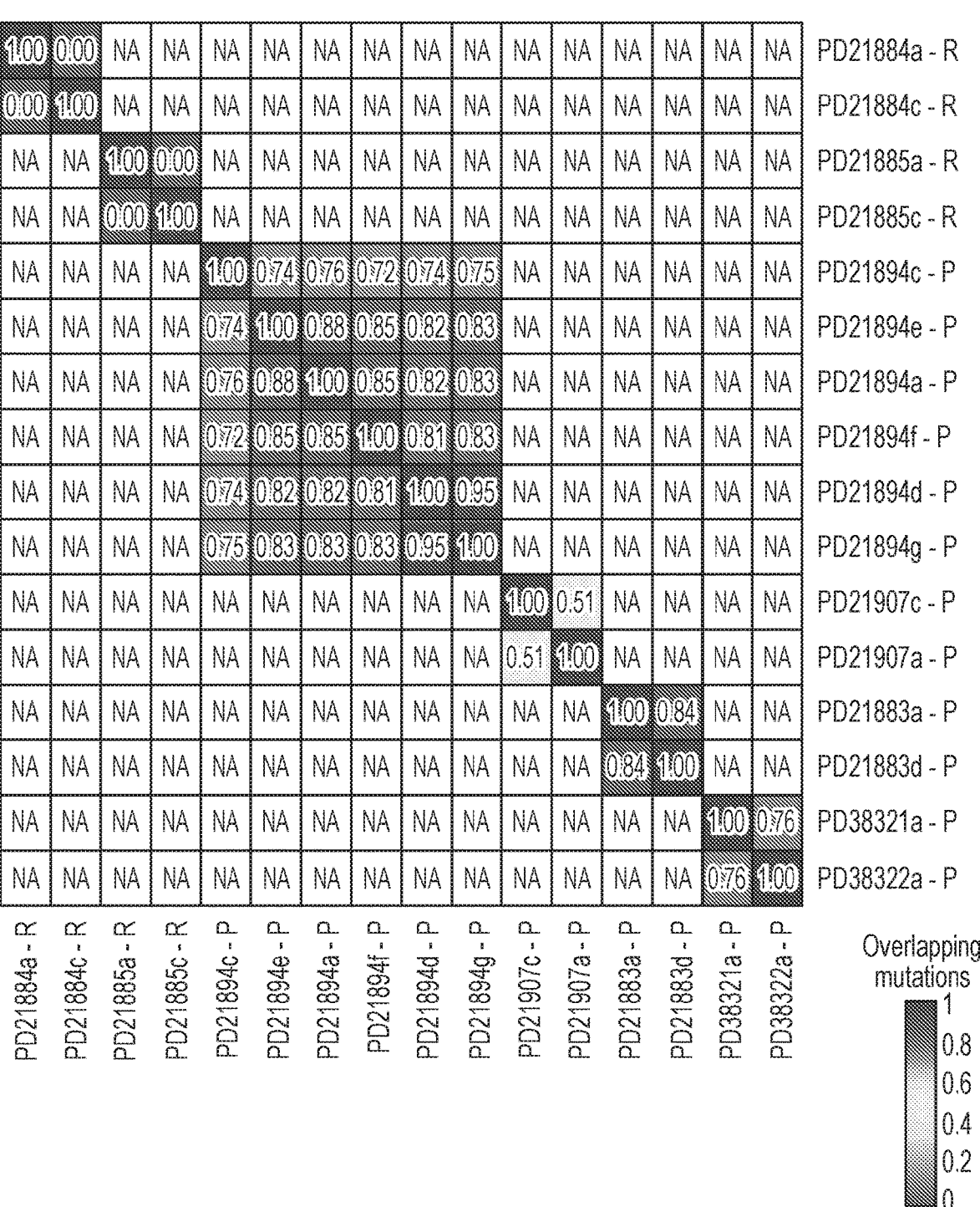

FIG. 12. Subclonal mutational structure in progressive and regressive CIS lesions. Heatmap showing the proportion of overlapping mutations between samples taken from the same patient. For four patients with lesions that would ultimately progress to cancer (denoted 'P'), over half the mutations were shared between any two given samples, suggesting that the lesions were derived from a common ancestral clone. By contrast, for two patients with lesions that would ultimately regress (denoted 'R'), almost no mutations were shared, suggesting that the lesions arose independently. Samples from the same patient are shown in the same colour; PD38321a and PD38322a do belong to the same patient and were mislabelled during processing.

Figure 13A:
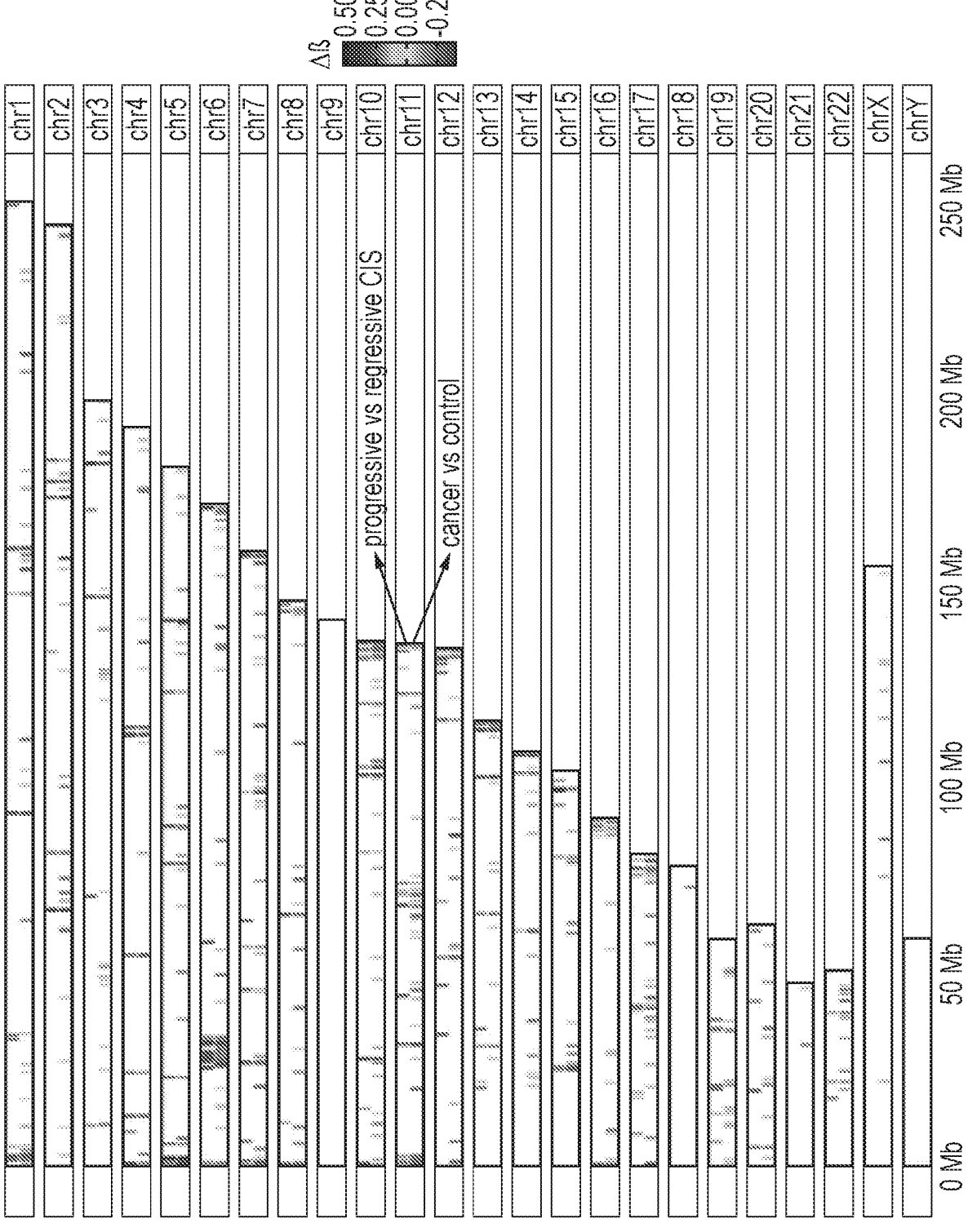
Figure 13B:
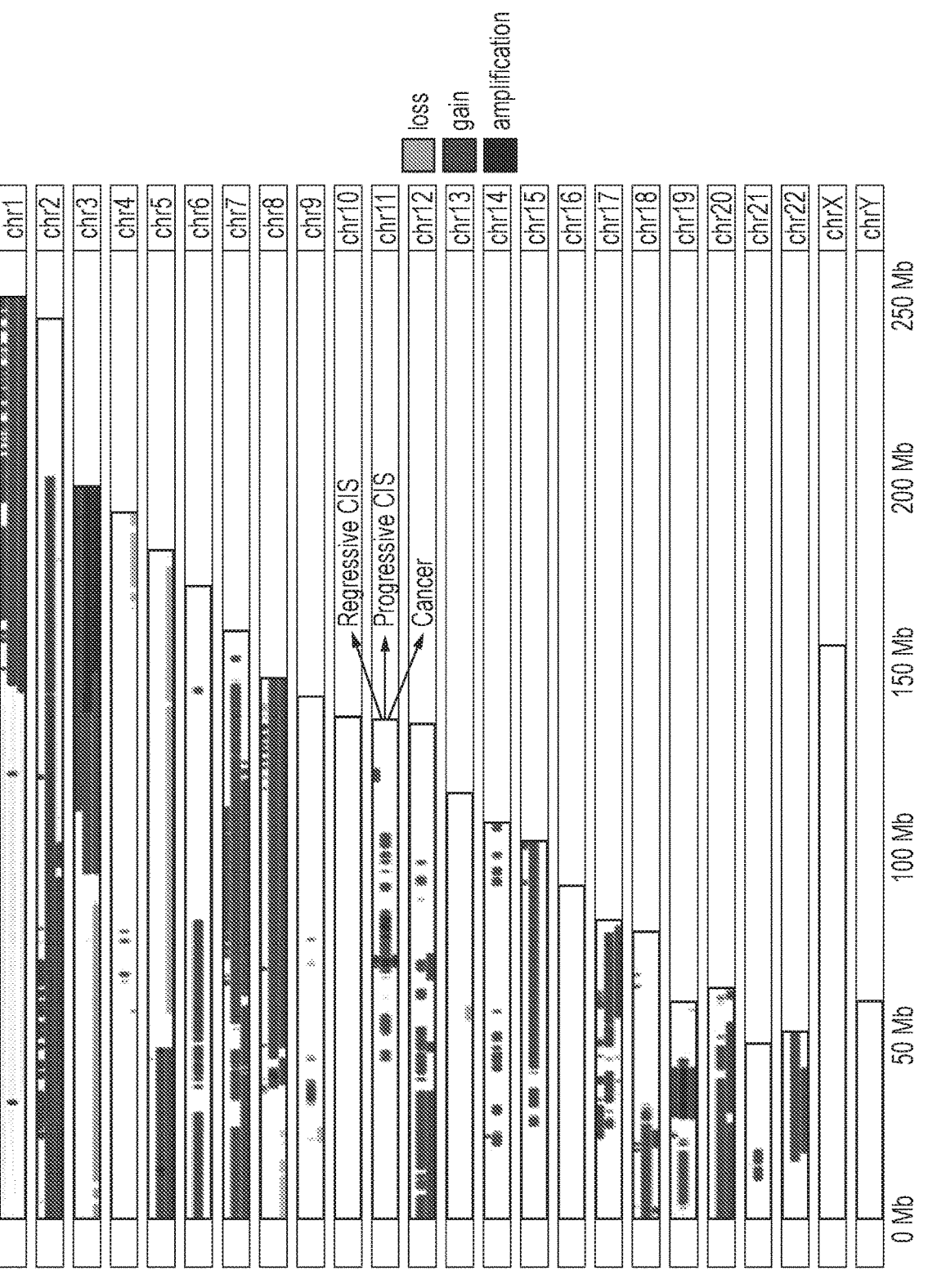

FIG. 13. Differential molecular changes between progressive and regressive lesions. Visualisation of differential changes across the genome. (A) shows all identified differentially methylated regions (DMRs) (hypermethylated regions in yellow, hypomethylated in blue) alongside a similar analysis comparing cancer and control samples from The Cancer Genome Atlas. It was observed that 58% of DMRs identified in the progressive vs regressive analysis are also identified in cancer vs control. (B) shows copy number changes across the genome in regressive CIS, progressive CIS and TCGA cancer samples. Congruency of copy number change was observed, suggesting similar processes in the two cohorts.

Figure 14F:
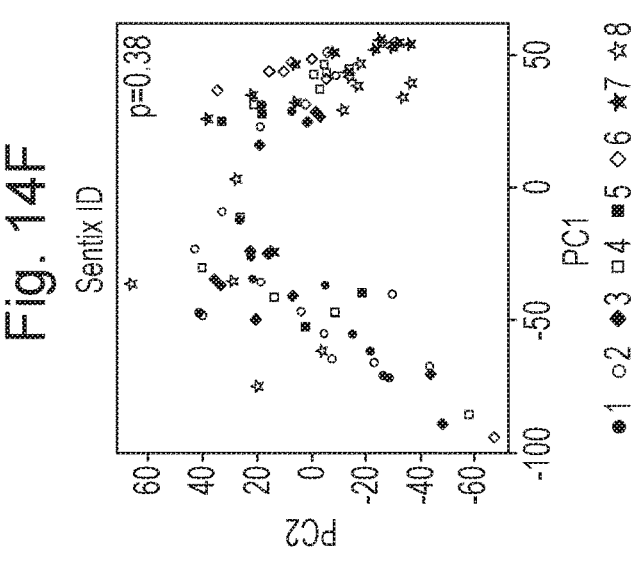
Figure 14E:
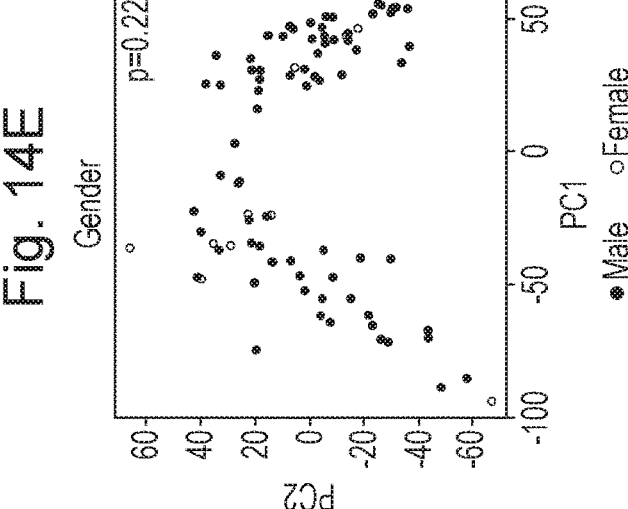
Figure 14D:
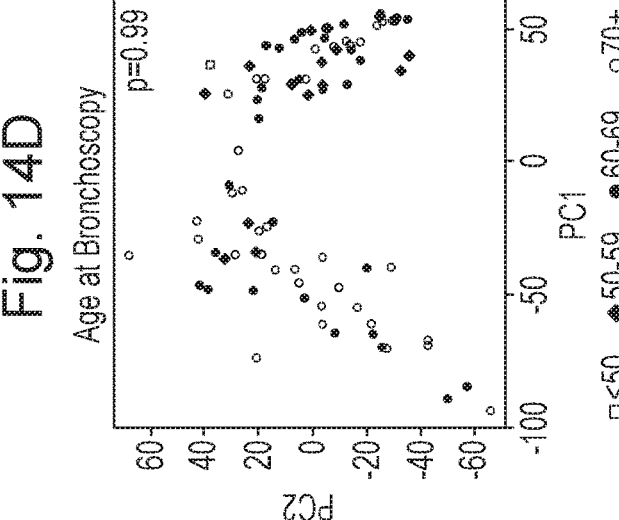
Figure 15A:
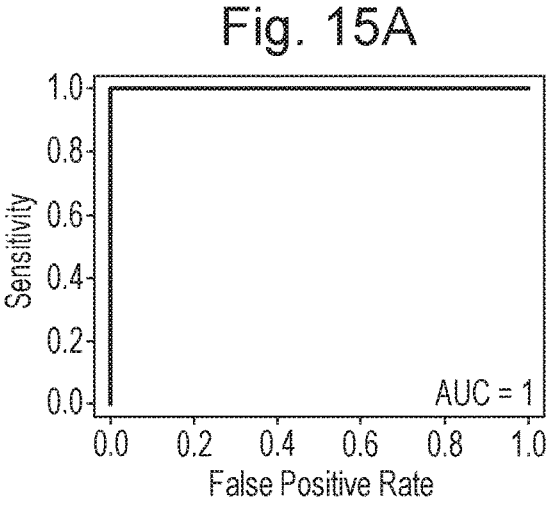
Figure 15B:
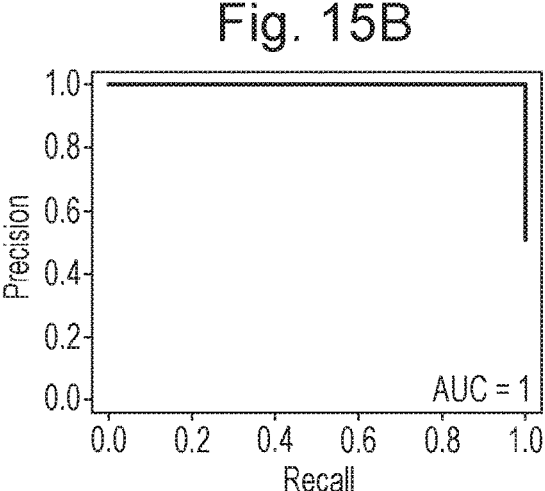
Figure 15C:
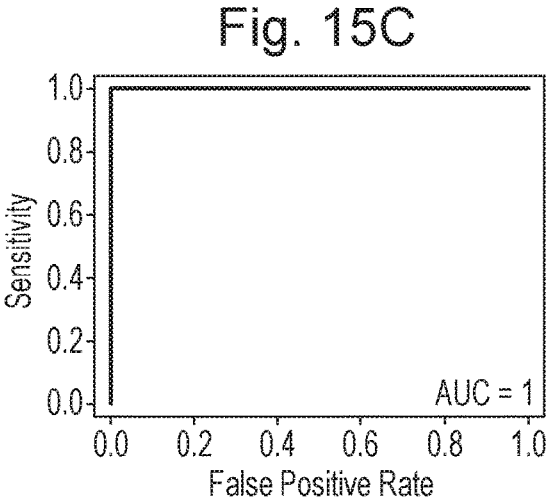
Figure 15D:
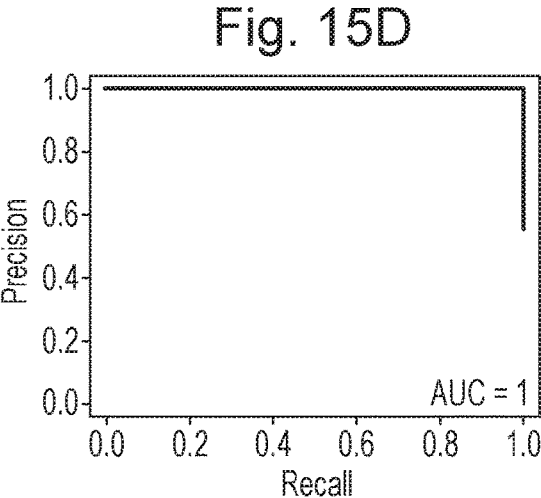
Figure 15E:
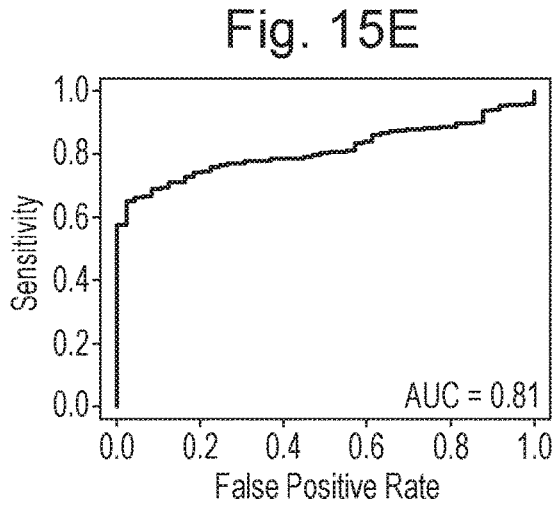
Figure 15F:
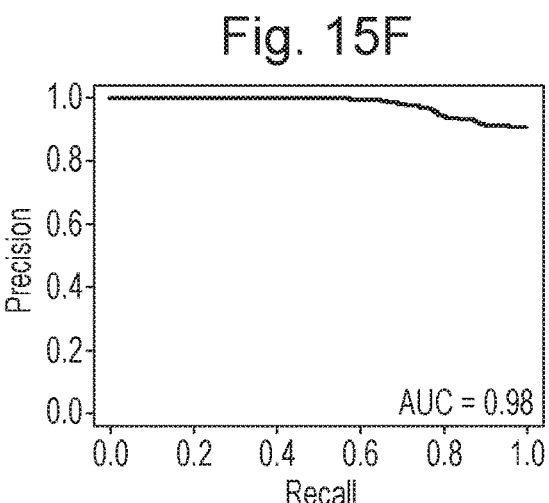

FIG. 14. Principal component analysis investigating effect of various biological, clinical and technical factors affecting correct case segregation for all differentially methylated positions (DMPs) and gene expression data. (A-F) Principal component analysis for all DMPs. (A) Smoking history (pack years). (B) Chronic obstructive pulmonary disease (COPD) status. (C) Previous lung cancer history referring to the presence of lung squamous cell cancer (LUSC) prior to identification of pre-invasive lesions. (D) Age at bronchoscopy (years); age of individual when pre-invasive lesion was first biopsied. (E) Gender. (F) Sentix ID. (G-K) Principal component analysis for all gene expression data. (G) Smoking history (pack years). (H) Chronic obstructive pulmonary disease (COPD) status. (I) Previous lung cancer history referring to the presence of lung squamous cell cancer (LUSC) prior to identification of pre-invasive lesions. (J) Age at bronchoscopy (years); age of individual when pre-invasive lesion was first biopsied. (K) Gender. P-values were calculated using multivariate ANOVA.

FIG. 15. ROC analytics of gene expression predictive model. ROC and precision-recall curves for the predictive model based on gene expression data shown in FIG. 5A-C. Curves are shown for the CIS discovery set (A-B), CIS validation set (C-D) and application to TCGA LUSC data (E-F).

FIG. 16. Predictive modelling of methylation data. In addition to the predictive modelling based on probe variation shown in FIG. 6, differentially expressed methylation probes were used to create a predictor using a Prediction Analysis for Microarrays (PAM) method. The model was trained on a training set (A-C) consisting of 26 progressive samples, 11 regressive samples and 23 control samples, shown in red, green and blue, respectively. A predictor based on 141 DMPs was created. This was applied to a validation set of 10 progressive, 7 regressive and 10 control samples (D-F), predicting outcome with AUC=0.99. (G-I) Application of the predictive model to TCGA methylation data.

Samples were correctly classified into TCGA LUSC and TCGA control samples with AUC=0.99. (J-M) ROC analytics and precision-recall curves for Methylation Heterogeneity Index (MHI) model presented in FIG. 5. Curves apply to cancer vs control (J-K) and progressive vs regressive (L-M), respectively. (N) Histogram of AUC values using MI model with random samples of 2000 probes, applied to progressive vs regressive data. This demonstrates that a similar AUC is achieved with a random sample of probes as when using the entire array.

FIG. 17. Predictive modelling of copy number alteration (CNA) data. Using an analogous method to gene expression and methylation copy number data derived from methylation arrays was used to predict lesion outcome. Probe-level copy number changes were aggregated over cytogenetic bands; these data were used as input to Prediction Analysis of Microarrays (PAM). (A-C) Probability plot based on a 154 cytogenetic band signature for correct class prediction (red circles indicate progressive lesions, green circles indicate regressive lesions). The area under the curve for the 154-cytogenetic band signature is 0.86. (D-F) Application of the predictive model to previously published data (van Boerdonk et al.) replicates those result, classifying all regressive and 9/12 progressive samples correctly. This dataset included pre-invasive samples of various histological grades, rather than only CIS. (G-I) Application of the predictive model to TCGA copy number data. Samples were correctly classified into TCGA LUSC and TCGA control samples with an AUC of 0.98.

Figure 18:
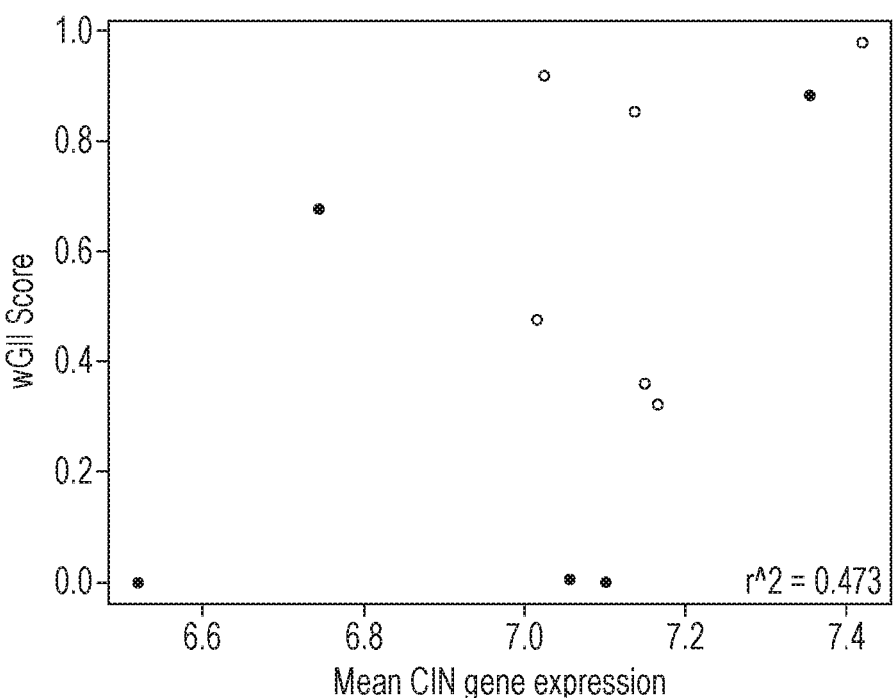

FIG. 18. wGII score correlates with mean CIN gene expression. To confirm an association between CIN gene expression and copy number change, Weighted Genome Integrity Index (wGII) was correlated with mean CIN gene expression for the 11 CIS samples where gene expression and whole-genome sequencing data was available. Pearson correlation coefficient r2=0.473.

DETAILED DESCRIPTION OF THE INVENTION

The early detection and treatment of pre-invasive lung disease, and the prevention of invasive lung cancers, such as LUSC, remains a major unmet need. The present inventors have extensively profiled the genome-wide gene expression and DNA methylation patterns associated with progressive pre-invasive lung disease as compared to regressive pre-invasive lung disease. Using these results, the present inventors have discovered molecular signatures that can be used to predict the clinical outcome of a pre-invasive lung lesion with a high degree of accuracy. The predictive molecular signatures provided by the present invention can be used to identify whether or not an individual has a progressive pre-invasive lung lesion i.e. a pre-invasive lesion that will progress or develop to an invasive lung cancer. Such an individual will benefit from preventative treatment of the pre-invasive lung lesion and/or treatment of the resultant invasive lung cancer. Conversely, the predictive molecular signatures provided by the present invention can be used to identify an individual as having a regressive pre-invasive lesion i.e a pre-invasive lesion that will not progress or develop into an invasive lung cancer. Such an individual would not benefit from preventative treatment of the pre-invasive lung lesion and/or treatment for lung cancer and therefore treatment and potentially harmful side-effects of e.g. chemotherapy/radiotherapy can be avoided.

The present invention relates to methods of identifying whether or not an individual has a pre-invasive lung lesion that will progress to an invasive lung cancer.

The present invention relates to a method of treating a pre-invasive lung lesion and/or treating and/or preventing an invasive lung cancer in an individual comprising:

identifying a pre-invasive lung lesion in an individual that will progress to an invasive lung cancer by performing a method according to any one of claims 1-11; and administering a lung cancer therapy to the individual, optionally wherein the therapy comprises surgical intervention.

The present invention also relates to a molecular signature described herein for identifying whether or not an individual has a pre-invasive lung lesion that will progress to an invasive lung cancer.

The present invention further relates to the use of a molecular signature described herein for identifying whether or not an individual has a pre-invasive lung lesion that will progress to an invasive lung cancer.

Definitions

The term "comprises" (comprise, comprising) should be understood to have its normal meaning in the art, i.e. that the stated feature or group of features is included, but that the term does not exclude any other stated feature or group of features from also being present. For example, a method comprising steps (a), (b) and (c) includes steps (a), (b) and (c) but may also include other steps.

The term "consists of" should also be understood to have its normal meaning in the art, i.e. that the stated feature or group of features is included, to the exclusion of further features. For example a method consisting of steps (a), (b) and (c) includes steps (a), (b) and (c) and no other steps.

For every embodiment in which "comprises" or "comprising" is used, the present invention provides a further embodiment in which "consists of" or "consisting of" is used. Thus, every disclosure of "comprises" should be considered to be a disclosure of "consists of".
Individual In any of the methods of the invention disclosed herein, the term "individual" may be a human. The most preferred individual to which the methods of the invention are applicable are humans.

In any of the methods of the invention disclosed herein, the individual may be a non-human animal. For example, methods of the invention disclosed herein may be applied to non-human animals to determine the efficacy of new therapeutics, new therapeutic strategies, new modes of administration of pre-existing therapeutic strategies, or surgical methods. Thus, in any of the methods of the invention disclosed herein the individual may be a rodent, such as a rat or a mouse. In any of the methods of the invention disclosed herein, the individual may be a non-human mammal, such as a primates, cats or pigs.

In any of the methods of the invention described herein, the individual can be one who:

(a) is not suspected of having cancer;

(b) is suspected of having a pre-invasive lung lesion but not suspected of having cancer;

(c) has a pre-invasive lesion but is not suspected of having cancer;

(d) has a pre-invasive lesion and is suspected of having cancer;

(e) is suspected of having cancer; or (f) has cancer.

The individual may be suspected of having a pre-invasive lung lesion and/or cancer on the basis of a clinical presentation, a diagnostic test and/or family history. The individual may have previously had a lung disease, a pre-invasive lung lesion and/or cancer. The individual may be in remission from a lung disease, a pre-invasive lung lesion and/or cancer e.g. an invasive lung cancer, such as LUSC. The individual may be, or have been, a smoker. The individual may be a non-smoker. The individual may be male. The individual may be female. The individual may be an infant. The individual may be an adult. The individual may be elderly.
Sample The methods of the invention described herein comprise the step of providing a sample of nucleic acid which has been taken from a tissue of the individual, wherein the tissue is suspected of harbouring a pre-invasive lung lesion.

The "nucleic acid sample which has been take from a tissue" may refer to a sample of nucleic acid which has been obtained from a material derived from a tissue, for example from whole blood, a blood fraction, plasma, serum, a bloodspot, a lung tissue biopsy, a lung tissue sample, lung mucus, sputum, or phlegm. Said sample of nucleic acid may be processed in any way that the user deems appropriate, such that a progression score can be determined using a molecular signature described herein.

The "nucleic acid" may be a DNA. The "nucleic acid" may be an RNA, such as a messenger RNA (mRNA).
Statistical Parameters for Predictive Molecular Signature Sensitivity and specificity metrics for identification of pre-invasive lung lesions that will progress to an invasive lung may be defined using standard receiver operating characteristic (ROC) statistical analysis. In ROC analysis, 100% sensitivity corresponds to a finding of no false negatives, and 100% specificity corresponds to a finding of no false positives.

As used herein the term "sensitivity" (also referred to as the true positive rate) refers to a measure of the proportion of actual positives that are correctly identified as such. In other words, the sensitivity of a diagnostic test may be expressed as the number of true positives i.e. individuals correctly identified as having a disease as a proportion of all the individuals having the disease in the test population (i.e. the sum of true positive and false negative outcomes). Thus, a high sensitivity diagnostic test is desirable as it rarely misidentifies individuals having the disease. This means that a negative result obtained by a highly sensitive test has a high likelihood of ruling out the disease.

In the field of medical diagnostics, and as used herein, the term "specificity" (also referred to as the true negative rate) refers to a measure of the proportion of actual negatives that are correctly identified as such. In other words, the specificity of a diagnostic test may be expressed as the number of true negatives (i.e. healthy individuals correctly identified as not having a disease) as a proportion of all the healthy individuals in the test population (i.e. the sum of true negative and false positive outcomes). Thus, a high specificity diagnostic test is desirable as it rarely misidentifies healthy individuals. This means that a positive result obtained by a highly specific test has a high likelihood of ruling in the disease.

In the field of medical diagnostics, and as used herein, a "Receiver Operating Characteristic (ROC) curve" refers to a plot of true positive rate (sensitivity) against the false positive rate (1−specificity) for all possible cut-off values. These terms are well known in the art and to the skilled person.

The specificity and/or sensitivity of a method may be determined by performing said method on a validation set of samples. For samples in the validation set it is known which samples are positive samples e.g. samples derived from pre-invasive lung lesions known to have progressed to an invasive lung cancer, such as a CIS that progressed to a LUSC. It is also know which samples of the validation set are negative samples e.g. samples derived from pre-invasive lung lesions which did not progress to an invasive cancer (i.e. pre-invasive lung lesions that regressed). The extent to which the method correctly identifies the known positive samples (i.e. the sensitivity/true positive rate of the method) and/or the known negative samples (i.e. the specificity/true negative rate of the method) can thus be determined.

A further metric which can be employed to classify the accuracy of the methods of the present invention is ROC AUC. In ROC analysis, the area under the curve of a ROC plot (AUC) is a metric for binary classification. In a random binary classifier the number of true positives and false positives will be approximately equal. In this situation the AUC score for the ROC plot will be 0.5. In a perfect binary classifier the number of true positives will be 100% and the number of false positives will be 0%. In this situation the AUC score for the ROC plot will be 1 which is therefore the highest AUC score a predictive classifier can achieve.

Predictive Molecular Signatures

The present invention relates to a method of identifying whether or not an individual has a pre-invasive lung lesion that will progress to an invasive lung cancer, the method comprising:

(a) providing a sample of nucleic acid which has been taken from a tissue of the individual, wherein the tissue is suspected of harbouring a pre-invasive lung lesion;

(b) performing an assay to determine a progression score for the sample; and (c) identifying whether or not the individual has a pre-invasive lung lesion that will progress to an invasive lung cancer by comparing the progression score to a threshold value;

wherein the progression score is determined using a molecular signature selected from:
i) a differentially expressed gene (DEG) signature;
ii) a differentially methylated position (DMP) signature;
iii) a copy number variation (CNV) signature; and
iv) combinations of (i) to (iii).

Thus, in some of the methods of the present invention described herein, the individual is identified as having a pre-invasive lung lesion that will progress to an invasive lung cancer based on a comparison of a progression score and a threshold value.

For example, the individual may be identified as having a pre-invasive lung lesion that will progress to an invasive lung cancer if the progression score determined for the sample is higher than the threshold; or the individual may be identified as not having a pre-invasive lung lesion that will progress to an invasive lung cancer if the progression score determined for the sample is lower than the threshold.

In any of the methods of the present invention described herein, the progression score may be determined using any of the molecular signatures described herein and combinations thereof, for example any of the DEG signatures provided in Tables 1-9 and/or any of the DMP signatures provided in Tables 11-17 and/or any of the CNV signatures provided in Tables 19-36. The gene weights provided in Tables 1-9 and/or the DMP weights provided Tables 11-17 and/or the CNV band weights provided in Tables 19-36 may be used as part of the molecular signature to determine a progression score for a sample.

Thus, the present invention provides a molecular signature for use in identifying whether or not an individual has a pre-invasive lung lesion that will progress to an invasive lung cancer. The molecular signature of the present invention may be a DEG signature as defined in any one of Tables 1-9 or combinations thereof. The molecular signature of the present invention may be a DMP signature as defined in any one of Tables 11-17 or combinations thereof. The molecular signature of the present invention may be a CNV signature as defined in any one of Tables 19-36 or combinations thereof.

As used herein, a "progression score" is a measure of the probability that an individual has a pre-invasive lung lesion that will progress to an invasive lung cancer. In the context of the present invention, a progression score has value between 0 and 1.

The PAM (prediction analysis of microarray data) method may be used to generate a progression score from differential gene expression data using a DEG signature described herein, from differential methylation data using a DMP signature described herein, or from copy number band variation data using a CNV signature described herein. Thus, in any of the methods of the present invention described herein, the progression score may be determined using the PAM method. In any of the methods of the present invention described herein, the progression score may be determined using the PAM method and molecular signature selected from:
i) a differentially expressed gene (DEG) signature;
ii) a differentially methylated position (DMP) signature;
iii) a copy number variation (CNV) signature; and
iv) combinations of (i) to (iii).

The PAM method is described Tibshirani, et al. "*Diagnosis of multiple cancer types by shrunken centroids of gene expression*" PNAS 2002 99:6567-6572 (the contents of which are incorporated herein by reference) and Tibshirani et al. (2002) "*Class prediction by nearest shrunken centroids, with applications to DNA microarrays*" Stanford tech report (the contents of which are incorporated herein by reference). A PAM software package (PAMR) is publically available at http://www.bioconductor.org/packages/2.7/bioc/html/pamr.html.

Briefly, by applying a molecular signature described herein to differential gene expression data or differential methylation data, discriminant scores can be calculated from which the probability of progression (i.e. the progression score) can be calculated, by analogy to Gaussian linear discriminant analysis, as implemented in the PAMR package (see equations [6]-[8] of Tibshirani, et al; PNAS 2002 99:6567-6572).

The progression score may be compared to a "threshold value", which is a numerical value between 0 and 1, in order to make a binary classification for a given sample. For example, where a threshold value of X is applied, samples having a progression score less than X should be classified as regressive i.e. the individual from which the sample was obtained will be identified as not having a pre-invasive lung lesion that will progress to an invasive cancer. Conversely, samples having a progression score greater than X should be classified as progressive i.e. the individual from which the sample was obtained should be identified as having a pre-invasive lung lesion that will progress to an invasive lung cancer.

As shown in FIG. 5, an example method using a DEG signature described herein (the DEG signature described in Table 2) generated progression scores of less than about 0.1 for the majority of regressive CIS lesions (plotted left of the vertical line in FIG. 5B) and the majority of non-cancerous control samples (plotted left of the vertical line in FIG. 5C). The majority of progressive CIS samples (plotted right of the vertical line in FIG. 5B) and cancerous samples (plotted right of the vertical line in FIG. 5B) had progression scores greater than about 0.1. Accordingly, based on this analysis, an appropriate "threshold value" would be about 0.1. Thus, in this situation, where a sample is determined to have a progression score of less than 0.1 the individual is identified as not having a pre-invasive lesion that will progress to an invasive lung cancer. Alternatively, where a sample is determined to have a progression score of greater than 0.1, the individual from which the sample was obtained will be identified as having a progressive pre-invasive lesion that will progress to an invasive lung cancer.

For any particular combination of molecular signature and threshold value, as applied to a differential gene expression dataset, a differential methylation dataset, or a copy number variation dataset, the skilled person using the PAMR methodology may determine an ROC AUC, sensitivity and/or specificity metrics. These metrics may be used to evaluate the usefulness of a particular method for a particular application. For example, a method that achieves a high sensitivity (few false negatives) at the expense of specificity (greater number of false positives) may be desirable if the method is to be used as a screening assay.

The skilled person will be able to select an appropriate an appropriate threshold value for use in a particular method. For example, where the method of the present invention involves determining a progression score using a DEG signature described herein, e.g. a DEG signature comprising the expression level of each of at least 10, at least 20, at least 30, at least 40, at least 50, at least 60, at least 75, at least 100, at least 150, at least 200, at least 250, at least 300, at least 325, least 350, at least 375, or 397 genes identified in Table 1, the threshold value may be from about 0.02 to about 0.06. Thus, in methods of the present invention where a progression score is determined using a DEG signature described herein e.g. a DEG signature comprising the expression level of each of at least 10, at least 20, at least 30, at least 40, at least 50, at least 60, at least 75, at least 100, at least 150, at least 200, at least 250, at least 300, at least 325, least 350, at least 375, or 397 genes identified in Table 1, the threshold value may be about 0.02, about 0.04, about 0.06, about 0.08, about 0.1, about 0.12, about 0.14, about 0.16, about 0.18, about 0.2, about 0.22, about 0.24, about 0.26, about 0.28, about 0.3, about 0.32, about 0.34, about 0.36, about 0.38, about 0.4, about 0.42, about 0.44, about 0.46, about 0.48, about 0.5, about 0.52, about 0.54, about 0.56, about 0.58, or about 0.6.

In other methods of the present invention, a progression score is determined using a DMP signature. Where the method of the present invention involves determining a progression score using a DMP signature described herein, e.g. a DMP signature comprising the methylation status (B) of least two, at least three, at least four, at least five, at least six, at least seven, at least eight, at least nine, at least 10, at least 12, least 14, at least 16, at least 18, at least 20, at least 25, at least 50, at least 75, at least 100, or differentially methylated positions (DMPs) selected from Table 11, the threshold value may be from about 0.3 to 0.6. Thus, in methods of the present invention where a progression score is determined using a DMP signature described herein, e.g. a DMP signature comprising the methylation status (B) of least two, at least three, at least four, at least five, at least six, at least seven, at least eight, at least nine, at least 10, at least 12, least 14, at least 16, at least 18, at least 20, at least 25, at least 50, at least 75, at least 100, at least 125, or differentially methylated positions (DMPs) selected from Table 11, the threshold value may be about 0.3, about 0.31, about 0.32, about 0.33, about 0.34, about 0.35, about 0.36, about 0.37, about 0.38, about 0.39, about 0.4, about 0.41, about 0.42, about 0.43, about 0.44, about 0.45, about 0.46, about 0.47, about 0.48, about 0.49, about 0.5, about 0.51, about 0.52, about 0.53, about 0.54, about 0.55, about 0.56, about 0.57, about 0.58, about 0.59, or about 0.6.

In other methods of the present invention, a progression score is determined using a CNV signature. Where the method of the present invention involves determining a progression score using a CNV signature described herein, e.g. a CNV signature comprising the amplification or loss of at least 5, at least 6, least 7, at least 8, at least 9, at least 10, at least 25, at least 50, at least 75, at least 100, at least 125, at least 150, at least 175, or at least 200 CNV bands identified in Table 19, the threshold value may be from about 0.05 to 0.6. Thus, in methods of the present invention where a progression score is determined using a CNV signature described herein, e.g. a CNV signature comprising the amplification or loss of at least 5, at least 6, least 7, at least 8, at least 9, at least 10, at least 25, at least 50, at least 75, at least 100, at least 125, at least 150, at least 175, or at least 200 CNV bands identified in Table 19, the threshold value may be about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.2, about 0.21, about 0.22, about 0.23, about 0.24, about 0.25, about 0.26, about 0.27, about 0.28, about 0.29, about 0.3, about 0.31, about 0.32, about 0.33, about 0.34, about 0.35, about 0.36, about 0.37, about 0.38, about 0.39, about 0.4, about 0.41, about 0.42, about 0.43, about 0.44, about 0.45, about 0.46, about 0.47, about 0.48, about 0.49, about 0.5, about 0.51, about 0.52, about 0.53, about 0.54, about 0.55, about 0.56, about 0.57, about 0.58, about 0.59, or about 0.6.

Assessment of Differentially Expressed Genes (DEGs)

In some of the methods of the present invention described herein, a progression score is determined using a DEG signature which comprises the expression levels of a plurality of differentially expressed genes (DEGs).

In any of the methods disclosed herein, the term "expression level" may refer to any measurable indicator of abundance of any number of the DEGs defined herein in the sample of nucleic acid which has been taken from a tissue of an individual. Thus, "expression level" of a DEG may refer an amount or quantity of a mRNA transcribed from said DEG defined herein or an amount or quantity of a cDNA reverse transcribed from said mRNA. Accordingly, the measurable indicator of abundance may, for example, be the concentration of a given mRNA or cDNA as determined using any technique suitable for use in a method of the invention. The measurable indicator of abundance may also be level of fluorescence, densitometry, colorimetry, or any assay indicator suitable for use in a method of the invention for providing a measurement of DEG, mRNA or cDNA expression level derived from the sample of nucleic acid.

A variety of techniques are available for determining the expression level of a DEG, as will be outlined briefly below. The methods described herein encompass any suitable technique for the determining the expression level of a differentially expressed gene.

Differential gene expression levels may be determined by a hybridisation assay using probes specific for a DEG of interest. The expression levels of multiple DEGs may be assayed in parallel using a plurality of probes, e.g. a plurality of probes provided together in a microarray. Typically, such microarrays will comprises a plurality of probes specific for labelled cDNAs prepared from mRNA isolated from a tissue. When hybridised to the microarray, the labelled cDNA generates a plurality of signals each of which is indicative of the concentration of a particular mRNA transcribed from a particular DEG.

The mRNA used to generate the cDNA by reverse transcription may be extracted from a formalin-fixed paraffin-embedded (FFPE) tissue sample. The expression level of DEGs may be assessed using a commercially available Human Whole-Genome DASL (cDNA-mediated Annealing, Selection, extension and Ligation) beadarray (Illumina). The expression level of DEGs may be assayed using a commercially available Clariom™ D Transcriptome Human Pico Assay 2.0 (transcriptome measurement assay) (Affymetrix).

Quantitative reverse transcription PCR (RT-qPCR) may also be used to determine the expression level of DEGs.

RNA sequencing (RNA-seq) methods may also be used to determine the expression level of DEGs. In such methods, total RNA may be isolated from the tissue sample taken from the individual. The total RNA sample may be purified to enrich for mRNAs prior to preparing an RNA library for sequencing. Library preparation may involve such steps as reverse transcription to cDNA, PCR amplification and may or may not preserve strandedness information. Next generation sequencing (NGS) may be used to sequence the cDNA library generated from the enriched mRNA in order to provide transcriptome information which can be compared against a reference in order to determine the expression levels of DEGs.

The skilled person may select any suitable available RNA-seq method available in the art. For example, any RNA-seq method described in Corney and Basturea (Materials and Methods 2013; 3:203; doi: 10.13070/mm.en.3.203; available at https://www.labome.com/method/RNA-seq-Using-Next-Generation-Sequencing.html, which is incorporated herein by reference). Various RNA-seq methods are commercially available. For example, an overview of RNA-seq methods available from Illumina is available at: https://www.illumina.com/content/dam/illumina-marketing/documents/products/other/rna-sequencing-workflow-buyers-guide-476-2015-003.pdf. The skilled person is able to select an appropriate RNA-seq method depending on the type of sample, for example a particular RNA-seq method may be appropriate for interrogation of fresh frozen (FF) samples and another RNA-seq method may be better suited for interrogation of formalin-fixed paraffin-embedded samples (FFPE). Nevertheless, it is routine for the skilled person to select a suitable RNA-seq method for evaluation of the expression levels of DEGs in any of the methods of the present invention disclosed herein.

Assessment of Differentially Methylated Position (DMP) Methylation Status (β)

In some of the methods of the present invention, described herein a progression score is determined using a DMP signature which comprises the methylation status (β) of a plurality of differentially methylated positions (DMPs), which may also be referred to as methylation variable positions (MVPs).

Methylation status (β) is a well know term in the art and the skilled person is readily able to determine the β value of given DMP. A single DMP on a single DNA molecule will either be methylated (M) or unmethylated (U). Thus, the β value for a single DMP, in a single DNA, is binary, i.e. M=1 or U=0. However, for a population comprising a plurality of DNA molecules, there will be multiple copies of the same DMP. Thus, there may be variation in methylation status between copies of the same DMP on different DNA molecules. Thus, for a sample comprising a population of DNA molecules, the β value is measure of the average methylation status across the entire population and can therefore have any value between 1 and 0.

Where β values are determined on the basis of signals (e.g. fluorescent signals) associated with methylated or unmethylated DMPs. For each sample, the β value may be calculated as the ratio of the signal intensity of the methylated (M) and unmethylated (U) DMPs. For example, according to the following formula:

$$\beta = \frac{\text{intensity of signal from } M \ DMPs}{\text{intensity of signal from } [U \ DMPs + M \ DMPs] + 100}$$

Methylation of DNA is a recognised form of epigenetic modification which has the capability of altering the expression of genes and other elements such as microRNAs. In cancer development and progression, methylation may have the effect of e.g. silencing tumor suppressor genes and/or increasing the expression of oncogenes. Other forms of dysregulation may occur as a result of methylation. Methylation of DNA occurs at discrete loci which are predominately dinucleotide consisting of a CpG motif, but may also occur at CHH motifs (where H is A, C, or T). During methylation, a methyl group is added to the fifth carbon of cytosine bases to create methylcytosine.

Methylation can occur throughout the genome and is not limited to regions with respect to an expressed sequence such as a gene. Methylation typically, but not always, occurs in a promoter or other regulatory region of an expressed sequence.

A DMP as defined herein is any dinucleotide locus which may show a variation in its methylation status between phenotypes, e.g. between a progressive pre-invasive lung lesion and a regressive pre-invasive lung lesion. A DMP is preferably a CpG or a CHH dinucleotide motif. A DMP as defined herein is not limited to the position of the locus with respect to a corresponding expressed sequence.

Typically, an assessment of DNA methylation status involves analysing the presence or absence of methyl groups in DNA, for example methyl groups on the 5$^{th}$ position of one or more cytosine nucleotides. Preferably, the methylation status of one or more cytosine nucleotides present as a CpG dinucleotide (where C stands for Cytosine, G for Guanine and p for the phosphate group attached to the backbone between the two) is assessed.

A variety of techniques are available for determining the methylation status (i.e. determine the β value) of a DMP, as will be outlined briefly below. The methods described herein encompass any suitable technique for the determination of DMP methylation status.

Methyl groups are lost from a starting DNA molecule during conventional in vitro handling steps such as PCR. To avoid this, techniques for the detection of methyl groups commonly involve the preliminary treatment of DNA prior to subsequent processing, in a way that preserves the methylation status information of the original DNA molecule. Such preliminary techniques involve three main categories of processing, i.e. bisulphite modification, restriction enzyme digestion and affinity-based analysis. Products of these techniques can then be coupled with sequencing or array-based platforms for subsequent identification or qualitative assessment of DMP methylation status.

Techniques involving bisulphite modification of DNA have become the most common methods for detection and assessment of methylation status of CpG dinucleotide. Treatment of DNA with bisulphite, e.g. sodium bisulphite, converts cytosine bases to uracil bases, but has no effect on 5-methylcytosines. Thus, the presence of a cytosine in bisulphite-treated DNA is indicative of the presence of a cytosine base which was previously methylated in the starting DNA molecule. Such cytosine bases can be detected by a variety of techniques. For example, primers specific for unmethylated versus methylated DNA can be generated and used for PCR-based identification of methylated CpG dinucleotides. A separation/capture step may be performed, e.g. using binding molecules such as complementary oligonucleotide sequences. Standard and next-generation DNA sequencing protocols can also be used.

In other approaches, methylation-sensitive enzymes can be employed which digest or cut only in the presence of methylated DNA. Analysis of resulting fragments is commonly carried out using microarrays.

Affinity-based techniques exploit binding interactions to capture fragments of methylated DNA for the purposes of enrichment. Binding molecules such as anti-5-methylcytosine antibodies are commonly employed prior to subsequent processing steps such as PCR and sequencing.

Olkhov-Mitsel and Bapat (2012) [46] provide a comprehensive review of techniques available for the identification and assessment of DMP-based biomarkers involving methylcytosine.

For the purposes of assessing the methylation status of the DMP-based biomarkers characterised and described herein, any suitable method can be employed.

Preferred methods involve bisulphite treatment of DNA, including amplification of the identified DMP loci for methylation specific PCR and/or sequencing and/or assessment of the methylation status of target loci using methylation-discriminatory microarrays.

Amplification of DMP loci can be achieved by a variety of approaches. Preferably, DMP loci are amplified using PCR. DMPs may also be amplified by other techniques such as multiplex ligation-dependent probe amplification (MLPA). A variety of PCR-based approaches may be used. For example, methylation-specific primers may be hybridized to DNA containing the DMP sequence of interest. Such primers may be designed to anneal to a sequence derived from either a methylated or non-methylated DMP locus. Following annealing, a PCR reaction is performed and the presence of a subsequent PCR product indicates the presence of an annealed DMP of identifiable sequence. In such methods, DNA is bisulphite converted prior to amplification. Such techniques are commonly referred to as methylation specific PCR (MSP) [47].

In other techniques, PCR primers may anneal to the DMP sequence of interest independently of the methylation status, and further processing steps may be used to determine the status of the DMP. Assays are designed so that the DMP site(s) are located between primer annealing sites. This method scheme is used in techniques such as bisulphite genomic sequencing [48], COBRA [49], Ms-SNuPE [50]. In such methods, DNA can be bisulphite converted before or after amplification.

Preferably, small-scale PCR approaches are used. Such approaches commonly involve mass partitioning of samples (e.g. digital PCR). These techniques offer robust accuracy and sensitivity in the context of a highly miniaturised system (pico-liter sized droplets), ideal for the subsequent handling of small quantities of DNA obtainable from the potentially small volume of cellular material present in biological samples, particularly urine samples. A variety of such small-scale PCR techniques are widely available. For example, microdroplet-based PCR instruments are available from a variety of suppliers, including RainDance Technologies, Inc. (Billerica, MA; http://raindancetech.com/) and Bio-Rad, Inc. (http://www.bio-rad.com/). Microarray platforms may also be used to carry out small-scale PCR. Such platforms may include microfluidic network-based arrays e.g. available from Fluidigm Corp. (www.fluidigm.com).

Following amplification of DMP loci, amplified PCR products may be coupled to subsequent analytical platforms in order to determine the methylation status of the DMPs of interest. For example, the PCR products may be directly sequenced to determine the presence or absence of a methylcytosine at the target DMP or analysed by array-based techniques.

Any suitable sequencing techniques may be employed to determine the sequence of target DNA. In the methods of the present invention the use of high-throughput, so-called "second generation", "third generation" and "next generation" techniques to sequence bisulphite-treated DNA are preferred.

In second generation techniques, large numbers of DNA molecules are sequenced in parallel. Typically, tens of thousands of molecules are anchored to a given location at high density and sequences are determined in a process dependent upon DNA synthesis. Reactions generally consist of successive reagent delivery and washing steps, e.g. to allow the incorporation of reversible labelled terminator bases, and scanning steps to determine the order of base incorporation. Array-based systems of this type are available commercially e.g. from Illumina, Inc. (San Diego, CA; http://www.illumina.com/).

Third generation techniques are typically defined by the absence of a requirement to halt the sequencing process between detection steps and can therefore be viewed as real-time systems. For example, the base-specific release of hydrogen ions, which occurs during the incorporation process, can be detected in the context of microwell systems (e.g. see the Ion Torrent system available from Life Technologies; http://www.lifetechnologies.com/). Similarly, in pyrosequencing the base-specific release of pyrophosphate (PPi) is detected and analysed. In nanopore technologies, DNA molecules are passed through or positioned next to nanopores, and the identities of individual bases are determined following movement of the DNA molecule relative to the nanopore. Systems of this type are available commercially e.g. from Oxford Nanopore (https://www.nanoporetech.com/). In an alternative method, a DNA polymerase enzyme is confined in a "zero-mode waveguide" and the identity of incorporated bases are determined with florescence detection of gamma-labeled phosphonucleotides (see e.g. Pacific Biosciences; http://www.pacificbiosciences.com/).

In other methods in accordance with the invention sequencing steps may be omitted. For example, amplified PCR products may be applied directly to hybridization arrays based on the principle of the annealing of two complementary nucleic acid strands to form a double-stranded molecule. Hybridization arrays may be designed to include probes which are able to hybridize to amplification products of a DMP and allow discrimination between methylated and non-methylated loci. For example, probes may be designed which are able to selectively hybridize to an DMP locus containing thymine, indicating the generation of uracil following bisulphite conversion of an unmethylated cytosine in the starting template DNA. Conversely, probes may be designed which are able to selectively hybridize to a DMP locus containing cytosine, indicating the absence of uracil conversion following bisulphite treatment. This corresponds with a methylated DMP locus in the starting template DNA.

Following the application of a suitable detection system to the array, computer-based analytical techniques can be used to determine the methylation status of an DMP. Detection systems may include, e.g. the addition of fluorescent molecules following a methylation status-specific probe extension reaction. Such techniques allow DMP status determination without the specific need for the sequencing of DMP amplification products. Such array-based discriminatory probes may be termed methylation-specific probes.

Any suitable methylation-discriminatory microarrays may be employed to assess the methylation status of the DMPs described herein. A preferred methylation-discriminatory microarray system is provided by Illumina, Inc. (San Diego, CA; http://www.illumina.com/).

In particular, the Infinium HumanMethylation450 Bead-Chip array system may be used to assess the methylation status of DMPs as described herein. Such a system exploits the chemical modifications made to DNA following bisulphite treatment of the starting DNA molecule. Briefly, the array comprises Type I beads to which are coupled oligonucleotide probes specific for DNA sequences corresponding to the unmethylated form of a DMP, as well as separate Type I beads to which are coupled oligonucleotide probes specific for DNA sequences corresponding to the methylated form of a DMP.

The Infinium HumanMethylation450 BeadChip array system also comprises Type II beads to which are coupled two different types of oligonucleotide probe: a first probe specific for DNA sequences corresponding to the unmethylated form of a DMP and a second probe specific for DNA sequences corresponding to the methylated form of the same DMP.

Candidate DNA molecules are applied to the array and selectively hybridize, under appropriate conditions, to the oligonucleotide probe corresponding to the relevant epigenetic form. Thus, a DNA molecule derived from a DMP which was methylated in the corresponding genomic DNA will selectively attach to methylation-specific oligonucleotide probes, but will fail to attach to the non-methylation-specific oligonucleotide probe. Single-base extension of only the hybridized probes incorporates a labeled ddNTP, which is subsequently stained with a fluorescence reagent and imaged. The methylation status of the DMP may be determined by calculating the ratio of the fluorescent signal derived from the methylated and unmethylated sites.

Because the DMPs of the DMP signatures defined herein were initially identified using the Illumina Infinium Human-Methylation450 BeadChip array system, the same chip system can be used to interrogate those same DMPs in the methods described herein. Alternative or customised arrays could, however, be employed to interrogate the diagnostic DMPs defined herein, provided that they comprise means for interrogating all DMPs for a given method, as defined herein.

Techniques involving combinations of the above-described methods may also be used. For example, DNA containing DMP sequences of interest may be hybridized to microarrays and then subjected to DNA sequencing to determine the status of the DMP as described above.

In the methods described above, sequences corresponding to DMP loci may also be subjected to an enrichment process. DNA containing DMP sequences of interest may be captured by binding molecules such as oligonucleotide probes complementary to the DMP target sequence of interest. Sequences corresponding to DMP loci may be captured before or after bisulphite conversion or before or after amplification. Probes may be designed to be complementary to bisulphite converted DNA. Captured DNA may then be subjected to further processing steps to determine the status of the DMP, such as DNA sequencing steps.

Capture/separation steps may be custom designed. Alternatively a variety of such techniques are available commercially, e.g. the SureSelect target enrichment system available from Agilent Technologies (http://www.agilent.com/home). In this system biotinylated "bait" or "probe" sequences (e.g. RNA) complementary to the DNA containing DMP sequences of interest are hybridized to sample nucleic acids. Streptavidin-coated magnetic beads are then used to capture sequences of interest hybridized to bait sequences. Unbound fractions are discarded. Bait sequences are then removed (e.g. by digestion of RNA) thus providing an enriched pool of DMP target sequences separated from non-DMP sequences. In a preferred method of the invention, template DNA is subjected to bisulphite conversion and target loci are then amplified by small-scale PCR such as microdroplet PCR using primers which are independent of the methylation status of the DMP. Following amplification, samples are subjected to a capture step to enrich for PCR products containing the target DMP, e.g. captured and purified using magnetic beads, as described above. Following capture, a standard PCR reaction is carried out to incorporate DNA sequencing barcodes into DMP-containing amplicons. PCR products are again purified and then subjected to DNA sequencing and analysis to determine the presence or absence of a methylcytosine at the target genomic DMP [32].

The DMP biomarker loci defined herein are identified e.g. by Illumina® identifiers (IlmnID), which are also referred to as DMP identifiers (DMP ID). These DMP loci identifiers refer to individual DMP sites used in the commercially available Illumina® Infinium Human Methylation450 Bead-Chip kit. The identity of each DMP site represented by each DMP loci identifier is publicly available from the Illumina, Inc. website under reference to the DMP sites used in the Infinium Human Methylation450 BeadChip kit.

Further information regarding DMP loci identification used in Illumina, Inc products is found in the technical note entitled "Technical Note: Epigenetics. CpG Loci Identification. A guide to Illumina's method for unambiguous CpG loci identification and tracking for the Golden Gate® and Infinium® Assay for Methylation" published in 2010 and found at:

http://www.illumina.com/documents/products/technotes/
      technote_cpg_loci_identification.pdf.
   Further information regarding the Illumina® Infinium Human Methylation450 BeadChip system can be found at:
   http://www.illumina.com/content/dam/illumina-market-
      ing/documents/products/datasheets/
      datasheet_humanmethylation450.pdf;
   and at:
   http://www.illumina.com/content/dam/illumina-market-
      ing/documents/products/technotes/
      technote_hm450_data analysis_optimization.pdf.

To complement evolving public databases to provide accurate DMP/CpG loci identifiers and strand orientation, Illumina® has developed a method to consistently designate DMP/CpG loci based on the actual or contextual sequence of each individual DMP/CpG locus. To unambiguously refer to DMP/CpG loci in any species, Illumina® has developed a consistent and deterministic DMP loci database to ensure uniformity in the reporting of methylation data. The Illumina® method takes advantage of sequences flanking a DMP locus to generate a unique DMP locus cluster ID. This number is based on sequence information only and is unaffected by genome version. Illumina's standardized nomenclature also parallels the TOP/BOT strand nomenclature (which indicates the strand orientation) commonly used for single nucleotide polymorphism (SNP) designation.

Illumina® Identifiers for the Infinium Human Methylation450 BeadChip system are also available from public repositories such as Gene Expression Omnibus (GEO) (http://www.ncbi.nlm.nih.gov/geo/). For example, at https://www.ncbi.nlm.nih.gov/geo/query/acc.cgi?acc=GPL13534 Provided herein are DMP signatures comprising two or more of the DMPs listed in Tables 12-17. Each of the DMPs listed in Tables 11-17 designated with a unique identifier termed a "DMP ID" (also known as an "Illumina ID") from which the skilled person can derive a genomic locus and nucleotide sequence said DMP, using for example the GEO database accessible at https://www.ncbi.nlm.nih.gov/geo/query/acc.cgi?acc=GPL13534. By way of example, the first DMP listed in Table 11 is designated "cg07716946" which corresponds to a DMP within chr15:67325986-67326256 and specifically at position 67326118 of chromosome 15. The second DMP listed in Table 11 is designated "cg04786287" which corresponds to a DMP within chr16:54970301-54972846 and specifically at position 54970523 of chromosome 16. The nucleotide sequences corresponding to DMP cg07716946 (with the CpG island designated using the notation [CG]) is:

```
                                    (SEQ ID NO: 1)
CCGGGACGCTGCTGGAGGCGCCGTCGCTCCGCGGCGGAGG

CGACCCAGTTTCCCAGCTCT[CG]TCCTCGCCACTTCCTC

TGCATGGGCTTCCAGGAGACTCGGCCTCCGTCGGCGACGC

TGGC
```

The nucleotide sequences corresponding to DMP cg04786287 (with the CpG island designated using the notation [CG]) is:

```
                                    (SEQ ID NO: 2)
GCTGTCCGCTGCCCGCATCCCTTCCGCCCTGGGCCTCTGC

ACGGTCTGCGGTTTTCTGTG[CG]CACTTGGTCTTCAGTA

CTAGCACCCAATTACGTCTGGGTTTTTCTTCTTTACAGAG

CTGG
```

Assessment of Copy Number Variation (CNV)

In some of the methods of the present invention described herein, a progression score is determined using a CNV signature which comprises the amplification or loss of a plurality of CNV bands, which are also referred to in the art as "cytogenetic bands".

CNV bands identified herein, such as the CNV bands identified in Tables 19-36, are designated using the standard nomenclature for cytogenetic bands. In this regard, each human chromosome has a short arm designated "p" and long arm designated "q", separated by a centromere. The ends of the chromosome are called telomeres. The telomere at the end of the p arm is referred to as "ptel" while the telomere at the end of the q arm designated "qtel". Each chromosome arm is divided into cytogenetic bands (i.e. CNV bands as referred to herein), which can be differentially stained and visualised using a microscope. The cytogenetic bands are labelled p1, p2, p3, etc. or q1, q2, q3, etc., counting from the centromere out toward the telomeres of either the p arm or the q arm. Each CNV band may comprise sub-bands, which in turn may comprise sub-sub-bands. The sub-bands and sub-sub-bands are also numbered from the centromere out toward the telomere. Accordingly, by way of example, if a CNV band has the designation 7q31.2 this indicates that the CNV band is on chromosome 7, q arm, band 3, sub-band 1, and sub-sub-band 2.

A variety of techniques are available for determining the status of a CNV band, as will be outlined briefly below. The methods described herein encompass any suitable technique for the determining the status of a CNV band, e.g. determining whether a particular CNV band has been amplified or lost.

Thus, in any of the methods of the present invention described herein, the amplification or loss of CNV bands may be determined using a method selected from the group consisting of next generation sequencing (NGS), the nCounter system (nanoString; https://www.nanostring.com/download file/view/323/3778), Multiplex Ligation-Dependent Probe Amplification (MLPA), real-time quantitative PCR, comparative genomic hybridization (CGH), Fluorescent In Situ Hybridization (FISH), and combinations thereof.

Pre-Invasive Lung Lesions and Lung Cancer

The methods of the present invention described herein may be used to determine whether or not an individual has a pre-invasive lung lesion that will progress to an invasive lung cancer.

As used herein the term "lung lesion" may refer to any population of cells derived from damaged or diseased lung tissue. The lesion may be cancerous. The lesion may be non-cancerous. Thus, in the context of the present invention the lesion lung lesion may present in the normal epithelium, tissue hyperplasia, dysplasia, or lung carcinoma in situ (CIS).

As used herein the term "pre-invasive" refers to a lesion or cell population which has not spread, or is not capable of spreading, beyond the tissue region in which said lesion or cell population originated. Conversely, as used herein, the term "invasive" refers to a cancer that has spread, or is capable of spreading, beyond the tissue region in which said cancer originated. The term "infiltrating" is also used in the art to refer to invasive cancer. The invasive lung cancer may be a lung squamous cell carcinoma (LUSC).

Methods of Treatment

The present invention also provides a method of treating a pre-invasive lung lesion and/or treating and/or preventing an invasive lung cancer in an individual comprising:

identifying a pre-invasive lung lesion in an individual that will progress to an invasive lung cancer by performing a method of the present invention; and administering a lung cancer therapy to the individual.

Thus, for example, the present invention provides a method of treating a pre-invasive lung lesion and/or treating and/or preventing an invasive lung cancer in an individual comprising:

identifying a pre-invasive lung lesion in an individual that will progress to an invasive lung cancer by performing an identification method; and administering a lung cancer therapy to the individual, wherein the identification method is a method of identifying whether or not an individual has a pre-invasive lung lesion that will progress to an invasive lung cancer, the method comprising:

(a) providing a sample of nucleic acid which has been taken from a tissue of the individual, wherein the tissue is suspected of harbouring a pre-invasive lung lesion;

(b) performing an assay to determine a progression score for the sample; and (c) identifying whether or not the individual has a pre-invasive lung lesion that will progress to an invasive lung cancer by comparing the progression score to a threshold value;

wherein the progression score is determined using a molecular signature selected from:

i) a differentially expressed gene (DEG) signature;

ii) a differentially methylated position (DMP) signature;

iii) a copy number variation (CNV) signature; and iv) combinations of (i) to (iii).

The present invention also provides a method for determining whether or not to provide a therapeutic method of treatment to an individual, the method comprising performing a method of identifying whether or not an individual has a pre-invasive lung lesion that will progress to an invasive lung cancer according to the present invention;

providing to the individual a therapeutic method of treatment if the individual is identified as having a pre-invasive lung lesion that will progress to an invasive lung cancer, optionally wherein the therapeutic method of treatment comprises administering to the individual a therapeutically effective amount of a lung cancer therapy.

The lung cancer therapy may comprise any known treatment or procedure known in the art.

Thus, the invention encompasses administration of one or more surgical procedures, one or more chemotherapeutic agents, one or more immunotherapeutic agents, one or more radiotherapeutic agents, one or more hormonal therapeutic agents or any combination of the above following the identification of a pre-invasive lung lesion in an individual that will progress to an invasive lung cancer.

Surgical procedures the removal or one or more lung lobe (lobectomy), removal of two lung lobes (bilobectomy) removal of a lung, a lung transplant, a lymphadenectomy, a wedge resection, a segmentectomy, and a sleeve resection.

Chemotherapeutic agents include the following. Alkylating agents, which include the nitrogen mustards, nitrosoureas, tetrazines, aziridines, cisplatin and platinum based derivatives, as well as the non-classical alkylating agents. Antimetabolites, which include the anti-folates, fluoropyrimidines, deoxynucleoside analogues and thiopurines. Microtubule disrupting agents, which include the *vinca* alkaloids and taxanes, as well as dolastatin 10 and derivatives thereof. Topoisomerase inhibitors, which include camptothecin, irinotecan and topotecan. Topoisomerase II poisons, which include etoposide, doxorubicin, mitoxantrone and teniposide. Topoisomerase II catalytic inhibitors, which include novobiocin, merbarone, and aclarubicin. Cytotoxic antibiotics, which include anthracyclines, actinomycin, bleomycin, plicamycin, and mitomycin.

Immunotherapeutics include monoclonal antibodies, antibody-drug conjugates, immune checkpoint inhibitors. For example, the lung cancer therapy may be selected from monoclonal antibodies directed against the VEGF/VEGFR pathway such as bevacizumab (Avastin), monoclonal antibodies directed against the EGFR pathway, such as Necitumumab (Portrazza), monoclonal antibodies that inhibit the PD-1. PD-L1 pathway, such as Atezolizumab (Tecentriq), Durvalumab (Imfinzi) Nivolumab (Opdivo) and Pembrolizumab (Keytruda).

Combination therapies include carboplatin-taxol and gemcitabine-cisplastin.

The lung cancer therapy may be selected from Abraxane (Paclitaxel Albumin-stabilized Nanoparticle Formulation), Afatinib Dimaleate, Afinitor (Everolimus), Alecensa (Alectinib), Alectinib, Alimta (Pemetrexed Disodium), Alunbrig (Brigatinib), Atezolizumab, Avastin (Bevacizumab), Bevacizumab, Brigatinib, Carboplatin, Ceritinib, Crizotinib, Cyramza (Ramucirumab), Dabrafenib, Dacomitinib, Docetaxel, Durvalumab, Erlotinib Hydrochloride, Everolimus, Gefitinib, Gilotrif (Afatinib Dimaleate), Gemcitabine Hydrochloride, Gemzar (Gemcitabine Hydrochloride), Imfinzi (Durvalumab), Iressa (Gefitinib), Keytruda (Pembrolizumab), Mechlorethamine Hydrochloride, Mekinist (Trametinib), Methotrexate, Mustargen (Mechlorethamine Hydrochloride), Navelbine (Vinorelbine Tartrate), Necitumumab, Nivolumab, Opdivo (Nivolumab), Osimertinib, Paclitaxel, Paclitaxel Albumin-stabilized Nanoparticle Formulation, Paraplat (Carboplatin), Paraplatin (Carboplatin), Pembrolizumab, Pemetrexed Disodium, Portrazza (Necitumumab), Ramucirumab, Tafinlar (Dabrafenib), Tagrisso (Osimertinib), Tarceva (Erlotinib Hydrochloride), Taxol (Paclitaxel), Taxotere (Docetaxel), Tecentriq (Atezolizumab), Trametinib, Trexall (Methotrexate), Vizimpro (Dacomitinib), Vinorelbine Tartrate, Xalkori (Crizotinib), Zykadia (Ceritinib), and combinations thereof.

The lung cancer therapy may comprise proton beam therapy. The lung cancer therapy may comprise photodynamic therapy.

The lung cancer therapy may be administered to an individual already having an invasive lung cancer, in an amount sufficient to cure, alleviate or partially arrest the lung cancer or one or more of its symptoms. Such therapeutic treatment may result in a decrease in severity of disease symptoms, or an increase in frequency or duration of symptom-free periods. An amount adequate to accomplish this is defined as "therapeutically effective amount". Effective amounts for a given purpose will depend on the severity of the disease as well as the weight and general state of the individual.

The lung cancer therapy may also be administered to an individual identified as having a pre-invasive lung lesion that will progress to an invasive lung cancer but who has not yet developed an invasive lung cancer. Such preventative treatment may prevent the progression of the pre-invasive lung lesion to an invasive cancer, delay the progression of the pre-invasive lung lesion to an invasive cancer, and/or lessen the severity or extent an invasive cancer derived from the identified pre-invasive lung lesion.

The following Examples are provided to illustrate the invention but not to limit the invention.

EXAMPLES

Example 1: General Study Design

It was reasoned that information on the future clinical trajectory of a pre-invasive lung lesion might be encoded in the genetic and epigenetic profile present at diagnosis. A prospective cohort study of patients with pre-invasive squamous airway lesions was therefore undertaken. Patients were managed conservatively, undergoing surveillance AFB with biopsy and CT scanning every 4 and 12 months, respectively, with definitive cancer treatment only performed at the earliest pathological evidence of progression to invasive tumours (FIG. 2A, B) [7]. When a CIS lesion either progressed to invasive cancer or regressed to normal epithelium/low-grade disease, molecular profiling was performed on the preceding CIS biopsy from the same lesion— the 'index biopsy' (FIG. 2C). Index biopsies all demonstrated histologically and morphologically indistinguishable CIS and were classified as either 'progressive' or 'regressive'. All such index CIS biopsies were subjected to a predetermined combination of transcriptomic, epigenetic and finally genomic profiling depending on DNA/RNA availability (FIG. 1; FIG. 2D; FIG. 7).

Example 2: Patient Characteristics

Patients with pre-invasive lung cancer lesions were recruited through University College London Hospitals (UCLH) Early Lung Cancer Surveillance Programme (ELCSP). Full details of the surveillance protocol including eligibility criteria for patient inclusion have been previously described [7]. Briefly, the programme has recruited 140 patients to date with pre-invasive lung cancer lesions of varying histological grades. 129 index CIS biopsies were obtained from 85 patients and subjected to molecular analysis. Dependent on stored tissue quantity, in total, 51 samples from 42 patients underwent gene expression profiling; 87 samples from 47 patients underwent methylation profiling; and 39 samples from 29 patients underwent whole genome sequencing. Methylation and gene expression datasets were divided into independent discovery and validation groups.

Clinical characteristics within each analysis group are shown in FIG. 1. In comparing progressive and regressive samples, it was found that progressive samples were associated with a higher pack-year smoking history in the methylation discovery group only (p<0.01) and with increased age in the WGS group (p=0.01). No clinical differences were consistently observed across the different analysis groups.

Example 3: Characterisation of CIS Genomic Profiles

Figure 3:
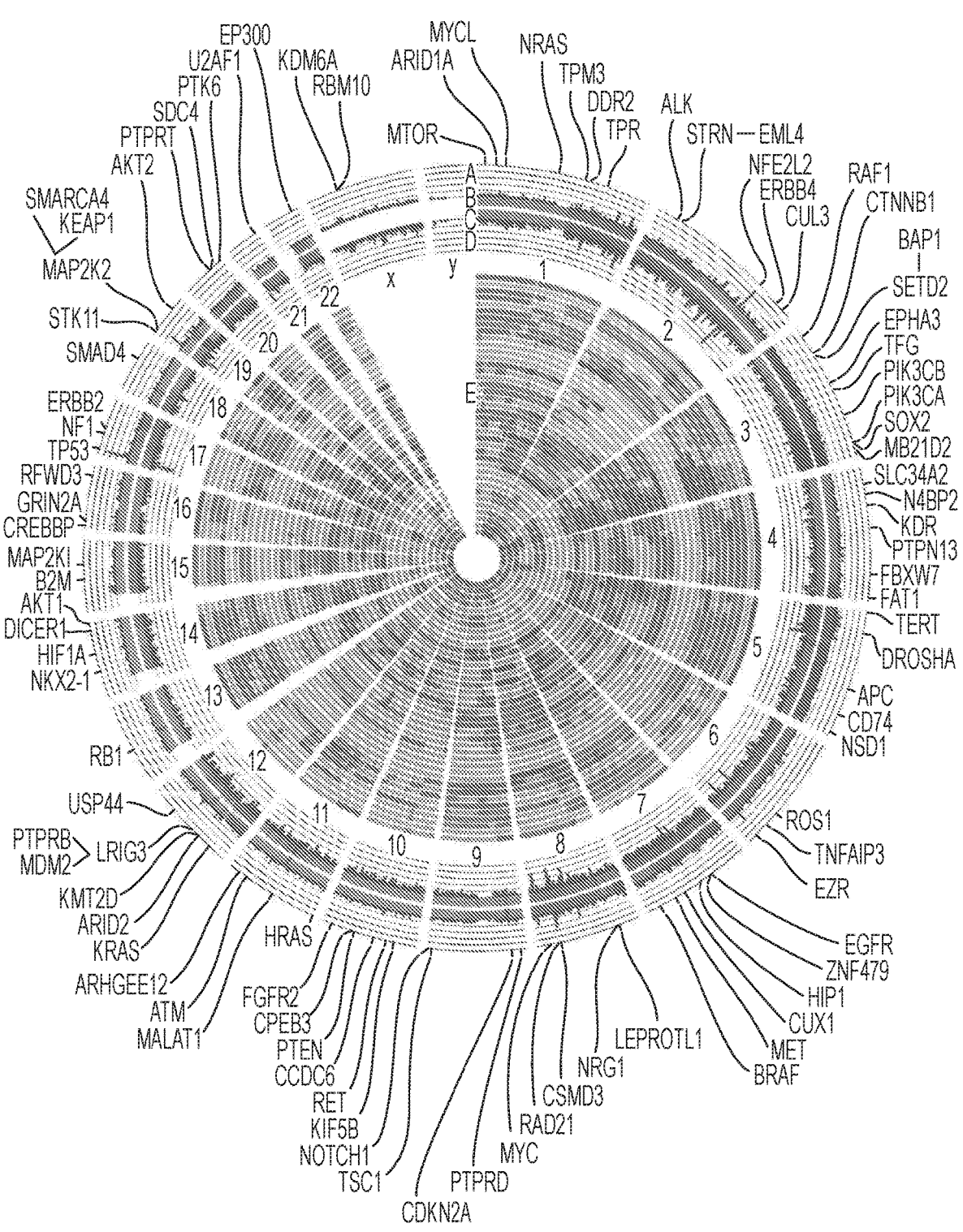
FIG. 3. Genomic aberrations in pre-invasive lung carcinoma-in-situ (CIS) lesions. Circos diagram comparing CIS genomic profiles with The Cancer Genome Atlas (TCGA) LUSC data. The outer histogram (A), shows mutation frequencies of all genes in TCGA data. The inner histogram (D) shows mutation frequencies in the CIS data presented herein. Profiles appear similar and no statistically significant differences were identified between the two datasets. Genes previously identified as potential drivers of lung cancer are labelled. Between the two histograms, average copy number changes are shown for TCGA data (B) and CIS data (C). Copy number gains are shown in red, losses in blue. Although there were some differences between whole-genome and whole-exome sequencing techniques, it was observed that many similar features between the two; for example, gains in 3q and 5p, which are well recognised features of squamous cell lung cancer. In the centre of the circos plot, 39 rings represent the copy number profiles of the 39 samples descried herein, illustrating the individual contribution of each sample to the average values presented (E).

The 39 CIS lesions are the first pre-invasive LUSC lesions to be whole-genome sequenced, so the burden and spectrum of mutations in CIS was compared with publicly available LUSC exome sequencing data from The Cancer Genome Atlas (TCGA). Due to differences between whole-genome and exome sequencing, only broad comparisons were made. A similar mutation burden and copy number profile between CIS samples and TCGA LUSC tumours was observed (FIG. 3). There is congruency of type and prevalence of potential driver mutations, broadly defined as any mutation in a gene previously implicated as a driver of lung cancer, between CIS and LUSC samples [8]. Frequent alterations in TP53, CDKN2A, SOX2 and AKT2, and less frequent alterations in FAT1, KMT2D, KEAP1, EGFR and NOTCH1 in CIS lesions were observed (FIG. 3). CIS mutational signatures [9],[10] showed a strong tobacco-associated signal and were similar to those found in LUSC (FIG. 8).

Marked aneuploidy was observed in CIS lesions, with somatic copy number alterations (CNAs) present across the genome (FIG. 3; FIG. 7). The most frequent changes were associated with gain and amplification of multiple locations on distal 3q: this is known to be the most common genomic aberration in LUSC11. Other recognised copy number associations identified in our data include gain/amplification in 5p, 8q and 19q and regions of loss/deletion in 3p, 4q, 5q, 8p, 9p and 13q.12-18.

Whilst most CIS samples had the genomic appearance of neoplasms, six lesions were observed which showed markedly lower mutational load and fewer copy number alterations than the others (FIG. 7; PD21884c, PD21885a, PD21885c, PD21904d, PD38317a, PD38319a). These samples had very few genomic changes, despite being CIS histologically. All of these six samples regressed to normal epithelium or low-grade dysplasia on subsequent biopsy. Four further samples met this end-point for regression, despite widespread mutational and copy number changes. However, with longer follow up one of these cases developed CIS recurrence (FIG. 10a; PD21893a), and two developed invasive cancer on further surveillance (FIG. 10B, C; PD21884a, PD38326a). Only one sample, PD21908a, showed sustained clinical regression after 9 years of follow up despite widespread molecular changes.

All but one progressive sample and all highly mutated regressive samples showed amplification in a small region of distal 3q (chr3:172516434-178440382). This region contains known driver genes (SOX2, PIK3CA), genes associated with chromosomal instability (ACTL6A) and methyltransferases (ECE2). Progressive sample PD38320a had little change outside this region and did not harbour a TP53 mutation, suggesting that this amplification may be a crucial early event in LUSC tumorigenesis.

Genomic features between the 29 progressive and 10 regressive lesions were compared. The three samples which showed evidence of progression after meeting the end-point for regression were excluded from this analysis. Comparisons of mutation burden between progressive and regressive lesions were performed by mixed effects modelling, allowing us to account for samples that come from the same patient. Even after correcting for patient age, smoking history and sample purity, progressive lesions had more somatically acquired mutations than those from regressive lesions, across base substitutions (p<0.001), indels (p=0.018), structural variants (p<0.001) and copy number changes (p<0.001) (FIG. 11A-D). When the analysis was restricted only to substitutions that were fully clonal in each lesion, there were still substantially more substitutions in progressive than regressive lesions (p<0.001) (FIG. 11E), suggesting that the increase in mutation burden is not due to recent subclonal diversification in progressive lesions. All the mutational processes (or signatures [9], [10]) identified in the CIS lesions contribute to the excess of mutations in progressive compared to regressive samples; however, only tobacco-associated signature 4 showed proportionally more mutations (p=0.017) (FIG. 8F-J). Progressive lesions contained more putative driver mutations than regressive lesions (p=0.001) (FIG. 11H). Importantly, no single cancer mutation perfectly discriminated between progressive and regressive lesions.

Figure 11I:
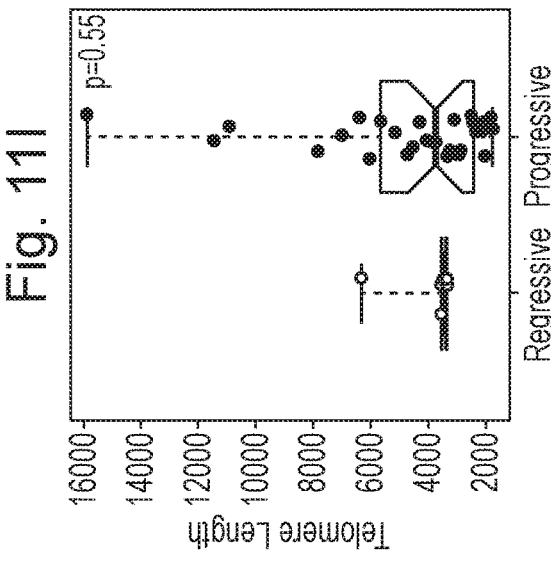
Figure 11H:
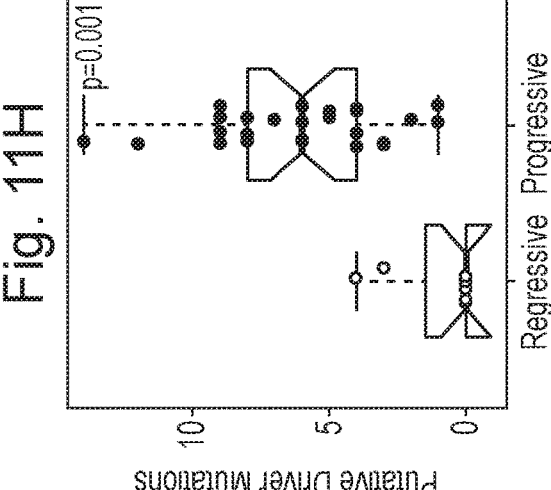
Figure 11G:
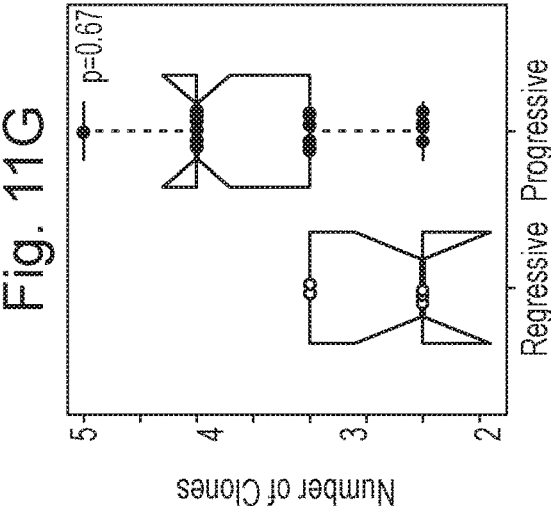

Within the biopsied lesions, clonal architecture was similar between progressive and regressive lesions (FIG. 11E-G). For four patients in whom we sequenced multiple progressive lesions, the lesions shared many somatic mutations despite their different locality in the bronchial tree, indicating their probable derivation from a common ancestral clone. By contrast, multiple regressive lesions from two further patients did not share common mutations and so are likely to have arisen independently (FIG. 12). There were no differences in telomere lengths between progressive and regressive lesions (p=0.59) (FIG. 11I).

Example 4: CIS Transcriptomic and Epigenetic Profiles

Figure 4A:
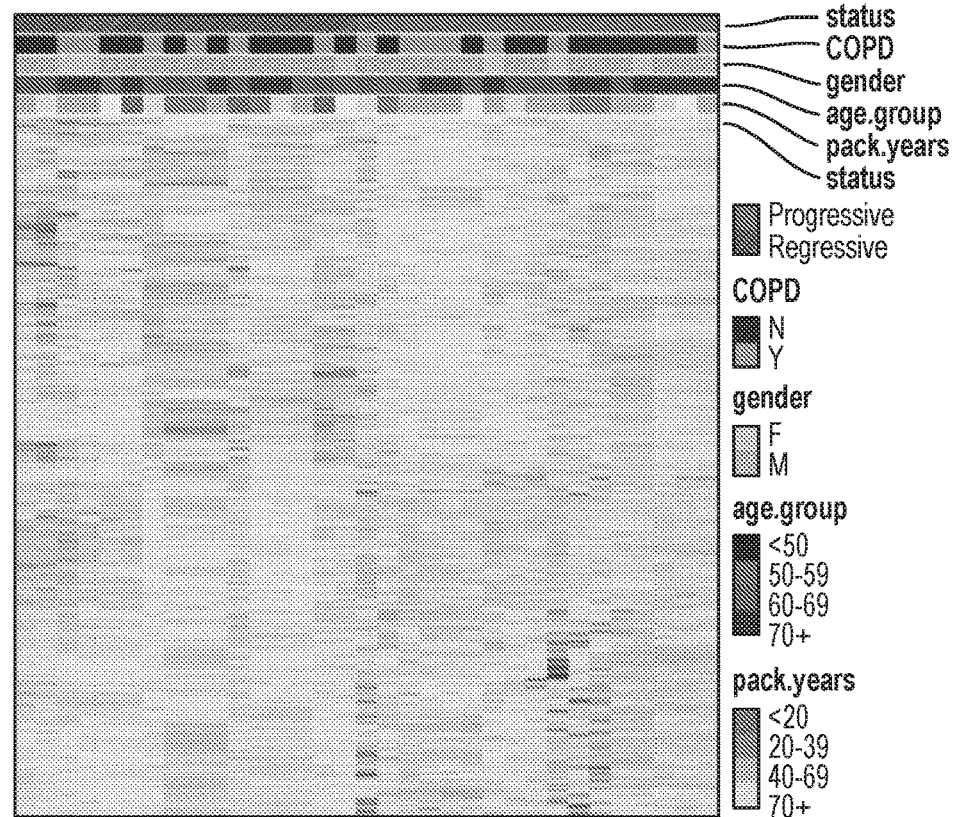
FIG. 4. Altered methylation and gene expression in lung carcinoma-in-situ (CIS) lesions. (A) Hierarchical clustering of 1335 significantly differentially expressed genes in progressive and regressive CIS lesions. Biological and clinical factors including age at diagnosis, gender, smoking history (pack years) and COPD status had no effect on CIS lesion gene expression profile (high expression=purple, e.g., the trend in the top left quadrant of (A), low expression=orange). (B) Hierarchical clustering of the top 1000 significantly differentially methylated positions (DMPs) between progressive and regressive CIS lesions and controls. Biological and clinical factors including age at diagnosis, gender and smoking history (pack years) status had no effect on the methylation profile (hypomethylated DMPs=blue, hypermethylated DMPs=orange, e.g., the trend in the bottom right quadrant of (B)). (C) Principle component analysis of all profiled genes in progressive and regressive CIS lesions showing a clear distinction between progressive and regressive groups (p=0.0017). (D) Principle component analysis of all methylation data in progressive, regressive and control CIS lesions showing a clear distinction between progressive and regressive groups (p=6.8×10-25). P values were calculated using multivariate ANOVA.

Gene expression microarrays were performed on a discovery set of 17 progressive and 16 regressive CIS lesions. Identified were 1335 genes with significant expression changes (FDR<0.01); 657 genes were up-regulated and 678 down-regulated in progressive CIS lesions (FIG. 4A).

Figure 4B:
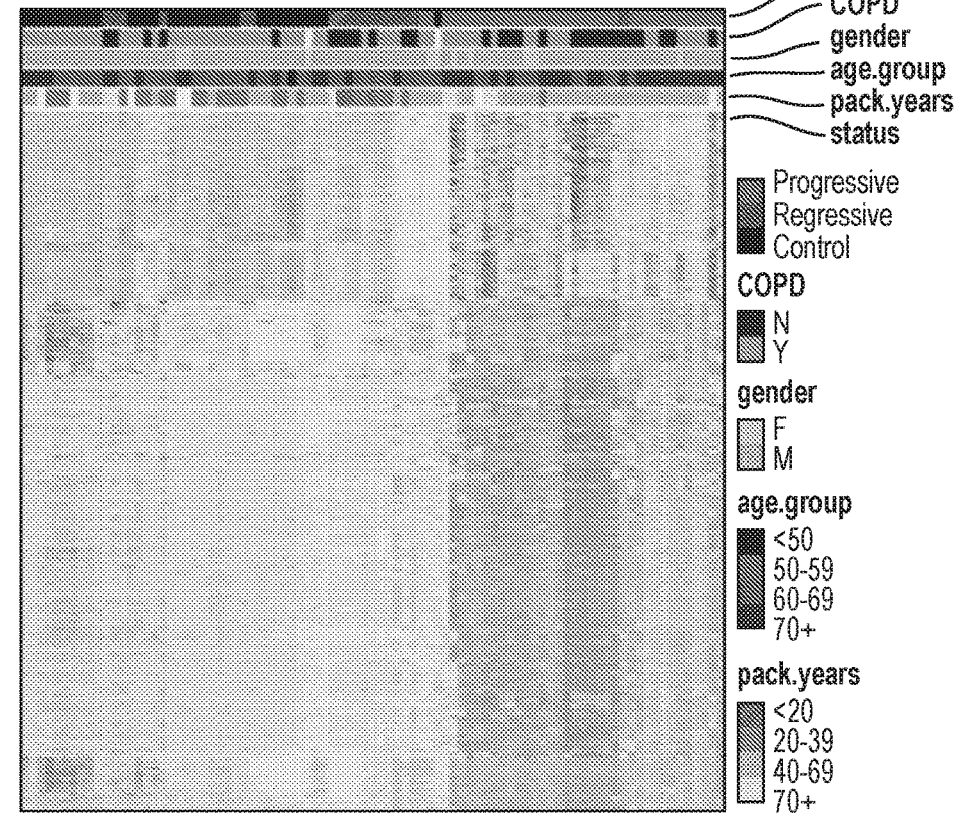

Differential analysis of methylation profiles was performed on a discovery set of 26 progressive, 11 regressive and 23 control samples. Widespread methylation changes were observed with 12,064 differentially methylated positions (DMPs), associated with 2,695 genes, at which methylation was significantly different between progressive and regressive samples (FDR<0.01; $|\Delta\beta|$>0.3). 6,314 DMPs were hypermethylated and 5,750 hypomethylated in progressive CIS (FIG. 4B). 260 differentially methylated regions (DMRs) were identified, of which 151 (58%) overlap with DMRs between TCGA cancer and control data (FIG. 13). Finally, identified were 36,620 differentially variable positions (DVPs) for which probe variance was markedly different between progressive and regressive groups.

Of the 1335 genes identified, TPM3, PTPRB, SLC34A2, KEAP1, NKX2-1, SMAD4 and SMARCA4 have previously been implicated as potential lung cancer drivers. Regarding methylation, the potential driver genes NKX2-1, TERT, DDR2, LRIG3, CUX1, EPHA3, CSMD3, MET, ZNF479, GRIN2A, PTPRD, NOTCH1, CD74, NSD1 and CDKN2A contain at least one significant DMP. Several genes which are significant in our gene expression analysis are also identified in our methylation data, including multiple genes in the homeobox family (HOXC8, HOXC9, HOXC10, HOXD10, HOXA11AS), previously implicated as an early epigenetic event in multiple cancers [19]. NKX2-1 (TTF-1) is the only putative driver gene to be identified in both gene expression and methylation analyses, and is also a member of the homeobox family. It is hypermethylated and underexpressed in progressive samples compared to regressive. This gene is widely used in diagnosis of lung adenocarcinoma and both underexpression and hypermethylation have been implicated in the development of this disease [20], [21]. NKX2-1 loss has been shown to drive squamous cancer formation in combination with SOX2 overexpression [22]; focal gains in the 3q region containing SOX2 are commonly observed in progressive CIS (FIG. 10).

Figure 4C:
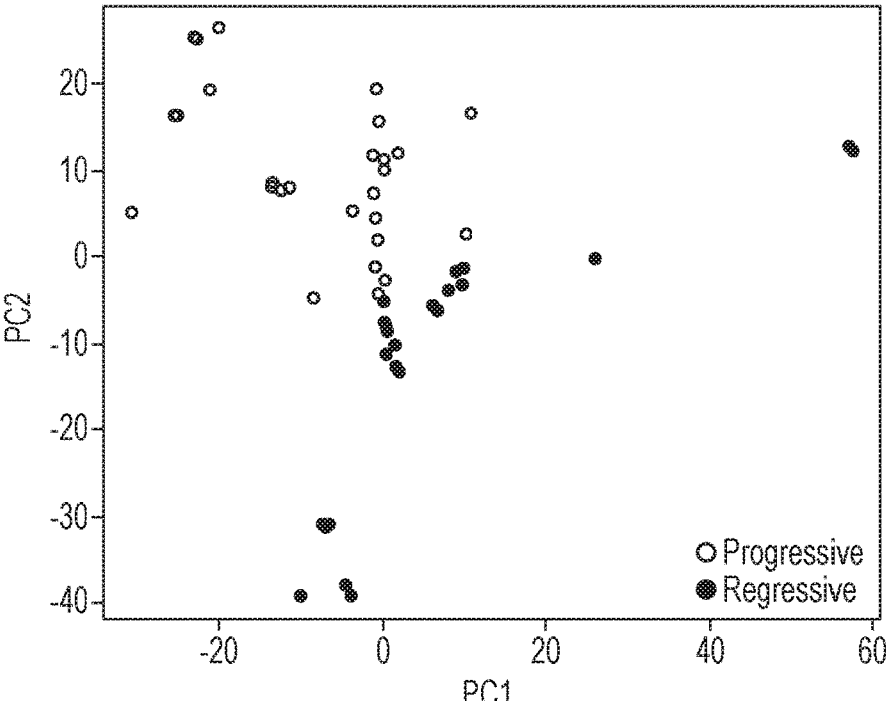

Principal component analysis of all gene expression and methylation data showed a clear distinction between the progressive and regressive subgroups (p=0.0017 and p=6.8× 10-25, respectively) (FIG. 4C,D). In the methylation dataset, the regressive lesions closely clustered with the control normal epithelial cells. A history of chronic obstructive pulmonary disease (COPD) had an effect on case segregation (p=1.2×10-5) but all other clinical and technical variables analysed, including smoking status and history of lung cancer, had no effect (FIG. 14). This was also the case for PCA analysis of the gene expression data (FIG. 14G-K).

Figure 4D:
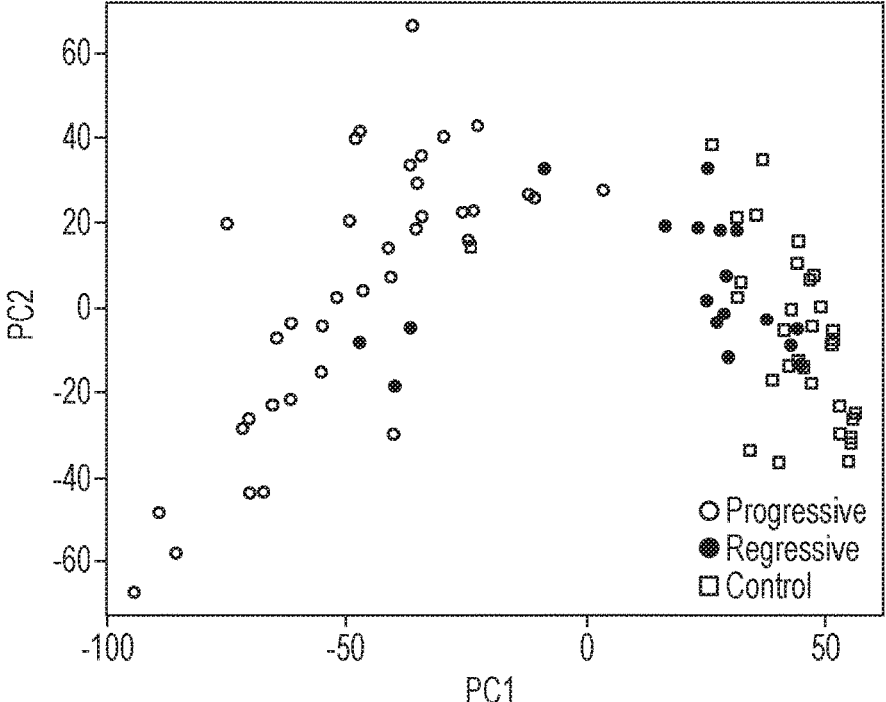

For methylation, one control and four regressive cases clustered with the progressive cases (FIG. 4D). Three of the four miss-classified regressive cases were subjected to whole-genome sequencing and were found to have more copy number alterations than other regressive samples (PD21884a, PD21893a, PD21908a). Two of these correspond to the samples discussed above, which showed signs of progression after meeting the clinical end point of regression (FIG. 10). For the control bronchial epithelium sample that was classified with the progressive lesions, CIS was detected in a biopsy specimen 12 months later from the same site. Thus, although these cases were formally treated as miss-classifications, it is likely that the molecular data underpinning the apparent errors indicate a cellular phenotype that is not consistent with a straightforward regressive lesion.

Example 5: Molecular Signatures Predict CIS Outcome

The ability to predict if a pre-invasive lesion will progress to cancer has important clinical implications. For gene expression, the above pre-defined discovery set to define our classifier were used (n=33; 17 progressive, 16 regressive; 10-fold cross-validation applied). This was applied to a separate validation set (n=18; 10 progressive, 8 regressive). All samples in the validation set were classified correctly. When applied to external data from TCGA (n=551: 502 LUSC, 49 control), the 291-gene model was able to classify LUSC vs control samples with AUC=0.81 (FIG. 5A-C; FIG. 15).

An analogous analysis was performed for methylation using a discovery set of 60 samples and a validation set of 27 samples. This classified validation samples with AUC=0.99 and classified external TCGA samples (n=412: 370 LUSC, 42 controls) into LUSC vs controls with AUC=0.99, based on a 141-DMP classifier (FIG. 16A-I).

Observed as an increased number of methylation probes with intermediate methylation in TCGA LUSC cancer vs TCGA control samples (FIG. 5D), reflecting methylation heterogeneity in these samples. We therefore developed a methylation heterogeneity index (MI), defined as the number of probes per sample with $t_{lo}<\beta<t_{hi}$. Optimisation based on the discovery set of 26 progressive and 11 regressive samples defined values of $t_{lo}$=0.26 and $t_{hi}$=0.88. Control samples were not used in this analysis. This model classified progressive vs regressive CIS samples in our validation set with AUC=0.74 and TCGA LUSC vs TCGA control samples with AUC=0.96 (FIG. 5E; FIG. 16J-N). Multivariate logistic regression in our CIS cohort demonstrated that this index was a predictor of progression status (p=0.017); previous history of lung cancer was also significantly associated (p=0.02), whereas smoking status, COPD status, age and gender were not.

Figure 16N:
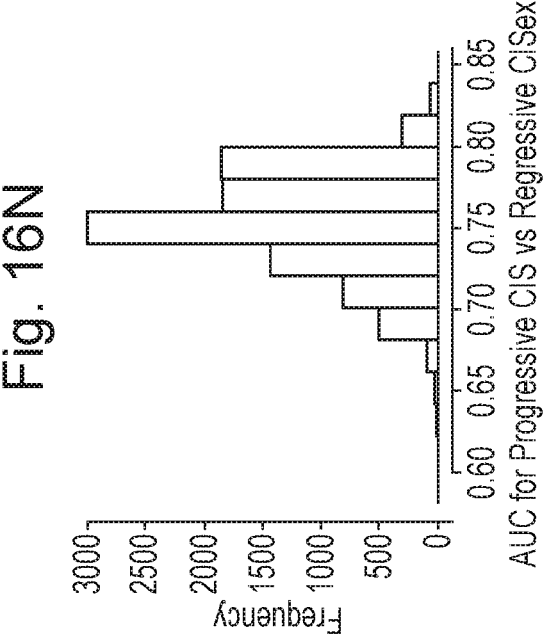
Figure 16M:
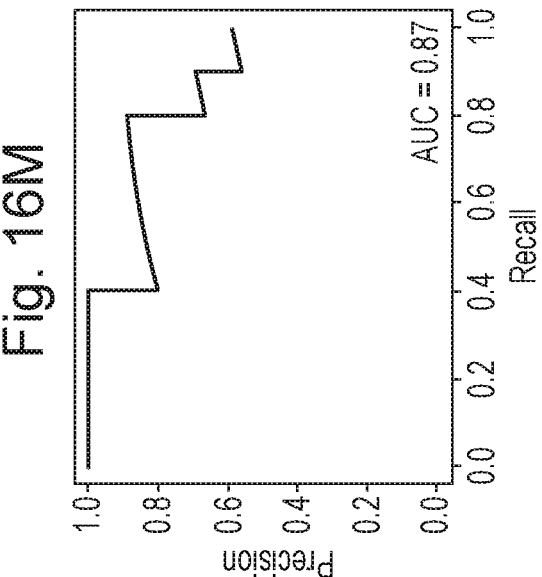

Given the widespread nature of methylation changes, it was hypothesised that this increase in heterogeneity may be a genome-wide process rather than specific to functional pathways. To test this theory, the predictive value of MII calculated from a sample of 2,000 probes, randomly selected from across the genome, was assessed. Running 10,000 simulations with each using a different random sample of 2,000 probes gave a mean AUC for TCGA LUSC vs TCGA control of 0.95 (95% CI 0.92-0.98) (FIG. 5F), and for progressive vs regressive CIS of 0.75 (95% CI 0.69-0.82) (FIG. 16N). These results are similar to those obtained using the entire set of 450,000 probes, suggesting that methylation heterogeneity is a genome-wide process. However, these AUC values are lower than those obtained from our predictive model based on just 141 differentially methylated positions, suggesting that specific methylation changes may be important, on this background of generalised change.

Figures 17G, 17H, 17I:
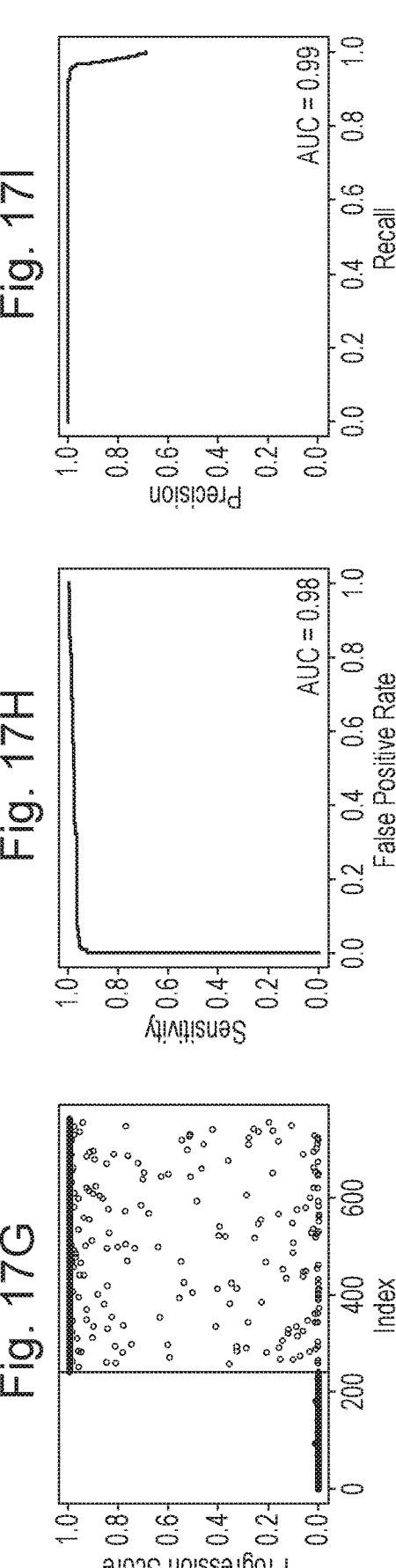

To build a predictive classifier based on copy number, copy number derived from methylation data was used to increase sample size and classified 46 of 54 samples correctly (FIG. 17A-C). A predictive classifier based on 154 predictive cytogenetic bands (CNV bands) that we identified classified 24/24 regressive samples and 9/12 progressive samples correctly (FIG. 17D-F). When applied to external data from TCGA (n=763: 524 LUSC, 239 control), this CNV model was able to classify LUSC vs control samples with AUC=0.98 (FIG. 17G-I).

Further analyses was performed using only one sample per patient to demonstrate that our results are not dependent on multiple sampling. The first available sample for each patient was selected, with CIS samples prioritised over control samples for methylation data. Results are similar to our analysis above, validating our initial results.

Although it cannot be fully excluded that lesions meeting the end point for regression will progress in future, most patients in this cohort now have several years of follow up. Of 35 regressive lesions undergoing molecular profiling, mean follow up was 67 months (median 57 months, range 11-150 months).

Example 6: CIN is an Early Marker of Progression to Cancer

Figure 6B:
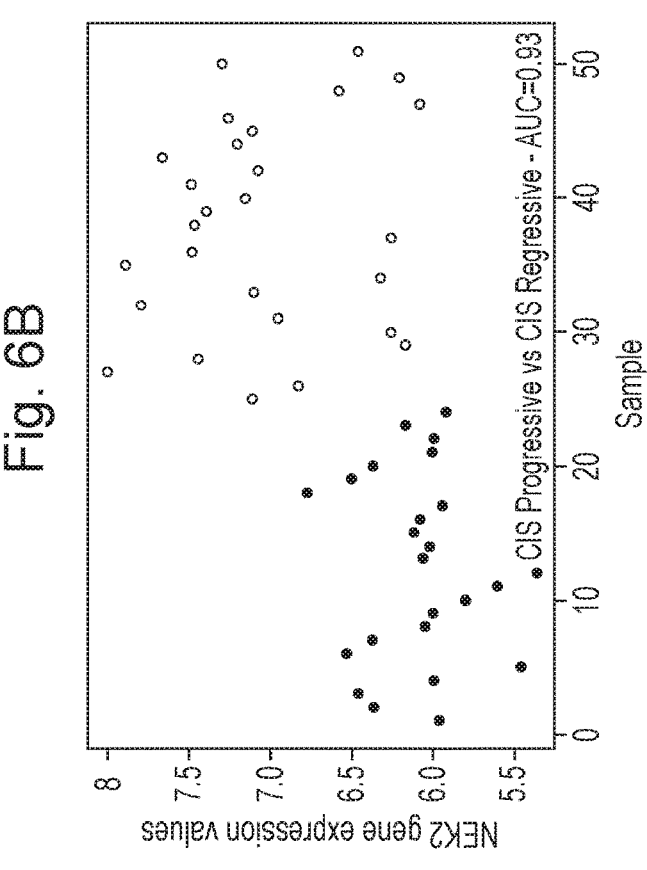
Figure 6A:
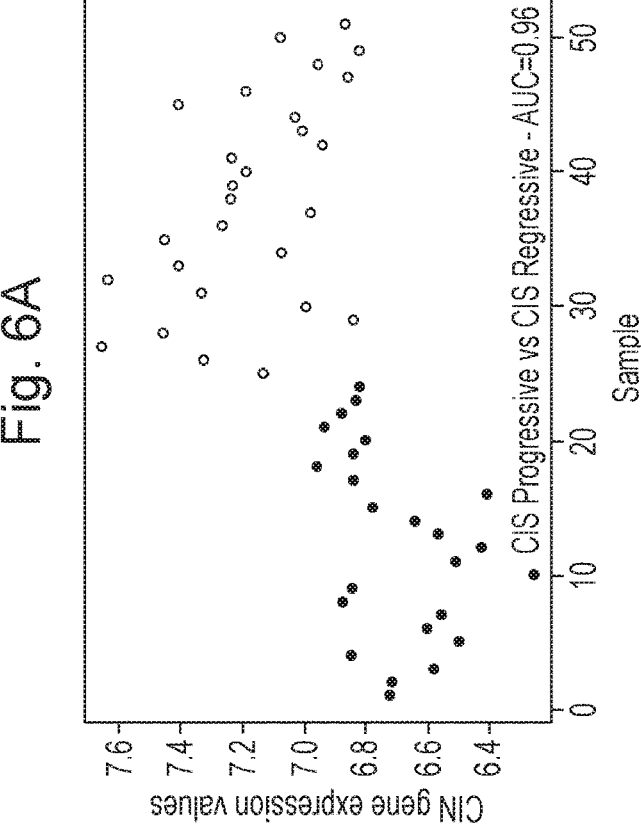

To investigate possible drivers of tumorigenic progression, a differential analysis of gene expression data between the progressive and regressive groups was performed. 5 of the top 100 genes identified have been previously associated with chromosomal instability (CIN) [24], as defined by the previously published CIN70 signature [25](ACTL6A, ELAVL1, MAD2L1, NEK2, OIP5). All five are up-regulated in progressive compared with regressive samples. CIN-related genes can predict progression (FIG. 6A); NEK2 expression alone predicts progression with AUC=0.93 (FIG. 6B).

Figure 6D:
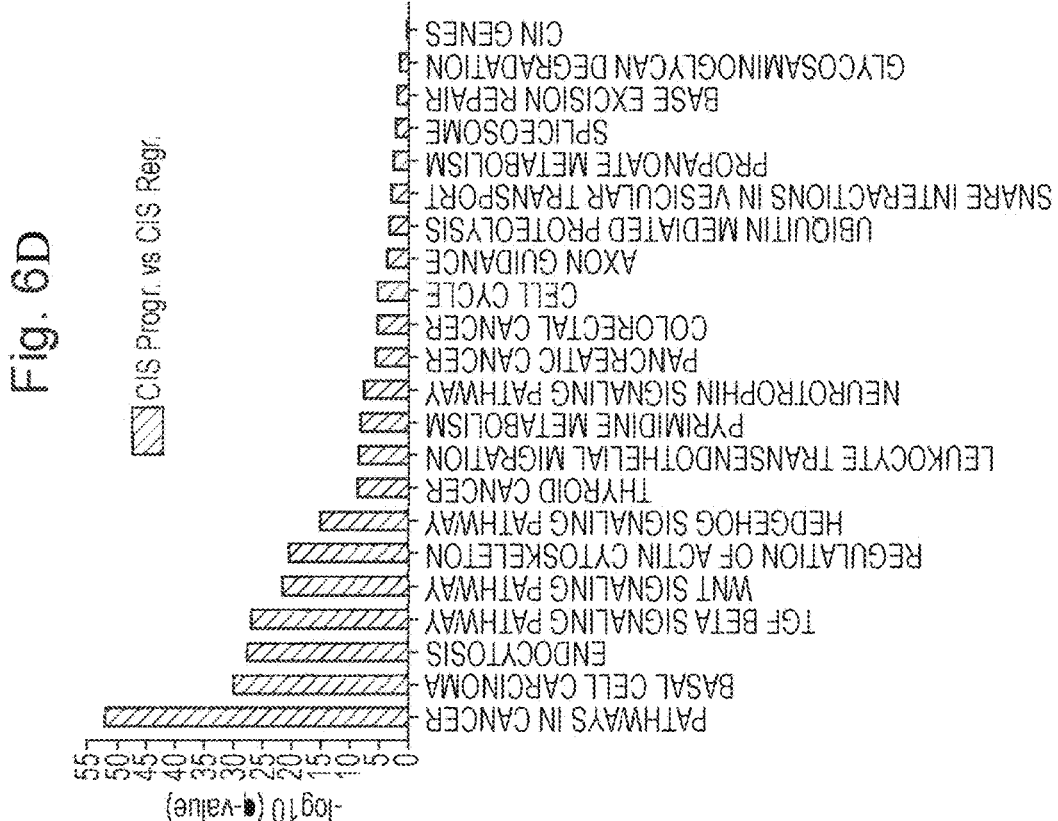
Figure 6C:
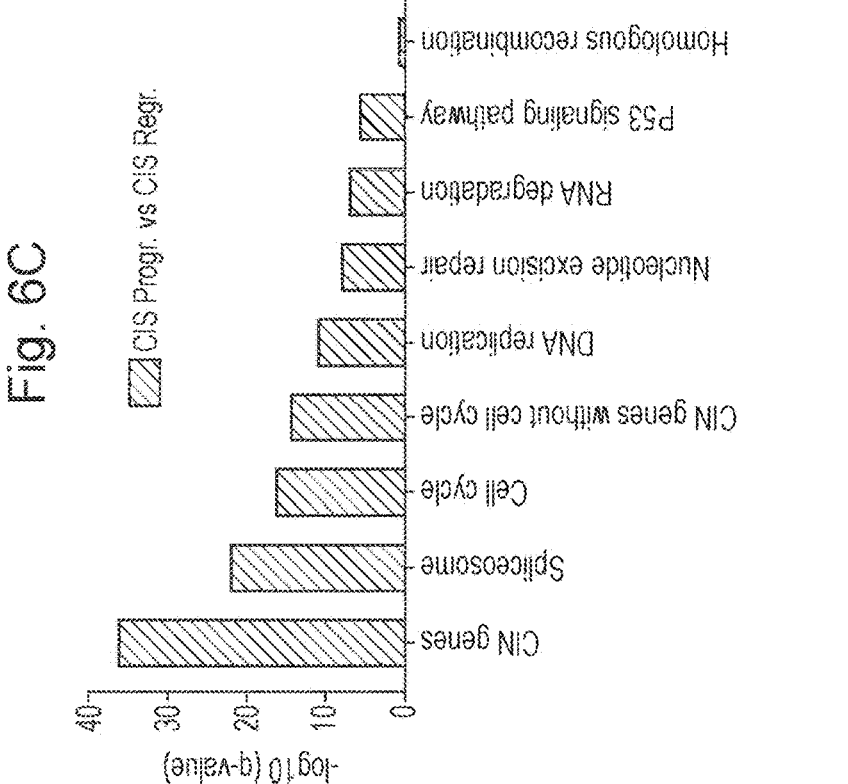

Pathway analysis was performed using the gage Bioconductor package [26] to compare the differentially expressed genes to KEGG gene sets. The CIN70 gene set was the most significant gene set identified (adjusted p value 8.9×10-32; up-regulated in progressive group), suggesting a role in early tumorigenesis. Cell cycle and DNA repair pathways were also implicated (FIG. 6C). Results were similar when cell-cycle associated genes were removed from the CIN70 signature, suggesting that this is a genuine CIN signal rather than a marker of proliferation.

Performing similar differential analysis of differentially methylated probes found widespread changes. The top probes identified were associated with cancer-associated cell signalling pathways, including TGF-beta, WNT and Hedgehog, as well as cell cycle and CIN-associated genes (FIG. 6D).

This CIN signal is consistent with the observed pattern of widespread copy number change (FIG. 3). Overall copy number variation for a sample, as measured by Weighted Genome Integrity Index (wGII) [27], correlates with mean CIN-associated gene expression of that sample (Pearson r2=0.473) (FIG. 18). It was also observed that a correlation between local copy number of a gene and expression of that gene, consistent with previous results [28], [29].

Example 7: Materials and Methods

Ethical Approval

All tissue and bronchial brushing samples were obtained under written informed patient consent and were fully anonymised. Study approval was provided by the UCL/ UCLH Local Ethics Committee (REC references 06/Q0505/ 12 and 01/0148).

Data Availability

Whole-genome sequencing data have been deposited at the European Genome Phenome Archive (https://www.ebi-.ac.uk/ega/at the EBI) with accession number EGAD00001003883. All gene expression and methylation microarray data reported in this study have been deposited in the National Center for Biotechnology Information Gene Expression Omnibus (GEO, http://www.ncbi.nlm.nih.gov/ geo/) public repository, and they are accessible through GEO accession number GSE108124.

Code Availability

All code used in our analysis will be made available at http://github.com/ucl-respiratory/preinvasive on publication. All software dependencies, full version information, and parameters used in our analysis can be found here.

Unless otherwise specified, all analyses were performed in an R statistical environment (v3.5.0; www.r-project.org/) using Bioconductor1 version 3.7.

Biological Samples

All patients with pre-invasive lung cancer lesions were recruited through University College London Hospitals (UCLH) Early Lung Cancer Surveillance Programme (ELCSP). Full details of the surveillance protocol including eligibility criteria for patient inclusion have been previously described [2]. Briefly, the programme has recruited 140 patients to date with pre-invasive lung cancer lesions of varying histological grades. Patients undergo autofluorescence bronchoscopy (AFB) and CT/PET scans every four to six months during which multiple biopsy specimens are collected. This longitudinal sequential AFB procedure provides biopsies of the same lesion sampled repeatedly over time, allowing us to monitor whether the individual lesions have progressed, regressed or remained static [2].

For a given CIS lesion under surveillance, when a biopsy from the same site showed evidence of progression to invasive cancer or regression to normal epithelium or low-grade dysplasia, we define the preceding CIS biopsy as the 'index' lesion. An index lesion was defined as progressive if the subsequent biopsy at the same site showed invasive cancer, or as regressive if the subsequent biopsy showed normal epithelium or low-grade disease (metaplasia, mild or moderate dysplasia). Lesions which do not satisfy one of these end-points were excluded from this study. Patients with multiple fresh-frozen (FF) and formalin-fixed, paraffin-embedded (FFPE) tissue biopsies were identified for DNA methylation and gene expression analysis, respectively. Laser-capture micro-dissection (LCM) was used to selectively isolate CIS cells for molecular analysis, reducing the extent of contamination by stromal cells.

The following protocol was used to determine which profiling methods were applied to a given CIS lesion during our initial data collection phase:

If FFPE samples were available, gene expression profiling was performed. For the first 33 samples (17 progressive and 16 regressive), gene expression profiles were generated using Illumina microarrays. Our predictive models are trained on this discovery set. Subsequently, a further set of 10 progressive and 8 regressive samples from 18 patients were profiled using a different microarray platform (Affymetrix) to validate our findings on an independent platform.

If FF samples were available, DNA from these samples was first used for methylation profiling. Samples with sufficient DNA after DNA profiling were additionally subjected to whole-genome sequencing. After acquisition of sufficient samples for our methylation dataset (54 samples; 36 progressive, 18 regressive), only 29 samples had sufficient DNA for WGS, therefore we prioritised WGS over methylation for the subsequent 10 samples.

Tissue Processing and Laser-Capture Micro-Dissection

FF or FFPE tissue sections (7-10 µM thickness) were mounted on a MembraneSlide 1.0 PEN. Prior to cryosectioning, the slides were heat-treated for 4 h at 180° C. in a drying cabinet to inactivate nucleases. To overcome the membrane's hydrophobic nature and to allow better section adherence, the slides were then UV-treated for 30 min at 254 nm. Prior to laser-capture micro-dissection (LCM), the slides containing the FF tissue sections for DNA extraction were washed in serial ethanol dilutions (50, 75, 100%) to remove the freezing medium (OCT) and to avoid any interference with the laser's efficiency. For RNA extraction, FFPE sections were dewaxed using the Arcturus® Paradise® PLUS Reagent System (Applied Biosystems, Foster City, CA, USA). For each case, epithelial areas of pre-invasive disease were identified by haematoxylin and eosin staining of the corresponding cryosection (~7 µM thick). The presence of epithelial areas of interest was confirmed by histological assessment of each case by two histopathologists. LCM to isolate the tissue area/cells of interest was performed with the PALM® Microbeamsystem (laser-capture microdissection system) (Carl Zeiss Microimaging, Munich, Germany) on unstained sections. The micro-dissected material was catapulted into a 500 µl AdhesiveCap that allows capture of the isolated tissue without applying any liquid into the cap prior to LCM, thus minimizing the risk of nuclease activity. The captured cells were stored at −80° C. until DNA extraction or processed immediately for RNA.

DNA Extraction

DNA from the micro-dissected tissue and bronchial brushing samples was extracted using QIAGEN's QIAmp DNA Mini and Micro kits, respectively (Crawley, UK). Soluble carrier RNA was used to increase tissue DNA yield. Concentration was measured using the QubitR dsDNA High-Sensitivity assay and QubitR 2.0 Fluorometer (Life Technologies, Paisley, UK). Nucleic acid quality and purity was estimated based on the A260/280 absorbance ratio readings using the NanoDrop-8000 UV-spectrophotometer (Thermo Scientific, Hertfordshire, UK). Only samples with an A260/280 ratio of 1.7-1.9 were included in the study.

RNA Extraction

RNA was extracted using the High Pure FFPE RNA Kit (Roche Applied Science, West Sussex, UK) according to manufacturer's protocol. Quantification was carried out using the Quant-iT RNA assay kit and the Qubit® 2.0 fluorometer (Life Technologies, Paisley, UK). RNA integrity was analysed using a BioAnalyzer 2100 (Agilent, Stockport, UK).

Bisulfite Conversion

For each sample undergoing methylation profiling, 200 ng of DNA were bisulfite converted using the EZ DNA methylation kit (Zymo Research Corp., Orange, CA, USA) according to the manufacturer's modified protocol for Illumina's Infinium 450K assay. This protocol incorporates a cyclic denaturation step to improve the conversion efficiency[3]. The 10 µl final conversion reaction was concentrated down to 4 µl with a vacufuge plus vacuum concentrator (Eppendorf AG, Hamburg, Germany) and sent to UCL's Genomics Core Facility for hybridization on the 450K BeadArray according to Illumina's Infinium HD protocol (Illumina Inc., San Diego, CA, USA) as previously described.4

Infinium HumanMethylation450K Raw Data Extraction and Pre-Processing

Illumina's iScan fluorescent system was used to scan and image the arrays. DNA methylation data were extracted as raw intensity signals without any prior background subtraction or data normalization and were stored as IDAT files.

CpG-specific methylation levels (β-values; continuous value ranging from 0 to 1) for each sample were calculated as the ratio of the fluorescent signal intensity of the methylated (M) and unmethylated (U) alleles according to the following formula:

$$\beta = \frac{\text{intensity of methylated allele } (M)}{\text{intensity of [unmethylated } (U) + \text{methylated } (M) \text{ allele]} + 100}\#$$

All subsequent raw β-value pre-processing, normalisation and down-stream analysis was performed using the Chip Analysis Methylation Pipeline (ChAMP) Bioconductor package with default settings [5].

Analysis of differentially variable positions (DVP) was performed using iEVORA6. Beta values from ChAMP were used as input to iEVORA following normalization and batch correction.

Genome-Wide Gene Expression Array

The extracted FFPE RNA used to generate the gene expression profiles on the discovery set was sent to UCL's Genomics Core Facility for hybridisation on the Human Whole-Genome DASL (cDNA-mediated Annealing, Selection, extension and Ligation) beadarrays according to Illumina's protocol (Illumina Inc., San Diego, CA, USA).

The extracted FFPE RNA used to generate the gene expression profiles on the validation set was sent to UK Bioinformatics Limited for hybridisation on the Clariom™ D Transcriptome Human Pico Assay 2.0 (transcriptome measurement assay) according to Affymetrix's protocol (Thermo Fisher Scientific Waltham, MA, USA).

Principal Component Analysis (PCA)

In order to identify any potential factors of variability affecting sample/group segregation, we applied principal component analysis on all probes passing filters defined above (implemented in the prcomp method of the R stats package). Technical and biological variation was investigated for batch arrays, smoking (pack-years), age at initial diagnosis, gender and previous lung cancer history. The ability of these features to predict the first principal component was quantified using ANOVA analysis, implemented in the R aov method. p-values quoted are derived from this method.

Gene Expression Analysis

Raw gene expression data were expressed as log 2 ratios of fluorescence intensities of the experimental samples. Quantile normalization was applied to Illumina data, using proprietary Illumina software. For Affymetrix data, RMA normalization was applied as defined in the affy Bioconductor package. For analyses utilizing both data sets, only genes represented on both arrays were included and ComBat7 was used to adjust for batch effects.

Differential expression analysis was performed using the limma8 Bioconductor package. Raw p-values were adjusted by the Benjamini-Hochberg procedure to give a FDR [9]. A significance threshold of FDR<0.01 was used to select differentially expressed genes. Cluster analysis and visualization was performed using the pheatmap [10] Bioconductor package.

Real Time PCR Validation

For microarray validation, total RNA from the 33 pre-invasive LUSC lesions undergoing Illumina gene expression profiling was reverse transcribed using qScript® cDNA Super-Mix (Polymerase chain reaction (PCR) reagents) (Quanta Biosciences, Lutterworth, UK) according to the manufacturer's protocol. Real-time quantitative PCR was carried out in eight genes using the SYBR-green master mix (Applied BioSystems, Bleiswijk, Netherlands) in an Eppendorf real-time PCR Machine (Eppendorf, Stevenage, UK). Findings were validated using quantitative PCR (qPCR) for four up-regulated (GAGE5, GPNMB, MMP12 and STC2) and four down-regulated (SPDEF, LM07, OBSCN and MT1E) genes. Gene-specific primers were designed inside or nearby the microarray sequence targeted, using Primer Express Software (PE Applied Biosystems, Bleiswijk, Netherlands). Relative gene expression was quantified using the threshold cycle (Ct) method and normalized to the amount of CTBL and CEP250, which met the criteria of less variation between samples and compatible expression level with the studied genes. Each sample was tested in triplicate and a sample without template was included in each run as a negative control. Correlations between microarrays and real time PCR data were measured using the Pearson coefficient. From microarray and real time PCR data, we calculated the progressive/regressive ratio for each gene expression. All eight genes tested were significant in our differential microarray analysis with FDR<0.05. A high degree of correlation (r=0.982) was observed between qPCR and array data.

Predictive Modelling

For methylation, gene expression and copy number data we applied Prediction Analysis of Microarrays (PAM)[11] to predict whether a sample was progressive or regressive based on its molecular profile. The Bioconductor PAMR package was used. In all presented analyses we select a threshold which minimizes the number of data inputs required whilst maintaining the minimum possible number of classification errors.

PAM calculates the probability of each sample being progressive. We describe this value as a 'Progression Score'. ROC analytics were performed on these progression scores to determine their value as a diagnostic test, using the pROC12 and PRROC13 Bioconductor packages.

For methylation and gene expression data a predictive model was trained on the training set and subsequently applied to an independent validation set. Regressive and control samples were grouped together for the methylation data analysis. ROC analytics were performed only on the validation set. Internal cross-validation was used for methylation-derived copy number data due to smaller sample size (control samples are used as a baseline to calculate copy number, therefore are excluded from predictive analysis).

When multiple lesions from one patient were included in an analysis, these were treated as independent events as they were always taken from different sites in the lung. The outcome of a lesion (whether it progressed or regressed) was determined on a per-lesion basis; the lesion was assigned to the progressive group only if cancer developed at the same site in the lung, and to the regressive group only if normal or low-grade dysplasia was obtained from the same site in the lung.

In some cases different technologies were used, for example our gene expression discovery set used Illumina microarrays whereas our validation set used Affymetrix. In such instances, both data sets were reduced to the subset of genes covered by probes in both platforms prior to creating a predictive model. The ComBat method from the sva Bioconductor package was used to correct for batch effects between the different platforms. In the case of RNAseq data, we used the voom transformation defined in the limma Bioconductor package to derive data comparable to expression data prior to batch correction with ComBat.

Copy Number Variation Analysis

For samples with whole-genome sequencing available we used ASCAT14 to derive local copy number estimates as described below. To increase our sample size for comparative analyses, copy number variation (CNV) data were obtained from non-normalised methylated and unmethylated signal intensities of probes in the 450K array as previously described [15] using the ChAMP Bioconductor package with default settings. Copy number (CN) profiles for progressive and regressive cases were obtained using the control cases for baseline normalisation. A previously defined threshold of ±0.3 was used for the identification of single CNV. Probes associated with highly polymorphic regions (e.g. major histocompatibility complex) were removed from the analysis. The analysis generated group CN frequency plots and CN profiles for each sample. For samples with both methylation and sequencing data available we observed good correlation between copy numbers derived from the two different methods.

For comparison with previous results, the ChAMP pipeline was then modified to return CNV values per-probe. Probe locations were matched to cytogenetic bands using the Ensembl GRCh37 assembly, obtained from http://grch37.rest.ensembl.org/info/assembly/homo_sapiens?content-type=application/json&bands=1, such that copy number variation could be assessed by cytogenetic band. The mean CNV value for each of 778 cytogenetic bands was calculated for each of our 54 samples. Limma analysis was used to identify bands that differed significantly between progressive and regressive samples with BH-adjusted p-value <0.05. Predictive modelling was performed using PAM to find bands predictive of progression, using the same method as for gene expression data. Due to the low number of regressive samples, an internal cross-validation method was used rather than separate discovery and validation sets.

Following identification of predictive cytogenetic bands, PAM modelling was repeated with the dataset limited to only those bands identified by van Boerdonk et al: 3q26.2-29, 3p26.3-p11.1 and 6p25.3-p24.3.16,17. This model was also accurate.

Finally, we applied our model to the validation data set of 24 regressive and 12 progressive samples used by van Boerdonk et al (GEO accession number GSE45287). These data were measured using a different microarray platform (arrayCGH). We assigned each probe to a cytogenetic band, and took the mean values to create a matrix of expression values by band. Our model was applied to the subset of chromosomal bands present in both data sets (760 of 778 bands). ComBat was used for batch correction between the two platforms. Our model correctly predicted 24/24 regressive samples and 9/12 progressive samples, replicating the results of van Boerdonk et al.

External Validation Using TCGA

Lung cancer methylation datasets publically available through The Cancer Genome Atlas (TCGA) were downloaded using GenomicDataCommons download tools [18]. We obtained the normalized β-values of 370 LUSC samples and 42 normal controls. ComBat was used to correct for batch effects between our data and TCGA data. These data were used as an external validation set to test our predictive models, and as input for our differential analysis of progression drivers from control through CIS to cancer.

Gene-expression microarray data sets comparable to our data were not publically available. RNAseq data was available from TCGA for 502 LUSC samples and 49 control samples. We applied a voom transformation [19] to these data, which uses normalized log-counts-per-million as an approximation for expression values, and hence allows comparison of RNAseq data with our gene expression pipeline. ComBat was used to correct for batch effects. The predictive model generated using PAM on our gene expression microarray data was applied to voom-transformed RNAseq data from TCGA and shown to be predictive (FIG. 5C). We therefore demonstrate the applicability of our model to this fully independent data set. These data were again used as input to our differential analysis of progression drivers.

Pathway Analysis

For gene expression data, the GAGE Bioconductor package [20] was used with KEGG gene sets [21]-[23] to identify pathways associated with genes differentially expressed in our analysis of progression to cancer (BH-adjusted p-value <0.01). In addition to these pathways we use the CIN70 signature defined by Carter et al. [24] to assess for a chromosomal instability signal. We also use a subset of the CIN70 genes with cell-cycle associated genes [25] removed to ensure that our signal is genuinely CIN-related, rather than a measure of proliferation.

Methylation data was analysed in the same way, using beta values as input to GAGE. In cases where there are multiple methylation probes for a single gene we use the mean beta value over that gene as input to pathway analysis. We acknowledge that using mean signal may be insensitive to single-probe methylation changes, however given the scale of changes observed we believe it will identify areas of large methylation change.

Genomic Sequencing

We created genome-wide shotgun libraries (insert size 331-367 bp) from native DNA using the Agilent Technologies Custom SureSelect Library Prep Kit library (cat no. 930075). 150 bp paired-end sequence data were generated using the Illumina HiSeq X Ten system.

Sequenced data were realigned to the human genome (NCBI build 37) using BWA-MEM. Unmapped reads and PCR duplicates were removed. A minimum sequencing depth of 40× was required.

Somatic Mutation Calling and Annotation

Single base somatic substitutions were identified by our in-house algorithm Cancer Variants through Expectation Maximisation (CaVEMan: https://github.com/cancerit/CaVEMan) [26]. This algorithm compares the sequence data from each tumour sample to its matched normal and calculates a mutation probability at each locus. This calculation incorporates information from aberrant cell fraction and copy number estimates from the Allele-Specific Copy number Analysis of Tumours (ASCAT) algorithm (https://www.crick.ac.uk/peter-van-loo/software/ASCAT) [14],[27]. Additional post-processing as described previously [28] was implemented. Any putative driver mutations were visually inspected with Jbrowse [29]. For every substitution that passed all filters in at least one sample, we counted the number of wild-type and mutant reads at the same position in all other samples from the same patient to see if that mutation was also present in related samples but had not been called.

Somatic Small Insertions and Deletions

These were identified using our in-house algorithm Pindel [30], [31]. As with substitutions, all putative driver mutations were visualised with Jbrowse.

Somatic Structural Variant Detection

Abnormally paired read pairs were grouped using an in-house tool, "Brass" [32]. Read groups overlapping genomic repeats, reads from the matched normal, or from a panel of unmatched normals were ignored. Read pair clusters were then filtered by read remapping. Read pair clusters with >50% of the reads mapping to microbial sequences were removed. Finally, candidate SV breakpoints were matched to copy number breakpoints as defined by ASCAT within 10 kb. Candidate SVs that were not associated with copy number segmentation breakpoints and with a copy number change of at least 0.3 were removed. All putative driver rearrangements were visually inspected using IGV [33], [34].

Somatic Copy Number Events, Ploidy, and Stromal Contamination

Copy number changes were derived from whole-genome sequencing data using the ASCAT algorithm. This algorithm compares the relative representation of heterozygous SNPs and the total read depth at these positions to estimate the aberrant cell fraction and ploidy for each sample, and then to determine allele-specific copy number.

Weighted Genome Integrity Index

To estimate the overall chromosomal instability of a sample, we use the Weighted Genome Integrity Index (wGII) score [35]. This is calculated by measuring the percentage of the genome which is abnormal, corrected such that each chromosome is equally weighted.

Mutation Annotation

Lung cancer driver genes were selected from the COSMIC Cancer Gene Census (CGC) v85 (cancer.sanger.ac.uk) [36]. CGC data was downloaded on 20 Jun. 2018. Genes annotated in the CGC as potential drivers in lung cancer or NSCLC were included. Those specific to adenocarcinoma were excluded as our samples are precursors to squamous cancers. Genes identified in two large studies of squamous cell cancer, and some additional genes based on expert curation of the literature (ARID1A, AKT2, FAT1, PTPRB) were included if they were present in the CGC—even if they were not annotated explicitly as implicated in lung cancer. Both Tier 1 and Tier 2 genes were included. A total of 96 genes were selected as putative lung squamous cell carcinoma drivers.

Mutations affecting these putative driver genes were annotated as driver mutations if they passed the following filters:

The mutation type (e.g. missense, frameshift, amplification) must have been validated in the CGC for the affected gene.

For genes annotated as tumour suppressors, mutations determined to have High or Moderate impact using Ensembl's Variant Effect Predictor [37] were classed as driver mutations.

For genes annotated as oncogenes, we checked the specific mutation against COSMIC mutation data for lung carcinomas. If the specific mutation occurred 3 or more times in this dataset it was classed as a driver mutation.

For genes annotated as fusion proteins, translocations with a translocation partner gene matching validated translocation partner genes in the CGC were classed as driver events.

Copy number amplifications and deletions were all classed as driver events if amplifications/deletions in the affected gene have been previously validated in the CGC. We included homozygous deletions of tumour suppressor genes and amplifications to more than double the sample ploidy for oncogenes.

Driver mutation discovery was also attempted using dndscv [38]. This was underpowered, however, and only yielded TP53 and CDKN2A as genes under positive selection. This package was also used to estimate the global dNdS for both progressive and regressive lesions.

Subclonality Analysis

The number of subclones contributing to a sample and their relative contribution was estimated by using a modified version of the sciClone Bioconductor package [39]. sciClone uses a Bayesian method to allocate mutations to clusters based on their variant allele frequency (VAF). By default, sciClone only considers regions that are copy number neutral and LOH-free. Given the significant aneuploidy in our data set we overcame this limitation by clustering on cancer cell fraction (CCF) rather than VAF. Briefly, cancer cell fraction represents the fraction of cancer cells in which a given mutation is present, therefore clonal mutations will have CCF=1. Following the method of McGranahan et al. [40], we estimated the CCF for each mutation with a 95% confidence interval. Mutations for which 1 lay within this confidence interval were labelled as 'clonal', other mutations as 'subclonal'.

CCF values for each mutation were then used as input to sciClone in place of VAF values to quantify clusters present (divided by 2 such that clonal mutations have a value of 0.5). As CCF corrects for local copy number, all regions were assumed to have copy number of 2, allowing sciClone to group mutations based only on their CCF estimates. A minimum tumour sequencing depth of 10 was required for each mutation.

Where more than one sample from a given patient was available, both one dimensional and multi-dimensional clustering were performed. Results from one dimensional clustering were used in the comparison of numbers of clones and proportion of clonal mutations between progressive and regressive lesions, in order to provide as fair a comparison as possible.

Extraction of Mutational Signatures

To obtain an approximate estimate of the contribution of different known mutational signatures to each sample, we used the MutationalPatterns Bioconductor package41. As a reference set of mutational signatures, we used a table with the relative frequency of each of the 96 trinucleotide substitutions across 30 known mutation signatures, [42], [43] available through the COSMIC website (http://cancer-.sanger.ac.uk/cosmic/signatures).

After a first run which indicated the most likely contribution of each signature, it seemed that the majority of substitutions were contributed by signatures 1, 2, 4, 5, and 13, which have been described to be the strongest signatures in lung squamous cell cancer [44]. Some contribution was identified from signatures 16, 8, 18 and 3 in our initial analysis; however, in this context it is likely that these represent overfitting given that signature 16 is similar to signature 5, and signatures 8, 18 and 3 are similar to signature 4. We therefore ran the algorithm a second time, this time only using a 5×96 matrix of mutational signatures 1, 2, 4, 5 and 13. All mutations were thus forced to belong to one of these five mutational signatures.

For a comparison of the clonal vs subclonal mutational processes in each sample, substitutions were annotated as clonal or subclonal based on CCF as described above. These were then run through the MutationalPatterns package.

Comparison of Mutational Burden and Signatures with Other Cancer Types

Signatures of mutations in our CIS dataset were compared with mutational signatures found in lung squamous cell cancer. Raw whole-exome sequencing data for this cancer type was downloaded from TCGA, and run through our substitution-calling algorithm CAVEMaN as described above. We then looked at the total number of substitutions called, and estimated the contribution of each mutational signature using the methods described above. Only coding regions of the CIS whole-genome sequencing data were compared to these exomes.

Estimation of Telomere Lengths

Telomere lengths were estimated using telomerecat [45], and were compared in progressive and regressive groups. Telomerecat is a de novo method for the estimation of telomere length (TL) from whole-genome sequencing samples. The algorithm works by comparing the ratio of full telomere reads to reads on the boundary between telomere and subtelomere. This ratio is transformed to a measure of length by taking into account the fragment length distribution. Telomerecat also corrects for error in sequencing reads by modelling the observed distribution of phred scores associated with mismatches in the telomere sequence. Samples were analysed in two groups corresponding to two separate sequencing batches, as per the telomerecat documentation.

All publications mentioned in the above specification are herein incorporated by reference. Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in genetics, epigenetics, molecular biology, cell biology, oncology or related fields are intended to be within the scope of the following claims.

Tables

TABLE 1

| Example DEG signature comprising 397 genes (gene weights are given in columns X0.score and X1.score) | | | | | | | | |
|---|---|---|---|---|---|---|---|---|
| GENE ID | X0.score | X1.score | GENE ID | X0.score | X1.score | GENE ID | X0.score | X1.score |
| KLK7 | 0.4684 | −0.4408 | GHR | −0.2436 | 0.2293 | CBS | −0.1736 | 0.1634 |
| SPNS2 | 0.4353 | −0.4097 | LHX9 | 0.2426 | −0.2284 | HTR2A | 0.173 | −0.1628 |
| CPVL | −0.3878 | 0.365 | ABCG4 | 0.2393 | −0.2252 | CD164L2 | 0.1705 | −0.1604 |
| FER1L6 | 0.3719 | −0.3501 | GABRB1 | 0.2331 | −0.2194 | SLC29A4 | −0.1704 | 0.1603 |
| ATP12A | 0.3663 | −0.3448 | ZIC2 | −0.2298 | 0.2163 | RPL7 | −0.1687 | 0.1588 |
| KLK12 | 0.3631 | −0.3418 | KRTAP13-1 | 0.2215 | −0.2085 | ZFP37 | −0.1685 | 0.1586 |
| ADCYAP1 | 0.344 | −0.3238 | LCE6A | 0.2119 | −0.1994 | SLC6A11 | 0.1685 | −0.1586 |
| RASIP1 | 0.3429 | −0.3227 | MIOX | 0.2066 | −0.1944 | PLAT | 0.168 | −0.1581 |

TABLE 1-continued

Example DEG signature comprising 397 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| KLK6 | 0.341 | −0.3209 | CHST6 | 0.2056 | −0.1935 | PRSS3 | 0.1666 | −0.1568 |
| KLK5 | 0.3229 | −0.3039 | RBAK | −0.2054 | 0.1933 | ELAVL1 | −0.1662 | 0.1564 |
| NCCRP1 | 0.3167 | −0.2981 | CSN3 | 0.2006 | −0.1888 | SOX17 | 0.1659 | −0.1562 |
| RHCG | 0.3159 | −0.2973 | ASCL2 | −0.1953 | 0.1838 | SLC13A5 | 0.1657 | −0.156 |
| IGFL1 | 0.3087 | −0.2905 | MPP6 | 0.1947 | −0.1832 | SLC6A14 | 0.1649 | −0.1552 |
| GDPD3 | 0.2877 | −0.2708 | LYPD3 | 0.1944 | −0.1829 | SMYD3 | −0.1599 | 0.1505 |
| MLPH | 0.2863 | −0.2695 | ZNF804B | 0.1939 | −0.1825 | ITPKA | −0.159 | 0.1497 |
| OR5B3 | 0.2846 | −0.2679 | RSRC1 | −0.1937 | 0.1823 | STAB2 | 0.1574 | −0.1482 |
| MT1F | −0.2805 | 0.264 | PANX3 | 0.1936 | −0.1822 | IFFO2 | 0.1559 | −0.1467 |
| OR52K1 | 0.2799 | −0.2634 | SPRR2B | 0.1913 | −0.1801 | MYNN | −0.1544 | 0.1453 |
| KRT23 | 0.2789 | −0.2625 | TMPRSS11D | 0.1906 | −0.1794 | PDE3B | −0.1539 | 0.1448 |
| DHRS9 | 0.2766 | −0.2603 | UNC93A | 0.1887 | −0.1776 | KLK10 | 0.1524 | −0.1434 |
| SULT2B1 | 0.2723 | −0.2563 | INO80B | −0.1864 | 0.1754 | HIST1H2AA | 0.1512 | −0.1423 |
| CST6 | 0.2614 | −0.246 | CLIC3 | 0.186 | −0.175 | ZNF614 | −0.1508 | 0.1419 |
| SBSN | 0.2552 | −0.2402 | MAD2L1 | −0.1854 | 0.1745 | H19 | 0.1497 | −0.1409 |
| PRAME | −0.2552 | 0.2402 | DNAJC19 | −0.1852 | 0.1743 | GPNMB | −0.149 | 0.1402 |
| NEK2 | −0.2518 | 0.237 | SNORD2 | −0.1757 | 0.1654 | E2F7 | −0.1486 | 0.1398 |
| SERPINB4 | 0.1475 | −0.1388 | ZNF721 | −0.1296 | 0.122 | SP6 | 0.1098 | −0.1034 |
| SLC4A11 | 0.1468 | −0.1382 | SKAP2 | −0.1266 | 0.1191 | PBOV1 | 0.109 | −0.1026 |
| HES5 | 0.1458 | −0.1372 | IRF7 | 0.1253 | −0.1179 | ID1 | 0.1087 | −0.1023 |
| ALOX12B | 0.1453 | −0.1367 | MEOX1 | 0.1252 | −0.1178 | ANLN | −0.1077 | 0.1014 |
| VAX2 | −0.1445 | 0.136 | TEX14 | 0.1248 | −0.1175 | MIPOL1 | −0.1076 | 0.1013 |
| FAM3D | 0.1438 | −0.1354 | G6PC | 0.124 | −0.1167 | C19orf33 | 0.1073 | −0.101 |
| OR52B6 | 0.1437 | −0.1353 | CCDC59 | −0.1234 | 0.1162 | SCEL | 0.1059 | −0.0997 |
| OR2B11 | 0.1429 | −0.1345 | SCML2 | −0.1223 | 0.1151 | ZNF284 | 0.1051 | −0.0989 |
| KLK8 | 0.1427 | −0.1343 | MAGEA9B | −0.1213 | 0.1142 | MIR554 | 0.103 | −0.0969 |
| NKAIN2 | −0.1425 | 0.1341 | ZSCAN4 | 0.1206 | −0.1135 | SH3TC1 | 0.1023 | −0.0963 |
| NOS1 | 0.1412 | −0.1329 | CRABP2 | 0.1199 | −0.1129 | STC2 | −0.1022 | 0.0962 |
| PEG10 | −0.1412 | 0.1329 | TRIM16 | 0.1198 | −0.1128 | DEFB122 | 0.1019 | −0.0959 |
| HOXC8 | −0.141 | 0.1327 | TFAP4 | −0.1197 | 0.1126 | OR14J1 | 0.1 | −0.0941 |
| ABHD8 | −0.1396 | 0.1314 | C19orf54 | −0.1179 | 0.111 | ZNF777 | −0.1 | 0.0941 |
| CLDN5 | 0.1386 | −0.1304 | HIST1H4F | 0.117 | −0.1101 | NRSN1 | 0.0999 | −0.094 |
| MCM10 | −0.1378 | 0.1297 | IFNA21 | 0.1163 | −0.1095 | FRAS1 | −0.0987 | 0.0929 |
| PI3 | 0.1378 | −0.1297 | CA1 | 0.1156 | −0.1088 | ECM1 | 0.0986 | −0.0928 |
| ADCY4 | 0.1367 | −0.1286 | ZYG11A | 0.115 | −0.1082 | ANGPT4 | 0.0984 | −0.0926 |
| HOXC9 | −0.1365 | 0.1285 | CDA | 0.1146 | −0.1079 | GABRP | 0.0979 | −0.0921 |
| FANCL | −0.1351 | 0.1271 | SERPINB3 | 0.1145 | −0.1078 | OIP5 | −0.0967 | 0.0911 |
| RDH13 | 0.1347 | −0.1268 | GRM3 | 0.1139 | −0.1072 | DNAJC5G | 0.0965 | −0.0908 |
| NOD2 | 0.1329 | −0.1251 | KRTDAP | 0.1129 | −0.1062 | HOXD10 | −0.0965 | 0.0908 |
| SORBS1 | 0.1328 | −0.125 | PRSS27 | 0.1109 | −0.1044 | B3GALT4 | 0.0965 | −0.0908 |
| KRTAP8-1 | 0.1328 | −0.1249 | VPS37D | −0.1105 | 0.104 | IGF2BP3 | −0.0947 | 0.0891 |
| E2F3 | −0.132 | 0.1235 | MYL3 | 0.11 | −0.1035 | UBL4B | 0.094 | −0.0884 |
| C2orf78 | 0.1305 | −0.1228 | EBF1 | 0.11 | −0.1035 | IL4R | 0.0938 | −0.0883 |
| ACTL6A | −0.0938 | 0.0882 | MUC16 | 0.0833 | −0.0784 | KRT16 | 0.0655 | −0.0616 |
| PCDHB13 | −0.0937 | 0.0882 | HOXC10 | −0.083 | 0.0781 | RNF126P1 | 0.0654 | −0.0616 |
| NKX2-1 | 0.0934 | −0.0879 | ZNF124 | −0.0822 | 0.0773 | PFN2 | −0.0641 | 0.0603 |
| SSX2 | 0.0933 | −0.0879 | PTPRB | 0.0813 | −0.0765 | PLD2 | 0.0634 | −0.0597 |
| HIST2H3A | −0.0932 | 0.0877 | TMEM41A | −0.0806 | 0.0759 | KCNS1 | 0.0631 | −0.0594 |
| MND1 | −0.0931 | 0.0877 | INPP4B | 0.0806 | −0.0759 | KCNJ3 | 0.0626 | −0.0589 |
| SCN8A | −0.0931 | 0.0876 | FBXO16 | 0.0796 | −0.0749 | CLCF1 | 0.062 | −0.0584 |
| OR5B12 | 0.0928 | −0.0874 | TMEM45B | 0.0788 | −0.0742 | TFB2M | −0.062 | 0.0583 |
| CLDN16 | −0.0923 | 0.0869 | MED28 | −0.0783 | 0.0737 | ZNF131 | −0.0619 | 0.0582 |
| SLC17A4 | 0.092 | −0.0866 | SORCS2 | 0.0782 | −0.0736 | ECT2 | −0.0617 | 0.058 |
| RRM2B | −0.0916 | 0.0862 | GSTM5 | 0.0782 | −0.0736 | CKAP2 | −0.0611 | 0.0575 |
| GATA4 | −0.0914 | 0.086 | OR51Q1 | 0.0777 | −0.0731 | TMEM40 | 0.0611 | −0.0575 |
| TGM5 | 0.0903 | −0.085 | OR4E2 | 0.0771 | −0.0725 | GADL1 | 0.0609 | −0.0573 |
| LOR | 0.0901 | −0.0848 | CXXC5 | 0.0767 | −0.0722 | ZDHHC13 | 0.0601 | −0.0566 |
| KRT78 | 0.09 | −0.0847 | NGEF | 0.0739 | −0.0695 | RAB36 | 0.0601 | −0.0566 |
| CRIP1 | 0.0896 | −0.0843 | SPACA5B | 0.0735 | −0.0691 | ALPL | 0.0601 | −0.0566 |
| ALDH7A1 | 0.0895 | −0.0843 | DUXAP3 | 0.0729 | −0.0687 | RAB26 | 0.0597 | −0.0562 |
| PALMD | 0.089 | −0.0837 | UBE2W | −0.0724 | 0.0682 | DLG1 | −0.0595 | 0.056 |
| S100A7 | 0.0888 | −0.0835 | EHHADH | −0.0713 | 0.0671 | RAB33B | −0.0593 | 0.0558 |
| REG1B | 0.0883 | −0.0831 | SPRR2E | 0.0686 | −0.0645 | PPOX | 0.0592 | −0.0557 |
| MID1 | −0.0878 | 0.0827 | ZNF121 | −0.0684 | 0.0644 | CYMP | 0.0589 | −0.0555 |
| CXCL10 | −0.0877 | 0.0826 | ECSCR | 0.0678 | −0.0638 | SIM2 | −0.0573 | 0.0539 |
| HSD17B3 | 0.0876 | −0.0824 | FOXI2 | 0.0677 | −0.0637 | OR4F4 | 0.0572 | −0.0538 |
| HCN1 | 0.0852 | −0.0802 | FGD5 | 0.0665 | −0.0626 | PAK2 | −0.0571 | 0.0538 |
| PRSS22 | 0.0834 | −0.0785 | LY6G6C | 0.0658 | −0.0619 | NMD3 | −0.0563 | 0.053 |
| SPP1 | −0.0834 | 0.0785 | INTS10 | 0.0658 | −0.0619 | FBN3 | −0.0559 | 0.0526 |
| PSCA | 0.0556 | −0.0523 | SNORD87 | −0.0471 | 0.0443 | NCBP2 | −0.0345 | 0.0324 |
| OR5AR1 | 0.0552 | −0.0519 | SCARA5 | 0.0461 | −0.0434 | TRIB1 | 0.0335 | −0.0315 |
| LCA5L | 0.0548 | −0.0516 | DHRS2 | −0.0455 | 0.0429 | ZNF10 | −0.0332 | 0.0312 |
| MMP12 | −0.0541 | 0.051 | ANKRD35 | 0.0452 | −0.0425 | TRIO | −0.033 | 0.0311 |
| TYW1 | −0.0536 | 0.0504 | LRP5 | −0.0441 | 0.0415 | SLC5A8 | 0.0322 | −0.0303 |
| MDH1B | 0.0535 | −0.0503 | OR52K2 | 0.044 | −0.0414 | FBXL18 | −0.0322 | 0.0303 |
| C15orf62 | 0.0533 | −0.0502 | RPL39L | −0.0438 | 0.0412 | MYH14 | 0.032 | −0.0301 |

TABLE 1-continued

Example DEG signature comprising 397 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| BTBD2 | −0.0532 | 0.05 | C1orf116 | 0.043 | −0.0405 | OR2AT4 | 0.0313 | −0.0295 |
| ZNF703 | −0.0531 | 0.05 | HLA-DQA2 | 0.0428 | −0.0402 | PQLC2 | −0.0312 | 0.0294 |
| PPFIA2 | 0.0529 | −0.0498 | OR52R1 | 0.0419 | −0.0394 | LRIG1 | 0.0312 | −0.0294 |
| MRAP | 0.0525 | −0.0494 | CEACAM5 | 0.0418 | −0.0394 | HLTF | −0.0309 | 0.0291 |
| MYOM3 | 0.0524 | −0.0493 | EIF2AK1 | −0.041 | 0.0386 | RAD51AP1 | −0.0308 | 0.029 |
| LCN2 | 0.0517 | −0.0487 | EPS8L1 | 0.0391 | −0.0368 | SDCBP2 | 0.0306 | −0.0288 |
| ZMYND15 | 0.0517 | −0.0486 | SLC22A8 | 0.039 | −0.0367 | GIPC2 | 0.0304 | −0.0286 |
| FUT3 | 0.0507 | −0.0477 | SNW1 | −0.0385 | 0.0363 | LACTB2 | −0.0304 | 0.0286 |
| GDF3 | 0.0505 | −0.0475 | C1QTNF1 | 0.0384 | −0.0362 | FAM133A | −0.0303 | 0.0285 |
| REM1 | 0.0502 | −0.0473 | MPV17L | 0.0382 | −0.036 | ACADVL | 0.0303 | −0.0285 |
| NOL10 | −0.05 | 0.0471 | ATP8A2 | 0.0375 | −0.0353 | SFTA3 | 0.0294 | −0.0277 |
| RUNDC3B | 0.05 | −0.047 | CD3EAP | −0.0371 | 0.0349 | BOC | 0.0293 | −0.0276 |
| MYOCD | 0.0495 | −0.0466 | ANXA1 | 0.037 | −0.0348 | CYP2E1 | 0.0287 | −0.027 |
| SPRR4 | 0.0494 | −0.0465 | B3GALNT1 | −0.0367 | 0.0346 | ZNF91 | −0.0286 | 0.0269 |
| KRT7 | 0.0487 | −0.0459 | TMEM183B | −0.0367 | 0.0345 | C1D | −0.0279 | 0.0263 |
| HIST1H2BH | −0.0487 | 0.0458 | GPR152 | 0.0361 | −0.034 | PNCK | −0.0277 | 0.0261 |
| MAB21L2 | 0.0483 | −0.0454 | CTSG | 0.0355 | −0.0334 | TM2D3 | −0.0275 | 0.0259 |
| MAS1 | 0.0477 | −0.0449 | RASL12 | 0.0354 | −0.0333 | OR11H6 | 0.0267 | −0.0252 |
| FZD4 | 0.0471 | −0.0444 | CLEC4G | 0.0347 | −0.0326 | RIOK1 | −0.0263 | 0.0247 |
| CRIP2 | 0.0262 | −0.0246 | SPINK5 | 0.0166 | −0.0156 | KRTAP4-7 | 0.0105 | −0.0098 |
| OR2L13 | 0.0261 | −0.0246 | CD300LD | 0.0164 | −0.0155 | ANKS6 | −0.0099 | 0.0093 |
| PGBD5 | 0.0259 | −0.0244 | FXR1 | −0.016 | 0.015 | C3orf30 | 0.0098 | −0.0092 |
| SERPINB1 | 0.0257 | −0.0242 | TMC5 | 0.0152 | −0.0143 | SFRP5 | 0.0095 | −0.009 |
| MTIF3 | 0.0246 | −0.0232 | DEFB125 | 0.0141 | −0.0132 | HIST1H3G | −0.0092 | 0.0087 |
| PIWIL3 | 0.0243 | −0.0229 | MIR548I1 | 0.014 | −0.0131 | USP11 | −0.009 | 0.0085 |
| VMO1 | 0.024 | −0.0226 | SNX32 | 0.0139 | −0.0131 | FES | 0.0072 | −0.0068 |
| TTC30A | −0.0238 | 0.0224 | IL33 | 0.0139 | −0.0131 | GPR68 | 0.0071 | −0.0067 |
| PNO1 | −0.0234 | 0.0221 | CDCA7L | −0.0129 | 0.0122 | PLCD1 | 0.0071 | −0.0066 |
| TTYH3 | −0.0223 | 0.021 | KCNG1 | −0.0129 | 0.0121 | TIAM1 | 0.0061 | −0.0057 |
| HIST3H2BB | −0.022 | 0.0207 | CTNS | 0.0128 | −0.0121 | KPNA2 | −0.0059 | 0.0055 |
| PLEKHH3 | 0.0217 | −0.0204 | RAB23 | −0.0128 | 0.012 | ACAP2 | −0.0059 | 0.0055 |
| NES | 0.0217 | −0.0204 | ETNK2 | −0.0128 | 0.012 | AGTPBP1 | −0.0058 | 0.0055 |
| SDK1 | −0.0216 | 0.0204 | BAG2 | −0.0128 | 0.012 | LMAN1 | −0.0057 | 0.0054 |
| GTF2H3 | −0.0214 | 0.0201 | DCUN1D5 | −0.0126 | 0.0119 | OR9I1 | 0.0055 | −0.0052 |
| SOX18 | 0.0211 | −0.0199 | XKR3 | 0.0124 | −0.0116 | CHI3L1 | 0.0053 | −0.005 |
| TRIM16L | 0.0206 | −0.0194 | ANXA2 | 0.0123 | −0.0116 | SLC6A5 | 0.0052 | −0.0049 |
| MYO1C | 0.0201 | −0.0189 | ARHGAP30 | 0.012 | −0.0113 | KLHL24 | −0.0052 | 0.0049 |
| TMEM139 | 0.0194 | −0.0183 | DSCC1 | −0.012 | 0.0112 | GALE | 0.005 | −0.0047 |
| LYPD2 | 0.0192 | −0.0181 | SERPINB8 | 0.0117 | −0.011 | MMP28 | 0.0046 | −0.0044 |
| KRT6B | 0.0189 | −0.0178 | LARP4 | −0.0115 | 0.0108 | CCL14 | 0.0046 | −0.0043 |
| KIF13B | 0.0188 | −0.0177 | KLHL13 | −0.0112 | 0.0105 | PROX2 | 0.004 | −0.0038 |
| ADAM29 | 0.0186 | −0.0175 | CSF2RB | 0.0109 | −0.0102 | IL23A | 0.0039 | −0.0036 |
| PSAT1 | −0.0183 | 0.0172 | FGD6 | −0.0108 | 0.0102 | ICA1 | 0.0032 | −0.003 |
| PLTP | −0.0174 | 0.0163 | CYB5R2 | 0.0108 | −0.0102 | PARP1 | −0.0031 | 0.0029 |
| LSM5 | −0.0173 | 0.0163 | BTN1A1 | 0.0107 | −0.0101 | NEK3 | 0.0029 | −0.0027 |
| PON1 | 0.0026 | −0.0024 | | | | | | |
| MTHFD2L | −0.0019 | 0.0018 | | | | | | |
| WDHD1 | −0.0013 | 0.0012 | | | | | | |
| HOXC6 | −0.0013 | 0.0012 | | | | | | |
| SWOP | 0.0013 | −0.0012 | | | | | | |
| ALOX12P2 | 0.0007 | −0.0006 | | | | | | |
| SNORD1A | −0.0006 | 0.0005 | | | | | | |
| C6orf89 | 0.0005 | −0.0005 | | | | | | |
| BIRC5 | −0.0003 | 0.0003 | | | | | | |

TABLE 2

Example DEG signature comprising 291 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| KLK7 | 0.4372 | −0.4115 | GHR | −0.2124 | 0.1999 | CBS | −0.1424 | 0.134 |
| SPNS2 | 0.4041 | −0.3803 | LHX9 | 0.2114 | −0.199 | HTR2A | 0.1417 | −0.1334 |
| CPVL | −0.3566 | 0.3356 | ABCG4 | 0.2081 | −0.1958 | CD164L2 | 0.1392 | −0.131 |
| FER1L6 | 0.3407 | −0.3207 | GABRB1 | 0.2019 | −0.19 | SLC29A4 | −0.1391 | 0.1309 |
| ATP12A | 0.3351 | −0.3154 | ZIC2 | −0.1986 | 0.1869 | RPL7 | −0.1375 | 0.1294 |
| KLK12 | 0.3319 | −0.3124 | KRTAP13-1 | 0.1903 | −0.1791 | ZFP37 | −0.1373 | 0.1292 |
| ADCYAP1 | 0.3128 | −0.2944 | LCE6A | 0.1806 | −0.17 | SLC6A11 | 0.1373 | −0.1292 |
| RASIP1 | 0.3117 | −0.2934 | MIOX | 0.1754 | −0.165 | PLAT | 0.1367 | −0.1287 |
| KLK6 | 0.3098 | −0.2915 | CHST6 | 0.1744 | −0.1641 | PRSS3 | 0.1353 | −0.1274 |
| KLK5 | 0.2917 | −0.2745 | RBAK | −0.1742 | 0.1639 | ELAVL1 | −0.135 | 0.127 |
| NCCRP1 | 0.2855 | −0.2687 | CSN3 | 0.1694 | −0.1594 | SOX17 | 0.1347 | −0.1268 |
| RHCG | 0.2847 | −0.2679 | ASCL2 | −0.164 | 0.1544 | SLC13A5 | 0.1345 | −0.1266 |

TABLE 2-continued

Example DEG signature comprising 291 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| IGFL1 | 0.2774 | −0.2611 | MPP6 | −0.1635 | 0.1539 | SLC6A14 | 0.1336 | −0.1258 |
| GDPD3 | 0.2565 | −0.2414 | LYPD3 | 0.1632 | −0.1536 | SMYD3 | −0.1287 | 0.1211 |
| MLPH | 0.2551 | −0.2401 | ZNF804B | 0.1627 | −0.1531 | ITPKA | −0.1278 | 0.1203 |
| OR5B3 | 0.2534 | −0.2385 | RSRC1 | −0.1625 | 0.1529 | STAB2 | 0.1262 | −0.1188 |
| MT1F | −0.2493 | 0.2346 | PANX3 | 0.1624 | −0.1528 | IFFO2 | 0.1247 | −0.1173 |
| OR52K1 | 0.2486 | −0.234 | SPRR2B | 0.1601 | −0.1507 | MYNN | −0.1232 | 0.116 |
| KRT23 | 0.2477 | −0.2331 | TMPRSS11D | 0.1594 | −0.15 | PDE3B | −0.1227 | 0.1155 |
| DHRS9 | 0.2454 | −0.2309 | UNC93A | 0.1574 | −0.1482 | KLK10 | 0.1211 | −0.114 |
| SULT2B1 | 0.241 | −0.2269 | INO80B | −0.1551 | 0.146 | HIST1H2AA | 0.12 | −0.1129 |
| CST6 | 0.2302 | −0.2166 | CLIC3 | 0.1548 | −0.1457 | ZNF614 | −0.1196 | 0.1126 |
| SBSN | 0.224 | −0.2108 | MAD2L1 | −0.1541 | 0.1451 | H19 | 0.1185 | −0.1115 |
| PRAME | −0.2239 | 0.2108 | DNAJC19 | −0.154 | 0.1449 | GPNMB | −0.1178 | 0.1108 |
| NEK2 | −0.2205 | 0.2076 | SNORD2 | −0.1445 | 0.136 | E2F7 | −0.1173 | 0.1104 |
| SERPINB4 | 0.1162 | −0.1094 | C2orf78 | 0.0992 | −0.0934 | MYL3 | 0.0787 | −0.0741 |
| SLC4A11 | 0.1156 | −0.1088 | ZNF721 | −0.0984 | 0.0926 | EBF1 | 0.0787 | −0.0741 |
| HES5 | 0.1145 | −0.1078 | SKAP2 | −0.0954 | 0.0898 | SP6 | 0.0786 | −0.074 |
| ALOX12B | 0.114 | −0.1073 | IRF7 | 0.094 | −0.0885 | PBOV1 | 0.0778 | −0.0732 |
| VAX2 | −0.1133 | 0.1066 | MEOX1 | 0.0939 | −0.0884 | ID1 | 0.0775 | −0.0729 |
| FAM3D | 0.1126 | −0.106 | TEX14 | 0.0936 | −0.0881 | ANLN | −0.0765 | 0.072 |
| OR52B6 | 0.1125 | −0.1059 | G6PC | 0.0927 | −0.0873 | MIPOL1 | −0.0764 | 0.0719 |
| OR2B11 | 0.1117 | −0.1051 | CCDC59 | −0.0922 | 0.0868 | C19orf33 | 0.0761 | −0.0716 |
| KLK8 | 0.1114 | −0.1049 | SCML2 | −0.091 | 0.0857 | SCEL | 0.0747 | −0.0703 |
| NKAIN2 | −0.1113 | 0.1047 | MAGEA9B | −0.0901 | 0.0848 | ZNF284 | 0.0739 | −0.0695 |
| NOS1 | 0.11 | −0.1035 | ZSCAN4 | 0.0894 | −0.0841 | MIR554 | 0.0718 | −0.0676 |
| PEG10 | −0.11 | 0.1035 | CRABP2 | 0.0887 | −0.0835 | SH3TC1 | 0.0711 | −0.0669 |
| HOXC8 | −0.1098 | 0.1033 | TRIM16 | 0.0886 | −0.0834 | STC2 | −0.0709 | 0.0668 |
| ABHD8 | −0.1083 | 0.102 | TFAP4 | −0.0885 | 0.0833 | DEFB122 | 0.0707 | −0.0665 |
| CLDN5 | 0.1073 | −0.101 | C19orf54 | −0.0867 | 0.0816 | OR14J1 | 0.0688 | −0.0647 |
| MCM10 | −0.1066 | 0.1003 | HIST1H4F | 0.0858 | −0.0807 | ZNF777 | −0.0687 | 0.0647 |
| PI3 | 0.1066 | −0.1003 | IFNA21 | 0.0851 | −0.0801 | NRSN1 | 0.0687 | −0.0646 |
| ADCY4 | 0.1055 | −0.0993 | CA1 | 0.0844 | −0.0794 | FRAS1 | −0.0675 | 0.0635 |
| HOXC9 | −0.1053 | 0.0991 | ZYG11A | 0.0838 | −0.0788 | ECM1 | 0.0674 | −0.0634 |
| FANCL | −0.1038 | 0.0977 | CDA | 0.0834 | −0.0785 | ANGPT4 | 0.0671 | −0.0632 |
| RDH13 | 0.1035 | −0.0974 | SERPINB3 | 0.0833 | −0.0784 | GABRP | 0.0667 | −0.0627 |
| NOD2 | 0.1017 | −0.0957 | GRM3 | 0.0827 | −0.0778 | OIP5 | −0.0655 | 0.0617 |
| SORBS1 | 0.1016 | −0.0956 | KRTDAP | 0.0817 | −0.0769 | DNAJC5G | 0.0653 | −0.0614 |
| KRTAP8-1 | 0.1015 | −0.0956 | PRSS27 | 0.0797 | −0.075 | HOXD10 | −0.0653 | 0.0614 |
| E2F3 | −0.1 | 0.0941 | VPS37D | −0.0792 | 0.0746 | B3GALT4 | 0.0652 | −0.0614 |
| IGF2BP3 | −0.0635 | 0.0597 | HSD17B3 | 0.0563 | −0.053 | ECSCR | 0.0365 | −0.0344 |
| UBL4B | 0.0627 | −0.0591 | HCN1 | 0.0539 | −0.0508 | FOXI2 | 0.0364 | −0.0343 |
| IL4R | 0.0625 | −0.0589 | PRSS22 | 0.0522 | −0.0491 | FGD5 | 0.0353 | −0.0332 |
| ACTL6A | −0.0625 | 0.0589 | SPP1 | −0.0521 | 0.0491 | LY6G6C | 0.0346 | −0.0326 |
| PCDHB13 | −0.0625 | 0.0588 | MUC16 | 0.0521 | −0.049 | INTS10 | 0.0345 | −0.0325 |
| NKX2-1 | 0.0622 | −0.0585 | HOXC10 | −0.0518 | 0.0487 | KRT16 | 0.0342 | −0.0322 |
| SSX2 | 0.0621 | −0.0585 | ZNF124 | −0.0509 | 0.0479 | RNF126P1 | 0.0342 | −0.0322 |
| HIST2H3A | −0.0619 | 0.0583 | PTPRB | 0.05 | −0.0471 | PFN2 | −0.0328 | 0.0309 |
| MND1 | −0.0619 | 0.0583 | TMEM41A | −0.0494 | 0.0465 | PLD2 | 0.0322 | −0.0303 |
| SCN8A | −0.0618 | 0.0582 | INPP4B | 0.0494 | −0.0465 | KCNS1 | 0.0319 | −0.03 |
| OR5B12 | 0.0616 | −0.058 | FBXO16 | 0.0484 | −0.0456 | KCNJ3 | 0.0314 | −0.0296 |
| CLDN16 | −0.0611 | 0.0575 | TMEM45B | 0.0476 | −0.0448 | CLCF1 | 0.0308 | −0.029 |
| SLC17A4 | 0.0608 | −0.0572 | MED28 | −0.0471 | 0.0443 | TFB2M | −0.0308 | 0.0289 |
| RRM2B | −0.0604 | 0.0568 | SORCS2 | 0.047 | −0.0442 | ZNF131 | −0.0307 | 0.0289 |
| GATA4 | −0.0602 | 0.0566 | GSTM5 | 0.047 | −0.0442 | ECT2 | −0.0304 | 0.0287 |
| TGM5 | 0.0591 | −0.0556 | OR51Q1 | 0.0465 | −0.0437 | CKAP2 | −0.0299 | 0.0281 |
| LOR | 0.0589 | −0.0554 | OR4E2 | 0.0458 | −0.0431 | TMEM40 | 0.0298 | −0.0281 |
| KRT78 | 0.0588 | −0.0553 | CXXC5 | 0.0455 | −0.0428 | GADL1 | 0.0297 | −0.0279 |
| CRIP1 | 0.0584 | −0.0549 | NGEF | 0.0427 | −0.0402 | ZDHHC13 | 0.0289 | −0.0272 |
| ALDH7A1 | 0.0583 | −0.0549 | SPACA5B | 0.0422 | −0.0398 | RAB36 | 0.0289 | −0.0272 |
| PALMD | 0.0577 | −0.0543 | DUXAP3 | 0.0417 | −0.0393 | ALPL | 0.0289 | −0.0272 |
| S100A7 | 0.0575 | −0.0541 | UBE2W | −0.0412 | 0.0388 | RAB26 | 0.0285 | −0.0268 |
| REG1B | 0.0571 | −0.0537 | EHHADH | −0.0401 | 0.0377 | DLG1 | −0.0283 | 0.0266 |
| MID1 | −0.0566 | 0.0533 | SPRR2E | 0.0373 | −0.0351 | RAB33B | −0.0281 | 0.0264 |
| CXCL10 | −0.0565 | 0.0532 | ZNF121 | −0.0372 | 0.035 | PPOX | 0.028 | −0.0263 |
| CYMP | 0.0277 | −0.0261 | MYOCD | 0.0183 | −0.0172 | CD3EAP | −0.0059 | 0.0055 |
| SIM2 | −0.0261 | 0.0245 | SPRR4 | 0.0182 | −0.0171 | ANXA1 | 0.0058 | −0.0054 |
| OR4F4 | 0.0259 | −0.0244 | KRT7 | 0.0175 | −0.0165 | B3GALNT1 | −0.0055 | 0.0052 |
| PAK2 | −0.0259 | 0.0244 | HIST1H2BH | −0.0175 | 0.0165 | TMEM183B | −0.0055 | 0.0051 |
| NMD3 | −0.0251 | 0.0236 | MAB21L2 | 0.0171 | −0.0161 | GPR152 | 0.0049 | −0.0046 |
| FBN3 | −0.0247 | 0.0232 | MAS1 | 0.0165 | −0.0155 | CTSG | 0.0042 | −0.004 |
| PSCA | 0.0243 | −0.0229 | FZD4 | 0.0159 | −0.015 | RASL12 | 0.0042 | −0.004 |
| OR5AR1 | 0.0239 | −0.0225 | SNORD87 | −0.0158 | 0.0149 | CLEC4G | 0.0034 | −0.0032 |
| LCA5L | 0.0236 | −0.0222 | SCARA5 | 0.0149 | −0.014 | NCBP2 | −0.0032 | 0.003 |
| MMP12 | −0.0229 | 0.0216 | DHRS2 | −0.0143 | 0.0135 | TRIB1 | 0.0023 | −0.0021 |
| TYW1 | −0.0223 | 0.021 | ANKRD35 | 0.014 | −0.0131 | ZNF10 | −0.0019 | 0.0018 |
| MDH1B | 0.0222 | −0.0209 | LRP5 | −0.0129 | 0.0121 | TRIO | −0.0018 | 0.0017 |
| C15orf62 | 0.0221 | −0.0208 | OR52K2 | 0.0127 | −0.012 | SLC5A8 | 0.001 | −0.0009 |

TABLE 2-continued

Example DEG signature comprising 291 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| BTBD2 | −0.0219 | 0.0206 | RPL39L | −0.0125 | 0.0118 | FBXL18 | −0.0009 | 0.0009 |
| ZNF703 | −0.0219 | 0.0206 | C1orf116 | 0.0118 | −0.0111 | MYH14 | 0.0008 | −0.0007 |
| PPFIA2 | 0.0217 | −0.0204 | HLA-DQA2 | 0.0115 | −0.0109 | OR2AT4 | 0.0001 | −0.0001 |
| MRAP | 0.0212 | −0.02 | OR52R1 | 0.0107 | −0.01 | | | |
| MYOM3 | 0.0212 | −0.0199 | CEACAM5 | 0.0106 | −0.01 | | | |
| LCN2 | 0.0205 | −0.0193 | EIF2AK1 | −0.0098 | 0.0092 | | | |
| ZMYND15 | 0.0205 | −0.0193 | EPS8L1 | 0.0079 | −0.0074 | | | |
| FUT3 | 0.0195 | −0.0183 | SLC22A8 | 0.0077 | −0.0073 | | | |
| GDF3 | 0.0193 | −0.0181 | SNW1 | −0.0073 | 0.0069 | | | |
| REM1 | 0.019 | −0.0179 | C1QTNF1 | 0.0072 | −0.0068 | | | |
| NOL10 | −0.0188 | 0.0177 | MPV17L | 0.007 | −0.0066 | | | |
| RUNDC3B | 0.0187 | −0.0176 | ATP8A2 | 0.0062 | −0.0059 | | | |

TABLE 3

Example DEG signature comprising 211 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| KLK7 | 0.4059 | −0.3821 | NEK2 | −0.1893 | 0.1782 | DNAJC19 | −0.1227 | 0.1155 |
| SPNS2 | 0.3728 | −0.3509 | GHR | −0.1812 | 0.1705 | SNORD2 | −0.1133 | 0.1066 |
| CPVL | −0.3254 | 0.3062 | LHX9 | 0.1802 | −0.1696 | CBS | −0.1111 | 0.1046 |
| FER1L6 | 0.3095 | −0.2913 | ABCG4 | 0.1768 | −0.1664 | HTR2A | 0.1105 | −0.104 |
| ATP12A | 0.3039 | −0.286 | GABRB1 | 0.1707 | −0.1606 | CD164L2 | 0.108 | −0.1017 |
| KLK12 | 0.3007 | −0.283 | ZIC2 | −0.1674 | 0.1575 | SLC29A4 | −0.1079 | 0.1016 |
| ADCYAP1 | 0.2816 | −0.265 | KRTAP13-1 | 0.159 | −0.1497 | RPL7 | −0.1062 | 0.1 |
| RASIP1 | 0.2805 | −0.264 | LCE6A | 0.1494 | −0.1406 | ZFP37 | −0.1061 | 0.0998 |
| KLK6 | 0.2785 | −0.2622 | MIOX | 0.1441 | −0.1357 | SLC6A11 | 0.106 | −0.0998 |
| KLK5 | 0.2604 | −0.2451 | CHST6 | 0.1431 | −0.1347 | PLAT | 0.1055 | −0.0993 |
| NCCRP1 | 0.2543 | −0.2393 | RBAK | −0.143 | 0.1345 | PRSS3 | 0.1041 | −0.098 |
| RHCG | 0.2535 | −0.2386 | CSN3 | 0.1382 | −0.13 | ELAVL1 | −0.1037 | 0.0976 |
| IGFL1 | 0.2462 | −0.2317 | ASCL2 | −0.1328 | 0.125 | SOX17 | 0.1035 | −0.0974 |
| GDPD3 | 0.2253 | −0.212 | MPP6 | −0.1322 | 0.1245 | SLC13A5 | 0.1033 | −0.0972 |
| MLPH | 0.2239 | −0.2107 | LYPD3 | 0.1319 | −0.1242 | SLC6A14 | 0.1024 | −0.0964 |
| OR5B3 | 0.2222 | −0.2091 | ZNF804B | 0.1315 | −0.1237 | SMYD3 | −0.0974 | 0.0917 |
| MT1F | −0.2181 | 0.2052 | RSRC1 | −0.1312 | 0.1235 | ITPKA | −0.0966 | 0.0909 |
| OR52K1 | 0.2174 | −0.2046 | PANX3 | 0.1312 | −0.1234 | STAB2 | 0.095 | −0.0894 |
| KRT23 | 0.2165 | −0.2037 | SPRR2B | 0.1289 | −0.1213 | IFFO2 | 0.0935 | −0.088 |
| DHRS9 | 0.2141 | −0.2015 | TMPRSS11D | 0.1281 | −0.1206 | MYNN | −0.092 | 0.0866 |
| SULT2B1 | 0.2098 | −0.1975 | UNC93A | 0.1262 | −0.1188 | PDE3B | −0.0914 | 0.0861 |
| CST6 | 0.199 | −0.1872 | INO80B | −0.1239 | 0.1166 | KLK10 | 0.0899 | −0.0846 |
| SBSN | 0.1927 | −0.1814 | CLIC3 | 0.1235 | −0.1163 | HIST1H2AA | 0.0888 | −0.0835 |
| PRAME | −0.1927 | 0.1814 | MAD2L1 | −0.1229 | 0.1157 | ZNF614 | −0.0884 | 0.0832 |
| H19 | 0.0872 | −0.0821 | NOD2 | 0.0705 | −0.0663 | SERPINB3 | 0.0521 | −0.049 |
| GPNMB | −0.0865 | 0.0815 | SORBS1 | 0.0703 | −0.0662 | GRM3 | 0.0515 | −0.0485 |
| E2F7 | −0.0861 | 0.081 | KRTAP8-1 | 0.0703 | −0.0662 | KRTDAP | 0.0504 | −0.0475 |
| SERPINB4 | 0.085 | −0.08 | E2F3 | −0.0688 | 0.0647 | PRSS27 | 0.0484 | −0.0456 |
| SLC4A11 | 0.0844 | −0.0794 | C2orf78 | 0.068 | −0.064 | VPS37D | −0.048 | 0.0452 |
| HES5 | 0.0833 | −0.0784 | ZNF721 | −0.0672 | 0.0632 | MYL3 | 0.0475 | −0.0447 |
| ALOX12B | 0.0828 | −0.0779 | SKAP2 | −0.0641 | 0.0604 | EBF1 | 0.0475 | −0.0447 |
| VAX2 | −0.0821 | 0.0773 | IRF7 | 0.0628 | −0.0591 | SP6 | 0.0474 | −0.0446 |
| FAM3D | 0.0814 | −0.0766 | MEOX1 | 0.0627 | −0.059 | PBOV1 | 0.0465 | −0.0438 |
| OR52B6 | 0.0813 | −0.0765 | TEX14 | 0.0624 | −0.0587 | ID1 | 0.0462 | −0.0435 |
| OR2B11 | 0.0805 | −0.0757 | G6PC | 0.0615 | −0.0579 | ANLN | −0.0453 | 0.0426 |
| KLK8 | 0.0802 | −0.0755 | CCDC59 | −0.061 | 0.0574 | MIPOL1 | −0.0452 | 0.0425 |
| NKAIN2 | −0.08 | 0.0753 | SCML2 | −0.0598 | 0.0563 | C19orf33 | 0.0448 | −0.0422 |
| NOS1 | 0.0788 | −0.0742 | MAGEA9B | −0.0589 | 0.0554 | SCEL | 0.0434 | −0.0409 |
| PEG10 | −0.0788 | 0.0741 | ZSCAN4 | 0.0581 | −0.0547 | ZNF284 | 0.0427 | −0.0401 |
| HOXC8 | −0.0785 | 0.0739 | CRABP2 | 0.0575 | −0.0541 | MIR554 | 0.0406 | −0.0382 |
| ABHD8 | −0.0771 | 0.0726 | TRIM16 | 0.0574 | −0.054 | SH3TC1 | 0.0399 | −0.0375 |
| CLDN5 | 0.0761 | −0.0716 | TFAP4 | −0.0572 | 0.0539 | STC2 | −0.0397 | 0.0374 |
| MCM10 | −0.0754 | 0.0709 | C19orf54 | −0.0555 | 0.0522 | DEFB122 | 0.0394 | −0.0371 |
| PI3 | 0.0753 | −0.0709 | HIST1H4F | 0.0545 | −0.0513 | OR14J1 | 0.0376 | −0.0354 |
| ADCY4 | 0.0742 | −0.0699 | IFNA21 | 0.0539 | −0.0507 | ZNF777 | −0.0375 | 0.0353 |
| HOXC9 | −0.074 | 0.0697 | CA1 | 0.0531 | −0.05 | NRSN1 | 0.0374 | −0.0352 |
| FANCL | −0.0726 | 0.0683 | ZYG11A | 0.0525 | −0.0494 | FRAS1 | −0.0363 | 0.0341 |
| RDH13 | 0.0722 | −0.068 | CDA | 0.0521 | −0.0491 | ECM1 | 0.0361 | −0.034 |
| ANGPT4 | 0.0359 | −0.0338 | CRIP1 | 0.0271 | −0.0256 | CXXC5 | 0.0143 | −0.0134 |
| GABRP | 0.0354 | −0.0333 | ALDH7A1 | 0.0271 | −0.0255 | NGEF | 0.0114 | −0.0108 |
| OIP5 | −0.0343 | 0.0323 | PALMD | 0.0265 | −0.025 | SPACA5B | 0.011 | −0.0104 |
| DNAJC5G | 0.034 | −0.032 | S100A7 | 0.0263 | −0.0248 | DUXAP3 | 0.0105 | −0.0099 |
| HOXD10 | −0.034 | 0.032 | REG1B | 0.0259 | −0.0243 | UBE2W | −0.01 | 0.0094 |
| B3GALT4 | 0.034 | −0.032 | MID1 | −0.0254 | 0.0239 | EHHADH | −0.0088 | 0.0083 |

TABLE 3-continued

Example DEG signature comprising 211 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| IGF2BP3 | −0.0323 | 0.0304 | CXCL10 | −0.0253 | 0.0238 | SPRR2E | 0.0061 | −0.0057 |
| UBL4B | 0.0315 | −0.0297 | HSD17B3 | 0.0251 | −0.0236 | ZNF121 | −0.0059 | 0.0056 |
| IL4R | 0.0313 | −0.0295 | HCN1 | 0.0227 | −0.0214 | ECSCR | 0.0053 | −0.005 |
| ACTL6A | −0.0313 | 0.0295 | PRSS22 | 0.021 | −0.0197 | FOXI2 | 0.0052 | −0.0049 |
| PCDHB13 | −0.0313 | 0.0294 | SPP1 | −0.0209 | 0.0197 | FGD5 | 0.0041 | −0.0038 |
| NKX2-1 | 0.031 | −0.0291 | MUC16 | 0.0209 | −0.0196 | LY6G6C | 0.0034 | −0.0032 |
| SSX2 | 0.0309 | −0.0291 | HOXC10 | −0.0206 | 0.0193 | INTS10 | 0.0033 | −0.0031 |
| HIST2H3A | −0.0307 | 0.0289 | ZNF124 | −0.0197 | 0.0185 | KRT16 | 0.003 | −0.0028 |
| MND1 | −0.0307 | 0.0289 | PTPRB | 0.0188 | −0.0177 | RNF126P1 | 0.003 | −0.0028 |
| SCN8A | −0.0306 | 0.0288 | TMEM41A | −0.0182 | 0.0171 | PFN2 | −0.0016 | 0.0015 |
| OR5B12 | 0.0304 | −0.0286 | INPP4B | 0.0182 | −0.0171 | PLD2 | 0.0009 | −0.0009 |
| CLDN16 | −0.0299 | 0.0281 | FBXO16 | 0.0172 | −0.0162 | KCNS1 | 0.0007 | −0.0006 |
| SLC17A4 | 0.0296 | −0.0279 | TMEM45B | 0.0164 | −0.0154 | KCNJ3 | 0.0002 | −0.0002 |
| RRM2B | −0.0292 | 0.0274 | MED28 | −0.0159 | 0.0149 | | | |
| GATA4 | −0.0289 | 0.0272 | SORCS2 | 0.0158 | −0.0148 | | | |
| TGM5 | 0.0279 | −0.0262 | GSTM5 | 0.0157 | −0.0148 | | | |
| LOR | 0.0277 | −0.0261 | OR51Q1 | 0.0153 | −0.0144 | | | |
| KRT78 | 0.0275 | −0.0259 | OR4E2 | 0.0146 | −0.0137 | | | |

TABLE 4

Example DEG signature comprising 155 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| KLK7 | 0.3747 | −0.3527 | NEK2 | −0.1581 | 0.1488 | DNAJC19 | −0.0915 | 0.0861 |
| SPNS2 | 0.3416 | −0.3215 | GHR | −0.15 | 0.1411 | SNORD2 | −0.082 | 0.0772 |
| CPVL | −0.2941 | 0.2768 | LHX9 | 0.149 | −0.1402 | CBS | −0.0799 | 0.0752 |
| FER1L6 | 0.2783 | −0.2619 | ABCG4 | 0.1456 | −0.137 | HTR2A | 0.0793 | −0.0746 |
| ATP12A | 0.2727 | −0.2566 | GABRB1 | 0.1395 | −0.1313 | CD164L2 | 0.0768 | −0.0723 |
| KLK12 | 0.2694 | −0.2536 | ZIC2 | −0.1361 | 0.1281 | SLC29A4 | −0.0767 | 0.0722 |
| ADCYAP1 | 0.2504 | −0.2356 | KRTAP13-1 | 0.1278 | −0.1203 | RPL7 | −0.075 | 0.0706 |
| RASIP1 | 0.2492 | −0.2346 | LCE6A | 0.1182 | −0.1112 | ZFP37 | −0.0748 | 0.0704 |
| KLK6 | 0.2473 | −0.2328 | MIOX | 0.1129 | −0.1063 | SLC6A11 | 0.0748 | −0.0704 |
| KLK5 | 0.2292 | −0.2157 | CHST6 | 0.1119 | −0.1053 | PLAT | 0.0743 | −0.0699 |
| NCCRP1 | 0.2231 | −0.2099 | RBAK | −0.1117 | 0.1052 | PRSS3 | 0.0729 | −0.0686 |
| RHCG | 0.2222 | −0.2092 | CSN3 | 0.1069 | −0.1006 | ELAVL1 | −0.0725 | 0.0682 |
| IGFL1 | 0.215 | −0.2023 | ASCL2 | −0.1016 | 0.0956 | SOX17 | 0.0723 | −0.068 |
| GDPD3 | 0.1941 | −0.1827 | MPP6 | −0.101 | 0.0951 | SLC13A5 | 0.072 | −0.0678 |
| MLPH | 0.1926 | −0.1813 | LYPD3 | 0.1007 | −0.0948 | SLC6A14 | 0.0712 | −0.067 |
| OR5B3 | 0.1909 | −0.1797 | ZNF804B | 0.1002 | −0.0944 | SMYD3 | −0.0662 | 0.0623 |
| MT1F | −0.1869 | 0.1759 | RSRC1 | −0.1 | 0.0941 | ITPKA | −0.0654 | 0.0615 |
| OR52K1 | 0.1862 | −0.1752 | PANX3 | 0.0999 | −0.0941 | STAB2 | 0.0637 | −0.06 |
| KRT23 | 0.1852 | −0.1743 | SPRR2B | 0.0977 | −0.0919 | IFFO2 | 0.0622 | −0.0586 |
| DHRS9 | 0.1829 | −0.1722 | TMPRSS11D | 0.0969 | −0.0912 | MYNN | −0.0608 | 0.0572 |
| SULT2B1 | 0.1786 | −0.1681 | UNC93A | 0.095 | −0.0894 | PDE3B | −0.0602 | 0.0567 |
| CST6 | 0.1677 | −0.1579 | INO80B | −0.0927 | 0.0872 | KLK10 | 0.0587 | −0.0552 |
| SBSN | 0.1615 | −0.152 | CLIC3 | 0.0923 | −0.0869 | HIST1H2AA | 0.0575 | −0.0541 |
| PRAME | −0.1615 | 0.152 | MAD2L1 | −0.0917 | 0.0863 | ZNF614 | −0.0571 | 0.0538 |
| H19 | 0.056 | −0.0527 | NOD2 | 0.0392 | −0.0369 | SERPINB3 | 0.0208 | −0.0196 |
| GPNMB | −0.0553 | 0.0521 | SORBS1 | 0.0391 | −0.0368 | GRM3 | 0.0203 | −0.0191 |
| E2F7 | −0.0549 | 0.0517 | KRTAP8-1 | 0.0391 | −0.0368 | KRTDAP | 0.0192 | −0.0181 |
| SERPINB4 | 0.0538 | −0.0506 | E2F3 | −0.0376 | 0.0353 | PRSS27 | 0.0172 | −0.0162 |
| SLC4A11 | 0.0532 | −0.05 | C2orf78 | 0.0368 | −0.0346 | VPS37D | −0.0168 | 0.0158 |
| HES5 | 0.0521 | −0.049 | ZNF721 | −0.0359 | 0.0338 | MYL3 | 0.0163 | −0.0153 |
| ALOX12B | 0.0516 | −0.0486 | SKAP2 | −0.0329 | 0.031 | EBF1 | 0.0163 | −0.0153 |
| VAX2 | −0.0509 | 0.0479 | IRF7 | 0.0316 | −0.0297 | SP6 | 0.0162 | −0.0152 |
| FAM3D | 0.0502 | −0.0472 | MEOX1 | 0.0315 | −0.0296 | PBOV1 | 0.0153 | −0.0144 |
| OR52B6 | 0.0501 | −0.0471 | TEX14 | 0.0312 | −0.0293 | ID1 | 0.015 | −0.0141 |
| OR2B11 | 0.0493 | −0.0464 | G6PC | 0.0303 | −0.0285 | ANLN | −0.014 | 0.0132 |
| KLK8 | 0.049 | −0.0461 | CCDC59 | −0.0297 | 0.028 | MIPOL1 | −0.014 | 0.0131 |
| NKAIN2 | −0.0488 | 0.0459 | SCML2 | −0.0286 | 0.0269 | C19orf33 | 0.0136 | −0.0128 |
| NOS1 | 0.0476 | −0.0448 | MAGEA9B | −0.0277 | 0.026 | SCEL | 0.0122 | −0.0115 |
| PEG10 | −0.0476 | 0.0448 | ZSCAN4 | 0.0269 | −0.0253 | ZNF284 | 0.0114 | −0.0108 |
| HOXC8 | −0.0473 | 0.0445 | CRABP2 | 0.0262 | −0.0247 | MIR554 | 0.0093 | −0.0088 |
| ABHD8 | −0.0459 | 0.0432 | TRIM16 | 0.0261 | −0.0246 | SH3TC1 | 0.0087 | −0.0082 |
| CLDN5 | 0.0449 | −0.0423 | TFAP4 | −0.026 | 0.0245 | STC2 | −0.0085 | 0.008 |
| MCM10 | −0.0441 | 0.0415 | C19orf54 | −0.0243 | 0.0228 | DEFB122 | 0.0082 | −0.0077 |
| PI3 | 0.0441 | −0.0415 | HIST1H4F | 0.0233 | −0.0219 | OR14J1 | 0.0063 | −0.006 |
| ADCY4 | 0.043 | −0.0405 | IFNA21 | 0.0227 | −0.0213 | ZNF777 | −0.0063 | 0.0059 |
| HOXC9 | −0.0428 | 0.0403 | CA1 | 0.0219 | −0.0206 | NRSN1 | 0.0062 | −0.0058 |
| FANCL | −0.0414 | 0.039 | ZYG11A | 0.0213 | −0.0201 | FRAS1 | −0.0051 | 0.0048 |
| RDH13 | 0.041 | −0.0386 | CDA | 0.0209 | −0.0197 | ECM1 | 0.0049 | −0.0046 |

TABLE 4-continued

| Example DEG signature comprising 155 genes (gene weights are given in columns X0.score and X1.score) | | | | | | | | |
|---|---|---|---|---|---|---|---|---|
| GENE ID | X0.score | X1.score | GENE ID | X0.score | X1.score | GENE ID | X0.score | X1.score |
| ANGPT4 | 0.0047 | −0.0044 | | | | | | |
| GABRP | 0.0042 | −0.004 | | | | | | |
| OIP5 | −0.0031 | 0.0029 | | | | | | |
| DNAJC5G | 0.0028 | −0.0026 | | | | | | |
| HOXD10 | −0.0028 | 0.0026 | | | | | | |
| B3GALT4 | 0.0028 | −0.0026 | | | | | | |
| IGF2BP3 | −0.001 | 0.001 | | | | | | |
| UBL4B | 0.0003 | −0.0003 | | | | | | |
| IL4R | 0.0001 | −0.0001 | | | | | | |
| ACTL6A | −0.0001 | 0.0001 | | | | | | |
| PCDHB13 | −0.0001 | 0.0001 | | | | | | |

TABLE 5

| Example DEG signature comprising 105 genes (gene weights are given in columns X0.score and X1.score) | | | | | | | | |
|---|---|---|---|---|---|---|---|---|
| GENE ID | X0.score | X1.score | GENE ID | X0.score | X1.score | GENE ID | X0.score | X1.score |
| KLK7 | 0.3435 | −0.3233 | NEK2 | −0.1269 | 0.1194 | DNAJC19 | −0.0603 | 0.0567 |
| SPNS2 | 0.3104 | −0.2921 | GHR | −0.1187 | 0.1118 | SNORD2 | −0.0508 | 0.0478 |
| CPVL | −0.2629 | 0.2475 | LHX9 | 0.1177 | −0.1108 | CBS | −0.0487 | 0.0458 |
| FER1L6 | 0.247 | −0.2325 | ABCG4 | 0.1144 | −0.1077 | HTR2A | 0.0481 | −0.0452 |
| ATP12A | 0.2414 | −0.2272 | GABRB1 | 0.1082 | −0.1019 | CD164L2 | 0.0456 | −0.0429 |
| KLK12 | 0.2382 | −0.2242 | ZIC2 | −0.1049 | 0.0987 | SLC29A4 | −0.0455 | 0.0428 |
| ADCYAP1 | 0.2191 | −0.2062 | KRTAP13-1 | 0.0966 | −0.0909 | RPL7 | −0.0438 | 0.0412 |
| RASIP1 | 0.218 | −0.2052 | LCE6A | 0.087 | −0.0818 | ZFP37 | −0.0436 | 0.041 |
| KLK6 | 0.2161 | −0.2034 | MIOX | 0.0817 | −0.0769 | SLC6A11 | 0.0436 | −0.041 |
| KLK5 | 0.198 | −0.1863 | CHST6 | 0.0807 | −0.0759 | PLAT | 0.0431 | −0.0405 |
| NCCRP1 | 0.1918 | −0.1806 | RBAK | −0.0805 | 0.0758 | PRSS3 | 0.0417 | −0.0392 |
| RHCG | 0.191 | −0.1798 | CSN3 | 0.0757 | −0.0713 | ELAVL1 | −0.0413 | 0.0389 |
| IGFL1 | 0.1837 | −0.1729 | ASCL2 | −0.0703 | 0.0662 | SOX17 | 0.041 | −0.0386 |
| GDPD3 | 0.1628 | −0.1533 | MPP6 | −0.0698 | 0.0657 | SLC13A5 | 0.0408 | −0.0384 |
| MLPH | 0.1614 | −0.1519 | LYPD3 | 0.0695 | −0.0654 | SLC6A14 | 0.0399 | −0.0376 |
| OR5B3 | 0.1597 | −0.1503 | ZNF804B | 0.069 | −0.065 | SMYD3 | −0.035 | 0.0329 |
| MT1F | −0.1556 | 0.1465 | RSRC1 | −0.0688 | 0.0647 | ITPKA | −0.0341 | 0.0321 |
| OR52K1 | 0.155 | −0.1458 | PANX3 | 0.0687 | −0.0647 | STAB2 | 0.0325 | −0.0306 |
| KRT23 | 0.154 | −0.1449 | SPRR2B | 0.0664 | −0.0625 | IFFO2 | 0.031 | −0.0292 |
| DHRS9 | 0.1517 | −0.1428 | TMPRSS11D | 0.0657 | −0.0618 | MYNN | −0.0295 | 0.0278 |
| SULT2B1 | 0.1474 | −0.1387 | UNC93A | 0.0637 | −0.06 | PDE3B | −0.029 | 0.0273 |
| CST6 | 0.1365 | −0.1285 | INO80B | −0.0615 | 0.0579 | KLK10 | 0.0274 | −0.0258 |
| SBSN | 0.1303 | −0.1226 | CLIC3 | 0.0611 | −0.0575 | HIST1H2AA | 0.0263 | −0.0248 |
| PRAME | −0.1303 | 0.1226 | MAD2L1 | −0.0605 | 0.0569 | ZNF614 | −0.0259 | 0.0244 |
| H19 | 0.0248 | −0.0233 | NOD2 | 0.008 | −0.0076 | | | |
| GPNMB | −0.0241 | 0.0227 | SORBS1 | 0.0079 | −0.0074 | | | |
| E2F7 | −0.0237 | 0.0223 | KRTAP8-1 | 0.0079 | −0.0074 | | | |
| SERPINB4 | 0.0226 | −0.0212 | E2F3 | −0.0063 | 0.006 | | | |
| SLC4A11 | 0.0219 | −0.0206 | C2orf78 | 0.0056 | −0.0052 | | | |
| HES5 | 0.0208 | −0.0196 | ZNF721 | −0.0047 | 0.0044 | | | |
| ALOX12B | 0.0204 | −0.0192 | SKAP2 | −0.0017 | 0.0016 | | | |
| VAX2 | −0.0196 | 0.0185 | IRF7 | 0.0004 | −0.0003 | | | |
| FAM3D | 0.0189 | −0.0178 | MEOX1 | 0.0003 | −0.0002 | | | |
| OR52B6 | 0.0188 | −0.0177 | | | | | | |
| OR2B11 | 0.018 | −0.017 | | | | | | |
| KLK8 | 0.0178 | −0.0167 | | | | | | |
| NKAIN2 | −0.0176 | 0.0165 | | | | | | |
| NOS1 | 0.0163 | −0.0154 | | | | | | |
| PEG10 | −0.0163 | 0.0154 | | | | | | |
| HOXC8 | −0.0161 | 0.0151 | | | | | | |
| ABHD8 | −0.0147 | 0.0138 | | | | | | |
| CLDN5 | 0.0137 | −0.0129 | | | | | | |
| MCM10 | −0.0129 | 0.0121 | | | | | | |
| PI3 | 0.0129 | −0.0121 | | | | | | |
| ADCY4 | 0.0118 | −0.0111 | | | | | | |
| HOXC9 | −0.0116 | 0.0109 | | | | | | |
| FANCL | −0.0102 | 0.0096 | | | | | | |
| RDH13 | 0.0098 | −0.0092 | | | | | | |

TABLE 6

Example DEG signature comprising 66 genes (gene weights are given in columns X0.score and X1.score)

| GENE ID | X0.score | X1.score | GENE ID | X0.score | X1.score | GENE ID | X0.score | X1.score |
|---|---|---|---|---|---|---|---|---|
| KLK7 | 0.3123 | −0.2939 | NEK2 | −0.0956 | 0.09 | DNAJC19 | −0.0291 | 0.0274 |
| SPNS2 | 0.2792 | −0.2627 | GHR | −0.0875 | 0.0824 | SNORD2 | −0.0196 | 0.0184 |
| CPVL | −0.2317 | 0.2181 | LHX9 | 0.0865 | −0.0814 | CBS | −0.0175 | 0.0164 |
| FER1L6 | 0.2158 | −0.2031 | ABCG4 | 0.0832 | −0.0783 | HTR2A | 0.0168 | −0.0158 |
| ATP12A | 0.2102 | −0.1978 | GABRB1 | 0.077 | −0.0725 | CD164L2 | 0.0143 | −0.0135 |
| KLK12 | 0.207 | −0.1948 | ZIC2 | −0.0737 | 0.0693 | SLC29A4 | −0.0142 | 0.0134 |
| ADCYAP1 | 0.1879 | −0.1768 | KRTAP13-1 | 0.0654 | −0.0615 | RPL7 | −0.0126 | 0.0118 |
| RASIP1 | 0.1868 | −0.1758 | LCE6A | 0.0557 | −0.0525 | ZFP37 | −0.0124 | 0.0116 |
| KLK6 | 0.1849 | −0.174 | MIOX | 0.0505 | −0.0475 | SLC6A11 | 0.0124 | −0.0116 |
| KLK5 | 0.1668 | −0.157 | CHST6 | 0.0494 | −0.0465 | PLAT | 0.0118 | −0.0111 |
| NCCRP1 | 0.1606 | −0.1512 | RBAK | −0.0493 | 0.0464 | PRSS3 | 0.0104 | −0.0098 |
| RHCG | 0.1598 | −0.1504 | CSN3 | 0.0445 | −0.0419 | ELAVL1 | −0.0101 | 0.0095 |
| IGFL1 | 0.1525 | −0.1436 | ASCL2 | −0.0391 | 0.0368 | SOX17 | 0.0098 | −0.0092 |
| GDPD3 | 0.1316 | −0.1239 | MPP6 | −0.0386 | 0.0363 | SLC13A5 | 0.0096 | −0.009 |
| MLPH | 0.1302 | −0.1225 | LYPD3 | 0.0383 | −0.036 | SLC6A14 | 0.0087 | −0.0082 |
| OR5B3 | 0.1285 | −0.1209 | ZNF804B | 0.0378 | −0.0356 | SMYD3 | −0.0037 | 0.0035 |
| MT1F | −0.1244 | 0.1171 | RSRC1 | −0.0376 | 0.0354 | ITPKA | −0.0029 | 0.0027 |
| OR52K1 | 0.1237 | −0.1165 | PANX3 | 0.0375 | −0.0353 | STAB2 | 0.0013 | −0.0012 |
| KRT23 | 0.1228 | −0.1156 | SPRR2B | 0.0352 | −0.0331 | | | |
| DHRS9 | 0.1205 | −0.1134 | TMPRSS11D | 0.0345 | −0.0324 | | | |
| SULT2B1 | 0.1161 | −0.1093 | UNC93A | 0.0325 | −0.0306 | | | |
| CST6 | 0.1053 | −0.0991 | INO80B | −0.0302 | 0.0285 | | | |
| SBSN | 0.099 | −0.0932 | CLIC3 | 0.0299 | −0.0281 | | | |
| PRAME | −0.099 | 0.0932 | MAD2L1 | −0.0292 | 0.0275 | | | |

TABLE 7

Example DEG signature comprising 45 genes (gene weights are given in columns X0.score and X1.score)

| GENE ID | X0.score | X1.score | GENE ID | X0.score | X1.score |
|---|---|---|---|---|---|
| KLK7 | 0.281 | −0.2645 | NEK2 | −0.0644 | 0.0606 |
| SPNS2 | 0.2479 | −0.2334 | GHR | −0.0563 | 0.053 |
| CPVL | −0.2005 | 0.1887 | LHX9 | 0.0553 | −0.052 |
| FER1L6 | 0.1846 | −0.1737 | ABCG4 | 0.0519 | −0.0489 |
| ATP12A | 0.179 | −0.1684 | GABRB1 | 0.0458 | −0.0431 |
| KLK12 | 0.1758 | −0.1654 | ZIC2 | −0.0424 | 0.04 |
| ADCYAP1 | 0.1567 | −0.1475 | KRTAP13-1 | 0.0341 | −0.0321 |
| RASIP1 | 0.1556 | −0.1464 | LCE6A | 0.0245 | −0.0231 |
| KLK6 | 0.1536 | −0.1446 | MIOX | 0.0192 | −0.0181 |
| KLK5 | 0.1355 | −0.1276 | CHST6 | 0.0182 | −0.0172 |
| NCCRP1 | 0.1294 | −0.1218 | RBAK | −0.0181 | 0.017 |
| RHCG | 0.1286 | −0.121 | CSN3 | 0.0133 | −0.0125 |
| IGFL1 | 0.1213 | −0.1142 | ASCL2 | −0.0079 | 0.0074 |
| GDPD3 | 0.1004 | −0.0945 | MPP6 | −0.0073 | 0.0069 |
| MLPH | 0.099 | −0.0931 | LYPD3 | 0.007 | −0.0066 |
| OR5B3 | 0.0973 | −0.0915 | ZNF804B | 0.0066 | −0.0062 |
| MT1F | −0.0932 | 0.0877 | RSRC1 | −0.0063 | 0.006 |
| OR52K1 | 0.0925 | −0.0871 | PANX3 | 0.0063 | −0.0059 |
| KRT23 | 0.0915 | −0.0862 | SPRR2B | 0.004 | −0.0038 |
| DHRS9 | 0.0892 | −0.084 | TMPRSS11D | 0.0032 | −0.003 |
| SULT2B1 | 0.0849 | −0.0799 | UNC93A | 0.0013 | −0.0012 |
| CST6 | 0.074 | −0.0697 | | | |
| SBSN | 0.0678 | −0.0638 | | | |
| PRAME | −0.0678 | 0.0638 | | | |

TABLE 8

Example DEG signature comprising 31 genes (gene weights are given in columns X0.score and X1.score)

| GENE ID | X0.score | X1.score | GENE ID | X0.score | X1.score |
|---|---|---|---|---|---|
| KLK7 | 0.2498 | −0.2351 | NEK2 | −0.0332 | 0.0312 |
| SPNS2 | 0.2167 | −0.204 | GHR | −0.0251 | 0.0236 |
| CPVL | −0.1692 | 0.1593 | LHX9 | 0.024 | −0.0226 |
| FER1L6 | 0.1534 | −0.1443 | ABCG4 | 0.0207 | −0.0195 |
| ATP12A | 0.1477 | −0.1391 | GABRB1 | 0.0146 | −0.0137 |

TABLE 8-continued

Example DEG signature comprising 31 genes (gene weights
are given in columns X0.score and X1.score)

| GENE ID | X0.score | X1.score | GENE ID | X0.score | X1.score |
|---|---|---|---|---|---|
| KLK12 | 0.1445 | −0.136 | ZIC2 | −0.0112 | 0.0106 |
| ADCYAP1 | 0.1254 | −0.1181 | KRTAP13-1 | 0.0029 | −0.0027 |
| RASIP1 | 0.1243 | −0.117 | | | |
| KLK6 | 0.1224 | −0.1152 | | | |
| KLK5 | 0.1043 | −0.0982 | | | |
| NCCRP1 | 0.0982 | −0.0924 | | | |
| RHCG | 0.0973 | −0.0916 | | | |
| IGFL1 | 0.0901 | −0.0848 | | | |
| GDPD3 | 0.0692 | −0.0651 | | | |
| MLPH | 0.0677 | −0.0638 | | | |
| OR5B3 | 0.066 | −0.0621 | | | |
| MT1F | −0.0619 | 0.0583 | | | |
| OR52K1 | 0.0613 | −0.0577 | | | |
| KRT23 | 0.0603 | −0.0568 | | | |
| DHRS9 | 0.058 | −0.0546 | | | |
| SULT2B1 | 0.0537 | −0.0505 | | | |
| CST6 | 0.0428 | −0.0403 | | | |
| SBSN | 0.0366 | −0.0344 | | | |
| PRAME | −0.0366 | 0.0344 | | | |

TABLE 9

Example DEG signature comprising 25 genes (gene weights
are given in columns X0.score and X1.score)

| GENE ID | X0.score | X1.score | GENE ID | X0.score | X1.score |
|---|---|---|---|---|---|
| KLK7 | 0.2186 | −0.2057 | NEK2 | −0.0019 | 0.0018 |
| SPNS2 | 0.1855 | −0.1746 | | | |
| CPVL | −0.138 | 0.1299 | | | |
| FER1L6 | 0.1221 | −0.1149 | | | |
| ATP12A | 0.1165 | −0.1097 | | | |
| KLK12 | 0.1133 | −0.1066 | | | |
| ADCYAP1 | 0.0942 | −0.0887 | | | |
| RASIP1 | 0.0931 | −0.0876 | | | |
| KLK6 | 0.0912 | −0.0858 | | | |
| KLK5 | 0.0731 | −0.0688 | | | |
| NCCRP1 | 0.0669 | −0.063 | | | |
| RHCG | 0.0661 | −0.0622 | | | |
| IGFL1 | 0.0588 | −0.0554 | | | |

TABLE 9-continued

Example DEG signature comprising 25 genes (gene weights
are given in columns X0.score and X1.score)

| GENE ID | X0.score | X1.score | GENE ID | X0.score | X1.score |
|---|---|---|---|---|---|
| GDPD3 | 0.0379 | −0.0357 | | | |
| MLPH | 0.0365 | −0.0344 | | | |
| OR5B3 | 0.0348 | −0.0328 | | | |
| MT1F | −0.0307 | 0.0289 | | | |
| OR52K1 | 0.0301 | −0.0283 | | | |
| KRT23 | 0.0291 | −0.0274 | | | |
| DHRS9 | 0.0268 | −0.0252 | | | |
| SULT2B1 | 0.0225 | −0.0211 | | | |
| CST6 | 0.0116 | −0.0109 | | | |
| SBSN | 0.0054 | −0.0051 | | | |
| PRAME | −0.0054 | 0.005 | | | |

TABLE 10

Characteristic parameters and metrics of example DEG signatures presented in Tables 1-9

| DEG Signature Table | Genes | AUC (validation) | AUC (TGCA) | Threshold value | Sensitivity (validation) | Specificity (validation) | Sensitivity (TCGA) | Specificity (TCGA) |
|---|---|---|---|---|---|---|---|---|
| 1 | 397 | 1 | 0.868323 | 0.14 | 1 | 0.621514 | 1 | 0.578378378 |
| 2 | 291 | 1 | 0.812221 | 0.105 | 0.959184 | 0.651394 | 1 | 0.578378378 |
| 3 | 211 | 1 | 0.758964 | 0.04 | 0.693878 | 0.705179 | 1 | 0.578378378 |
| 4 | 155 | 1 | 0.698837 | 0.035 | 0.408163 | 0.756972 | 1 | 0.578378378 |
| 5 | 105 | 1 | 0.636393 | 0.3 | 0.55102 | 0.609562 | 1 | 0.578378378 |
| 6 | 66 | 1 | 0.576795 | 0.34 | 0.428571 | 0.611554 | 1 | 0.578378378 |
| 7 | 45 | 1 | 0.537523 | 0.355 | 0.326531 | 0.621514 | 1 | 0.578378378 |
| 8 | 31 | 1 | 0.520124 | 0.4124 | 0.326531 | 0.593625 | 1 | 0.578378378 |
| 9 | 25 | 1 | 0.510285 | 0.51 | 0.44898 | 0.505976 | 1 | 0.578378378 |

TABLE 11

Example DMP signature comprising 141 DMPs (DMP weights are given in columns X0.score and X1.score)

| DMP ID | X0.score | X1.score | DMP ID | X0.score | X1.score | DMP ID | X0.score | X1.score |
|---|---|---|---|---|---|---|---|---|
| cg07716946 | −0.2803 | 0.3666 | cg09968620 | −0.0861 | 0.1126 | cg10364040 | −0.053 | 0.0693 |
| cg04786287 | −0.2741 | 0.3584 | cg19664945 | −0.0839 | 0.1097 | cg22991101 | −0.0522 | 0.0683 |

TABLE 11-continued

Example DMP signature comprising 141 DMPs (DMP weights are given in columns X0.score and X1.score)

| DMP ID | X0.score | X1.score | DMP ID | X0.score | X1.score | DMP ID | X0.score | X1.score |
|---|---|---|---|---|---|---|---|---|
| cg03782157 | −0.1916 | 0.2505 | cg06685968 | −0.0801 | 0.1048 | cg03222323 | −0.0516 | 0.0675 |
| cg12368188 | −0.1907 | 0.2494 | cg11362010 | −0.079 | 0.1033 | cg21425842 | −0.0502 | 0.0656 |
| cg25829490 | −0.1711 | 0.2237 | cg10759602 | −0.0754 | 0.0986 | cg04233770 | −0.0498 | 0.0651 |
| cg09628195 | −0.1611 | 0.2107 | cg26053832 | −0.0752 | 0.0984 | cg00503383 | −0.0491 | 0.0642 |
| cg20674701 | −0.1581 | 0.2068 | cg27071152 | −0.0749 | 0.098 | cg06530490 | −0.0466 | 0.0609 |
| cg22549870 | −0.1403 | 0.1835 | cg17975443 | −0.0741 | 0.0969 | cg21811143 | −0.0458 | 0.0598 |
| cg02020945 | −0.1384 | 0.181 | cg03366986 | −0.0731 | 0.0956 | cg22674699 | −0.0455 | 0.0595 |
| cg14164044 | −0.1363 | 0.1783 | cg00332153 | −0.0711 | 0.093 | cg00217080 | 0.0452 | −0.0591 |
| cg10210594 | −0.1353 | 0.177 | cg05317090 | −0.0702 | 0.0918 | cg16971668 | −0.0447 | 0.0584 |
| cg22974982 | −0.1241 | 0.1622 | cg00459623 | −0.0692 | 0.0905 | cg13406145 | −0.0445 | 0.0582 |
| cg15545035 | −0.1217 | 0.1591 | cg27622679 | −0.0691 | 0.0904 | cg14290904 | −0.0439 | 0.0574 |
| cg03843000 | −0.1189 | 0.1555 | cg04490714 | −0.0691 | 0.0903 | cg13294849 | −0.0436 | 0.0571 |
| cg16332610 | −0.1059 | 0.1385 | cg20501518 | −0.0689 | 0.09 | cg06316886 | −0.0435 | 0.0569 |
| cg20627174 | −0.1009 | 0.1319 | cg04164058 | −0.0661 | 0.0864 | cg14765959 | −0.0434 | 0.0567 |
| cg07524679 | −0.1008 | 0.1319 | cg14239111 | 0.0647 | −0.0847 | cg18235734 | −0.0433 | 0.0567 |
| cg09570682 | −0.1002 | 0.1311 | cg25371634 | −0.0643 | 0.0841 | cg15281710 | −0.0394 | 0.0516 |
| cg18891712 | −0.0994 | 0.13 | cg01783662 | −0.0636 | 0.0832 | cg26666835 | −0.0393 | 0.0514 |
| cg03892356 | −0.0991 | 0.1296 | cg15888290 | −0.0595 | 0.0777 | cg22669623 | −0.039 | 0.0511 |
| cg26470798 | −0.0984 | 0.1286 | cg14631910 | −0.0593 | 0.0775 | cg12254845 | −0.0384 | 0.0503 |
| cg12144497 | −0.097 | 0.1268 | cg04689080 | −0.0571 | 0.0746 | cg14428048 | −0.0382 | 0.05 |
| cg04153740 | −0.0916 | 0.1198 | cg11123595 | −0.054 | 0.0706 | cg04018288 | −0.0381 | 0.0499 |
| cg04828133 | −0.0891 | 0.1165 | cg22541735 | −0.0539 | 0.0705 | cg25023994 | −0.0363 | 0.0475 |
| cg19006220 | 0.036 | −0.0471 | cg08260959 | −0.0244 | 0.0319 | cg09387749 | −0.009 | 0.0118 |
| cg21319932 | −0.0359 | 0.047 | cg07265743 | −0.0232 | 0.0304 | cg00005847 | −0.0088 | 0.0116 |
| cg00901051 | −0.0354 | 0.0462 | cg01558212 | −0.0228 | 0.0298 | cg04472725 | −0.0075 | 0.0098 |
| cg04094811 | −0.0349 | 0.0456 | cg08548396 | −0.0221 | 0.0289 | cg09181792 | −0.0074 | 0.0096 |
| cg09165441 | −0.0347 | 0.0453 | cg21591742 | −0.0219 | 0.0286 | cg07345734 | −0.0073 | 0.0095 |
| cg03731303 | −0.0345 | 0.0452 | cg18096722 | −0.021 | 0.0274 | cg26590744 | −0.0068 | 0.0089 |
| cg21865150 | −0.0345 | 0.0452 | cg17204129 | −0.0209 | 0.0273 | cg06733794 | −0.0054 | 0.0071 |
| cg12506930 | −0.0338 | 0.0441 | cg13158481 | −0.0207 | 0.0271 | cg04819096 | −0.0053 | 0.0069 |
| cg23475625 | −0.0329 | 0.0431 | cg09323727 | −0.0196 | 0.0257 | cg21545862 | −0.0052 | 0.0068 |
| cg20177650 | −0.0306 | 0.04 | cg01466288 | −0.0194 | 0.0253 | cg18630667 | −0.0048 | 0.0063 |
| cg00414898 | −0.0305 | 0.0399 | cg18698788 | −0.0187 | 0.0245 | cg24269074 | −0.0046 | 0.006 |
| cg11095319 | −0.0302 | 0.0394 | cg00689492 | −0.0185 | 0.0241 | cg04415798 | −0.0046 | 0.006 |
| cg10288510 | −0.0293 | 0.0383 | cg06966660 | −0.0165 | 0.0216 | cg27103296 | −0.0043 | 0.0056 |
| cg25392692 | −0.0292 | 0.0381 | cg05020604 | −0.0163 | 0.0213 | cg25702780 | −0.0033 | 0.0043 |
| cg08529345 | −0.0286 | 0.0375 | cg02469909 | −0.0163 | 0.0213 | cg17588266 | −0.0032 | 0.0042 |
| cg24864887 | −0.0285 | 0.0373 | cg20762861 | −0.0152 | 0.0199 | cg12384499 | −0.003 | 0.004 |
| cg14720773 | −0.0284 | 0.0371 | cg09670128 | −0.0148 | 0.0193 | cg08594218 | −0.0029 | 0.0039 |
| cg20295992 | −0.0277 | 0.0362 | cg09170112 | 0.0145 | −0.019 | cg01414185 | −0.0026 | 0.0034 |
| cg00040312 | −0.0265 | 0.0346 | cg05857758 | −0.0136 | 0.0178 | cg16794506 | −0.0024 | 0.0032 |
| cg08404009 | −0.0263 | 0.0344 | cg13217260 | −0.0127 | 0.0166 | cg25960893 | −0.0008 | 0.001 |
| cg20312687 | 0.0259 | −0.0339 | cg14537533 | −0.0126 | 0.0165 | cg16305379 | −0.0007 | 0.0009 |
| cg06890747 | −0.0257 | 0.0336 | cg07378762 | −0.0112 | 0.0147 | | | |
| cg06822689 | −0.0253 | 0.0331 | cg26509715 | −0.011 | 0.0144 | | | |
| cg02164225 | −0.0253 | 0.0331 | cg14087921 | 0.01 | −0.0131 | | | |

TABLE 12

Example DMP signature comprising 65 DMPs (DMP weights are given in columns X0.score and X1.score)

| DMP ID | X0.score | X1.score | DMP ID | X0.score | X1.score | DMP ID | X0.score | X1.score |
|---|---|---|---|---|---|---|---|---|
| cg07716946 | −0.2403 | 0.3142 | cg09968620 | −0.0461 | 0.0603 | cg10364040 | −0.013 | 0.017 |
| cg04786287 | −0.234 | 0.306 | cg19664945 | −0.0439 | 0.0573 | cg22991101 | −0.0122 | 0.0159 |
| cg03782157 | −0.1515 | 0.1982 | cg06685968 | −0.0401 | 0.0524 | cg03222323 | −0.0116 | 0.0151 |
| cg12368188 | −0.1507 | 0.197 | cg11362010 | −0.0389 | 0.0509 | cg21425842 | −0.0101 | 0.0133 |
| cg25829490 | −0.131 | 0.1713 | cg10759602 | −0.0353 | 0.0462 | cg04233770 | −0.0097 | 0.0127 |
| cg09628195 | −0.1211 | 0.1583 | cg26053832 | −0.0352 | 0.046 | cg00503383 | −0.0091 | 0.0119 |
| cg20674701 | −0.1181 | 0.1544 | cg27071152 | −0.0349 | 0.0456 | cg06530490 | −0.0065 | 0.0085 |
| cg22549870 | −0.1003 | 0.1311 | cg17975443 | −0.034 | 0.0445 | cg21811143 | −0.0057 | 0.0075 |
| cg02020945 | −0.0984 | 0.1287 | cg03366986 | −0.033 | 0.0432 | cg22674699 | −0.0054 | 0.0071 |
| cg14164044 | −0.0963 | 0.1259 | cg00332153 | −0.031 | 0.0406 | cg00217080 | 0.0051 | −0.0067 |
| cg10210594 | −0.0953 | 0.1246 | cg05317090 | −0.0302 | 0.0395 | cg16971668 | −0.0046 | 0.006 |
| cg22974982 | −0.084 | 0.1099 | cg00459623 | −0.0291 | 0.0381 | cg13406145 | −0.0045 | 0.0058 |
| cg15545035 | −0.0816 | 0.1067 | cg27622679 | −0.0291 | 0.038 | cg14290904 | −0.0039 | 0.0051 |
| cg03843000 | −0.0788 | 0.1031 | cg04490714 | −0.029 | 0.0379 | cg13294849 | −0.0036 | 0.0047 |
| cg16332610 | −0.0659 | 0.0862 | cg20501518 | −0.0288 | 0.0377 | cg06316886 | −0.0035 | 0.0046 |
| cg20627174 | −0.0608 | 0.0795 | cg04164058 | −0.026 | 0.034 | cg14765959 | −0.0033 | 0.0043 |
| cg07524679 | −0.0608 | 0.0795 | cg14239111 | 0.0247 | −0.0323 | cg18235734 | −0.0033 | 0.0043 |
| cg09570682 | −0.0602 | 0.0787 | cg25371634 | −0.0243 | 0.0317 | | | |
| cg18891712 | −0.0594 | 0.0777 | cg01783662 | −0.0236 | 0.0308 | | | |

TABLE 12-continued

Example DMP signature comprising 65 DMPs (DMP weights are given in columns X0.score and X1.score)

| DMP ID | X0.score | X1.score | DMP ID | X0.score | X1.score | DMP ID | X0.score | X1.score |
|---|---|---|---|---|---|---|---|---|
| cg03892356 | −0.059 | 0.0772 | cg15888290 | −0.0194 | 0.0254 | | | |
| cg26470798 | −0.0583 | 0.0763 | cg14631910 | −0.0192 | 0.0251 | | | |
| cg12144497 | −0.0569 | 0.0744 | cg04689080 | −0.017 | 0.0222 | | | |
| cg04153740 | −0.0516 | 0.0674 | cg11123595 | −0.014 | 0.0183 | | | |
| cg04828133 | −0.049 | 0.0641 | cg22541735 | −0.0139 | 0.0182 | | | |

TABLE 13

Example DMP signature comprising 27 DMPs (DMP weights are given in columns X0.score and X1.score)

| DMP ID | X0.score | X1.score | DMP ID | X0.score | X1.score |
|---|---|---|---|---|---|
| cg07716946 | −0.2002 | 0.2619 | cg09968620 | −0.006 | 0.0079 |
| cg04786287 | −0.194 | 0.2536 | cg19664945 | −0.0038 | 0.005 |
| cg03782157 | −0.1115 | 0.1458 | cg06685968 | 0 | 0 |
| cg12368188 | −0.1106 | 0.1447 | | | |
| cg25829490 | −0.091 | 0.119 | | | |
| cg09628195 | −0.081 | 0.106 | | | |
| cg20674701 | −0.078 | 0.102 | | | |
| cg22549870 | −0.0602 | 0.0788 | | | |
| cg02020945 | −0.0583 | 0.0763 | | | |
| cg14164044 | −0.0562 | 0.0736 | | | |
| cg10210594 | −0.0552 | 0.0722 | | | |
| cg22974982 | −0.044 | 0.0575 | | | |
| cg15545035 | −0.0416 | 0.0543 | | | |
| cg03843000 | −0.0388 | 0.0507 | | | |
| cg16332610 | −0.0259 | 0.0338 | | | |
| cg20627174 | −0.0208 | 0.0272 | | | |
| cg07524679 | −0.0207 | 0.0271 | | | |
| cg09570682 | −0.0201 | 0.0263 | | | |
| cg18891712 | −0.0193 | 0.0253 | | | |
| cg03892356 | −0.019 | 0.0248 | | | |
| cg26470798 | −0.0183 | 0.0239 | | | |
| cg12144497 | −0.0169 | 0.0221 | | | |
| cg04153740 | −0.0115 | 0.0151 | | | |
| cg04828133 | −0.009 | 0.0118 | | | |

TABLE 14

Example DMP signature comprising 13 DMPs (DMP weights are given in columns X0.score and X1.score)

| DMP ID | X0.score | X1.score |
|---|---|---|
| cg07716946 | −0.1602 | 0.2095 |
| cg04786287 | −0.1539 | 0.2013 |
| cg03782157 | −0.0714 | 0.0934 |
| cg12368188 | −0.0706 | 0.0923 |
| cg25829490 | −0.0509 | 0.0666 |
| cg09628195 | −0.041 | 0.0536 |
| cg20674701 | −0.038 | 0.0497 |
| cg22549870 | −0.0202 | 0.0264 |
| cg02020945 | −0.0183 | 0.0239 |
| cg14164044 | −0.0162 | 0.0212 |
| cg10210594 | −0.0152 | 0.0199 |
| cg22974982 | −0.0039 | 0.0051 |
| cg15545035 | −0.0015 | 0.002 |
| cg04828133 | −0.009 | 0.0118 |

TABLE 15

Example DMP signature comprising 6 DMPs (DMP weights are given in columns X0.score and X1.score)

| DMP ID | X0.score | X1.score |
|---|---|---|
| cg07716946 | −0.1201 | 0.1571 |
| cg04786287 | −0.1139 | 0.1489 |
| cg03782157 | −0.0314 | 0.041 |
| cg12368188 | −0.0305 | 0.0399 |
| cg25829490 | −0.0109 | 0.0142 |
| cg09628195 | −0.0009 | 0.0012 |

TABLE 16

Example DMP signature comprising 2 DMPs (DMP weights are given in columns X0.score and X1.score)

| DMP ID | X0.score | X1.score |
|---|---|---|
| cg07716946 | −0.0801 | 0.1047 |
| cg04786287 | −0.0738 | 0.0965 |

TABLE 17

Example DMP signature comprising 2 DMPs (DMP weights
are given in columns X0.score and X1.score)

| DMP ID | X0.score | X1.score |
|---|---|---|
| cg07716946 | −0.04 | 0.0524 |
| cg04786287 | −0.0338 | 0.0442 |

5

TABLE 18

Summary of characteristic parameters and metrics of example DMP signatures presented in Tables 11-17

| DMP Signature Table | DMPs | AUC (Validation) | AUV (TCGA) | Threshold Value | Sensitivity (Validation) | Specificity (Validation) | Sensitivity (TCGA) | Specificity (TCGA) |
|---|---|---|---|---|---|---|---|---|
| 11 | 141 | 0.994118 | 0.998263 | 0.5 | 0.882353 | 1 | 1 | 0.583784 |
| 12 | 65 | 0.994118 | 0.998649 | 0.475 | 0.882353 | 1 | 1 | 0.581081 |
| 13 | 27 | 0.976471 | 0.995817 | 0.455 | 0.882353 | 1 | 1 | 0.578378 |
| 14 | 13 | 0.976471 | 0.987259 | 0.45 | 0.882353 | 1 | 1 | 0.564865 |
| 15 | 6 | 0.982353 | 0.956113 | 0.45 | 0.882353 | 1 | 1 | 0.545946 |
| 16 | 2 | 0.982353 | 0.939833 | 0.44 | 0.882353 | 1 | 1 | 0.559459 |
| 17 | 2 | 0.982353 | 0.940412 | 0.43 | 0.882353 | 1 | 1 | 0.613514 |

TABLE 19

Example CNV signature comprising 219 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.4346 | 0.2173 | 5q11.2 | 0.2415 | −0.1208 | 5p15.33 | −0.1984 | 0.0992 |
| 3q26.31 | −0.4068 | 0.2034 | 3p24.1 | 0.2412 | −0.1206 | 3p14.1 | 0.1955 | −0.0978 |
| 3q26.2 | −0.3878 | 0.1939 | 3p24.2 | 0.2373 | −0.1187 | 19q13.12 | −0.1922 | 0.0961 |
| 3q26.33 | −0.3864 | 0.1932 | 3p23 | 0.2317 | −0.1158 | 5q21.3 | 0.191 | −0.0955 |
| 3q28 | −0.3754 | 0.1877 | 3p26.3 | 0.2313 | −0.1157 | 5q23.1 | 0.1904 | −0.0952 |
| 5q13.2 | 0.3718 | −0.1859 | 5p15.1 | −0.2313 | 0.1156 | 5q14.1 | 0.1867 | −0.0934 |
| 3q26.1 | −0.3491 | 0.1745 | 3p22.1 | 0.2288 | −0.1144 | 3q25.33 | −0.184 | 0.092 |
| 5q12.3 | 0.3344 | −0.1672 | 9p23 | 0.2246 | −0.1123 | 3q25.32 | −0.1839 | 0.092 |
| 3q27.3 | −0.3254 | 0.1627 | 3p26.1 | 0.2238 | −0.1119 | 3p25.1 | 0.1793 | −0.0896 |
| 3q29 | −0.3223 | 0.1612 | 19q13.13 | −0.2172 | 0.1086 | 9p24.2 | 0.1792 | −0.0896 |
| 3q27.2 | −0.3162 | 0.1581 | 3p24.3 | 0.2163 | −0.1081 | 5q33.3 | 0.1787 | −0.0894 |
| 3q27.1 | −0.3105 | 0.1552 | 3p22.2 | 0.2151 | −0.1075 | 2p25.3 | −0.1783 | 0.0891 |
| 5q12.1 | 0.3078 | −0.1539 | 2q34 | 0.2123 | −0.1062 | 3q25.1 | −0.1778 | 0.0889 |
| 5q13.1 | 0.2884 | −0.1442 | 3p21.33 | 0.2109 | −0.1054 | 3q25.31 | −0.1773 | 0.0886 |
| 5q22.1 | 0.2878 | −0.1439 | 9p22.1 | 0.2085 | −0.1042 | 19q11 | −0.1757 | 0.0879 |
| 21q21.2 | 0.2744 | −0.1372 | 3p21.32 | 0.2077 | −0.1038 | 3p14.2 | 0.1748 | −0.0874 |
| 3p22.3 | 0.2592 | −0.1296 | 9p24.1 | 0.207 | −0.1035 | 3p21.1 | 0.1746 | −0.0873 |
| 9p22.2 | 0.2584 | −0.1292 | 3p14.3 | 0.2069 | −0.1035 | 5p15.32 | −0.1715 | 0.0857 |
| 5q13.3 | 0.2578 | −0.1289 | 5q23.2 | 0.2068 | −0.1034 | 3p21.31 | 0.1706 | −0.0853 |
| 3p26.2 | 0.2566 | −0.1283 | 5q15 | 0.2064 | −0.1032 | 5p12 | −0.17 | 0.085 |
| 5q14.3 | 0.2547 | −0.1273 | 5q21.1 | 0.2063 | −0.1031 | 5q33.1 | 0.1699 | −0.0849 |
| 5q22.2 | 0.2538 | −0.1269 | 5p14.1 | −0.2036 | 0.1018 | 4q32.2 | 0.1698 | −0.0849 |
| 5q22.3 | 0.2498 | −0.1249 | 5p15.2 | −0.2019 | 0.101 | 5p13.3 | −0.1658 | 0.0829 |
| 9p22.3 | 0.2424 | −0.1212 | 3p13 | 0.2009 | −0.1005 | 5p13.1 | −0.1657 | 0.0829 |
| 19q13.2 | −0.165 | 0.0825 | 19q12 | −0.1319 | 0.0659 | 6q11.1 | −0.0949 | 0.0474 |
| 9p21.3 | 0.1632 | −0.0816 | 4p15.31 | 0.1315 | −0.0658 | 20p11.22 | −0.0945 | 0.0473 |
| 4p15.2 | 0.1627 | −0.0814 | 4q31.3 | 0.1274 | −0.0637 | 2q33.3 | 0.0933 | −0.0467 |
| 3p21.2 | 0.1626 | −0.0813 | 22q11.1 | −0.1265 | 0.0633 | 11q13.3 | −0.0911 | 0.0456 |
| 3p25.2 | 0.1618 | −0.0809 | 8p22 | 0.1228 | −0.0614 | 4q26 | 0.0879 | −0.0439 |
| 5q14.2 | 0.161 | −0.0805 | 8p21.2 | 0.1197 | −0.0599 | 9p24.3 | 0.0853 | −0.0426 |
| 3p25.3 | 0.1586 | −0.0793 | 4q23 | 0.1163 | −0.0582 | 2q36.2 | 0.0843 | −0.0421 |
| 5q33.2 | 0.1573 | −0.0787 | 5q31.1 | 0.1158 | −0.0579 | 6p25.3 | −0.0831 | 0.0416 |
| 4q31.23 | 0.1545 | −0.0773 | 4p14 | 0.1128 | −0.0564 | 4q31.21 | 0.0829 | −0.0415 |
| 5p13.2 | −0.1542 | 0.0771 | 8p21.1 | 0.1117 | −0.0558 | 21q21.3 | 0.08 | −0.04 |
| 5p15.31 | −0.1502 | 0.0751 | 4q34.2 | 0.1114 | −0.0557 | 15q25.3 | −0.0795 | 0.0397 |
| 4q32.1 | 0.1461 | −0.0731 | 8p23.2 | 0.111 | −0.0555 | 6p11.2 | −0.0766 | 0.0383 |
| 4p15.1 | 0.1456 | −0.0728 | 9p21.2 | 0.1104 | −0.0552 | 15q22.32 | −0.0764 | 0.0382 |
| 4q32.3 | 0.1442 | −0.0721 | 3p12.2 | 0.1097 | −0.0548 | 4q27 | 0.0757 | −0.0378 |
| 3q24 | −0.1419 | 0.0709 | 5q34 | 0.1085 | −0.0542 | 10q21.1 | 0.0752 | −0.0376 |
| 4q28.2 | 0.1412 | −0.0706 | 4q22.3 | 0.1055 | −0.0528 | 1p13.3 | 0.075 | −0.0375 |
| 8p12 | 0.1407 | −0.0703 | 4q31.22 | 0.1035 | −0.0517 | 5p14.3 | −0.0715 | 0.0358 |
| 5q32 | 0.1375 | −0.0687 | 5q31.2 | 0.1019 | −0.051 | 5q31.3 | 0.0679 | −0.034 |
| 15q26.3 | −0.1366 | 0.0683 | 4q24 | 0.1003 | −0.0502 | 15q26.1 | −0.0649 | 0.0324 |
| 5q23.3 | 0.1347 | −0.0673 | 4q28.1 | 0.1001 | −0.05 | 2q36.3 | 0.0639 | −0.032 |

TABLE 19-continued

Example CNV signature comprising 219 CNV bands (CNV band weights are given in columns X0.score and X1.score)

| CNV band | X0.score | X1.score | CNV band | X0.score | X1.score | CNV band | X0.score | X1.score |
|---|---|---|---|---|---|---|---|---|
| 3q25.2 | -0.1346 | 0.0673 | 15q26.2 | -0.0996 | 0.0498 | 8q24.3 | -0.0638 | 0.0319 |
| 5q21.2 | 0.1345 | -0.0673 | 17p11.1 | -0.0995 | 0.0498 | 2p16.3 | -0.0634 | 0.0317 |
| 4q33 | 0.1327 | -0.0663 | 3p12.1 | 0.0976 | -0.0488 | 2q36.1 | 0.0633 | -0.0316 |
| 19q13.11 | -0.1325 | 0.0663 | 1p13.2 | 0.0973 | -0.0487 | 8p21.3 | 0.0627 | -0.0314 |
| 2q35 | 0.0615 | -0.0308 | 8q24.22 | -0.0318 | 0.0159 | 2p16.2 | -0.0154 | 0.0077 |
| 4q31.1 | 0.061 | -0.0305 | 1q22 | -0.0309 | 0.0155 | 4p13 | 0.0149 | -0.0075 |
| 4q25 | 0.058 | -0.029 | 4p15.32 | 0.0286 | -0.0143 | 1p21.3 | 0.0133 | -0.0066 |
| 1q42.13 | -0.0563 | 0.0281 | 22q12.1 | -0.0277 | 0.0139 | 2q32.3 | -0.0132 | 0.0066 |
| 8q24.21 | -0.0555 | 0.0277 | 13q21.2 | 0.0275 | -0.0137 | 1p32.2 | 0.0117 | -0.0059 |
| 13q12.12 | 0.0546 | -0.0273 | 1q41 | -0.0273 | 0.0137 | 3q22.3 | -0.0106 | 0.0053 |
| 4q34.1 | 0.054 | -0.027 | 1q21.3 | -0.027 | 0.0135 | 2p24.1 | -0.0105 | 0.0052 |
| 5q11.1 | 0.0539 | -0.0269 | 2q14.2 | -0.0258 | 0.0129 | 22q11.22 | -0.0099 | 0.005 |
| 20p11.1 | -0.0527 | 0.0263 | 1q21.2 | -0.0249 | 0.0124 | 15q24.3 | -0.0085 | 0.0043 |
| 2q31.1 | -0.0505 | 0.0253 | 1p21.1 | 0.0247 | -0.0123 | 1q42.2 | -0.0076 | 0.0038 |
| 2q33.2 | 0.0499 | -0.025 | 4q34.3 | 0.0243 | -0.0122 | 2q12.2 | -0.0072 | 0.0036 |
| 2p25.1 | -0.048 | 0.024 | 22q11.21 | -0.0232 | 0.0116 | 2p11.2 | -0.0071 | 0.0036 |
| 2p22.1 | -0.0472 | 0.0236 | 3p11.2 | 0.023 | -0.0115 | 1q42.3 | -0.007 | 0.0035 |
| 2p14 | -0.0465 | 0.0232 | 4q22.2 | 0.0227 | -0.0113 | 2p16.1 | -0.0069 | 0.0035 |
| 2p22.2 | -0.046 | 0.023 | 8p23.3 | 0.0225 | -0.0113 | 1p22.1 | 0.0068 | -0.0034 |
| 3p12.3 | 0.0453 | -0.0227 | 8p23.1 | 0.0212 | -0.0106 | 4q28.3 | 0.0062 | -0.0031 |
| 1p32.1 | 0.0432 | -0.0216 | 1q32.3 | -0.02 | 0.01 | 1p36.11 | 0.0055 | -0.0028 |
| 13q12.11 | 0.0427 | -0.0213 | 1p31.1 | 0.0199 | -0.0099 | 1q32.2 | -0.0037 | 0.0018 |
| 2p25.2 | -0.0414 | 0.0207 | 1q44 | -0.0187 | 0.0093 | 3q23 | -0.0035 | 0.0017 |
| 2p15 | -0.0394 | 0.0197 | 2p21 | -0.0176 | 0.0088 | 13q33.1 | 0.003 | -0.0015 |
| 1p22.3 | 0.0376 | -0.0188 | 2p23.2 | -0.0176 | 0.0088 | 2q11.2 | -0.0029 | 0.0014 |
| 21q22.11 | 0.0362 | -0.0181 | 2p24.3 | -0.0172 | 0.0086 | 2q12.3 | -0.0026 | 0.0013 |
| 3p11.1 | 0.0337 | -0.0168 | 2q31.3 | -0.0165 | 0.0083 | 15q25.2 | -0.0023 | 0.0011 |
| 18q22.1 | 0.0333 | -0.0166 | 6p22.3 | -0.0159 | 0.0079 | 10q11.23 | 0.0021 | -0.0011 |
| 2p13.2 | -0.0005 | 0.0003 | | | | | | |
| 1q31.3 | -0.0005 | 0.0002 | | | | | | |
| 1p21.2 | 0.0003 | -0.0001 | | | | | | |

TABLE 20

Example CNV signature comprising 179 CNV bands (CNV band weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | -0.4104 | 0.2052 | 5q11.2 | 0.2174 | -0.1087 | 5p15.33 | -0.1743 | 0.0871 |
| 3q26.31 | -0.3827 | 0.1913 | 3p24.1 | 0.2171 | -0.1085 | 3p14.1 | 0.1714 | -0.0857 |
| 3q26.2 | -0.3637 | 0.1818 | 3p24.2 | 0.2132 | -0.1066 | 19q13.12 | -0.168 | 0.084 |
| 3q26.33 | -0.3623 | 0.1811 | 3p23 | 0.2075 | -0.1038 | 5q21.3 | 0.1668 | -0.0834 |
| 3q28 | -0.3513 | 0.1756 | 3p26.3 | 0.2072 | -0.1036 | 5q23.1 | 0.1662 | -0.0831 |
| 5q13.2 | 0.3477 | -0.1739 | 5p15.1 | -0.2071 | 0.1036 | 5q14.1 | 0.1626 | -0.0813 |
| 3q26.1 | -0.325 | 0.1625 | 3p22.1 | 0.2046 | -0.1023 | 3q25.33 | -0.1598 | 0.0799 |
| 5q12.3 | 0.3102 | -0.1551 | 9p23 | 0.2005 | -0.1002 | 3q25.32 | -0.1598 | 0.0799 |
| 3q27.3 | -0.3012 | 0.1506 | 3p26.1 | 0.1997 | -0.0998 | 3p25.1 | 0.1551 | -0.0776 |
| 3q29 | -0.2982 | 0.1491 | 19q13.13 | -0.1931 | 0.0965 | 9p24.2 | 0.1551 | -0.0776 |
| 3q27.2 | -0.292 | 0.146 | 3p24.3 | 0.1921 | -0.0961 | 5q33.3 | 0.1546 | -0.0773 |
| 3q27.1 | -0.2863 | 0.1432 | 3p22.2 | 0.1909 | -0.0955 | 2p25.3 | -0.1541 | 0.0771 |
| 5q12.1 | 0.2836 | -0.1418 | 2q34 | 0.1882 | -0.0941 | 3q25.1 | -0.1536 | 0.0768 |
| 5q13.1 | 0.2643 | -0.1321 | 3p21.33 | 0.1867 | -0.0934 | 3q25.31 | -0.1531 | 0.0766 |
| 5q22.1 | 0.2637 | -0.1318 | 9p22.1 | 0.1843 | -0.0922 | 19q11 | -0.1516 | 0.0758 |
| 21q21.2 | 0.2502 | -0.1251 | 3p21.32 | 0.1835 | -0.0918 | 3p14.2 | 0.1507 | -0.0753 |
| 3p22.3 | 0.2351 | -0.1175 | 9p24.1 | 0.1829 | -0.0915 | 3p21.1 | 0.1505 | -0.0753 |
| 9p22.2 | 0.2343 | -0.1171 | 3p14.3 | 0.1828 | -0.0914 | 5p15.32 | -0.1473 | 0.0737 |
| 5q13.3 | 0.2336 | -0.1168 | 5q23.2 | 0.1826 | -0.0913 | 3p21.31 | 0.1465 | -0.0732 |
| 3p26.2 | 0.2325 | -0.1162 | 5q15 | 0.1823 | -0.0911 | 5p12 | -0.1459 | 0.0729 |
| 5q14.3 | 0.2305 | -0.1153 | 5q21.1 | 0.1821 | -0.0911 | 5q33.1 | 0.1457 | -0.0729 |
| 5q22.2 | 0.2296 | -0.1148 | 5p14.1 | -0.1795 | 0.0897 | 4q32.2 | 0.1457 | -0.0728 |
| 5q22.3 | 0.2257 | -0.1128 | 5p15.2 | -0.1778 | 0.0889 | 5p13.3 | -0.1417 | 0.0708 |
| 9p22.3 | 0.2182 | -0.1091 | 3p13 | 0.1768 | -0.0884 | 5p13.1 | -0.1416 | 0.0708 |
| 19q13.2 | -0.1409 | 0.0704 | 19q12 | -0.1077 | 0.0539 | 6q11.1 | -0.0708 | 0.0354 |
| 9p21.3 | 0.139 | -0.0695 | 4p15.31 | 0.1074 | -0.0537 | 20p11.22 | -0.0704 | 0.0352 |
| 4p15.2 | 0.1386 | -0.0693 | 4q31.3 | 0.1033 | -0.0516 | 2q33.3 | 0.0692 | -0.0346 |
| 3p21.2 | 0.1384 | -0.0692 | 22q11.1 | -0.1024 | 0.0512 | 11q13.3 | -0.067 | 0.0335 |
| 3p25.2 | 0.1376 | -0.0688 | 8p22 | 0.0986 | -0.0493 | 4q26 | 0.0637 | -0.0319 |
| 5q14.2 | 0.1369 | -0.0684 | 8p21.2 | 0.0956 | -0.0478 | 9p24.3 | 0.0611 | -0.0306 |
| 3p25.3 | 0.1344 | -0.0672 | 4q23 | 0.0922 | -0.0461 | 2q36.2 | 0.0601 | -0.0301 |
| 5q33.2 | 0.1332 | -0.0666 | 5q31.1 | 0.0917 | -0.0458 | 6p25.3 | -0.059 | 0.0295 |
| 4q31.23 | 0.1304 | -0.0652 | 4p14 | 0.0886 | -0.0443 | 4q31.21 | 0.0588 | -0.0294 |

TABLE 20-continued

Example CNV signature comprising 179 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 5p13.2 | −0.13 | 0.065 | 8p21.1 | 0.0876 | −0.0438 | 21q21.3 | 0.0558 | −0.0279 |
| 5p15.31 | −0.1261 | 0.063 | 4q34.2 | 0.0872 | −0.0436 | 15q25.3 | −0.0553 | 0.0277 |
| 4q32.1 | 0.122 | −0.061 | 8p23.2 | 0.0868 | −0.0434 | 6p11.2 | −0.0525 | 0.0263 |
| 4p15.1 | 0.1215 | −0.0607 | 9p21.2 | 0.0862 | −0.0431 | 15q22.32 | −0.0523 | 0.0262 |
| 4q32.3 | 0.1201 | −0.06 | 3p12.2 | 0.0855 | −0.0428 | 4q27 | 0.0516 | −0.0258 |
| 3q24 | −0.1177 | 0.0589 | 5q34 | 0.0843 | −0.0422 | 10q21.1 | 0.051 | −0.0255 |
| 4q28.2 | 0.117 | −0.0585 | 4q22.3 | 0.0814 | −0.0407 | 1p13.3 | 0.0508 | −0.0254 |
| 8p12 | 0.1165 | −0.0583 | 4q31.22 | 0.0793 | −0.0397 | 5p14.3 | −0.0474 | 0.0237 |
| 5q32 | 0.1133 | −0.0567 | 5q31.2 | 0.0778 | −0.0389 | 5q31.3 | 0.0438 | −0.0219 |
| 15q26.3 | −0.1124 | 0.0562 | 4q24 | 0.0762 | −0.0381 | 15q26.1 | −0.0407 | 0.0204 |
| 5q23.3 | 0.1105 | −0.0553 | 4q28.1 | 0.0759 | −0.038 | 2q36.3 | 0.0398 | −0.0199 |
| 3q25.2 | −0.1104 | 0.0552 | 15q26.2 | −0.0755 | 0.0377 | 8q24.3 | −0.0396 | 0.0198 |
| 5q21.2 | 0.1104 | −0.0552 | 17p11.1 | −0.0754 | 0.0377 | 2p16.3 | −0.0392 | 0.0196 |
| 4q33 | 0.1085 | −0.0543 | 3p12.1 | 0.0735 | −0.0367 | 2q36.1 | 0.0391 | −0.0196 |
| 19q13.11 | −0.1084 | 0.0542 | 1p13.2 | 0.0732 | −0.0366 | 8p21.3 | 0.0386 | −0.0193 |

20

TABLE 20

(continued)

| CNV band | X0.score | X1.score | CNV band | X0.score | X1.score |
|---|---|---|---|---|---|
| 2q35 | 0.0374 | −0.0187 | 8q24.22 | −0.0076 | 0.0038 |
| 4q31.1 | 0.0369 | −0.0184 | 1q22 | −0.0068 | 0.0034 |
| 4q25 | 0.0339 | −0.0169 | 4p15.32 | 0.0044 | −0.0022 |
| 1q42.13 | −0.0321 | 0.0161 | 22q12.1 | −0.0036 | 0.0018 |
| 8q24.21 | −0.0313 | 0.0157 | 13q21.2 | 0.0033 | −0.0017 |
| 13q12.12 | 0.0305 | −0.0152 | 1q41 | −0.0032 | 0.0016 |
| 4q34.1 | 0.0298 | −0.0149 | 1q21.3 | −0.0029 | 0.0015 |
| 5q11.1 | 0.0297 | −0.0149 | 2q14.2 | −0.0017 | 0.0008 |
| 20p11.1 | −0.0285 | 0.0143 | 1q21.2 | −0.0007 | 0.0004 |
| 2q31.1 | −0.0264 | 0.0132 | 1p21.1 | 0.0006 | −0.0003 |
| 2q33.2 | 0.0258 | −0.0129 | 4q34.3 | 0.0002 | −0.0001 |
| 2p25.1 | −0.0239 | 0.0119 | | | |
| 2p22.1 | −0.0231 | 0.0115 | | | |

TABLE 20-continued (continued)

| CNV band | X0.score | X1.score | CNV band | X0.score | X1.score |
|---|---|---|---|---|---|
| 2p14 | −0.0223 | 0.0112 | | | |
| 2p22.2 | −0.0218 | 0.0109 | | | |
| 3p12.3 | 0.0212 | −0.0106 | | | |
| 1p32.1 | 0.0191 | −0.0095 | | | |
| 13q12.11 | 0.0185 | −0.0093 | | | |
| 2p25.2 | −0.0172 | 0.0086 | | | |
| 2p15 | −0.0153 | 0.0076 | | | |
| 1p22.3 | 0.0135 | −0.0067 | | | |
| 21q22.11 | 0.0121 | −0.006 | | | |
| 3p11.1 | 0.0095 | −0.0048 | | | |
| 18q22.1 | 0.0092 | −0.0046 | | | |

TABLE 21

Example CNV signature comprising 155 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.3863 | 0.1931 | 5q11.2 | 0.1932 | −0.0966 | 5p15.33 | −0.1501 | 0.0751 |
| 3q26.31 | −0.3585 | 0.1793 | 3p24.1 | 0.1929 | −0.0965 | 3p14.1 | 0.1472 | −0.0736 |
| 3q26.2 | −0.3395 | 0.1698 | 3p24.2 | 0.1891 | −0.0945 | 19q13.12 | −0.1439 | 0.0719 |
| 3q26.33 | −0.3381 | 0.1691 | 3p23 | 0.1834 | −0.0917 | 5q21.3 | 0.1427 | −0.0713 |
| 3q28 | −0.3272 | 0.1636 | 3p26.3 | 0.183 | −0.0915 | 5q23.1 | 0.1421 | −0.0711 |
| 5q13.2 | 0.3236 | −0.1618 | 5p15.1 | −0.183 | 0.0915 | 5q14.1 | 0.1384 | −0.0692 |
| 3q26.1 | −0.3008 | 0.1504 | 3p22.1 | 0.1805 | −0.0902 | 3q25.33 | −0.1357 | 0.0678 |
| 5q12.3 | 0.2861 | −0.1431 | 9p23 | 0.1763 | −0.0882 | 3q25.32 | −0.1357 | 0.0678 |
| 3q27.3 | −0.2771 | 0.1385 | 3p25.1 | 0.1755 | −0.0878 | 3p25.1 | 0.131 | −0.0655 |
| 3q29 | −0.274 | 0.137 | 19q13.13 | −0.1689 | 0.0845 | 9p24.2 | 0.131 | −0.0655 |
| 3q27.2 | −0.2679 | 0.1339 | 3p24.3 | 0.168 | −0.084 | 5q33.3 | 0.1304 | −0.0652 |
| 3q27.1 | −0.2622 | 0.1311 | 3p22.2 | 0.1668 | −0.0834 | 2p25.3 | −0.13 | 0.065 |
| 5q12.1 | 0.2595 | −0.1297 | 2q34 | 0.164 | −0.082 | 3q25.1 | −0.1295 | 0.0647 |
| 5q13.1 | 0.2401 | −0.1201 | 3p21.33 | 0.1626 | −0.0813 | 3q25.31 | −0.129 | 0.0645 |
| 5q22.1 | 0.2395 | −0.1198 | 9p22.1 | 0.1602 | −0.0801 | 19q11 | −0.1274 | 0.0637 |
| 21q21.2 | 0.2261 | −0.113 | 3p21.32 | 0.1594 | −0.0797 | 3p14.2 | 0.1265 | −0.0633 |
| 3p22.3 | 0.2109 | −0.1055 | 9p24.1 | 0.1588 | −0.0794 | 3p21.1 | 0.1264 | −0.0632 |
| 9p22.2 | 0.2101 | −0.1051 | 3p14.3 | 0.1586 | −0.0793 | 5p15.32 | −0.1232 | 0.0616 |
| 5q13.3 | 0.2095 | −0.1047 | 5q23.2 | 0.1585 | −0.0792 | 3p21.31 | 0.1223 | −0.0612 |
| 3p26.2 | 0.2083 | −0.1042 | 5q15 | 0.1581 | −0.0791 | 5p12 | −0.1217 | 0.0609 |
| 5q14.3 | 0.2064 | −0.1032 | 5q21.1 | 0.158 | −0.079 | 5q33.1 | 0.1216 | −0.0608 |
| 5q22.2 | 0.2055 | −0.1027 | 5p14.1 | −0.1554 | 0.0777 | 4q32.2 | 0.1215 | −0.0608 |
| 5q22.3 | 0.2015 | −0.1008 | 5p15.2 | −0.1537 | 0.0768 | 5p13.3 | −0.1175 | 0.0588 |
| 9p22.3 | 0.1941 | −0.0971 | 3p13 | 0.1527 | −0.0763 | 5p13.1 | −0.1174 | 0.0587 |
| 19q13.2 | −0.1167 | 0.0584 | 19q12 | −0.0836 | 0.0418 | 6q11.1 | −0.0466 | 0.0233 |
| 9p21.3 | 0.1149 | −0.0574 | 4p15.31 | 0.0832 | −0.0416 | 20p11.22 | −0.0462 | 0.0231 |
| 4p15.2 | 0.1145 | −0.0572 | 4q31.3 | 0.0791 | −0.0396 | 2q33.3 | 0.045 | −0.0225 |
| 3p21.2 | 0.1143 | −0.0571 | 22q11.1 | −0.0783 | 0.0391 | 11q13.3 | −0.0428 | 0.0214 |

TABLE 21-continued

Example CNV signature comprising 155 CNV bands (CNV band weights are given in columns X0.score and X1.score)

| CNV band | X0.score | X1.score | CNV band | X0.score | X1.score | CNV band | X0.score | X1.score |
|---|---|---|---|---|---|---|---|---|
| 3p25.2 | 0.1135 | −0.0567 | 8p22 | 0.0745 | −0.0372 | 4q26 | 0.0396 | −0.0198 |
| 5q14.2 | 0.1127 | −0.0564 | 8p21.2 | 0.0714 | −0.0357 | 9p24.3 | 0.037 | −0.0185 |
| 3p25.3 | 0.1103 | −0.0551 | 4q23 | 0.068 | −0.034 | 2q36.2 | 0.036 | −0.018 |
| 5q33.2 | 0.109 | −0.0545 | 5q31.1 | 0.0675 | −0.0338 | 6p25.3 | −0.0348 | 0.0174 |
| 4q31.23 | 0.1062 | −0.0531 | 4p14 | 0.0645 | −0.0323 | 4q31.21 | 0.0346 | −0.0173 |
| 5p13.2 | −0.1059 | 0.0529 | 8p21.1 | 0.0634 | −0.0317 | 21q21.3 | 0.0317 | −0.0159 |
| 5p15.31 | −0.1019 | 0.051 | 4q34.2 | 0.0631 | −0.0315 | 15q25.3 | −0.0312 | 0.0156 |
| 4q32.1 | 0.0978 | −0.0489 | 8p23.2 | 0.0627 | −0.0313 | 6p11.2 | −0.0284 | 0.0142 |
| 4p15.1 | 0.0973 | −0.0487 | 9p21.2 | 0.0621 | −0.031 | 15q22.32 | −0.0282 | 0.0141 |
| 4q32.3 | 0.0959 | −0.048 | 3p12.2 | 0.0614 | −0.0307 | 4q27 | 0.0274 | −0.0137 |
| 3q24 | −0.0936 | 0.0468 | 5q34 | 0.0602 | −0.0301 | 10q21.1 | 0.0269 | −0.0134 |
| 4q28.2 | 0.0929 | −0.0464 | 4q22.3 | 0.0572 | −0.0286 | 1p13.3 | 0.0267 | −0.0133 |
| 8p12 | 0.0924 | −0.0462 | 4q31.22 | 0.0552 | −0.0276 | 5p14.3 | −0.0232 | 0.0116 |
| 5q32 | 0.0892 | −0.0446 | 5q31.2 | 0.0537 | −0.0268 | 5q31.3 | 0.0197 | −0.0098 |
| 15q26.3 | −0.0883 | 0.0442 | 4q24 | 0.052 | −0.026 | 15q26.1 | −0.0166 | 0.0083 |
| 5q23.3 | 0.0864 | −0.0432 | 4q28.1 | 0.0518 | −0.0259 | 2q36.3 | 0.0156 | −0.0078 |
| 3q25.2 | −0.0863 | 0.0431 | 15q26.2 | −0.0513 | 0.0257 | 8q24.3 | −0.0155 | 0.0077 |
| 5q21.2 | 0.0862 | −0.0431 | 17p11.1 | −0.0512 | 0.0256 | 2p16.3 | −0.0151 | 0.0075 |
| 4q33 | 0.0844 | −0.0422 | 3p12.1 | 0.0493 | −0.0247 | 2q36.1 | 0.015 | −0.0075 |
| 19q13.11 | −0.0842 | 0.0421 | 1p13.2 | 0.0491 | −0.0245 | 8p21.3 | 0.0144 | −0.0072 |
| 2q35 | 0.0132 | −0.0066 | | | | | | |
| 4q31.1 | 0.0127 | −0.0064 | | | | | | |
| 4q25 | 0.0097 | −0.0049 | | | | | | |
| 1q42.13 | −0.008 | 0.004 | | | | | | |
| 8q24.21 | −0.0072 | 0.0036 | | | | | | |
| 13q12.12 | 0.0064 | −0.0032 | | | | | | |
| 4q34.1 | 0.0057 | −0.0028 | | | | | | |
| 5q11.1 | 0.0056 | −0.0028 | | | | | | |
| 20p11.1 | −0.0044 | 0.0022 | | | | | | |
| 2q31.1 | −0.0022 | 0.0011 | | | | | | |
| 2q33.2 | 0.0016 | −0.0008 | | | | | | |

TABLE 22

Example CNV signature comprising 136 CNV bands (CNV band weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.3621 | 0.1811 | 5q11.2 | 0.1691 | −0.0845 | 5p15.33 | −0.126 | 0.063 |
| 3q26.31 | −0.3344 | 0.1672 | 3p24.1 | 0.1688 | −0.0844 | 3p14.1 | 0.1231 | −0.0615 |
| 3q26.2 | −0.3154 | 0.1577 | 3p24.2 | 0.1649 | −0.0825 | 19q13.12 | −0.1197 | 0.0599 |
| 3q26.33 | −0.314 | 0.157 | 3p23 | 0.1593 | −0.0796 | 5q21.3 | 0.1185 | −0.0593 |
| 3q28 | −0.303 | 0.1515 | 3p26.3 | 0.1589 | −0.0794 | 5q23.1 | 0.118 | −0.059 |
| 5q13.2 | 0.2994 | −0.1497 | 5p15.1 | −0.1588 | 0.0794 | 5q14.1 | 0.1143 | −0.0571 |
| 3q26.1 | −0.2767 | 0.1383 | 3p22.1 | 0.1564 | −0.0782 | 3q25.33 | −0.1116 | 0.0558 |
| 5q12.3 | 0.262 | −0.131 | 9p23 | 0.1522 | −0.0761 | 3q25.32 | −0.1115 | 0.0558 |
| 3q27.3 | −0.2529 | 0.1265 | 3p26.1 | 0.1514 | −0.0757 | 3p25.1 | 0.1068 | −0.0534 |
| 3q29 | −0.2499 | 0.1249 | 19q13.13 | −0.1448 | 0.0724 | 9p24.2 | 0.1068 | −0.0534 |
| 3q27.2 | −0.2437 | 0.1219 | 3p24.3 | 0.1438 | −0.0719 | 5q33.3 | 0.1063 | −0.0531 |
| 3q27.1 | −0.2381 | 0.119 | 3p22.2 | 0.1426 | −0.0713 | 2p25.3 | −0.1059 | 0.0529 |
| 5q12.1 | 0.2353 | −0.1177 | 2q34 | 0.1399 | −0.07 | 3q25.1 | −0.1053 | 0.0527 |
| 5q13.1 | 0.216 | −0.108 | 3p21.33 | 0.1384 | −0.0692 | 3q25.31 | −0.1048 | 0.0524 |
| 5q22.1 | 0.2154 | −0.1077 | 9p22.1 | 0.136 | −0.068 | 19q11 | −0.1033 | 0.0516 |
| 21q21.2 | 0.2019 | −0.101 | 3p21.32 | 0.1353 | −0.0676 | 3p14.2 | 0.1024 | −0.0512 |
| 3p22.3 | 0.1868 | −0.0934 | 9p24.1 | 0.1346 | −0.0673 | 3p21.1 | 0.1022 | −0.0511 |
| 9p22.2 | 0.186 | −0.093 | 3p14.3 | 0.1345 | −0.0672 | 5p15.32 | −0.099 | 0.0495 |
| 5q13.3 | 0.1854 | −0.0927 | 5q23.2 | 0.1343 | −0.0672 | 3p21.31 | 0.0982 | −0.0491 |
| 3p26.2 | 0.1842 | −0.0921 | 5q15 | 0.134 | −0.067 | 5p12 | −0.0976 | 0.0488 |
| 5q14.3 | 0.1822 | −0.0911 | 5q21.1 | 0.1338 | −0.0669 | 5q33.1 | 0.0975 | −0.0487 |
| 5q22.2 | 0.1814 | −0.0907 | 5p14.1 | −0.1312 | 0.0656 | 4q32.2 | 0.0974 | −0.0487 |
| 5q22.3 | 0.1774 | −0.0887 | 5p15.2 | −0.1295 | 0.0648 | 5p13.3 | −0.0934 | 0.0467 |
| 9p22.3 | 0.17 | −0.085 | 3p13 | 0.1285 | −0.0643 | 5p13.1 | −0.0933 | 0.0466 |
| 19q13.2 | −0.0926 | 0.0463 | 19q12 | −0.0594 | 0.0297 | 6q11.1 | −0.0225 | 0.0112 |
| 9p21.3 | 0.0907 | −0.0454 | 4p15.31 | 0.0591 | −0.0295 | 20p11.22 | −0.0221 | 0.0111 |
| 4p15.2 | 0.0903 | −0.0452 | 4q31.3 | 0.055 | −0.0275 | 2q33.3 | 0.0209 | −0.0104 |
| 3p21.2 | 0.0901 | −0.0451 | 22q11.1 | −0.0541 | 0.0271 | 11q13.3 | −0.0187 | 0.0093 |
| 3p25.2 | 0.0893 | −0.0447 | 8p22 | 0.0504 | −0.0252 | 4q26 | 0.0154 | −0.0077 |
| 5q14.2 | 0.0886 | −0.0443 | 8p21.2 | 0.0473 | −0.0236 | 9p24.3 | 0.0128 | −0.0064 |
| 3p25.3 | 0.0862 | −0.0431 | 4q23 | 0.0439 | −0.0219 | 2q36.2 | 0.0118 | −0.0059 |
| 5q33.2 | 0.0849 | −0.0425 | 5q31.1 | 0.0434 | −0.0217 | 6p25.3 | −0.0107 | 0.0054 |
| 4q31.23 | 0.0821 | −0.041 | 4p14 | 0.0404 | −0.0202 | 4q31.21 | 0.0105 | −0.0052 |

TABLE 22-continued

Example CNV signature comprising 136 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 5p13.2 | −0.0817 | 0.0409 | 8p21.1 | 0.0393 | −0.0196 | 21q21.3 | 0.0076 | −0.0038 |
| 5p15.31 | −0.0778 | 0.0389 | 4q34.2 | 0.0389 | −0.0195 | 15q25.3 | −0.007 | 0.0035 |
| 4q32.1 | 0.0737 | −0.0369 | 8p23.2 | 0.0386 | −0.0193 | 6p11.2 | −0.0042 | 0.0021 |
| 4p15.1 | 0.0732 | −0.0366 | 9p21.2 | 0.0379 | −0.019 | 15q22.32 | −0.004 | 0.002 |
| 4q32.3 | 0.0718 | −0.0359 | 3p12.2 | 0.0373 | −0.0186 | 4q27 | 0.0033 | −0.0016 |
| 3q24 | −0.0695 | 0.0347 | 5q34 | 0.036 | −0.018 | 10q21.1 | 0.0028 | −0.0014 |
| 4q28.2 | 0.0687 | −0.0344 | 4q22.3 | 0.0331 | −0.0165 | 1p13.3 | 0.0026 | −0.0013 |
| 8p12 | 0.0682 | −0.0341 | 4q31.22 | 0.031 | −0.0155 | | | |
| 5q32 | 0.0651 | −0.0325 | 5q31.2 | 0.0295 | −0.0148 | | | |
| 15q26.3 | −0.0642 | 0.0321 | 4q24 | 0.0279 | −0.0139 | | | |
| 5q23.3 | 0.0622 | −0.0311 | 4q28.1 | 0.0277 | −0.0138 | | | |
| 3q25.2 | −0.0621 | 0.0311 | 15q26.2 | −0.0272 | 0.0136 | | | |
| 5q21.2 | 0.0621 | −0.031 | 17p11.1 | −0.0271 | 0.0135 | | | |
| 4q33 | 0.0602 | −0.0301 | 3p12.1 | 0.0252 | −0.0126 | | | |
| 19q13.11 | −0.0601 | 0.03 | 1p13.2 | 0.0249 | −0.0125 | | | |

TABLE 23

Example CNV signature comprising 120 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.338 | 0.169 | 5q11.2 | 0.145 | −0.0725 | 5p15.33 | −0.1018 | 0.0509 |
| 3q26.31 | −0.3102 | 0.1551 | 3p24.1 | 0.1446 | −0.0723 | 3p14.1 | 0.0989 | −0.0495 |
| 3q26.2 | −0.2912 | 0.1456 | 3p24.2 | 0.1408 | −0.0704 | 19q13.12 | −0.0956 | 0.0478 |
| 3q26.33 | −0.2898 | 0.1449 | 3p23 | 0.1351 | −0.0676 | 5q21.3 | 0.0944 | −0.0472 |
| 3q28 | −0.2789 | 0.1394 | 3p26.3 | 0.1347 | −0.0674 | 5q23.1 | 0.0938 | −0.0469 |
| 5q13.2 | 0.2753 | −0.1376 | 5p15.1 | −0.1347 | 0.0673 | 5q14.1 | 0.0901 | −0.0451 |
| 3q26.1 | −0.2525 | 0.1263 | 3p22.1 | 0.1322 | −0.0661 | 3q25.33 | −0.0874 | 0.0437 |
| 5q12.3 | 0.2378 | −0.1189 | 9p23 | 0.1281 | −0.064 | 3q25.32 | −0.0874 | 0.0437 |
| 3q27.3 | −0.2288 | 0.1144 | 3p26.1 | 0.1273 | −0.0636 | 3p25.1 | 0.0827 | −0.0413 |
| 3q29 | −0.2258 | 0.1129 | 19q13.13 | −0.1206 | 0.0603 | 9p24.2 | 0.0827 | −0.0413 |
| 3q27.2 | −0.2196 | 0.1098 | 3p24.3 | 0.1197 | −0.0598 | 5q33.3 | 0.0821 | −0.0411 |
| 3q27.1 | −0.2139 | 0.107 | 3p22.2 | 0.1185 | −0.0592 | 2p25.3 | −0.0817 | 0.0409 |
| 5q12.1 | 0.2112 | −0.1056 | 2q34 | 0.1158 | −0.0579 | 3q25.1 | −0.0812 | 0.0406 |
| 5q13.1 | 0.1919 | −0.0959 | 3p21.33 | 0.1143 | −0.0571 | 3q25.31 | −0.0807 | 0.0403 |
| 5q22.1 | 0.1913 | −0.0956 | 9p22.1 | 0.1119 | −0.056 | 19q11 | −0.0792 | 0.0396 |
| 21q21.2 | 0.1778 | −0.0889 | 3p21.32 | 0.1111 | −0.0556 | 3p14.2 | 0.0783 | −0.0391 |
| 3p22.3 | 0.1626 | −0.0813 | 9p24.1 | 0.1105 | −0.0552 | 3p21.1 | 0.0781 | −0.039 |
| 9p22.2 | 0.1619 | −0.0809 | 3p14.3 | 0.1104 | −0.0552 | 5p15.32 | −0.0749 | 0.0375 |
| 5q13.3 | 0.1612 | −0.0806 | 5q23.2 | 0.1102 | −0.0551 | 3p21.31 | 0.0741 | −0.037 |
| 3p26.2 | 0.16 | −0.08 | 5q15 | 0.1099 | −0.0549 | 5p12 | −0.0734 | 0.0367 |
| 5q14.3 | 0.1581 | −0.079 | 5q21.1 | 0.1097 | −0.0549 | 5q33.1 | 0.0733 | −0.0367 |
| 5q22.2 | 0.1572 | −0.0786 | 5p14.1 | −0.1071 | 0.0535 | 4q32.2 | 0.0733 | −0.0366 |
| 5q22.3 | 0.1532 | −0.0766 | 5p15.2 | −0.1054 | 0.0527 | 5p13.3 | −0.0693 | 0.0346 |
| 9p22.3 | 0.1458 | −0.0729 | 3p13 | 0.1044 | −0.0522 | 5p13.1 | −0.0691 | 0.0346 |
| 19q13.2 | −0.0684 | 0.0342 | 19q12 | −0.0353 | 0.0176 | | | |
| 9p21.3 | 0.0666 | −0.0333 | 4p15.31 | 0.035 | −0.0175 | | | |
| 4p15.2 | 0.0662 | −0.0331 | 4q31.3 | 0.0309 | −0.0154 | | | |
| 3p21.2 | 0.066 | −0.033 | 22q11.1 | −0.03 | 0.015 | | | |
| 3p25.2 | 0.0652 | −0.0326 | 8p22 | 0.0262 | −0.0131 | | | |
| 5q14.2 | 0.0644 | −0.0322 | 8p21.2 | 0.0231 | −0.0116 | | | |
| 3p25.3 | 0.062 | −0.031 | 4q23 | 0.0197 | −0.0099 | | | |
| 5q33.2 | 0.0608 | −0.0304 | 5q31.1 | 0.0192 | −0.0096 | | | |
| 4q31.23 | 0.0579 | −0.029 | 4p14 | 0.0162 | −0.0081 | | | |
| 5p13.2 | −0.0576 | 0.0288 | 8p21.1 | 0.0151 | −0.0076 | | | |
| 5p15.31 | −0.0536 | 0.0268 | 4q34.2 | 0.0148 | −0.0074 | | | |
| 4q32.1 | 0.0496 | −0.0248 | 8p23.2 | 0.0144 | −0.0072 | | | |
| 4p15.1 | 0.049 | −0.0245 | 9p21.2 | 0.0138 | −0.0069 | | | |
| 4q32.3 | 0.0476 | −0.0238 | 3p12.2 | 0.0131 | −0.0066 | | | |
| 3q24 | −0.0453 | 0.0227 | 5q34 | 0.0119 | −0.0059 | | | |
| 4q28.2 | 0.0446 | −0.0223 | 4q22.3 | 0.0089 | −0.0045 | | | |
| 8p12 | 0.0441 | −0.022 | 4q31.22 | 0.0069 | −0.0034 | | | |
| 5q32 | 0.0409 | −0.0205 | 5q31.2 | 0.0054 | −0.0027 | | | |
| 15q26.3 | −0.04 | 0.02 | 4q24 | 0.0038 | −0.0019 | | | |
| 5q23.3 | 0.0381 | −0.0191 | 4q28.1 | 0.0035 | −0.0018 | | | |
| 3q25.2 | −0.038 | 0.019 | 15q26.2 | −0.0031 | 0.0015 | | | |
| 5q21.2 | 0.0379 | −0.019 | 17p11.1 | −0.0029 | 0.0015 | | | |
| 4q33 | 0.0361 | −0.018 | 3p12.1 | 0.001 | −0.0005 | | | |
| 19q13.11 | −0.0359 | 0.018 | 1p13.2 | 0.0008 | −0.0004 | | | |

TABLE 24

Example CNV signature comprising 101 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.3138 | 0.1569 | 5q11.2 | 0.1208 | −0.0604 | 5p15.33 | −0.0777 | 0.0388 |
| 3q26.31 | −0.2861 | 0.1431 | 3p24.1 | 0.1205 | −0.0602 | 3p14.1 | 0.0748 | −0.0374 |
| 3q26.2 | −0.2671 | 0.1335 | 3p24.2 | 0.1166 | −0.0583 | 19q13.12 | −0.0714 | 0.0357 |
| 3q26.33 | −0.2657 | 0.1329 | 3p23 | 0.111 | −0.0555 | 5q21.3 | 0.0702 | −0.0351 |
| 3q28 | −0.2547 | 0.1274 | 3p26.3 | 0.1106 | −0.0553 | 5q23.1 | 0.0697 | −0.0348 |
| 5q13.2 | 0.2511 | −0.1256 | 5p15.1 | −0.1106 | 0.0553 | 5q14.1 | 0.066 | −0.033 |
| 3q26.1 | −0.2284 | 0.1142 | 3p22.1 | 0.1081 | −0.054 | 3q25.33 | −0.0633 | 0.0316 |
| 5q12.3 | 0.2137 | −0.1068 | 9p23 | 0.1039 | −0.052 | 3q25.32 | −0.0632 | 0.0316 |
| 3q27.3 | −0.2047 | 0.1023 | 3p26.1 | 0.1031 | −0.0516 | 3p25.1 | 0.0585 | −0.0293 |
| 3q29 | −0.2016 | 0.1008 | 19q13.13 | −0.0965 | 0.0482 | 9p24.2 | 0.0585 | −0.0293 |
| 3q27.2 | −0.1955 | 0.0977 | 3p24.3 | 0.0956 | −0.0478 | 5q33.3 | 0.058 | −0.029 |
| 3q27.1 | −0.1898 | 0.0949 | 3p22.2 | 0.0944 | −0.0472 | 2p25.3 | −0.0576 | 0.0288 |
| 5q12.1 | 0.1871 | −0.0935 | 2q34 | 0.0916 | −0.0458 | 3q25.1 | −0.0571 | 0.0285 |
| 5q13.1 | 0.1677 | −0.0839 | 3p21.33 | 0.0901 | −0.0451 | 3q25.31 | −0.0566 | 0.0283 |
| 5q22.1 | 0.1671 | −0.0836 | 9p22.1 | 0.0878 | −0.0439 | 19q11 | −0.055 | 0.0275 |
| 21q21.2 | 0.1537 | −0.0768 | 3p21.32 | 0.087 | −0.0435 | 3p14.2 | 0.0541 | −0.0271 |
| 3p22.3 | 0.1385 | −0.0692 | 9p24.1 | 0.0863 | −0.0432 | 3p21.1 | 0.0539 | −0.027 |
| 9p22.2 | 0.1377 | −0.0689 | 3p14.3 | 0.0862 | −0.0431 | 5p15.32 | −0.0508 | 0.0254 |
| 5q13.3 | 0.1371 | −0.0685 | 5q23.2 | 0.0861 | −0.043 | 3p21.31 | 0.0499 | −0.025 |
| 3p26.2 | 0.1359 | −0.0679 | 5q15 | 0.0857 | −0.0429 | 5p12 | −0.0493 | 0.0246 |
| 5q14.3 | 0.1339 | −0.067 | 5q21.1 | 0.0856 | −0.0428 | 5q33.1 | 0.0492 | −0.0246 |
| 5q22.2 | 0.1331 | −0.0665 | 5p14.1 | −0.0829 | 0.0415 | 4q32.2 | 0.0491 | −0.0246 |
| 5q22.3 | 0.1291 | −0.0645 | 5p15.2 | −0.0812 | 0.0406 | 5p13.3 | −0.0451 | 0.0226 |
| 9p22.3 | 0.1217 | −0.0608 | 3p13 | 0.0802 | −0.0401 | 5p13.1 | −0.045 | 0.0225 |
| 19q13.2 | −0.0443 | 0.0222 | 19q12 | −0.0112 | 0.0056 | | | |
| 9p21.3 | 0.0425 | −0.0212 | 4p15.31 | 0.0108 | −0.0054 | | | |
| 4p15.2 | 0.042 | −0.021 | 4q31.3 | 0.0067 | −0.0034 | | | |
| 3p21.2 | 0.0418 | −0.0209 | 22q11.1 | −0.0058 | 0.0029 | | | |
| 3p25.2 | 0.0411 | −0.0205 | 8p22 | 0.0021 | −0.001 | | | |
| 5q14.2 | 0.0403 | −0.0201 | | | | | | |
| 3p25.3 | 0.0379 | −0.0189 | | | | | | |
| 5q33.2 | 0.0366 | −0.0183 | | | | | | |
| 4q31.23 | 0.0338 | −0.0169 | | | | | | |
| 5p13.2 | −0.0335 | 0.0167 | | | | | | |
| 5p15.31 | −0.0295 | 0.0147 | | | | | | |
| 4q32.1 | 0.0254 | −0.0127 | | | | | | |
| 4p15.1 | 0.0249 | −0.0124 | | | | | | |
| 4q32.3 | 0.0235 | −0.0117 | | | | | | |
| 3q24 | −0.0212 | 0.0106 | | | | | | |
| 4q28.2 | 0.0204 | −0.0102 | | | | | | |
| 8p12 | 0.02 | −0.01 | | | | | | |
| 5q32 | 0.0168 | −0.0084 | | | | | | |
| 15q26.3 | −0.0159 | 0.0079 | | | | | | |
| 5q23.3 | 0.014 | −0.007 | | | | | | |
| 3q25.2 | −0.0139 | 0.0069 | | | | | | |
| 5q21.2 | 0.0138 | −0.0069 | | | | | | |
| 4q33 | 0.012 | −0.006 | | | | | | |
| 19q13.11 | −0.0118 | 0.0059 | | | | | | |

TABLE 25

Example CNV signature comprising 85 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.2897 | 0.1449 | 5q11.2 | 0.0967 | −0.0483 | 5p15.33 | −0.0536 | 0.0268 |
| 3q26.31 | −0.262 | 0.131 | 3p24.1 | 0.0964 | −0.0482 | 3p14.1 | 0.0507 | −0.0253 |
| 3q26.2 | −0.2429 | 0.1215 | 3p24.2 | 0.0925 | −0.0462 | 19q13.12 | −0.0473 | 0.0237 |
| 3q26.33 | −0.2416 | 0.1208 | 3p23 | 0.0868 | −0.0434 | 5q21.3 | 0.0461 | −0.0231 |
| 3q28 | −0.2306 | 0.1153 | 3p26.3 | 0.0865 | −0.0432 | 5q23.1 | 0.0455 | −0.0228 |
| 5q13.2 | 0.227 | −0.1135 | 5p15.1 | −0.0864 | 0.0432 | 5q14.1 | 0.0419 | −0.0209 |
| 3q26.1 | −0.2042 | 0.1021 | 3p22.1 | 0.0839 | −0.042 | 3q25.33 | −0.0391 | 0.0196 |
| 5q12.3 | 0.1895 | −0.0948 | 9p23 | 0.0798 | −0.0399 | 3q25.32 | −0.0391 | 0.0195 |
| 3q27.3 | −0.1805 | 0.0903 | 3p26.1 | 0.079 | −0.0395 | 3p25.1 | 0.0344 | −0.0172 |
| 3q29 | −0.1775 | 0.0887 | 19q13.13 | −0.0723 | 0.0362 | 9p24.2 | 0.0344 | −0.0172 |
| 3q27.2 | −0.1713 | 0.0857 | 3p24.3 | 0.0714 | −0.0357 | 5q33.3 | 0.0339 | −0.0169 |
| 3q27.1 | −0.1656 | 0.0828 | 3p22.2 | 0.0702 | −0.0351 | 2p25.3 | −0.0334 | 0.0167 |
| 5q12.1 | 0.1629 | −0.0815 | 2q34 | 0.0675 | −0.0337 | 3q25.1 | −0.0329 | 0.0165 |
| 5q13.1 | 0.1436 | −0.0718 | 3p21.33 | 0.066 | −0.033 | 3q25.31 | −0.0324 | 0.0162 |
| 5q22.1 | 0.143 | −0.0715 | 9p22.1 | 0.0636 | −0.0318 | 19q11 | −0.0309 | 0.0154 |

TABLE 25-continued

Example CNV signature comprising 85 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 21q21.2 | 0.1295 | −0.0648 | 3p21.32 | 0.0628 | −0.0314 | 3p14.2 | 0.03 | −0.015 |
| 3p22.3 | 0.1144 | −0.0572 | 9p24.1 | 0.0622 | −0.0311 | 3p21.1 | 0.0298 | −0.0149 |
| 9p22.2 | 0.1136 | −0.0568 | 3p14.3 | 0.0621 | −0.031 | 5p15.32 | −0.0266 | 0.0133 |
| 5q13.3 | 0.1129 | −0.0565 | 5q23.2 | 0.0619 | −0.031 | 3p21.31 | 0.0258 | −0.0129 |
| 3p26.2 | 0.1118 | −0.0559 | 5q15 | 0.0616 | −0.0308 | 5p12 | −0.0251 | 0.0126 |
| 5q14.3 | 0.1098 | −0.0549 | 5q21.1 | 0.0614 | −0.0307 | 5q33.1 | 0.025 | −0.0125 |
| 5q22.2 | 0.1089 | −0.0545 | 5p14.1 | −0.0588 | 0.0294 | 4q32.2 | 0.025 | −0.0125 |
| 5q22.3 | 0.105 | −0.0525 | 5p15.2 | −0.0571 | 0.0285 | 5p13.3 | −0.021 | 0.0105 |
| 9p22.3 | 0.0975 | −0.0488 | 3p13 | 0.0561 | −0.028 | 5p13.1 | −0.0209 | 0.0104 |
| 19q13.2 | −0.0202 | 0.0101 | | | | | | |
| 9p21.3 | 0.0183 | −0.0092 | | | | | | |
| 4p15.2 | 0.0179 | −0.0089 | | | | | | |
| 3p21.2 | 0.0177 | −0.0089 | | | | | | |
| 3p25.2 | 0.0169 | −0.0085 | | | | | | |
| 5q14.2 | 0.0161 | −0.0081 | | | | | | |
| 3p25.3 | 0.0137 | −0.0069 | | | | | | |
| 5q33.2 | 0.0125 | −0.0062 | | | | | | |
| 4q31.23 | 0.0097 | −0.0048 | | | | | | |
| 5p13.2 | −0.0093 | 0.0047 | | | | | | |
| 5p15.31 | −0.0054 | 0.0027 | | | | | | |
| 4q32.1 | 0.0013 | −0.0006 | | | | | | |
| 4p15.1 | 0.0007 | −0.0004 | | | | | | |

TABLE 26

Example CNV signature comprising 70 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.2656 | 0.1328 | 5q11.2 | 0.0725 | −0.0363 | 5p15.33 | −0.0294 | 0.0147 |
| 3q26.31 | −0.2378 | 0.1189 | 3p24.1 | 0.0722 | −0.0361 | 3p14.1 | 0.0265 | −0.0133 |
| 3q26.2 | −0.2188 | 0.1094 | 3p24.2 | 0.0684 | −0.0342 | 19q13.12 | −0.0232 | 0.0116 |
| 3q26.33 | −0.2174 | 0.1087 | 3p23 | 0.0627 | −0.0313 | 5q21.3 | 0.022 | −0.011 |
| 3q28 | −0.2064 | 0.1032 | 3p26.3 | 0.0623 | −0.0312 | 5q23.1 | 0.0214 | −0.0107 |
| 5q13.2 | 0.2029 | −0.1014 | 5p15.1 | −0.0623 | 0.0311 | 5q14.1 | 0.0177 | −0.0089 |
| 3q26.1 | −0.1801 | 0.0901 | 3p22.1 | 0.0598 | −0.0299 | 3q25.33 | −0.015 | 0.0075 |
| 5q12.3 | 0.1654 | −0.0827 | 9p23 | 0.0556 | −0.0278 | 3q25.32 | −0.015 | 0.0075 |
| 3q27.3 | −0.1564 | 0.0782 | 3p26.1 | 0.0548 | −0.0274 | 3p25.1 | 0.0103 | −0.0051 |
| 3q29 | −0.1533 | 0.0767 | 19q13.13 | −0.0482 | 0.0241 | 9p24.2 | 0.0103 | −0.0051 |
| 3q27.2 | −0.1472 | 0.0736 | 3p24.3 | 0.0473 | −0.0236 | 5q33.3 | 0.0097 | −0.0049 |
| 3q27.1 | −0.1415 | 0.0707 | 3p22.2 | 0.0461 | −0.023 | 2p25.3 | −0.0093 | 0.0046 |
| 5q12.1 | 0.1388 | −0.0694 | 2q34 | 0.0433 | −0.0217 | 3q25.1 | −0.0088 | 0.0044 |
| 5q13.1 | 0.1194 | −0.0597 | 3p21.33 | 0.0419 | −0.0209 | 3q25.31 | −0.0083 | 0.0041 |
| 5q22.1 | 0.1188 | −0.0594 | 9p22.1 | 0.0395 | −0.0197 | 19q11 | −0.0067 | 0.0034 |
| 21q21.2 | 0.1054 | −0.0527 | 3p21.32 | 0.0387 | −0.0193 | 3p14.2 | 0.0058 | −0.0029 |
| 3p22.3 | 0.0902 | −0.0451 | 9p24.1 | 0.0381 | −0.019 | 3p21.1 | 0.0057 | −0.0028 |
| 9p22.2 | 0.0894 | −0.0447 | 3p14.3 | 0.0379 | −0.019 | 5p15.32 | −0.0025 | 0.0012 |
| 5q13.3 | 0.0888 | −0.0444 | 5q23.2 | 0.0378 | −0.0189 | 3p21.31 | 0.0016 | −0.0008 |
| 3p26.2 | 0.0876 | −0.0438 | 5q15 | 0.0374 | −0.0187 | 5p12 | −0.001 | 0.0005 |
| 5q14.3 | 0.0857 | −0.0428 | 5q21.1 | 0.0373 | −0.0186 | 5q33.1 | 0.0009 | −0.0004 |
| 5q22.2 | 0.0848 | −0.0424 | 5p14.1 | −0.0346 | 0.0173 | 4q32.2 | 0.0008 | −0.0004 |
| 5q22.3 | 0.0808 | −0.0404 | 5p15.2 | −0.0329 | 0.0165 | | | |
| 9p22.3 | 0.0734 | −0.0367 | 3p13 | 0.032 | −0.016 | | | |

TABLE 27

Example CNV signature comprising 50 CNV bands (CNV band
weights are given in columns X0.score and X1.score)

| CNV band | X0.score | X1.score | CNV band | X0.score | X1.score | CNV band | X0.score | X1.score |
|---|---|---|---|---|---|---|---|---|
| 3q26.32 | −0.2414 | 0.1207 | 5q11.2 | 0.0484 | −0.0242 | 5p15.33 | −0.0053 | 0.0026 |
| 3q26.31 | −0.2137 | 0.1068 | 3p24.1 | 0.0481 | −0.024 | 3p14.1 | 0.0024 | −0.0012 |
| 3q26.2 | −0.1947 | 0.0973 | 3p24.2 | 0.0442 | −0.0221 | | | |
| 3q26.33 | −0.1933 | 0.0966 | 3p23 | 0.0385 | −0.0193 | | | |

TABLE 27-continued

Example CNV signature comprising 50 CNV bands (CNV band weights are given in columns X0.score and X1.score)

| CNV band | X0.score | X1.score | CNV band | X0.score | X1.score | CNV band | X0.score | X1.score |
|---|---|---|---|---|---|---|---|---|
| 3q28 | −0.1823 | 0.0912 | 3p26.3 | 0.0382 | −0.0191 | | | |
| 5q13.2 | 0.1787 | −0.0894 | 5p15.1 | −0.0381 | 0.0191 | | | |
| 3q26.1 | −0.156 | 0.078 | 3p22.1 | 0.0356 | −0.0178 | | | |
| 5q12.3 | 0.1413 | −0.0706 | 9p23 | 0.0315 | −0.0157 | | | |
| 3q27.3 | −0.1322 | 0.0661 | 3p26.1 | 0.0307 | −0.0153 | | | |
| 3q29 | −0.1292 | 0.0646 | 19q13.13 | −0.0241 | 0.012 | | | |
| 3q27.2 | −0.123 | 0.0615 | 3p24.3 | 0.0231 | −0.0116 | | | |
| 3q27.1 | −0.1174 | 0.0587 | 3p22.2 | 0.0219 | −0.011 | | | |
| 5q12.1 | 0.1146 | −0.0573 | 2q34 | 0.0192 | −0.0096 | | | |
| 5q13.1 | 0.0953 | −0.0476 | 3p21.33 | 0.0177 | −0.0089 | | | |
| 5q22.1 | 0.0947 | −0.0473 | 9p22.1 | 0.0153 | −0.0077 | | | |
| 21q21.2 | 0.0812 | −0.0406 | 3p21.32 | 0.0146 | −0.0073 | | | |
| 3p22.3 | 0.0661 | −0.033 | 9p24.1 | 0.0139 | −0.007 | | | |
| 9p22.2 | 0.0653 | −0.0326 | 3p14.3 | 0.0138 | −0.0069 | | | |
| 5q13.3 | 0.0646 | −0.0323 | 5q23.2 | 0.0136 | −0.0068 | | | |
| 3p26.2 | 0.0635 | −0.0317 | 5q15 | 0.0133 | −0.0066 | | | |
| 5q14.3 | 0.0615 | −0.0308 | 5q21.1 | 0.0131 | −0.0066 | | | |
| 5q22.2 | 0.0606 | −0.0303 | 5p14.1 | −0.0105 | 0.0053 | | | |
| 5q22.3 | 0.0567 | −0.0283 | 5p15.2 | −0.0088 | 0.0044 | | | |
| 9p22.3 | 0.0493 | −0.0246 | 3p13 | 0.0078 | −0.0039 | | | |

TABLE 28

Example CNV signature comprising 33 CNV bands (CNV band weights are given in columns X0.score and X1.score)

| CNV band | X0.score | X1.score | CNV band | X0.score | X1.score |
|---|---|---|---|---|---|
| 3q26.32 | −0.2173 | 0.1086 | 5q11.2 | 0.0242 | −0.0121 |
| 3q26.31 | −0.1895 | 0.0948 | 3p24.1 | 0.0239 | −0.012 |
| 3q26.2 | −0.1705 | 0.0853 | 3p24.2 | 0.0201 | −0.01 |
| 3q26.33 | −0.1691 | 0.0846 | 3p23 | 0.0144 | −0.0072 |
| 3q28 | −0.1582 | 0.0791 | 3p26.3 | 0.014 | −0.007 |
| 5q13.2 | 0.1546 | −0.0773 | 5p15.1 | −0.014 | 0.007 |
| 3q26.1 | −0.1318 | 0.0659 | 3p22.1 | 0.0115 | −0.0058 |
| 5q12.3 | 0.1171 | −0.0586 | 9p23 | 0.0073 | −0.0037 |
| 3q27.3 | −0.1081 | 0.054 | 3p26.1 | 0.0066 | −0.0033 |
| 3q29 | −0.105 | 0.0525 | | | |
| 3q27.2 | −0.0989 | 0.0494 | | | |
| 3q27.1 | −0.0932 | 0.0466 | | | |
| 5q12.1 | 0.0905 | −0.0452 | | | |
| 5q13.1 | 0.0712 | −0.0356 | | | |
| 5q22.1 | 0.0705 | −0.0353 | | | |
| 21q21.2 | 0.0571 | −0.0285 | | | |
| 3p22.3 | 0.0419 | −0.021 | | | |
| 9p22.2 | 0.0411 | −0.0206 | | | |
| 5q13.3 | 0.0405 | −0.0203 | | | |
| 3p26.2 | 0.0393 | −0.0197 | | | |
| 5q14.3 | 0.0374 | −0.0187 | | | |
| 5q22.2 | 0.0365 | −0.0183 | | | |
| 5q22.3 | 0.0325 | −0.0163 | | | |
| 9p22.3 | 0.0251 | −0.0126 | | | |

TABLE 29

Example CNV signature comprising 25 CNV bands (CNV band weights are given in columns X0.score and X1.score)

| CNV band | X0.score | X1.score | CNV band | X0.score | X1.score |
|---|---|---|---|---|---|
| 3q26.32 | −0.1931 | 0.0966 | 5q11.2 | 0.0001 | −0.0001 |
| 3q26.31 | −0.1654 | 0.0827 | | | |
| 3q26.2 | −0.1464 | 0.0732 | | | |
| 3q26.33 | −0.145 | 0.0725 | | | |
| 3q28 | −0.134 | 0.067 | | | |
| 5q13.2 | 0.1304 | −0.0652 | | | |
| 3q26.1 | −0.1077 | 0.0538 | | | |
| 5q12.3 | 0.093 | −0.0465 | | | |
| 3q27.3 | −0.084 | 0.042 | | | |
| 3q29 | −0.0809 | 0.0405 | | | |

TABLE 29-continued

Example CNV signature comprising 25 CNV bands (CNV band weights are given in columns X0.score and X1.score)

| CNV band | X0.score | X1.score | CNV band | X0.score | X1.score |
|---|---|---|---|---|---|
| 3q27.2 | −0.0748 | 0.0374 | | | |
| 3q27.1 | −0.0691 | 0.0345 | | | |
| 5q12.1 | 0.0663 | −0.0332 | | | |
| 5q13.1 | 0.047 | −0.0235 | | | |
| 5q22.1 | 0.0464 | −0.0232 | | | |
| 21q21.2 | 0.0329 | −0.0165 | | | |
| 3p22.3 | 0.0178 | −0.0089 | | | |
| 9p22.2 | 0.017 | −0.0085 | | | |
| 5q13.3 | 0.0164 | −0.0082 | | | |
| 3p26.2 | 0.0152 | −0.0076 | | | |
| 5q14.3 | 0.0132 | −0.0066 | | | |
| 5q22.2 | 0.0124 | −0.0062 | | | |
| 5q22.3 | 0.0084 | −0.0042 | | | |
| 9p22.3 | 0.001 | −0.0005 | | | |

TABLE 30

Example CNV signature comprising 16 CNV bands (CNV band weights are given in columns X0.score and X1.score)

| CNV band | X0.score | X1.score |
|---|---|---|
| 3q26.32 | −0.169 | 0.0845 |
| 3q26.31 | −0.1413 | 0.0706 |
| 3q26.2 | −0.1222 | 0.0611 |
| 3q26.33 | −0.1209 | 0.0604 |
| 3q28 | −0.1099 | 0.0549 |
| 5q13.2 | 0.1063 | −0.0531 |
| 3q26.1 | −0.0835 | 0.0418 |
| 5q12.3 | 0.0688 | −0.0344 |
| 3q27.3 | −0.0598 | 0.0299 |
| 3q29 | −0.0568 | 0.0284 |
| 3q27.2 | −0.0506 | 0.0253 |
| 3q27.1 | −0.0449 | 0.0225 |
| 5q12.1 | 0.0422 | −0.0211 |
| 5q13.1 | 0.0229 | −0.0114 |
| 5q22.1 | 0.0223 | −0.0111 |
| 21q21.2 | 0.0088 | −0.0044 |

TABLE 31

Example CNV signature comprising 13 CNV bands (CNV band
weights are given in columns X0.score and X1.score)

| CNV band | X0.score | X1.score |
|---|---|---|
| 3q26.32 | −0.1449 | 0.0724 |
| 3q26.31 | −0.1171 | 0.0586 |
| 3q26.2 | −0.0981 | 0.049 |
| 3q26.33 | −0.0967 | 0.0484 |
| 3q28 | −0.0857 | 0.0429 |
| 5q13.2 | 0.0821 | −0.0411 |
| 3q26.1 | −0.0594 | 0.0297 |
| 5q12.3 | 0.0447 | −0.0223 |
| 3q27.3 | −0.0357 | 0.0178 |
| 3q29 | −0.0326 | 0.0163 |
| 3q27.2 | −0.0265 | 0.0132 |
| 3q27.1 | −0.0208 | 0.0104 |
| 5q12.1 | 0.0181 | −0.009 |

TABLE 32

Example CNV signature comprising 11 CNV bands (CNV band
weights are given in columns X0.score and X1.score)

| CNV band | X0.score | X1.score |
|---|---|---|
| 3q26.32 | −0.1207 | 0.0604 |
| 3q26.31 | −0.093 | 0.0465 |
| 3q26.2 | −0.074 | 0.037 |
| 3q26.33 | −0.0726 | 0.0363 |
| 3q28 | −0.0616 | 0.0308 |
| 5q13.2 | 0.058 | −0.029 |
| 3q26.1 | −0.0353 | 0.0176 |
| 5q12.3 | 0.0205 | −0.0103 |
| 3q27.3 | −0.0115 | 0.0058 |
| 3q29 | −0.0085 | 0.0042 |
| 3q27.2 | −0.0023 | 0.0012 |

TABLE 33

Example CNV signature comprising 7 CNV bands (CNV band
weights are given in columns X0.score and X1.score)

| CNV band | X0.score | X1.score |
|---|---|---|
| 3q26.32 | −0.0966 | 0.0483 |
| 3q26.31 | −0.0688 | 0.0344 |
| 3q26.2 | −0.0498 | 0.0249 |

TABLE 33-continued

Example CNV signature comprising 7 CNV bands (CNV band
weights are given in columns X0.score and X1.score)

| CNV band | X0.score | X1.score |
|---|---|---|
| 3q26.33 | −0.0484 | 0.0242 |
| 3q28 | −0.0375 | 0.0187 |
| 5q13.2 | 0.0339 | −0.0169 |
| 3q26.1 | −0.0111 | 0.0056 |

TABLE 34

Example CNV signature comprising 6 CNV bands (CNV band
weights are given in columns X0.score and X1.score)

| CNV band | X0.score | X1.score |
|---|---|---|
| 3q26.32 | −0.0724 | 0.0362 |
| 3q26.31 | −0.0447 | 0.0223 |
| 3q26.2 | −0.0257 | 0.0128 |
| 3q26.33 | −0.0243 | 0.0121 |
| 3q28 | −0.0133 | 0.0067 |
| 5q13.2 | 0.0097 | −0.0049 |

TABLE 35

Example CNV signature comprising 4 CNV bands (CNV band
weights are given in columns X0.score and X1.score)

| CNV band | X0.score | X1.score |
|---|---|---|
| 3q26.32 | −0.0483 | 0.0241 |
| 3q26.31 | −0.0205 | 0.0103 |
| 3q26.2 | −0.0015 | 0.0008 |
| 3q26.33 | −0.0001 | 0.0001 |

TABLE 36

Example CNV signature comprising 1 CNV band (CNV band
weights are given in columns X0.score and X1.score)

| CNV band | X0.score | X1.score |
|---|---|---|
| 3q26.32 | −0.0241 | 0.0121 |

TABLE 37

Summary of characteristic parameters and metrics of example CNV signatures

| CNV Signature Table | CNV Bands | AUC (Validation) | AUV (TCGA) | Threshold Value | Sensitivity (Validation) | Specificity (Validation) | Sensitivity (TCGA) | Specificity (TCGA) |
|---|---|---|---|---|---|---|---|---|
| 19 | 219 | 0.885417 | 0.981012 | 0.015 | 1 | 0.75 | 1 | 0.908396947 |
| 20 | 179 | 0.881944 | 0.980237 | 0.01 | 1 | 0.75 | 1 | 0.923664122 |
| 21 | 155 | 0.878472 | 0.979527 | 0.015 | 1 | 0.75 | 0.9958159 | 0.929389313 |
| 22 | 136 | 0.881944 | 0.978976 | 0.01 | 0.791666667 | 0.833333333 | 0.991631799 | 0.946564885 |
| 23 | 120 | 0.885417 | 0.978473 | 0.01 | 0.083333333 | 0.916666667 | 0.966527197 | 0.958015267 |
| 24 | 101 | 0.888889 | 0.977706 | 0.02 | 0.041666667 | 1 | 0.920502092 | 0.961832061 |
| 25 | 85 | 0.885417 | 0.976492 | 0.06 | 0.041666667 | 1 | 0.941422594 | 0.958015267 |
| 26 | 70 | 0.895833 | 0.974456 | 0.12 | 0 | 1 | 0.907949791 | 0.959923664 |
| 27 | 50 | 0.920139 | 0.972013 | 0.185 | 0 | 1 | 0.820083682 | 0.961832061 |
| 28 | 33 | 0.930556 | 0.966735 | 0.31 | 0 | 1 | 0.907949791 | 0.942748092 |
| 29 | 25 | 0.954861 | 0.963174 | 0.405 | 0 | 1 | 0.912133891 | 0.940839695 |
| 30 | 16 | 0.958333 | 0.960123 | 0.48 | 0.041666667 | 1 | 0.933054393 | 0.927480916 |
| 31 | 13 | 0.965278 | 0.957281 | 0.555 | 0.5 | 1 | 0.979079498 | 0.893129771 |
| 32 | 11 | 0.958333 | 0.953919 | 0.6 | 0.75 | 0.916666667 | 0.987447699 | 0.879770992 |
| 33 | 7 | 0.958333 | 0.951715 | 0.65 | 1 | 0.666666667 | 1 | 0.753816794 |
| 34 | 6 | 0.888889 | 0.949871 | 0.66 | 1 | 0.666666667 | 1 | 0.709923664 |

TABLE 37-continued

| Summary of characteristic parameters and metrics of example CNV signatures | | | | | | | |
|---|---|---|---|---|---|---|---|
| CNV Signature Table | CNV Bands | AUC (Validation) | AUV (TCGA) | Threshold Value | Sensitivity (Validation) | Specificity (Validation) | Sensitivity (TCGA) | Specificity (TCGA) |
| 35 | 4 | 0.861111 | 0.940896 | 0.545 | 0 | 1 | 0 | 1 |
| 36 | 1 | 0.84375 | 0.948861 | 0.62 | 0 | 1 | 0 | 1 |

REFERENCES

1 Huber, W. et al. Orchestrating high-throughput genomic analysis with Bioconductor. Nat Methods 12, 115-121, doi:10.1038/nmeth.3252 (2015).

2 Jeremy George, P. et al. Surveillance for the detection of early lung cancer in patients with bronchial dysplasia. Thorax 62, 43-50, doi:10.1136/thx.2005.052191 (2007).

3 Bibikova, M. et al. High density DNA methylation array with single CpG site resolution. Genomics 98, 288-295, doi: 10.1016/j.ygeno.2011.07.007 (2011).

4 Sandoval, J. et al. Validation of a DNA methylation microarray for 450,000 CpG sites in the human genome. Epigenetics 6, 692-702 (2011).

5 Morris, T. J. et al. ChAMP: 450k Chip Analysis Methylation Pipeline. Bioinformatics 30, 428-430, doi:10.1093/bioinformatics/btt684 (2014).

6 Teschendorff, A. E. et al. DNA methylation outliers in normal breast tissue identify field defects that are enriched in cancer. Nat Commun 7, 10478, doi:10.1038/ncomms10478 (2016).

7 Johnson, W. E., Li, C. & Rabinovic, A. Adjusting batch effects in microarray expression data using empirical Bayes methods. Biostatistics 8, 118-127, doi:10.1093/biostatistics/kxj037 (2007).

8 Ritchie, M. E. et al. limma powers differential expression analyses for RNA-sequencing and microarray studies. Nucleic acids research 43, e47, doi:10.1093/nar/gkv007 (2015).

9 Benjamini, Y., Drai, D., Elmer, G., Kafkafi, N. & Golani, I. Controlling the false discovery rate in behavior genetics research. Behav Brain Res 125, 279-284 (2001).

10 Kolde, R. Pheatmap: pretty heatmaps. R package version 61 (2012).

11 Tibshirani, R., Hastie, T., Narasimhan, B. & Chu, G. Diagnosis of multiple cancer types by shrunken centroids of gene expression. Proceedings of the National Academy of Sciences of the United States of America 99, 6567-6572, doi:10.1073/pnas.082099299 (2002).

12 Robin, X. et al. pROC: an open-source package for R and S+ to analyze and compare ROC curves. BMC Bioinformatics 12, 77, doi: 10.1186/1471-2105-12-77 (2011).

13 Keilwagen, J., Grosse, I. & Grau, J. Area under precision-recall curves for weighted and unweighted data. PLoS One 9, e92209, doi:10.1371/journal.pone.0092209 (2014).

14 Raine, K. M. et al. ascatNgs: Identifying Somatically Acquired Copy-Number Alterations from Whole-Genome Sequencing Data. Current protocols in bioinformatics 56, 15 19 11-15 19 17, doi:10.1002/cpbi.17 (2016).

15 Feber, A. et al. Using high-density DNA methylation arrays to profile copy number alterations. Genome Biol 15, R30, doi:10.1186/gb-2014-15-2-r30 (2014).

16 van Boerdonk, R. A. et al. DNA copy number alterations in endobronchial squamous metaplastic lesions predict lung cancer. American journal of respiratory and critical care medicine 184, 948-956, doi:10.1164/rccm.201102-02180C (2011).

17 van Boerdonk, R. A. et al. DNA copy number aberrations in endobronchial lesions: a validated predictor for cancer. Thorax 69, 451-457, doi:10.1136/thoraxjnl-2013-203821 (2014).

18 Grossman, R. L. et al. Toward a Shared Vision for Cancer Genomic Data. N Engl J Med 375, 1109-1112, doi: 10.1056/NEJMp1607591 (2016).

19 Law, C. W., Chen, Y., Shi, W. & Smyth, G. K. voom: Precision weights unlock linear model analysis tools for RNA-seq read counts. Genome biology 15, R29, doi: 10.1186/gb-2014-15-2-r29 (2014).

20 Luo, W., Friedman, M. S., Shedden, K., Hankenson, K. D. & Woolf, P. J. GAGE: generally applicable gene set enrichment for pathway analysis. BMC Bioinformatics 10, 161, doi:10.1186/1471-2105-10-161 (2009).

21 Kanehisa, M. & Goto, S. KEGG: kyoto encyclopedia of genes and genomes. Nucleic acids research 28, 27-30 (2000).

22 Kanehisa, M., Sato, Y., Kawashima, M., Furumichi, M. & Tanabe, M. KEGG as a reference resource for gene and protein annotation. Nucleic acids research 44, D457-462, doi:10.1093/nar/gkv1070 (2016).

23 Kanehisa, M., Furumichi, M., Tanabe, M., Sato, Y. & Morishima, K. KEGG: new perspectives on genomes, pathways, diseases and drugs. Nucleic acids research 45, D353-D361, doi:10.1093/nar/gkw1092 (2017).

24 Carter, S. L., Eklund, A. C., Kohane, I. S., Harris, L. N. & Szallasi, Z. A signature of chromosomal instability inferred from gene expression profiles predicts clinical outcome in multiple human cancers. Nat Genet 38, 1043-1048, doi:10.1038/ng1861 (2006).

25 Whitfield, M. L. et al. Identification of genes periodically expressed in the human cell cycle and their expression in tumors. Mol Biol Cell 13, 1977-2000, doi:10.1091/mbc.02-02-0030. (2002).

26 Jones, D. et al. cgpCaVEManWrapper: Simple Execution of CaVEMan in Order to Detect Somatic Single Nucleotide Variants in NGS Data. Current protocols in bioinformatics 56, 15 10 11-15 10 18, doi:10.1002/cpbi.20 (2016).

27 Van Loo, P. et al. Allele-specific copy number analysis of tumors. Proc Natl Acad Sci USA 107, 16910-16915, doi:10.1073/pnas.1009843107 (2010).

28 Nik-Zainal, S. et al. The life history of 21 breast cancers. Cell 149, 994-1007, doi:10.1016/j.cell.2012.04.023 (2012).

29 Skinner, M. E., Uzilov, A. V., Stein, L. D., Mungall, C. J. & Holmes, I. H. JBrowse: a next-generation genome browser. Genome Res 19, 1630-1638, doi:10.1101/gr.094607.109 (2009).

30 Raine, K. M. et al. cgpPindel: Identifying Somatically Acquired Insertion and Deletion Events from Paired End Sequencing. Curr Protoc Bioinformatics 52, 15 17 11-12, doi:10.1002/0471250953.bi1507s52 (2015).

31 Ye, K., Schulz, M. H., Long, Q., Apweiler, R. & Ning, Z. Pindel: a pattern growth approach to detect break points of large deletions and medium sized insertions from paired-end short reads. Bioinformatics 25, 2865-2871, doi:10.1093/bioinformatics/btp394 (2009).

32 Papaemmanuil, E. et al. RAG-mediated recombination is the predominant driver of oncogenic rearrangement in ETV6-RUNX1 acute lymphoblastic leukemia. Nature genetics 46, 116-125, doi:10.1038/ng.2874 (2014).

33 Robinson, J. T. et al. Integrative genomics viewer. Nat Biotechnol 29, 24-26, doi:10.1038/nbt.1754 (2011).

34 Thorvaldsdottir, H., Robinson, J. T. & Mesirov, J. P. Integrative Genomics Viewer (IGV): high-performance genomics data visualization and exploration. Brief Bioinform 14, 178-192, doi:10.1093/bib/bbs017 (2013).

35 Endesfelder, D. et al. Chromosomal instability selects gene copy-number variants encoding core regulators of proliferation in ER+ breast cancer. Cancer Res 74, 4853-4863, doi: 10.1158/0008-5472.CAN-13-2664 (2014).

36 Forbes, S. A. et al. COSMIC: somatic cancer genetics at high-resolution. Nucleic acids research 45, D777-D783, doi: 10.1093/nar/gkwl 121 (2017).

37 McLaren, W. et al. The Ensembl Variant Effect Predictor. Genome Biol 17, 122, doi: 10.1186/si 3059-016-0974-4 (2016).

38 Martincorena, I. et al. Universal Patterns of Selection in Cancer and Somatic Tissues. Cell 171, 1029-1041 e1021, doi:10.1016/j.cell.2017.09.042 (2017).

39 Miller, C. A. et al. SciClone: inferring clonal architecture and tracking the spatial and temporal patterns of tumor evolution. PLoS Comput Biol 10, e1003665, doi:10.1371/journal.pcbi.1003665 (2014).

40 McGranahan, N. et al. Clonal neoantigens elicit T cell immunoreactivity and sensitivity to immune checkpoint blockade. Science 351, 1463-1469, doi:10.1126/science.aaf1490 (2016).

41 Blokzijl, F., Janssen, R., van Boxtel, R. & Cuppen, E. MutationalPatterns: comprehensive genome-wide analysis of mutational processes. Genome Med 10, 33, doi: 10.1186/si 3073-018-0539-0 (2018).

42 Alexandrov, L. B. et al. Clock-like mutational processes in human somatic cells. Nat Genet 47, 1402-1407, doi: 10.1038/ng.3441 (2015).

43 Alexandrov, L. B. et al. Signatures of mutational processes in human cancer. Nature 500, 415-421, doi: 10.1038/nature12477 (2013).

44 Martincorena, I. & Campbell, P. J. Somatic mutation in cancer and normal cells. Science 349, 1483-1489, doi: 10.1126/science.aab4082 (2015).

45 Farmery, J. H. R., Smith, M. L. & Lynch, A. G. Telomerecat: A Ploidy-Agnostic Method For Estimating Telomere Length From Whole Genome Sequencing Data. bioRxiv, doi:10.1101/139972 (2017).

46 Olkhov-Mitsel, E and Bapat, B: Strategies for discovery and validation of methylated and hydroxymethylated DNA biomarkers. *Cancer Medicine* 2012, 1(2): 237-260.

47 Herman, J. G., Graff, J. R., Myohanen, S., Nelkin, B. D. & Baylin, S. B.: Methylation-specific PCR: a novel PCR assay for methylation status of CpG islands. *Proc. Natl Acad. Sci. USA* 1996, 93: 9821-9826.

48 Frommer, M. et al.: A genomic sequencing protocol that yields a positive display of 5-methylcytosine residues in individual DNA strands. *Proc. Natl Acad. Sci. USA* 1992, 89: 1827-1831.

49 Xiong, Z. & Laird, P. W.: COBRA: a sensitive and quantitative DNA methylation assay. *Nucleic Acids Res.* 1997, 25: 2532-2534.

50 Gonzalgo, M. L. & Jones, P. A.: Rapid quantitation of methylation differences at specific sites using methylation sensitive single nucleotide primer extension (Ms-SNuPE). *Nucleic Acids Res.* 1997, 25: 2529-2531.

51 Paul D S, Guilhamon P, Karpathakis A, Butcher L M, Thirlwell C, Feber A, Beck S: Assessment of RainDrop BS-seq as a method for large-scale, targeted bisulfite sequencing. *Epigenetics* 2014, 9.

The invention claimed is:

1. A method comprising:
(a) providing a sample of nucleic acid which has been taken from a lung squamous cell carcinoma (LUSC) tissue of a subject;
(b) measuring a differentially methylated position (DMP) signature comprising positions cg07716946 and cg04786287 in the sample;
(c) detecting a change in methylation status at positions cg07716946 and cg04786287 compared to control samples; and
(d) administering an effective amount of lung cancer therapy to the subject with a change in methylation status at positions cg07716946 and cg04786287.

2. A method comprising:
(a) providing a sample of nucleic acid which has been taken from a pre-invasive lung lesion tissue of a subject;
(b) measuring a differentially methylated position (DMP) signature comprising positions cg07716946 and cg04786287 in the sample;
(c) detecting a change in methylation status at positions cg07716946 and cg04786287 compared to control samples; and
(d) administering an effective amount of lung cancer therapy to the subject with a change in methylation status at positions cg07716946 and cg04786287.

3. The method of claim 2, wherein the lung cancer therapy comprises one or more surgical procedures, one or more chemotherapeutic agents, one or more immunotherapeutic agents, one or more radiotherapeutic agents, one or more hormonal therapeutic agents or any combination thereof.

4. The method of claim 3, wherein the one or more surgical procedures comprises lobectomy, bilobectomy, removal of a lung, a lung transplant, a lymphadenectomy, a wedge resection, a segmentectomy, or a sleeve resection.

5. The method of claim 3, wherein the one or more chemotherapeutic agents comprises alkylating agents, antimetabolites, microtubule disrupting agents, topoisomerase inhibitors, topoisomerase II poisons, topoisomerase II catalytic inhibitors, or cytotoxic antibiotics.

6. The method of claim 3, wherein the one or more immunotherapeutic agents comprises monoclonal antibodies, antibody-drug conjugates, or immune checkpoint inhibitors.

7. The method of claim 2, wherein the lung cancer therapy comprises proton beam therapy or photodynamic therapy.

8. The method of claim 1, wherein the lung cancer therapy comprises one or more surgical procedures, one or more chemotherapeutic agents, one or more immunotherapeutic agents, one or more radiotherapeutic agents, one or more hormonal therapeutic agents or any combination thereof.

9. The method of claim 8, wherein the one or more surgical procedures comprises lobectomy, bilobectomy, removal of a lung, a lung transplant, a lymphadenectomy, a wedge resection, a segmentectomy, or a sleeve resection.

10. The method of claim 8, wherein the one or more chemotherapeutic agents comprises alkylating agents, antimetabolites, microtubule disrupting agents, topoisomerase inhibitors, topoisomerase II poisons, topoisomerase II catalytic inhibitors, or cytotoxic antibiotics.

11. The method of claim 8, wherein the one or more immunotherapeutic agents comprises monoclonal antibodies, antibody-drug conjugates, or immune checkpoint inhibitors.

12. The method of claim 1, wherein the lung cancer therapy comprises proton beam therapy or photodynamic therapy.

13. The method of claim 1, further comprising measuring differentially methylation positions of at least one or more of the following positions:

cg03782157, cg12368188, cg25829490, cg09628195, cg20674701, cg22549870, cg02020945, cg14164044, cg10210594, cg22974982, cg15545035, cg03843000, cg16332610, c20627174, cg07524679, cg09570682, cg18891712, cg03892356, cg26470798, cg12144497, cg04153740, cg04828133, cg09968620, cg19664945, cg06685968, cg11362010, cg10759602, cg26053832, cg27071152, cg17975443, cg03366986, cg00332153, cg05317090, cg00459623, cg27622679, cg04490714, cg20501518, cg04164058, cg14239111, cg25371634, cg01783662, cg15888290, cg14631910, cg04689080, cg11123595, cg22541735, cg10364040, cg22991101, cg03222323, cg21425842, cg04233770, cg00503383, cg06530490, cg21811143, cg22674699, cg00217080, cg16971668, cg13406145, cg14290904, cg13294849, cg06316886, cg14765959, cg18235734, cg15281710, cg26666835, cg22669623, cg12254845, cg14428048, cg04018288, cg25023994, cg19006220, cg21319932, cg00901051, cg04094811, cg09165441, cg03731303, cg21865150, cg12506930, cg23475625, cg20177650, cg00414898, cg11095319, cg10288510, cg25392692, cg08529345, cg24864887, cg14720773, cg20295992, cg00040312, cg08404009, cg20312687, cg06890747, cg06822689, cg02164225, cg08260959, cg07265743, cg01558212, cg08548396, cg21591742, cg18096722, cg17204129, cg13158481, cg09323727, cg01466288, cg18698788, cg00689492, cg06966660, cg05020604, cg02469909, cg20762861, cg09670128, cg09170112, cg05857758, cg13217260, cg14537533, cg07378762, cg26509715, cg14087921, cg09387749, cg00005847, cg04472725, cg09181792, cg07345734, cg26590744, cg06733794, cg04819096, cg21545862, cg18630667, cg24269074, cg04415798, cg27103296, cg25702780, cg17588266, cg12384499, cg08594218, cg01414185, cg16794506, cg25960893, cg16305379, cg07716946, cg04786287, cg03782157, cg12368188, cg25829490, cg09628195, cg20674701, cg22549870, cg02020945, cg14164044, cg10210594, cg22974982, cg15545035, cg03843000, cg16332610, cg20627174, cg07524679, cg09570682, cg18891712, cg03892356, cg26470798, cg12144497, cg04153740, cg04828133, cg09968620, cg19664945, cg06685968, cg11362010, cg10759602, cg26053832, cg27071152, cg17975443, cg03366986, cg00332153, cg05317090, cg00459623, cg27622679, cg04490714, cg20501518, cg04164058, cg14239111, cg25371634, cg01783662, cg15888290, cg14631910, cg04689080, cg11123595, cg22541735, cg10364040, cg22991101, cg03222323, c21425842, cg04233770, cg00503383, cg06530490, cg21811143, cg22674699, cg00217080, cg16971668, cg13406145, cg14290904, cg13294849, cg06316886, cg14765959, cg18235734, cg07716946, cg04786287, cg03782157, cg12368188, cg25829490, cg09628195, cg20674701, cg22549870, cg02020945, cg14164044, cg10210594, cg22974982, cg15545035, cg03843000, c16332610, c 2O627174, cg07524679, cg09570682, cg18891712, cg03892356, cg26470798, cg12144497, cg04153740, cg04828133, cg09968620, cg19664945, cg06685968, cg07716946, cg04786287, cg03782157, cg12368188, cg25829490, cg09628195, cg20674701, cg22549870, cg02020945, cg14164044, cg10210594, cg22974982, cg15545035, cg04828133, cg07716946, cg04786287, cg03782157, cg12368188, cg25829490, cg09628195, cg07716946, cg04786287.

14. The method of claim 2, further comprising measuring differentially methylation positions of at least one or more of the following positions:

cg03782157, cg12368188, cg25829490, cg09628195, cg20674701, cg22549870, cg02020945, cg14164044, cg10210594, cg22974982, cg15545035, cg03843000, cg16332610, c20627174, cg07524679, cg09570682, cg18891712, cg03892356, cg26470798, cg12144497, cg04153740, cg04828133, cg09968620, cg19664945, cg06685968, cg11362010, cg10759602, cg26053832, cg27071152, cg17975443, cg03366986, cg00332153, cg05317090, cg00459623, cg27622679, cg04490714, cg20501518, cg04164058, cg14239111, cg25371634, cg01783662, cg15888290, cg14631910, cg04689080, cg11123595, cg22541735, cg10364040, cg22991101, cg03222323, cg21425842, cg04233770, cg00503383, cg06530490, cg21811143, cg22674699, cg00217080, cg16971668, cg13406145, cg14290904, cg13294849, cg06316886, cg14765959, cg18235734, cg15281710, cg26666835, cg22669623, cg12254845, cg14428048, cg04018288, cg25023994, cg19006220, cg21319932, cg00901051, cg04094811, cg09165441, cg03731303, cg21865150, cg12506930, cg23475625, cg20177650, cg00414898, cg11095319, cg10288510, cg25392692, cg08529345, cg24864887, cg14720773, cg20295992, cg00040312, cg08404009, cg20312687, cg06890747, cg06822689, cg02164225, cg08260959, cg07265743, cg01558212, cg08548396, cg21591742, cg18096722, cg17204129, cg13158481, cg09323727, cg01466288, cg18698788, cg00689492, cg06966660, cg05020604, cg02469909, cg20762861, cg09670128, cg09170112, cg05857758, cg13217260, cg14537533, cg07378762, cg26509715, cg14087921, cg09387749, cg00005847, cg04472725, cg09181792, cg07345734, cg26590744, cg06733794, cg04819096, cg21545862, cg18630667, cg24269074, cg04415798, cg27103296, cg25702780, cg17588266, cg12384499, cg08594218, cg01414185, cg16794506, cg25960893, cg16305379, cg07716946, cg04786287, cg03782157, cg12368188, cg25829490, cg09628195, cg20674701, cg22549870, cg02020945, cg14164044, cg10210594, cg22974982, cg15545035, cg03843000, cg16332610, cg20627174, cg07524679, cg09570682, cg18891712, cg03892356, cg26470798, cg12144497, cg04153740, cg04828133, cg09968620, cg19664945, cg06685968, cg11362010, cg10759602, cg26053832, cg27071152, cg17975443, cg03366986, cg00332153, cg05317090, cg00459623, cg27622679, cg04490714, cg20501518, cg04164058, cg14239111, cg25371634, cg01783662, cg15888290, cg14631910, cg04689080, cg11123595, cg22541735, cg10364040, cg22991101, cg03222323, c21425842, cg04233770, cg00503383, cg06530490, cg21811143, cg22674699, cg00217080, cg16971668, cg13406145, cg14290904, cg13294849, cg06316886, cg14765959, cg18235734, cg07716946, cg04786287, cg03782157, cg12368188, cg25829490, cg09628195, cg20674701, cg22549870, cg02020945, cg14164044, cg10210594, cg22974982, cg15545035, cg03843000, c16332610, c 2O627174, cg07524679, cg09570682, cg18891712, cg03892356, cg26470798, cg12144497, cg04153740, cg04828133, cg09968620, cg19664945, cg06685968, cg07716946, cg04786287, cg03782157, cg12368188, cg25829490, cg09628195, cg20674701, cg22549870, cg02020945, cg14164044, cg10210594, cg22974982, cg15545035, cg04828133, cg07716946, cg04786287, cg03782157, cg12368188, cg25829490, cg09628195, cg07716946, cg04786287.

\* \* \* \* \*

SEQUENCE LISTING

```
<160> NUMBER OF SEQ ID NOS: 2

<210> SEQ ID NO 1
<211> LENGTH: 122
<212> TYPE: DNA
<213> ORGANISM: Artificial Sequence
<220> FEATURE:
<223> OTHER INFORMATION: DMP cg07716946
<220> FEATURE:
<221> NAME/KEY: misc_feature
<222> LOCATION: (61)..(62)
<223> OTHER INFORMATION: CpG island

<400> SEQUENCE: 1
ccgggacgct gctggaggcg ccgtcgctcc gcggcggagg cgacccagtt tcccagctct        60
cgtcctcgcc acttcctctg catgggcttc caggagactc ggcctccgtc ggcgacgctg       120
gc                                                                      122

<210> SEQ ID NO 2
<211> LENGTH: 122
<212> TYPE: DNA
<213> ORGANISM: Artificial Sequence
<220> FEATURE:
<223> OTHER INFORMATION: DMP cg04786287
<220> FEATURE:
<221> NAME/KEY: misc_feature
```

-continued

```
<222> LOCATION: (61)..(62)
<223> OTHER INFORMATION: CpG island

<400> SEQUENCE: 2
gctgtccgct gcccgcatcc cttccgccct gggcctctgc acggtctgcg gttttctgtg          60
cgcacttggt cttcagtact agcacccaat tacgtctggg tttttcttct ttacagagct         120
gg                                                                        122
```